US011827623B2

(12) United States Patent
Park et al.

(10) Patent No.: US 11,827,623 B2
(45) Date of Patent: Nov. 28, 2023

(54) HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

(71) Applicant: LT MATERIALS CO., LTD., Yongin (KR)

(72) Inventors: Geon-Yu Park, Yongin (KR); Seung-Gyu Yang, Yongin (KR); Eui-Jeong Choi, Yongin (KR); Dong-Jun Kim, Yongin (KR)

(73) Assignee: LT MATERIALS CO., LTD., Yongin (KR)

(*) Notice: Subject to any disclaimer, the term of this patent is extended or adjusted under 35 U.S.C. 154(b) by 443 days.

(21) Appl. No.: 17/054,355

(22) PCT Filed: Jun. 18, 2019

(86) PCT No.: PCT/KR2019/007335
§ 371 (c)(1),
(2) Date: Nov. 10, 2020

(87) PCT Pub. No.: WO2019/245263
PCT Pub. Date: Dec. 26, 2019

(65) Prior Publication Data

US 2021/0188816 A1 Jun. 24, 2021

(30) Foreign Application Priority Data

Jun. 19, 2018 (KR) ........................ 10-2018-0070358

(51) Int. Cl.
*C07D 403/10* (2006.01)
*C07D 209/82* (2006.01)
(Continued)

(52) U.S. Cl.
CPC ......... *C07D 403/10* (2013.01); *C07D 209/82* (2013.01); *C07D 251/24* (2013.01);
(Continued)

(58) Field of Classification Search
None
See application file for complete search history.

(56) References Cited

U.S. PATENT DOCUMENTS

| | | | | |
|---|---|---|---|---|
| 9,972,789 B2 | 5/2018 | Cho et al. | | |
| 2010/0108997 A1* | 5/2010 | Kim | ..................... | C07D 215/06 564/426 |

(Continued)

FOREIGN PATENT DOCUMENTS

| | | | | |
|---|---|---|---|---|
| JP | 2009114068 A * | 5/2009 | ............. | C07C 13/66 |
| KR | 10-2009-0132352 A | 12/2009 | | |

(Continued)

OTHER PUBLICATIONS

Machine translation of KR-203078749, translation generated Mar. 2023, 36 pages. (Year: 2023).*

(Continued)

*Primary Examiner* — Robert S Loewe
(74) *Attorney, Agent, or Firm* — Birch, Stewart, Kolasch & Birch, LLP

(57) ABSTRACT

The present specification relates to a heterocyclic compound represented by Chemical Formula 1, and an organic light emitting device comprising the same.

17 Claims, 2 Drawing Sheets

(51) Int. Cl.

| | |
|---|---|
| ***C07D 251/24*** | (2006.01) |
| ***C07D 403/14*** | (2006.01) |
| ***C07D 405/14*** | (2006.01) |
| ***C07D 409/14*** | (2006.01) |
| ***C07D 487/04*** | (2006.01) |
| ***C07D 491/048*** | (2006.01) |
| ***C07D 495/04*** | (2006.01) |
| ***H10K 85/40*** | (2023.01) |
| ***H10K 85/60*** | (2023.01) |
| *H10K 50/15* | (2023.01) |
| *H10K 50/16* | (2023.01) |
| *H10K 50/18* | (2023.01) |
| *H10K 50/17* | (2023.01) |

(52) U.S. Cl.

CPC ......... *C07D 403/14* (2013.01); *C07D 405/14* (2013.01); *C07D 409/14* (2013.01); *C07D 487/04* (2013.01); *C07D 491/048* (2013.01); *C07D 495/04* (2013.01); *H10K 85/40* (2023.02); *H10K 85/622* (2023.02); *H10K 85/633* (2023.02); *H10K 85/654* (2023.02); *H10K 85/6572* (2023.02); *H10K 85/6574* (2023.02); *H10K 85/6576* (2023.02); *H10K 50/15* (2023.02); *H10K 50/16* (2023.02); *H10K 50/171* (2023.02); *H10K 50/18* (2023.02)

(56) References Cited

U.S. PATENT DOCUMENTS

| | | | | |
|---|---|---|---|---|
| 2012/0118802 | A1 | 5/2012 | Takai | |
| 2013/0256637 | A1 | 10/2013 | Seo et al. | |
| 2014/0158992 | A1* | 6/2014 | Xia | C07D 403/14 544/216 |
| 2015/0171357 | A1* | 6/2015 | Takada | H10K 85/622 546/276.7 |
| 2016/0181524 | A1 | 6/2016 | Lee et al. | |
| 2017/0294613 | A1* | 10/2017 | Cho | H10K 85/615 |
| 2019/0157569 | A1* | 5/2019 | Lee | H10K 85/615 |
| 2019/0237674 | A1* | 8/2019 | Cha | C07D 409/10 |
| 2019/0319197 | A1 | 10/2019 | Pan et al. | |
| 2020/0203624 | A1 | 6/2020 | Stoessel et al. | |

FOREIGN PATENT DOCUMENTS

| | | | | | |
|---|---|---|---|---|---|
| KR | 10-2010-0041043 | A | | 4/2010 | |
| KR | 10-2010-0045587 | A | | 5/2010 | |
| KR | 2013078749 | A | * | 7/2013 | C07C 15/38 |
| KR | 10-2015-0085772 | A | | 7/2015 | |
| KR | 10-2016-0076010 | A | | 6/2016 | |
| KR | 10-2017-0129599 | A | | 11/2017 | |
| KR | 20170129599 | A | † | 11/2017 | |
| TW | 201114990 | A1 | | 5/2011 | |
| WO | WO-2017200210 | A1 | * | 11/2017 | C07D 251/24 |
| WO | WO 2018/087346 | A1 | | 5/2018 | |
| WO | WO 2018/095390 | A1 | | 5/2018 | |

OTHER PUBLICATIONS

Machine translation of JP-2009114068-A, translation generated Jun. 2023, 13 pages. (Year: 2023).*

International Search Report issued in PCT/KR2019/007335 (PCT/ISA/210), dated Sep. 18, 2019.

Kuwabara et al., "Thermally Stable Multilayered Organic Electroluminescent Devices Using Novel Starburst Molecules, 4,4' ,4"-Tri(N-carbazolyl)triphenylamine (TCTA) and 4,4' ,4"-Tris(3-methylphenylphenylamino)triphenylamine (m-MTDATA), as Hole-Transport Materials", Advanced Materials, vol. 6, No. 9, 1994, pp. 677-679.

* cited by examiner
† cited by third party

【FIG. 1】
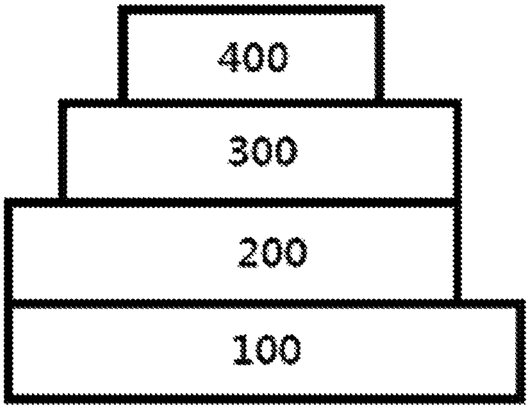
【FIG. 2】
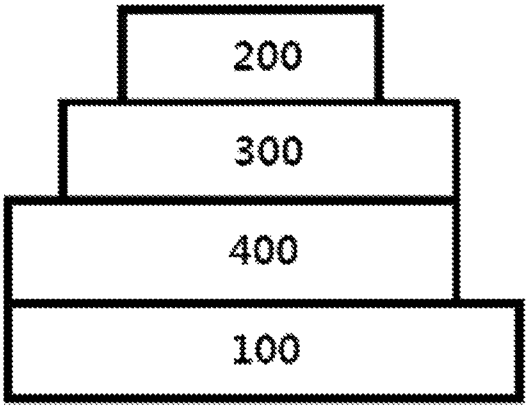

【FIG. 3】
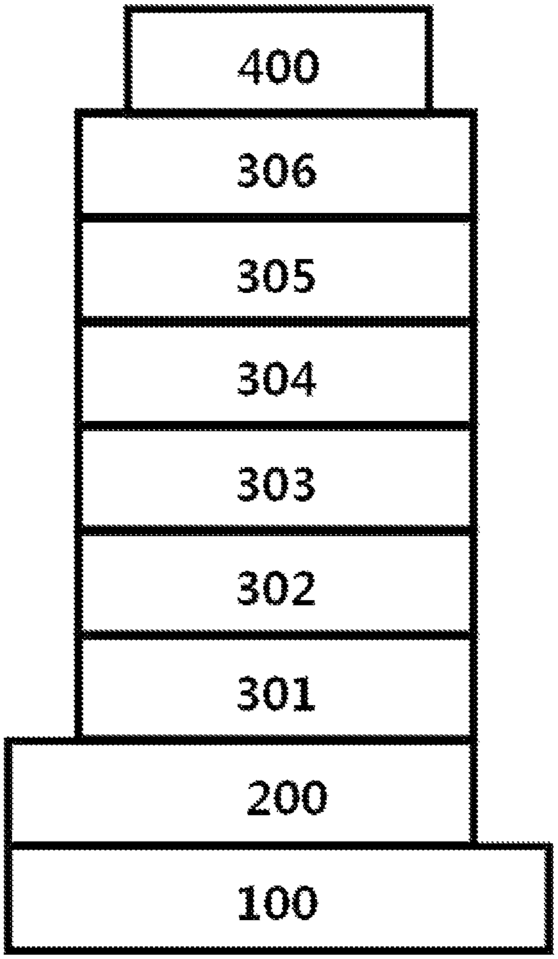

HETEROCYCLIC COMPOUND, ORGANIC LIGHT EMITTING DIODE COMPRISING SAME, COMPOSITION FOR ORGANIC LAYER OF ORGANIC LIGHT EMITTING DIODE, AND METHOD FOR MANUFACTURING ORGANIC LIGHT EMITTING DIODE

TECHNICAL FIELD

This application claims priority to and the benefits of Korean Patent Application No. 10-2018-0070358, filed with the Korean Intellectual Property Office on Jun. 19, 2018, the entire contents of which are incorporated herein by reference.

The present specification relates to a heterocyclic compound, and an organic light emitting device comprising the same.

BACKGROUND ART

An electroluminescent device is one type of self-emissive display devices, and has an advantage of having a wide viewing angle, and a high response speed as well as having an excellent contrast.

An organic light emitting device has a structure disposing an organic thin film between two electrodes. When a voltage is applied to an organic light emitting device having such a structure, electrons and holes injected from the two electrodes bind and pair in the organic thin film, and light emits as these annihilate. The organic thin film may be formed in a single layer or a multilayer as necessary.

A material of the organic thin film may have a light emitting function as necessary. For example, as a material of the organic thin film, compounds capable of forming a light emitting layer themselves alone may be used, or compounds capable of performing a role of a host or a dopant of a host-dopant-based light emitting layer may also be used. In addition thereto, compounds capable of performing roles of hole injection, hole transfer, electron blocking, hole blocking, electron transfer, electron injection and the like may also be used as a material of the organic thin film.

Development of an organic thin film material has been continuously required for enhancing performance, lifetime or efficiency of an organic light emitting device.

PRIOR ART DOCUMENTS

Patent Documents

U.S. Pat. No. 4,356,429

DISCLOSURE

Technical Problem

The present disclosure is directed to providing a heterocyclic compound, and an organic light emitting device comprising the same.

Technical Solution

One embodiment of the present application provides a heterocyclic compound represented by the following Chemical Formula 1.

[Chemical Formula 1]

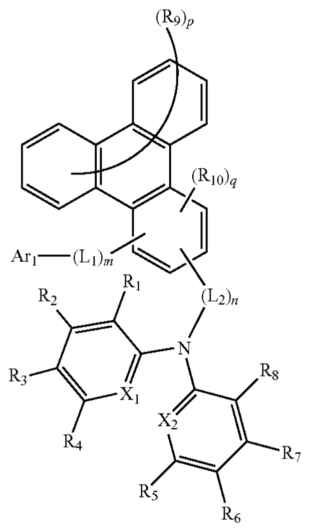

In Chemical Formula 1, $L_1$ and $L_2$ are a direct bond; a substituted or unsubstituted arylene group; or a substituted or unsubstituted heteroarylene group, $Ar_1$ is a substituted or unsubstituted alkyl group; a substituted or unsubstituted aryl group; a substituted or unsubstituted heteroaryl group; —SiRR'R"; or —P(═O)RR', $X_1$ is $CR_x$, $X_2$ is $CR_y$, $R_x$ and $R_y$ are the same as or different from each other, and each independently hydrogen; a substituted or unsubstituted aryl group; or a substituted or unsubstituted heteroaryl group, or bond to each other to form a direct bond, $R_1$ to $R_8$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(═O)RR'; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring, $R_9$ and $R_{10}$ are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; SiRR'R"; —P(═O)RR'; and an amine group unsubstituted or substituted with a substituted or unsubstituted alkyl group, a substituted or unsubstituted aryl group or a substituted or unsubstituted heteroaryl group, R, R' and R" are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, p is an integer of 0 to 8, q is an integer of 0 to 2, m and n are an integer of 0 to 5, and when p, q, m and n are each an integer of 2 or greater, substituents in the parentheses are the same as or different from each other.

In addition, one embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

Another embodiment of the present application provides an organic light emitting device, wherein the organic material layer comprising the heterocyclic compound of Chemical Formula 1 further comprises a heterocyclic compound represented by the following Chemical Formula 2.

[Chemical Formula 2]

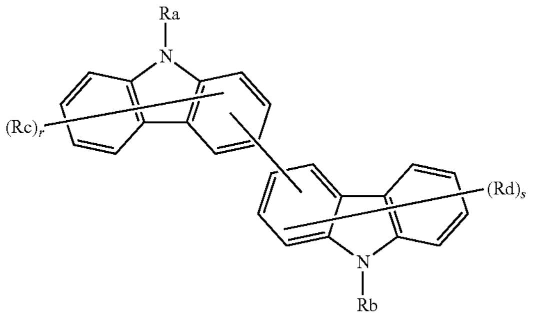

In Chemical Formula 2,

Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; $-SiR_{101}R_{102}R_{103}$; $-P(=O)R_{101}R_{102}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring, $R_{101}$, $R_{102}$ and $R_{103}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, Ra and Rb are the same as or different from each other, and each independently a substituted or unsubstituted aryl group; or a substituted or unsubstituted heteroaryl group, r and s are an integer of 0 to 7, and when r and s are each an integer of 2 or greater, substituents in the parentheses are the same as or different from each other.

In addition, another embodiment of the present application provides a composition for an organic material layer of an organic light emitting device comprising the heterocyclic compound represented by Chemical Formula 1 and the heterocyclic compound represented by Chemical Formula 2.

Lastly, one embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

Advantageous Effects

A compound described in the present specification can be used as a material of an organic material layer of an organic light emitting device. The compound is capable of performing a role of a hole injection material, a hole transfer material, a light emitting material, an electron transfer material, an electron injection material and the like in the organic light emitting device. Particularly, the compound can be used as a light emitting layer material of the organic light emitting device.

Specifically, the compound alone can be used as a light emitting material, or the compound can be used as a host material or a dopant material of a light emitting layer. When using the compound represented by Chemical Formula 1 in an organic material layer, a driving voltage of a device can be lowered, light efficiency can be enhanced, and lifetime properties of a device can be enhanced by thermal stability of the compound.

Particularly, the heterocyclic compound represented by Chemical Formula 1 and the heterocyclic compound represented by Chemical Formula 2 can be simultaneously used as a material of a light emitting layer of an organic light emitting device. In this case, a driving voltage of a device can be lowered, light efficiency can be enhanced, and lifetime properties of a device can be enhanced by thermal stability of the compound.

DESCRIPTION OF DRAWINGS

FIG. 1 to FIG. 3 are diagrams each schematically illustrating a lamination structure of an organic light emitting device according to one embodiment of the present application.

REFERENCE NUMERAL

100: Substrate
200: Anode
300: Organic Material Layer
301: Hole Injection Layer
302: Hole Transfer Layer
303: Light Emitting Layer

304: Hole Blocking Layer
305: Electron Transfer Layer
306: Electron Injection Layer
400: Cathode

MODE FOR DISCLOSURE

Hereinafter, the present application will be described in detail.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, the halogen may be fluorine, chlorine, bromine or iodine.

In the present specification, the alkyl group includes linear or branched having 1 to 60 carbon atoms, and may be further substituted with other substituents. The number of carbon atoms of the alkyl group may be from 1 to 60, specifically from 1 to 40 and more specifically from 1 to 20. Specific examples thereof may include a methyl group, an ethyl group, a propyl group, an n-propyl group, an isopropyl group, a butyl group, an n-butyl group, an isobutyl group, a tert-butyl group, a sec-butyl group, a 1-methyl-butyl group, a 1-ethyl-butyl group, a pentyl group, an n-pentyl group, an isopentyl group, a neopentyl group, a tert-pentyl group, a hexyl group, an n-hexyl group, a 1-methylpentyl group, a 2-methylpentyl group, a 4-methyl-2-pentyl group, a 3,3-dimethylbutyl group, a 2-ethylbutyl group, a heptyl group, an n-heptyl group, a 1-methylhexyl group, a cyclopentylmethyl group, a cyclohexylmethyl group, an octyl group, an n-octyl group, a tert-octyl group, a 1-methylheptyl group, a 2-ethylhexyl group, a 2-propylpentyl group, an n-nonyl group, a 2,2-dimethylheptyl group, a 1-ethyl-propyl group, a 1,1-dimethyl-propyl group, an isohexyl group, a 2-methylpentyl group, a 4-methylhexyl group, a 5-methylhexyl group and the like, but are not limited thereto.

In the present specification, the alkenyl group includes linear or branched having 2 to 60 carbon atoms, and may be further substituted with other substituents. The number of carbon atoms of the alkenyl group may be from 2 to 60, specifically from 2 to 40 and more specifically from 2 to 20. Specific examples thereof may include a vinyl group, a 1-propenyl group, an isopropenyl group, a 1-butenyl group, a 2-butenyl group, a 3-butenyl group, a 1-pentenyl group, a 2-pentenyl group, a 3-pentenyl group, a 3-methyl-1-butenyl group, a 1,3-butadienyl group, an allyl group, a 1-phenylvinyl-1-yl group, a 2-phenylvinyl-1-yl group, a 2,2-diphenylvinyl-1-yl group, a 2-phenyl-2-(naphthyl-1-yl)vinyl-1-yl group, a 2,2-bis(diphenyl-1-yl)vinyl-1-yl group, a stilbenyl group, a styrenyl group and the like, but are not limited thereto.

In the present specification, the alkynyl group includes linear or branched having 2 to 60 carbon atoms, and may be further substituted with other substituents. The number of carbon atoms of the alkynyl group may be from 2 to 60, specifically from 2 to 40 and more specifically from 2 to 20.

In the present specification, the alkoxy group may be linear, branched or cyclic. The number of carbon atoms of the alkoxy group is not particularly limited, but is preferably from 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benxyloxy, p-methylbenzyloxy and the like, but are not limited thereto.

In the present specification, the cycloalkyl group includes monocyclic or polycyclic having 3 to 60 carbon atoms, and may be further substituted with other substituents. Herein, the polycyclic means a group in which the cycloalkyl group is directly linked to or fused with other cyclic groups. Herein, the other cyclic groups may be a cycloalkyl group, but may also be different types of cyclic groups such as a heterocycloalkyl group, an aryl group and a heteroaryl group. The number of carbon groups of the cycloalkyl group may be from 3 to 60, specifically from 3 to 40 and more specifically from 5 to 20. Specific examples thereof may include a cyclopropyl group, a cyclobutyl group, a cyclopentyl group, a 3-methylcyclopentyl group, a 2,3-dimethylcyclopentyl group, a cyclohexyl group, a 3-methylcyclohexyl group, a 4-methylcyclohexyl group, a 2,3-dimethylcyclohexyl group, a 3,4,5-trimethylcyclohexyl group, a 4-tert-butylcyclohexyl group, a cycloheptyl group, a cyclooctyl group and the like, but are not limited thereto.

In the present specification, the heterocycloalkyl group includes O, S, Se, N or Si as a heteroatom, includes monocyclic or polycyclic having 2 to 60 carbon atoms, and may be further substituted with other substituents. Herein, the polycyclic means a group in which the heterocycloalkyl group is directly linked to or fused with other cyclic groups. Herein, the other cyclic groups may be a heterocycloalkyl group, but may also be different types of cyclic groups such as a cycloalkyl group, an aryl group and a heteroaryl group. The number of carbon atoms of the heterocycloalkyl group may be from 2 to 60, specifically from 2 to 40 and more specifically from 3 to 20.

In the present specification, the aryl group includes monocyclic or polycyclic having 6 to 60 carbon atoms, and may be further substituted with other substituents. Herein, the polycyclic means a group in which the aryl group is directly linked to or fused with other cyclic groups. Herein, the other cyclic groups may be an aryl group, but may also be different types of cyclic groups such as a cycloalkyl group, a heterocycloalkyl group and a heteroaryl group. The aryl group includes a spiro group. The number of carbon atoms of the aryl group may be from 6 to 60, specifically from 6 to 40 and more specifically from 6 to 25. Specific examples of the aryl group may include a phenyl group, a biphenyl group, a triphenyl group, a naphthyl group, an anthryl group, a chrysenyl group, a phenanthrenyl group, a perylenyl group, a fluoranthenyl group, a triphenylenyl group, a phenalenyl group, a pyrenyl group, a tetracenyl group, a pentacenyl group, a fluorenyl group, an indenyl group, an acenaphthylenyl group, a benzofluorenyl group, a spirobifluorenyl group, a 2,3-dihydro-1H-indenyl group, a fused ring thereof, and the like, but are not limited thereto.

In the present specification, the silyl group is a substituent including Si, having the Si atom directly linked as a radical, and is represented by $-SiR_{104}R_{105}R_{106}$. $R_{104}$ to $R_{106}$ are the same as or different from each other, and may be each independently a substituent formed with at least one of hydrogen; deuterium; a halogen group; an alkyl group; an alkenyl group; an alkoxy group; a cycloalkyl group; an aryl group; and a heterocyclic group. Specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the fluorenyl group may be substituted, and adjacent substituents may bond to each other to form a ring.

When the fluorenyl group is substituted,

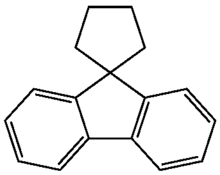
,
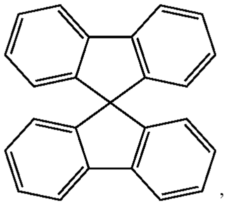
,
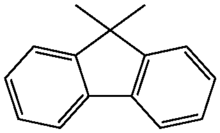
,
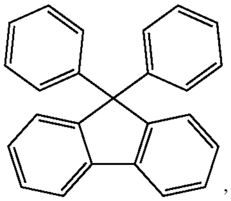
,
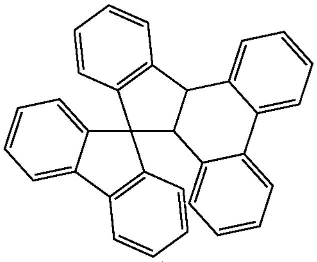
,
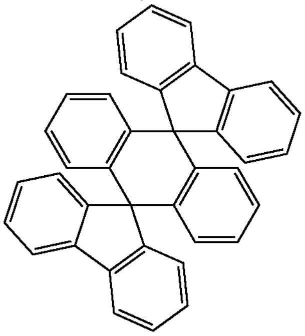

and the like may be included, however, the structure is not limited thereto.

In the present specification, the heteroaryl group includes O, S, Se, N or Si as a heteroatom, includes monocyclic or polycyclic having 2 to 60 carbon atoms, and may be further substituted with other substituents. Herein, the polycyclic means a group in which the heteroaryl group is directly linked to or fused with other cyclic groups. Herein, the other cyclic groups may be a heteroaryl group, but may also be different types of cyclic groups such as a cycloalkyl group, a heterocycloalkyl group and an aryl group. The number of carbon atoms of the heteroaryl group may be from 2 to 60, specifically from 2 to 40 and more specifically from 3 to 25. Specific examples of the heteroaryl group may include a pyridyl group, a pyrrolyl group, a pyrimidyl group, a pyridazinyl group, a furanyl group, a thiophene group, an imidazolyl group, a pyrazolyl group, an oxazolyl group, an isoxazolyl group, a thiazolyl group, an isothiazolyl group, a triazolyl group, a furazanyl group, an oxadiazolyl group, a thiadiazolyl group, a dithiazolyl group, a tetrazolyl group, a pyranyl group, a thiopyranyl group, a diazinyl group, an oxazinyl group, a thiazinyl group, a dioxynyl group, a triazinyl group, a tetrazinyl group, a quinolyl group, an isoquinolyl group, a quinazolinyl group, an isoquinazolinyl group, a qninozolinyl group, a naphthyridyl group, an acridinyl group, a phenanthridinyl group, an imidazopyridinyl group, a diazanaphthalenyl group, a triazaindene group, an indolyl group, an indolizinyl group, a benzothiazolyl group, a benzoxazolyl group, a benzimidazolyl group, a benzothiophene group, a benzofuran group, a dibenzothiophene group, a dibenzofuran group, a carbazolyl group, a benzocarbazolyl group, a dibenzocarbazolyl group, a phenazinyl group, a dibenzosilole group, spirobi(dibenzosilole), a dihydrophenazinyl group, a phenoxazinyl group, a phenanthridyl group, an imidazopyridinyl group, a thienyl group, an indolo[2,3-a]carbazolyl group, an indolo[2,3-b]carbazolyl group, an indolinyl group, a 10,11-dihydro-dibenzo[b,f]azepine group, a 9,10-dihydroacridinyl group, a phenanthrazinyl group, a phenothiathiazinyl group, a phthalazinyl group, a naphthylidinyl group, a phenanthrolinyl group, a benzo[c][1,2,5]thiadiazolyl group, a 5,10-dihydrobenzo[b,e][1,4]azasilinyl, a pyrazolo[1,5-c]quinazolinyl group, a pyrido[1,2-b]indazolyl group, a pyrido[1,2-a]imidazo[1,2-e]indolinyl group, a 5,11-dihydroindeno[1,2-b]carbazolyl group and the like, but are not limited thereto.

In the present specification, the amine group may be selected from the group consisting of a monoalkylamine group; a monoarylamine group; a monoheteroarylamine group; $-NH_2$; a dialkylamine group; a diarylamine group; a diheteroarylamine group; an alkylarylamine group; an alkylheteroarylamine group; and an arylheteroarylamine group, and although not particularly limited thereto, the number of carbon atoms is preferably from 1 to 30. Specific examples of the amine group may include a methylamine group, a dimethylamine group, an ethylamine group, a diethylamine group, a phenylamine group, a naphthylamine group, a biphenylamine group, a dibiphenylamine group, an anthracenylamine group, a 9-methyl-anthracenylamine group, a diphenylamine group, a phenylnaphthylamine group, a ditolylamine group, a phenyltolylamine group, a triphenylamine group, a biphenylnaphthylamine group, a phenylbiphenylamine group, a biphenylfluorenylamine group, a phenyltriphenylenylamine group, a biphenyltriphenylenylamine group and the like, but are not limited thereto.

In the present specification, the arylene group means the aryl group having two bonding sites, that is, a divalent group. Descriptions on the aryl group provided above may be applied thereto except for those that are each a divalent. In addition, the heteroarylene group means the heteroaryl group having two bonding sites, that is, a divalent group. Descriptions on the heteroaryl group provided above may be applied thereto except for those that are each a divalent.

In the present specification, specific examples of the phosphine oxide group may include a diphenylphosphine oxide group, a dinaphthylphosphine oxide group and the like, but are not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

In the present specification, "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; P(═O)RR'; C1 to C20 alkylamine; C6 to C60 monocyclic or polycyclic arylamine; and C2 to C60 monocyclic or polycyclic heteroarylamine, or being unsubstituted, or being substituted with a substituent linking two or more substituents selected from among the substituents illustrated above, or being unsubstituted.

One embodiment of the present application provides a compound represented by Chemical Formula 1.

In one embodiment of the present application, Chemical Formula 1 may be represented by the following Chemical Formula 3 or 4.

[Chemical Formula 3]

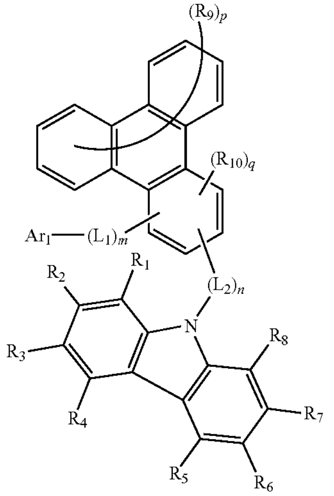

[Chemical Formula 4]

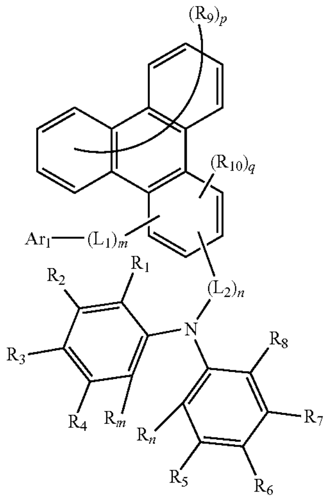

In Chemical Formulae 3 and 4, $R_1$ to $R_{10}$, $Ar_1$, $L_1$, $L_2$, p, q and m have the same definitions as in Chemical Formula 1, $R_m$ and $R_n$ are the same as or different from each other, and may be each independently hydrogen; a substituted or unsubstituted aryl group; or a substituted or unsubstituted heteroaryl group.

In one embodiment of the present application, $R_m$ and $R_n$ may be hydrogen.

In one embodiment of the present application, $R_x$ and $R_y$ are the same as or different from each other, and each independently hydrogen; a substituted or unsubstituted aryl group; or a substituted or unsubstituted heteroaryl group, or may bond to each other to form a direct bond.

In another embodiment, $R_x$ and $R_y$ are hydrogen, or may bond to each to form a direct bond.

In one embodiment of the present application, $L_1$ and $L_2$ may be a direct bond; a substituted or unsubstituted arylene group; or a substituted or unsubstituted heteroarylene group.

In another embodiment, $L_1$ and $L_2$ may be a direct bond; a substituted or unsubstituted C6 to C60 arylene group; or a substituted or unsubstituted C2 to C60 heteroarylene group.

In another embodiment, $L_1$ and $L_2$ may be a direct bond; a substituted or unsubstituted C6 to C40 arylene group; or a substituted or unsubstituted C2 to C40 heteroarylene group.

In another embodiment, $L_1$ and $L_2$ may be a direct bond; a C6 to C40 arylene group; or a C2 to C40 heteroarylene group.

In another embodiment, $L_1$ and $L_2$ may be a direct bond; a C6 to C20 arylene group; or a C2 to C20 heteroarylene group.

In another embodiment, $L_1$ and $L_2$ may be a direct bond; a phenylene group; a biphenylene group; a naphthylene group; or a divalent pyridine group.

In one embodiment of the present application, $L_2$ may be a direct bond.

In one embodiment of the present application, $R_9$ and $R_{10}$ are the same as or different from each other, and may be each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; SiRR'R"; —P(═O)RR'; and an amine group unsubstituted or substituted with a substituted or unsubstituted alkyl group, a substituted or unsubstituted aryl group or a substituted or unsubstituted heteroaryl group.

In another embodiment, $R_9$ and $R_{10}$ are the same as or different from each other, and may be each independently hydrogen; a substituted or unsubstituted aryl group; or a substituted or unsubstituted heteroaryl group.

In another embodiment, $R_9$ and $R_{10}$ are the same as or different from each other, and may be each independently hydrogen; a substituted or unsubstituted C6 to C60 aryl group; or a substituted or unsubstituted C2 to C60 heteroaryl group.

In another embodiment, $R_9$ and $R_{10}$ are the same as or different from each other, and may be each independently hydrogen.

In one embodiment of the present application, $R_1$ to $R_8$ are the same as or different from each other, and each independently selected from the group consisting of hydrogen; deuterium; a substituted or unsubstituted alkyl group; a substituted or unsubstituted aryl group; a substituted or unsubstituted heteroaryl group; —SiRR'R"; —P(=O)RR'; and an amine group unsubstituted or substituted with a substituted or unsubstituted alkyl group, a substituted or unsubstituted aryl group or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_1$ to $R_8$ are the same as or different from each other, and each independently selected from the group consisting of hydrogen; a substituted or unsubstituted aryl group; a substituted or unsubstituted heteroaryl group; and an amine group unsubstituted or substituted with a substituted or unsubstituted alkyl group, a substituted or unsubstituted aryl group or a substituted or unsubstituted heteroaryl group, or two or more groups adjacent to each other may bond to each other to form a substituted or unsubstituted aromatic hydrocarbon ring or a substituted or unsubstituted heteroring.

In another embodiment, $R_1$ to $R_8$ are the same as or different from each other, and each independently selected from the group consisting of hydrogen; a substituted or unsubstituted C6 to C60 aryl group; a substituted or unsubstituted C2 to C60 heteroaryl group; and an amine group unsubstituted or substituted with a substituted or unsubstituted C6 to C60 aryl group, or two or more groups adjacent to each other may bond to each other to form a substituted or unsubstituted C6 to C60 aromatic hydrocarbon ring or a substituted or unsubstituted C2 to C60 heteroring.

In another embodiment, $R_1$ to $R_8$ are the same as or different from each other, and each independently selected from the group consisting of hydrogen; a substituted or unsubstituted C6 to C40 aryl group; a substituted or unsubstituted C2 to C40 heteroaryl group; and an amine group unsubstituted or substituted with a substituted or unsubstituted C6 to C40 aryl group, or two or more groups adjacent to each other may bond to each other to form a substituted or unsubstituted C6 to C40 aromatic hydrocarbon ring or a substituted or unsubstituted C2 to C40 heteroring.

In another embodiment, $R_1$ to $R_8$ are the same as or different from each other, and each independently selected from the group consisting of hydrogen; a C6 to C40 aryl group unsubstituted or substituted with a C1 to C40 alkyl group; a C2 to C40 heteroaryl group unsubstituted or substituted with a C6 to C40 aryl group; and an amine group unsubstituted or substituted with a C6 to C40 aryl group, or two or more groups adjacent to each other may bond to each other to form a C6 to C40 aromatic hydrocarbon ring unsubstituted or substituted with a C1 to C40 alkyl group, or a C2 to C40 heteroring unsubstituted or substituted with a C6 to C40 aryl group.

In another embodiment, $R_1$ to $R_8$ are the same as or different from each other, and each independently selected from the group consisting of hydrogen; a phenyl group; a naphthyl group; a triphenylenyl group; a dimethylfluorenyl group; a dibenzothiophene group; a dibenzofuran group; a carbazole group unsubstituted or substituted with a phenyl group; a benzo[c]carbazole group unsubstituted or substituted with a phenyl group; a diphenylamine group; and a dibiphenylamine group, or two or more groups adjacent to each other may bond to each other to form a benzene ring; an indene ring unsubstituted or substituted with a methyl group; an indole ring unsubstituted or substituted with a phenyl group; a benzofuran ring; or a benzothiophene ring.

In one embodiment of the present application, $Ar_1$ may be a substituted or unsubstituted alkyl group; a substituted or unsubstituted aryl group; a substituted or unsubstituted heteroaryl group; —SiRR'R"; or —P(=O)RR'.

In another embodiment, $Ar_1$ may be a substituted or unsubstituted C6 to C60 aryl group; a substituted or unsubstituted C2 to C60 heteroaryl group; or —SiRR'R".

In another embodiment, $Ar_1$ may be a substituted or unsubstituted C6 to C40 aryl group; a substituted or unsubstituted C2 to C40 heteroaryl group; or —SiRR'R".

In another embodiment, $Ar_1$ may be a C6 to C40 aryl group unsubstituted or substituted with a C6 to C40 alkyl group; a C2 to C40 heteroaryl group unsubstituted or substituted with one or more substituents selected from the group consisting of a C6 to C40 aryl group and a C2 to C40 heteroaryl group; or —SiRR'R".

In another embodiment, $Ar_1$ may be a phenyl group; a dimethylfluorenyl group; a triphenylenyl group; a pyridine group unsubstituted or substituted with a phenyl group; a pyrimidine group unsubstituted or substituted with a phenyl group; a triazine group unsubstituted or substituted with one or more substituents selected from the group consisting of a phenyl group, a biphenyl group, a naphthyl group, a dimethylfluorene group, a triphenylenyl group, a dibenzothiophene group and a dibenzofuran group; a phenanthroline group; a benzimidazole group unsubstituted or substituted with a phenyl group; a quinol group unsubstituted or substituted with a phenyl group; a quinazoline group unsubstituted or substituted with a phenyl group; a dibenzofuran group; a dibenzothiophene group; a benzo[4.5]thieno[3,2-d]pyrimidine group unsubstituted or substituted with a phenyl group; or a benzofuro[3,2-d]pyrimidine group unsubstituted or substituted with a phenyl group.

In one embodiment of the present application, $Ar_1$ may be substituted again with —CN or a methyl group.

In one embodiment of the present application, R, R' and R" are the same as or different from each other, and may be each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group.

In another embodiment, R, R' and R" are the same as or different from each other, and may be each independently a substituted or unsubstituted aryl group.

In another embodiment, R, R' and R" are the same as or different from each other, and may be each independently a substituted or unsubstituted C6 to C60 aryl group.

In another embodiment, R, R' and R" are the same as or different from each other, and may be each independently a substituted or unsubstituted C6 to C40 aryl group.

In another embodiment, R, R' and R" are the same as or different from each other, and may be each independently a C6 to C40 aryl group.

In another embodiment, R, R' and R" may be a phenyl group.

In one embodiment of the present application, Chemical Formula 1 may be represented by the following Chemical Formula 5 or 6.

[Chemical Formula 5]

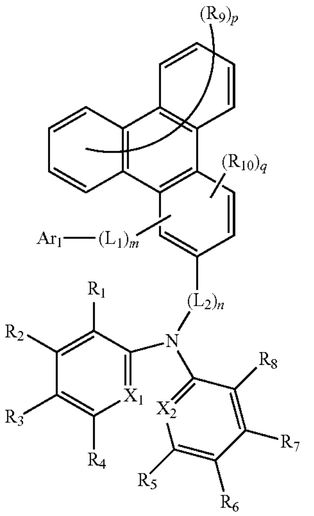

[Chemical Formula 6]

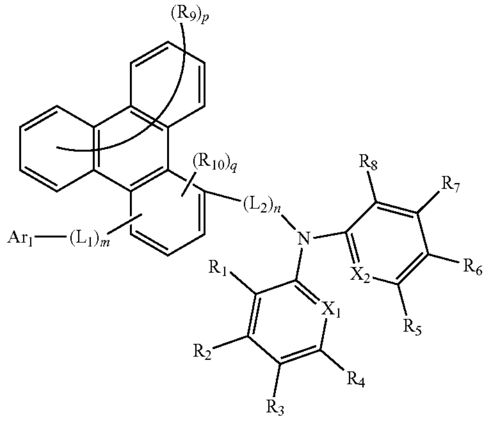

In Chemical Formulae 5 and 6, $L_1$, $L_2$, $Ar_1$, $R_1$ to $R_{10}$, $X_1$, $X_2$, p, q, m and n have the same definitions as in Chemical Formula 1.

In one embodiment of the present application, Chemical Formula 1 may be represented by any one of the following Chemical Formulae 7 to 12.

[Chemical Formula 7]

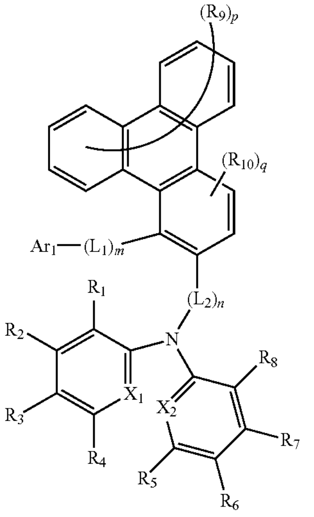

-continued

[Chemical Formula 8]

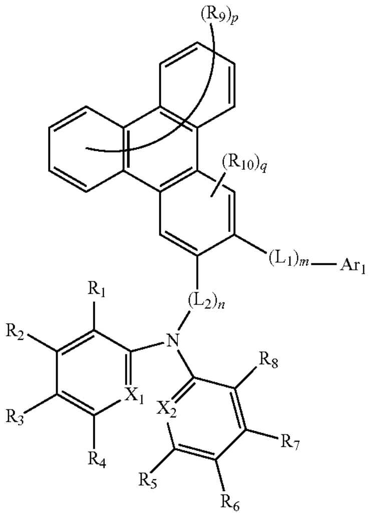

[Chemical Formula 9]

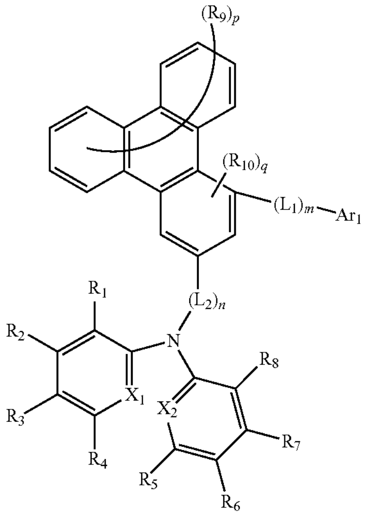

[Chemical Formula 10]

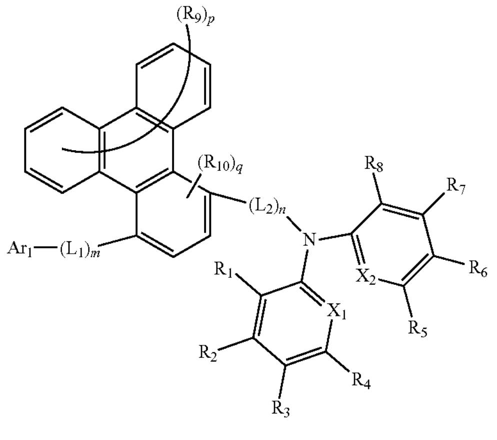

-continued
[Chemical Formula 11]
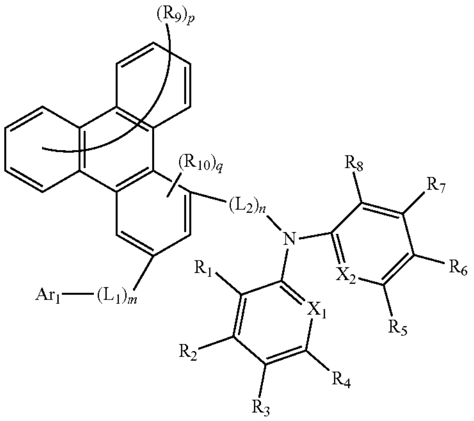
-continued
[Chemical Formula 12]
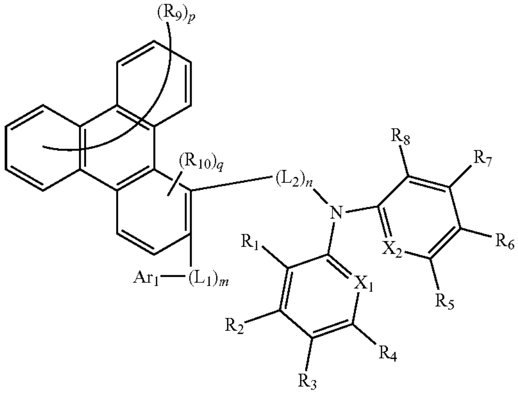
In Chemical Formulae 7 to 12,
$L_1$, $L_2$, $Ar_1$, $R_1$ to $R_{10}$, $X_1$, $X_2$, p, q, m and n have the same definitions as in Chemical Formula 1.
In the heterocyclic compound provided in one embodiment of the present application, Chemical Formula 1 is represented by any one of the following compounds.
1-1
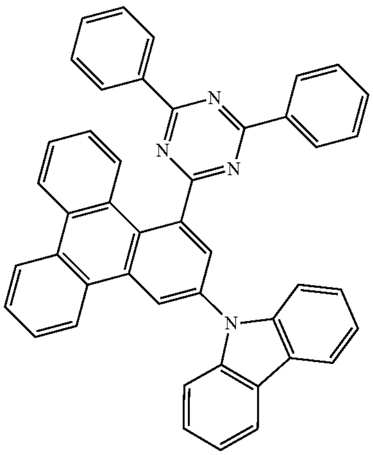
1-2
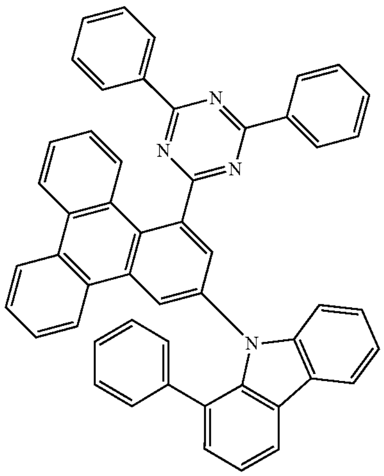
1-3
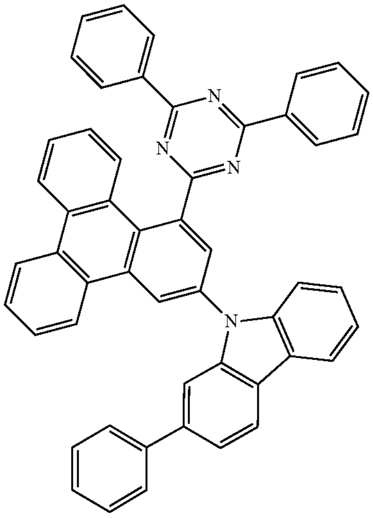
1-4
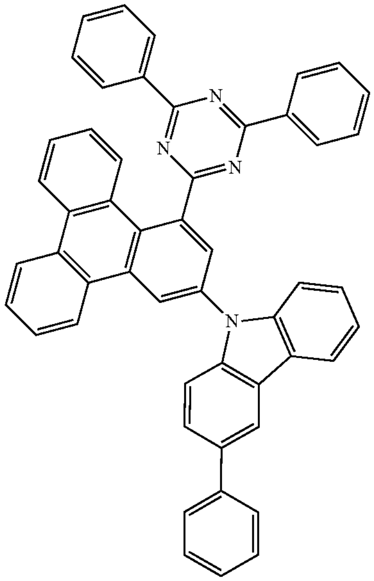

-continued
1-5
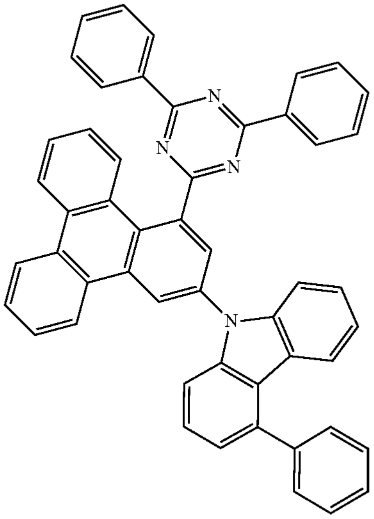
1-6
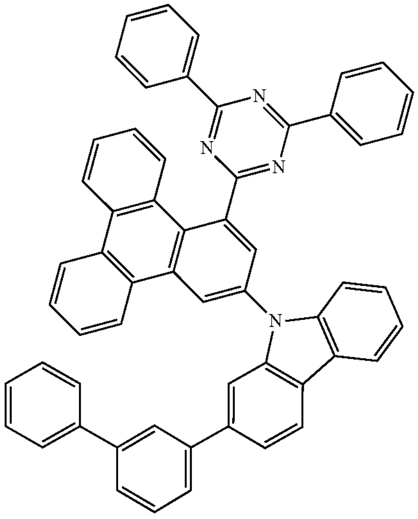
1-7
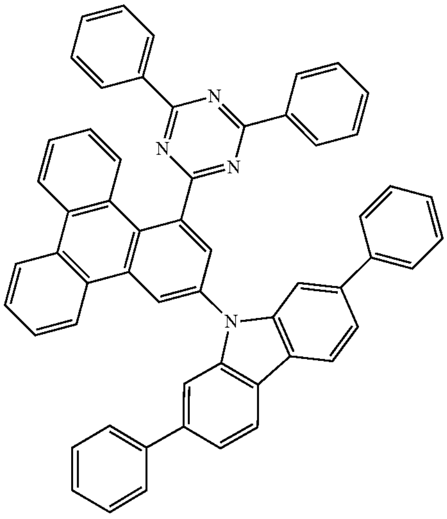
1-8
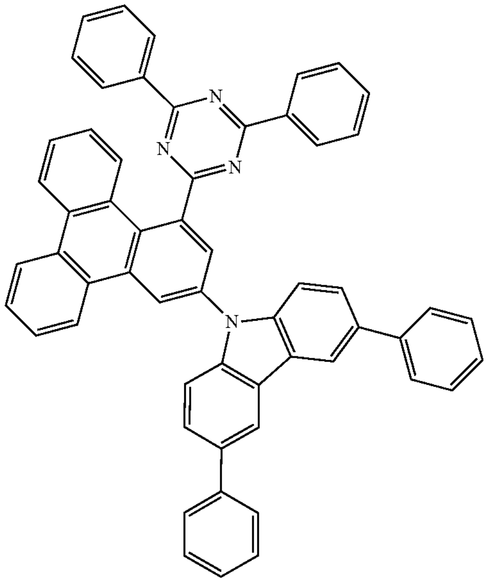

-continued
1-9
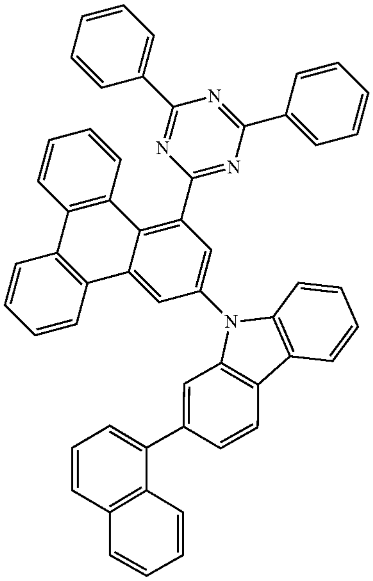
1-10
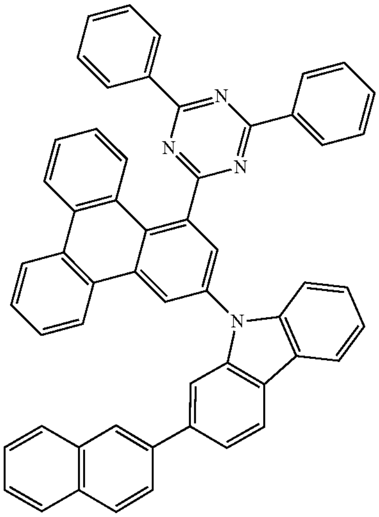
1-11
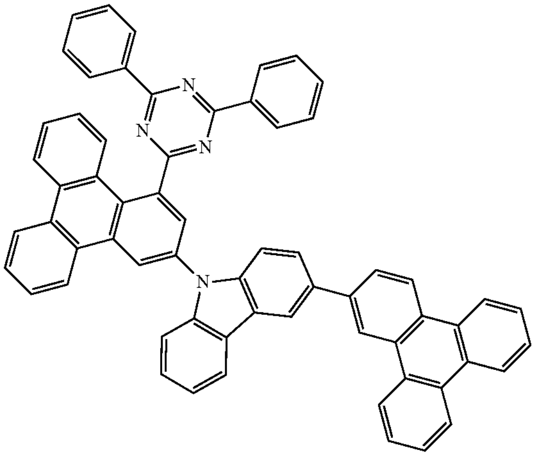
1-12
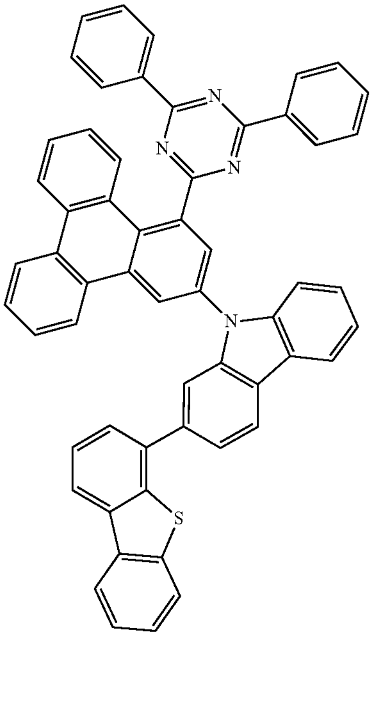

-continued
1-13
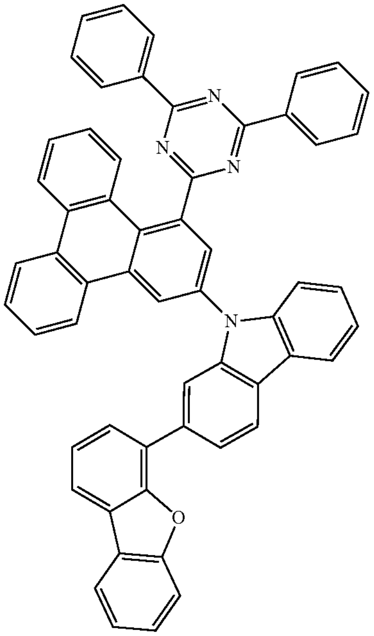
1-14
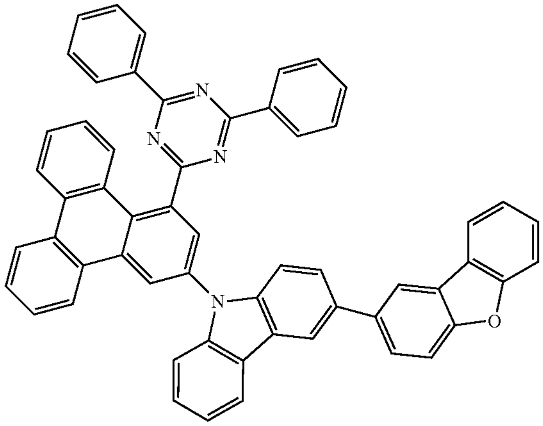
1-15
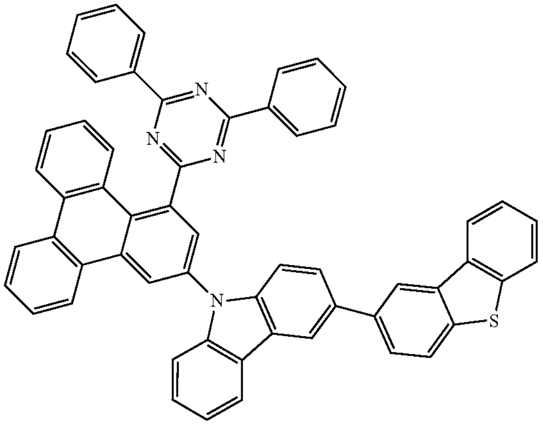
1-16
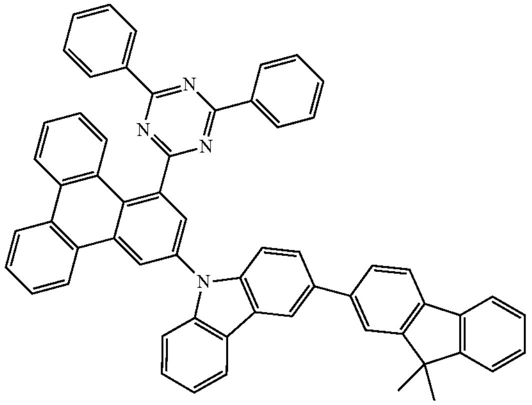

-continued
1-17
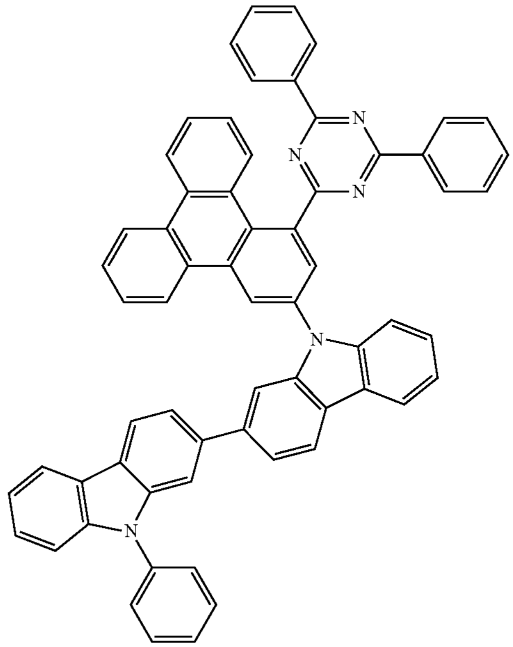
1-18
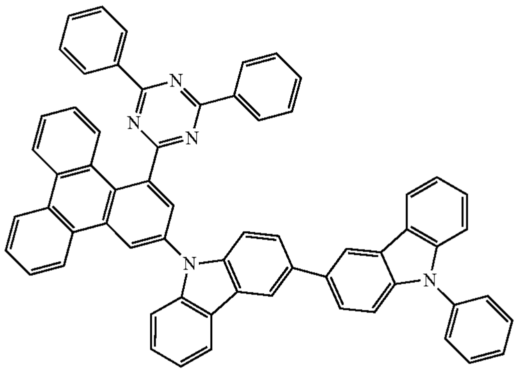
1-19
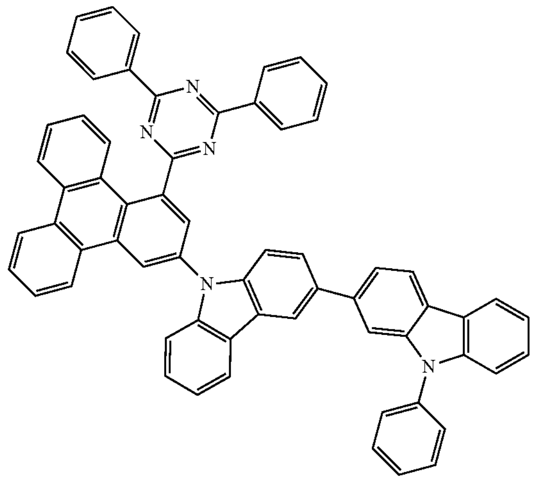
1-20
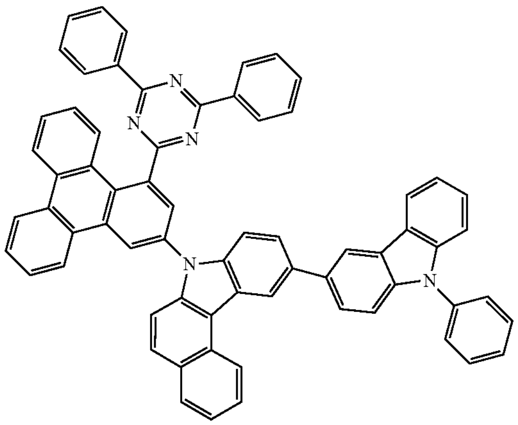
1-21
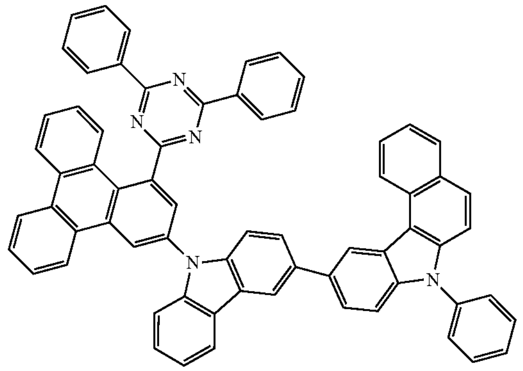
1-22
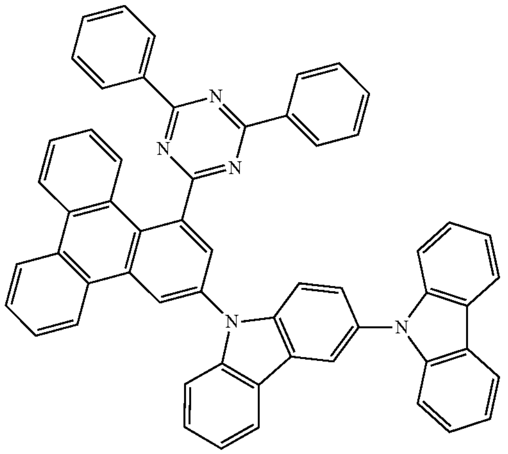

-continued
1-23
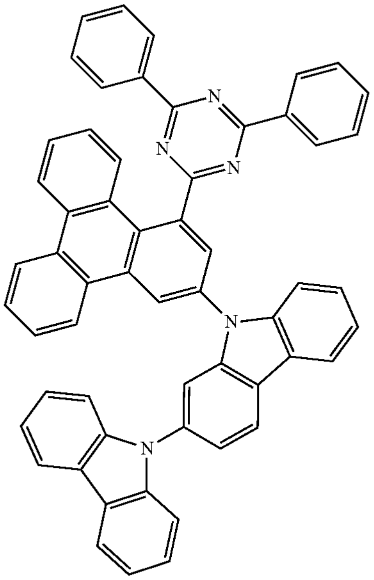
1-24
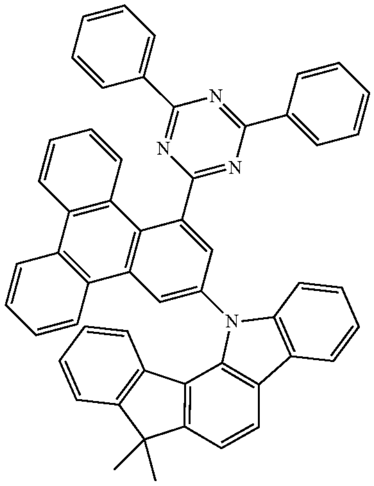
1-25
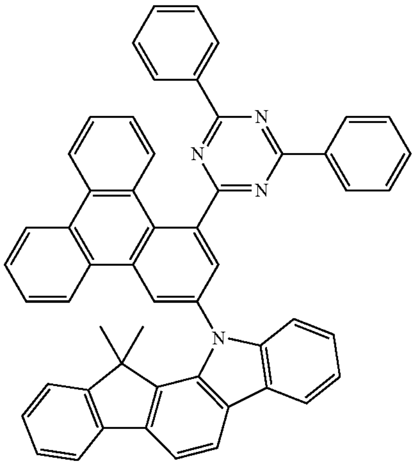
1-26
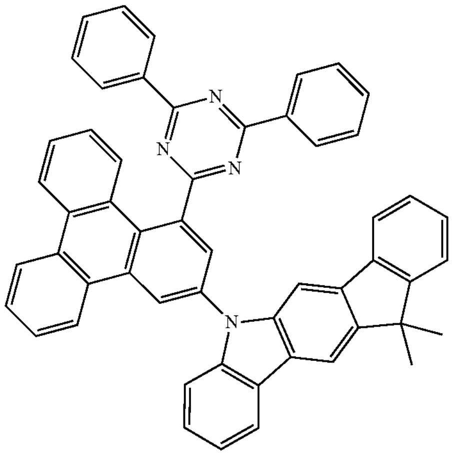
1-27
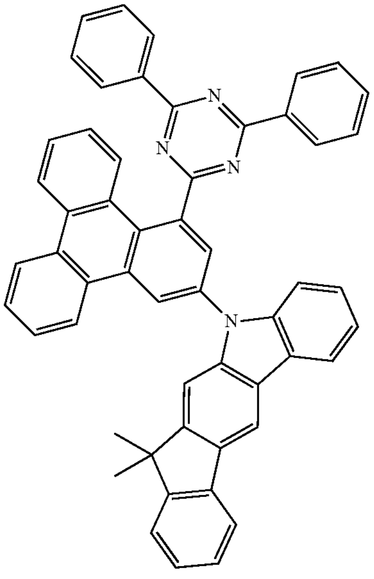
1-28
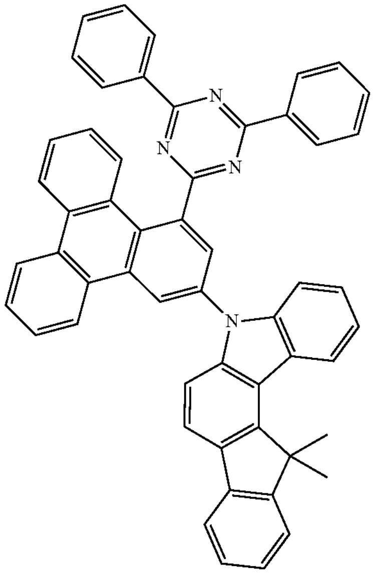

-continued
1-29
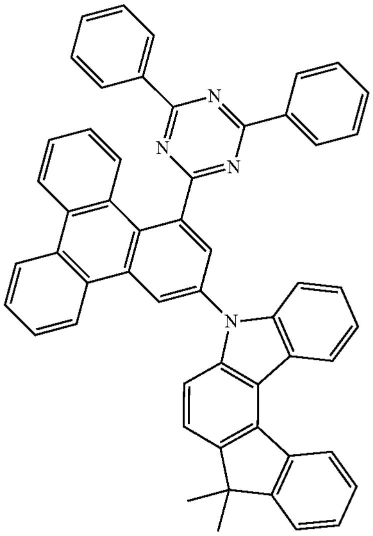
1-30
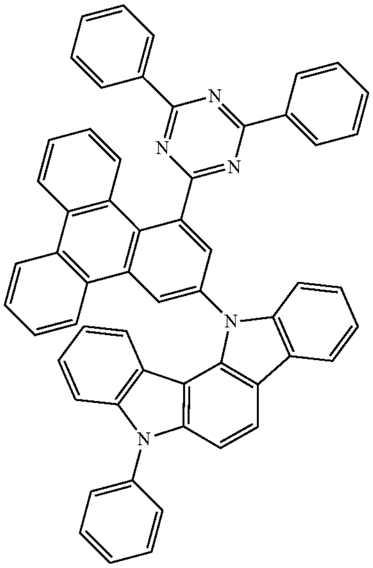
1-31
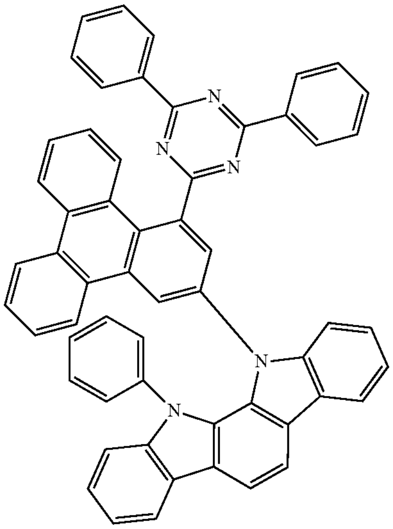
1-32
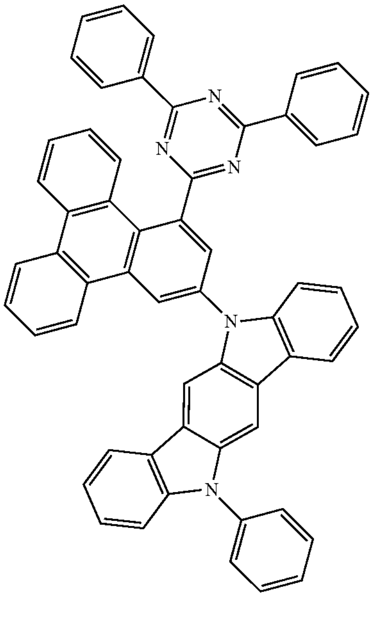

-continued
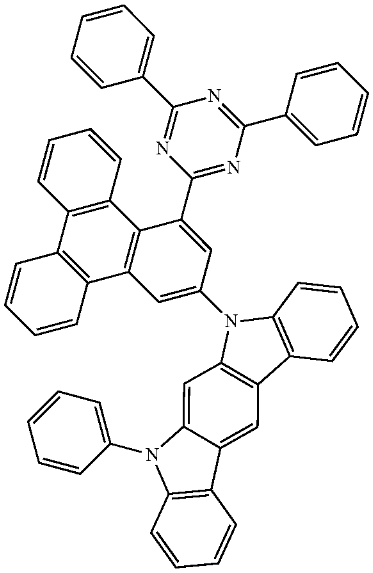
1-33
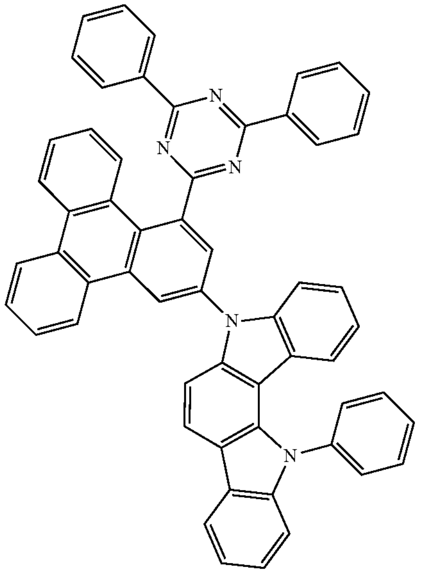
1-34
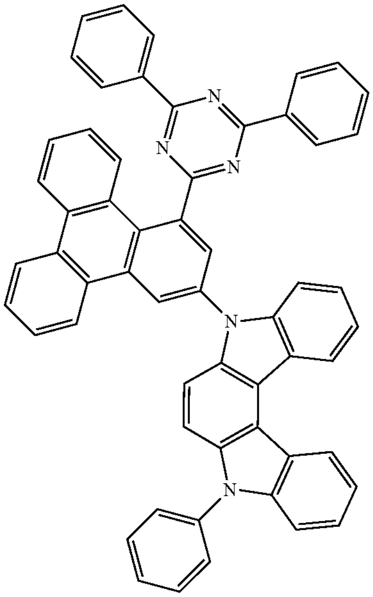
1-35
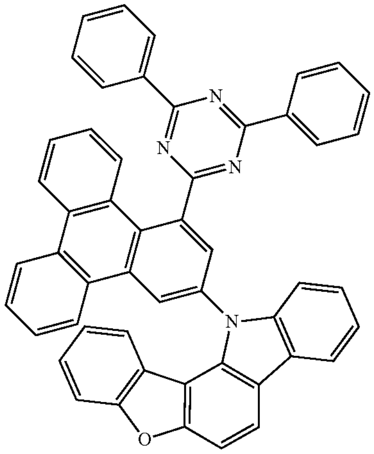
1-36
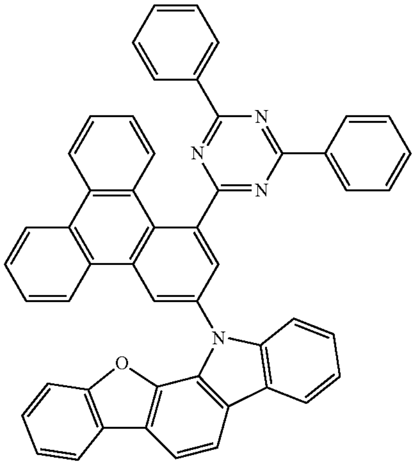
1-37
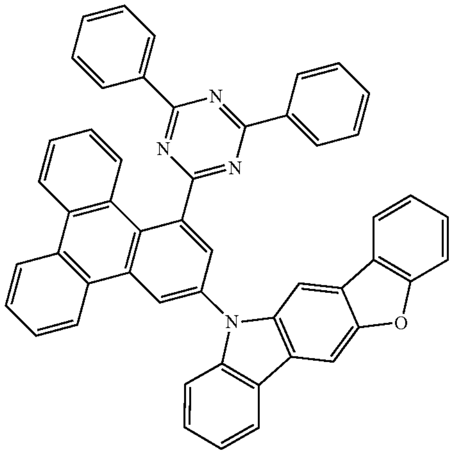
1-38

-continued
1-39
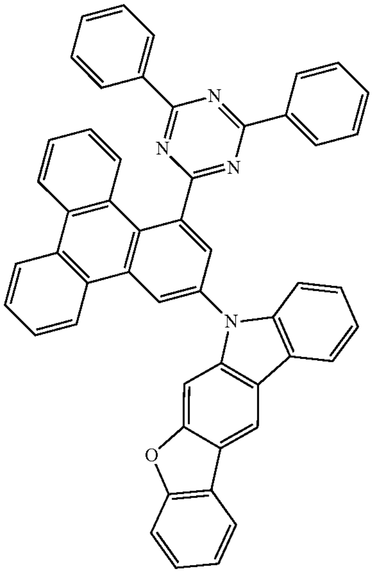
1-40
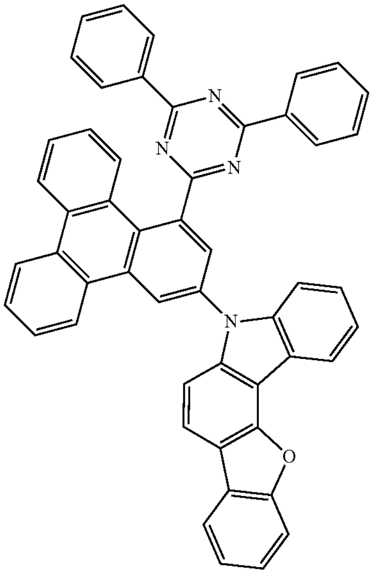
1-41
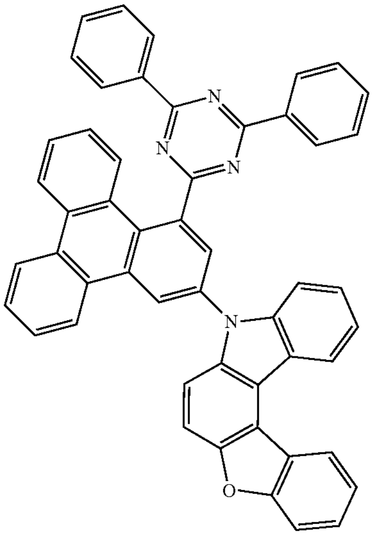
1-42
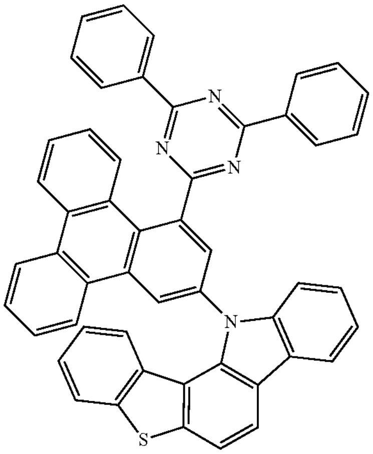
1-43
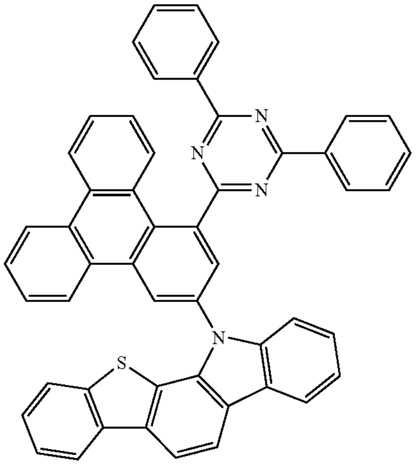
1-44
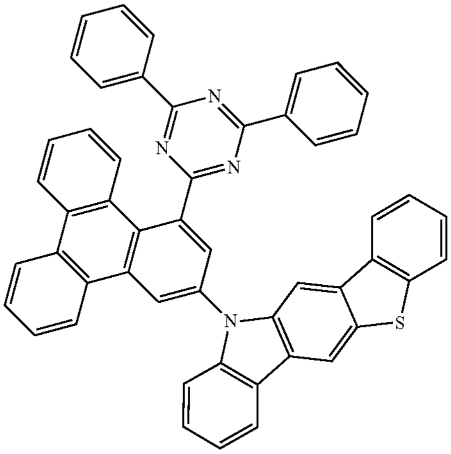

-continued
1-45
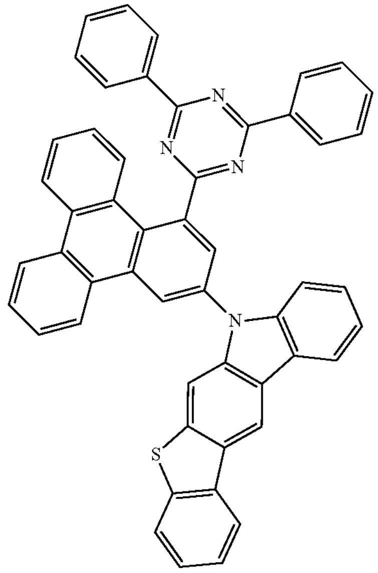
1-46
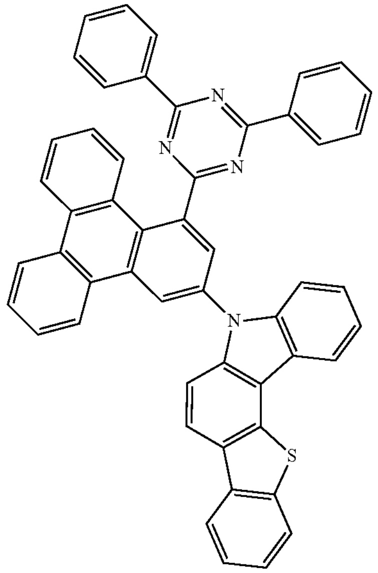
1-47
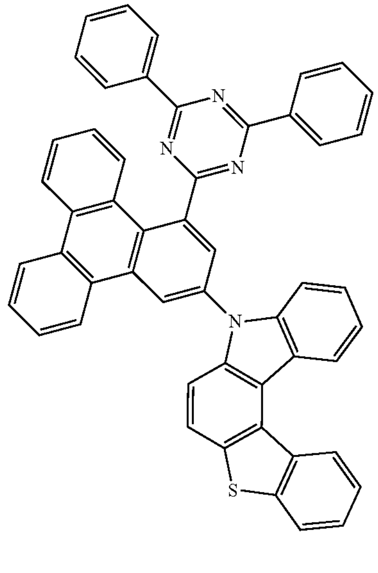
1-48
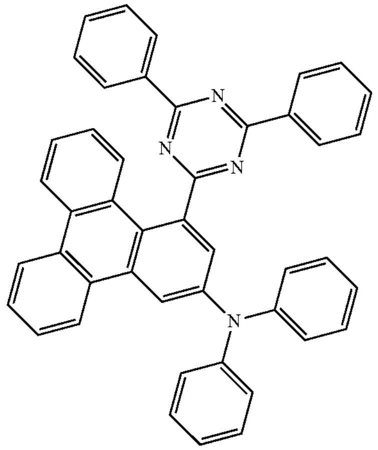

-continued
1-49
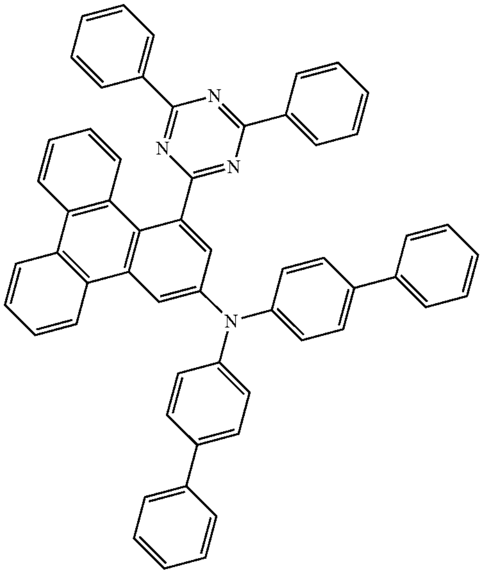
1-50
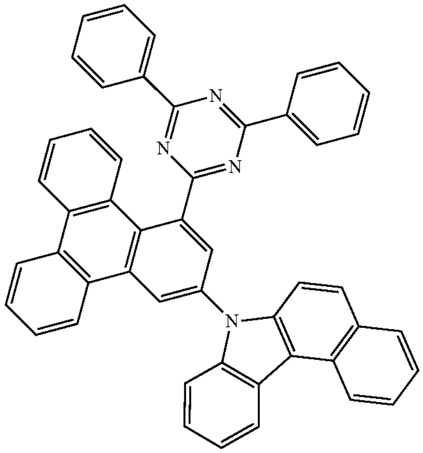
1-51
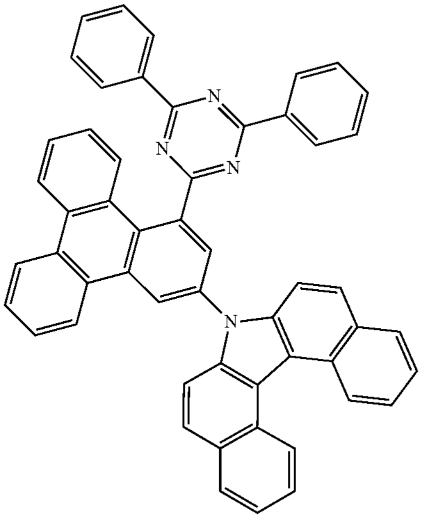
1-52
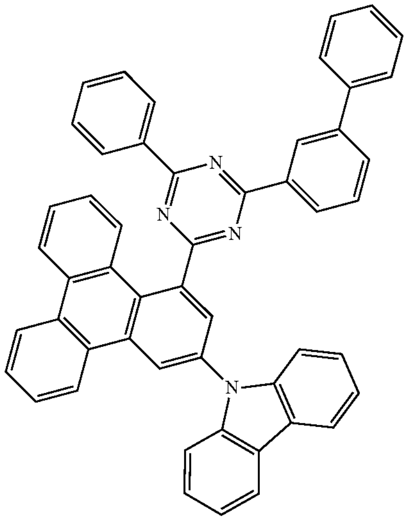

-continued
1-53
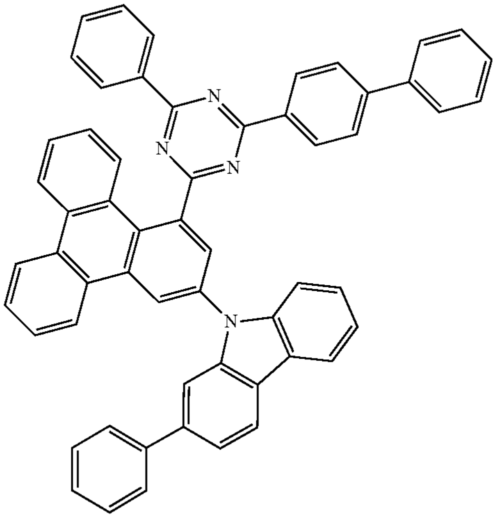
1-54
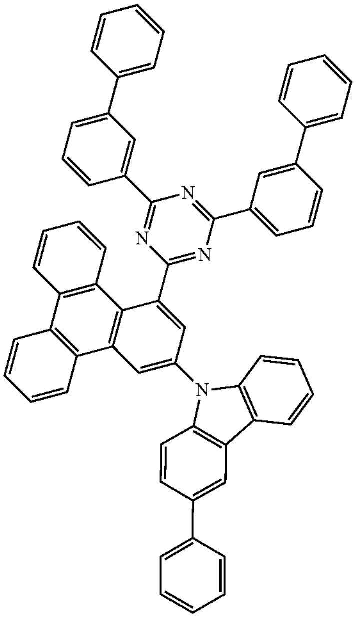
1-55
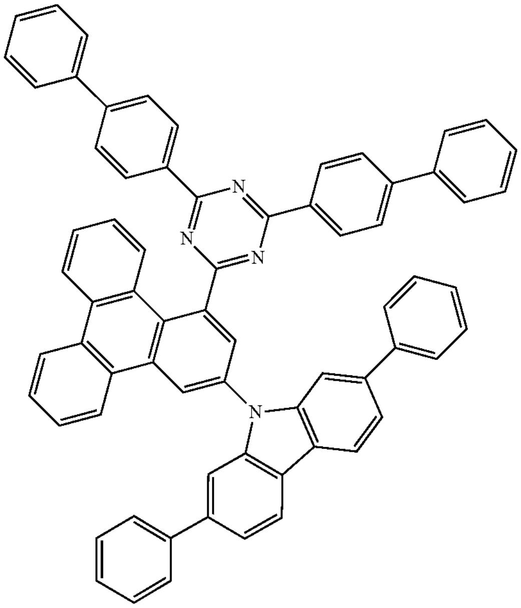
1-56
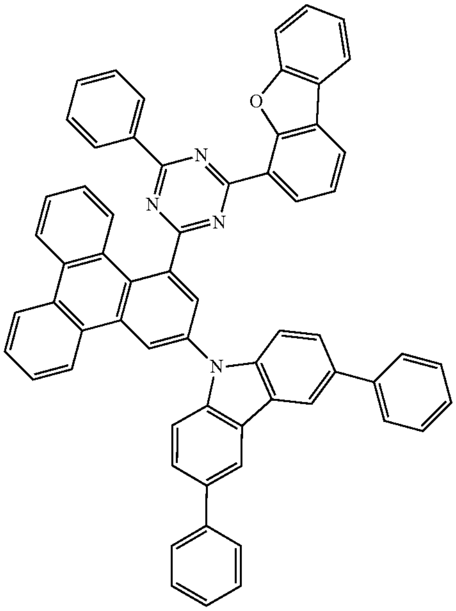

-continued
1-57
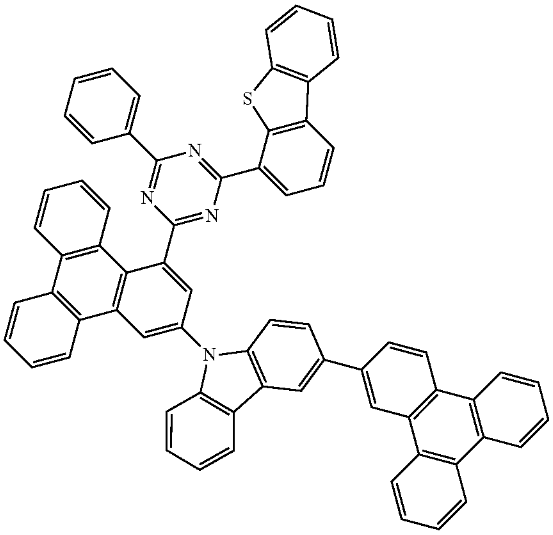
1-58
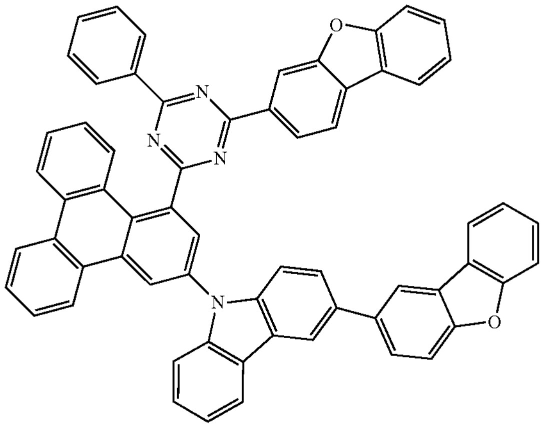
1-59
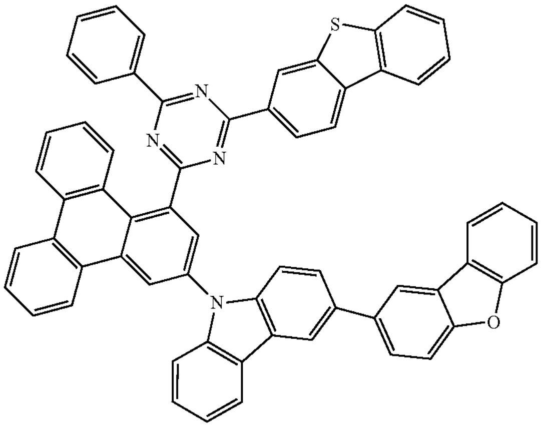
1-60
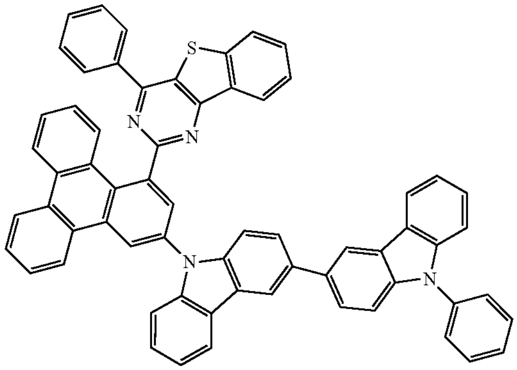
1-61
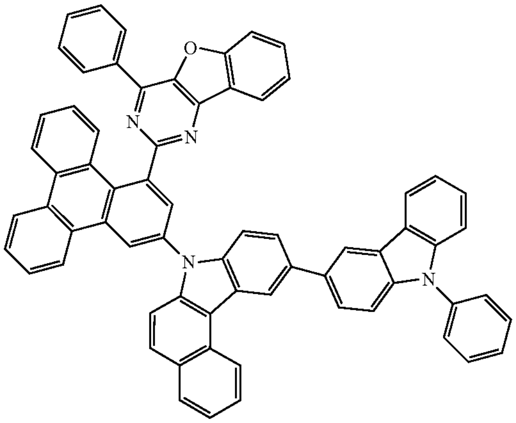
1-62
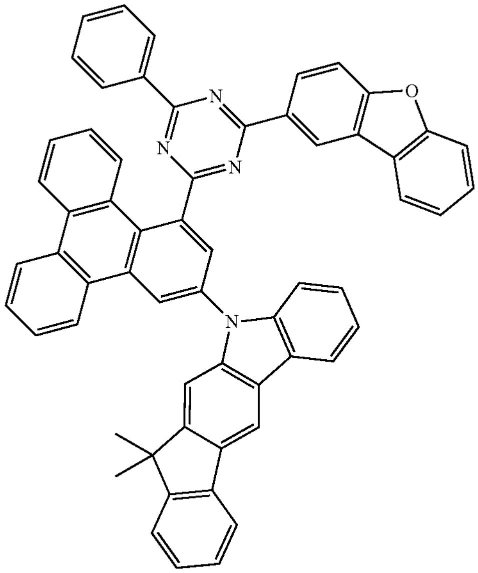

-continued
1-63
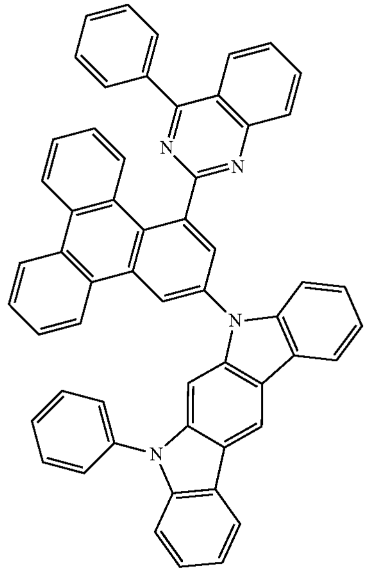
1-64
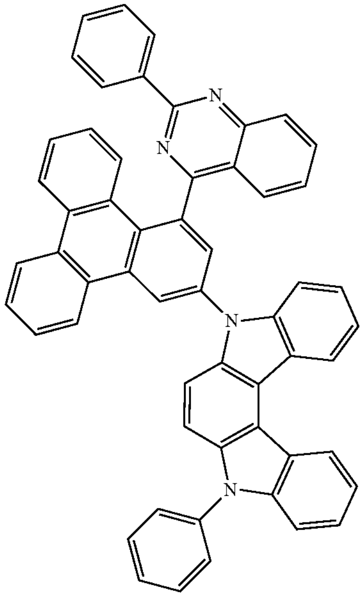
1-65
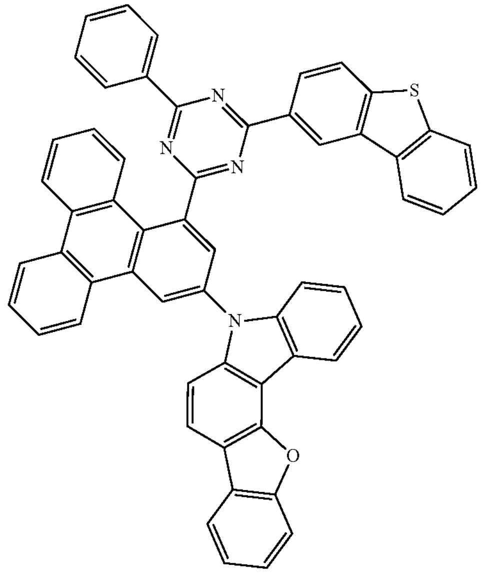
1-66
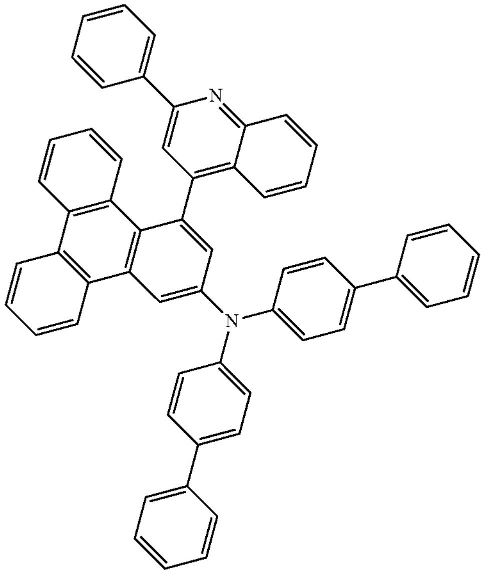

-continued
1-67
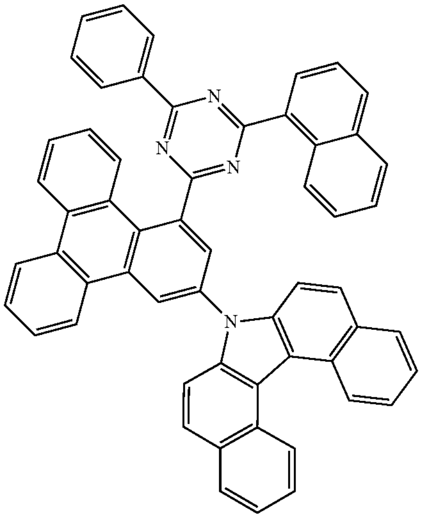
1-68
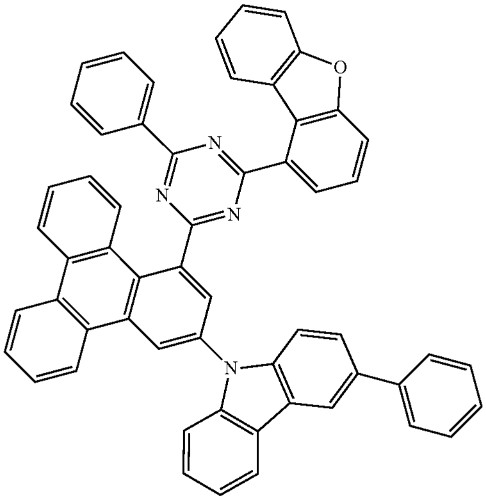
1-69
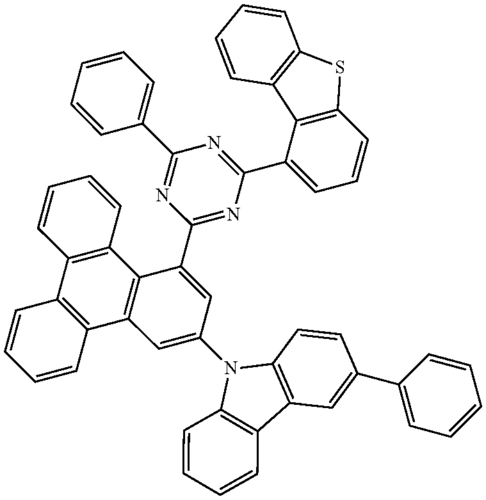
1-70
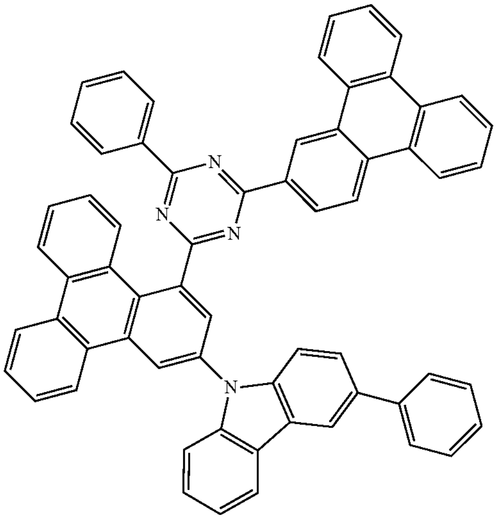
1-71
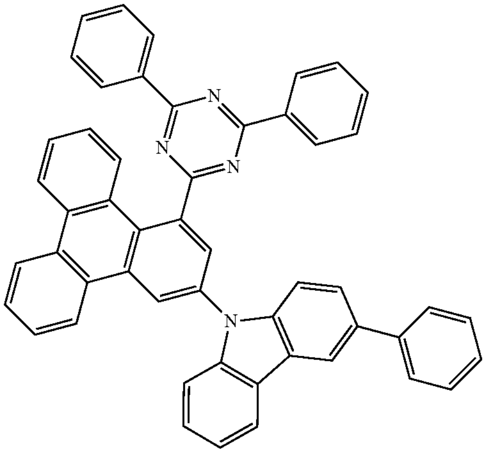
1-72
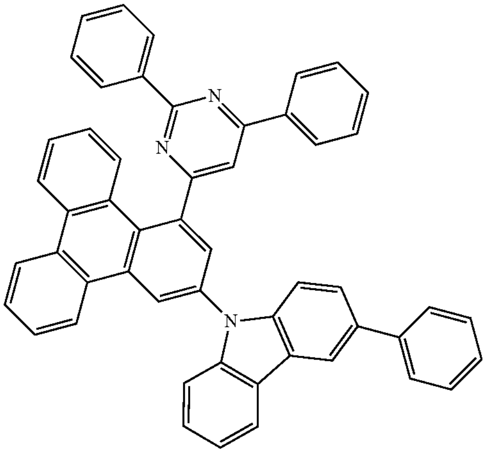

-continued
1-73
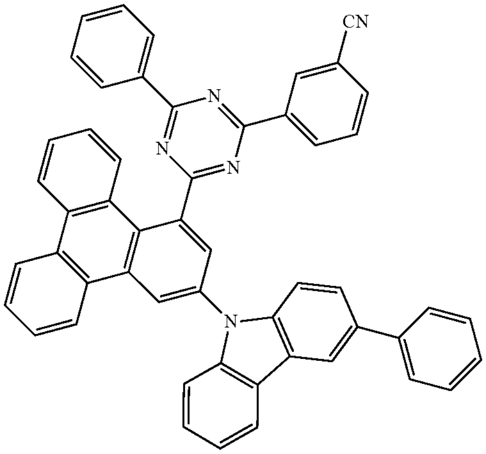
1-74
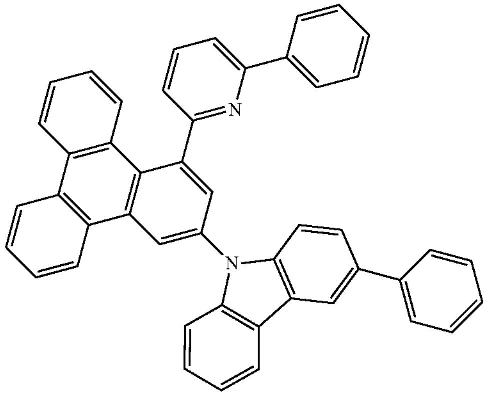
1-75
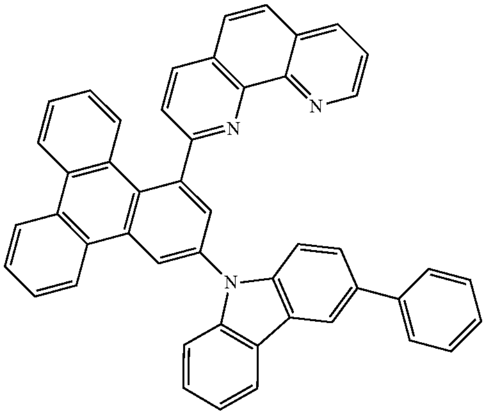
1-76
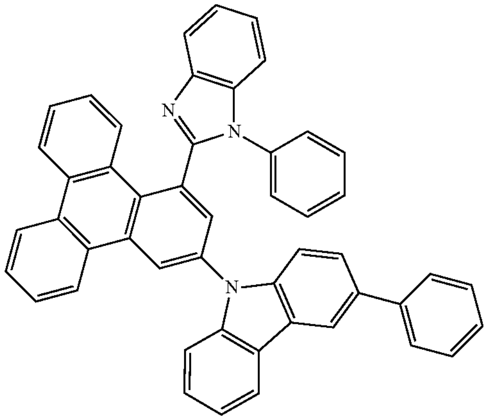
1-77
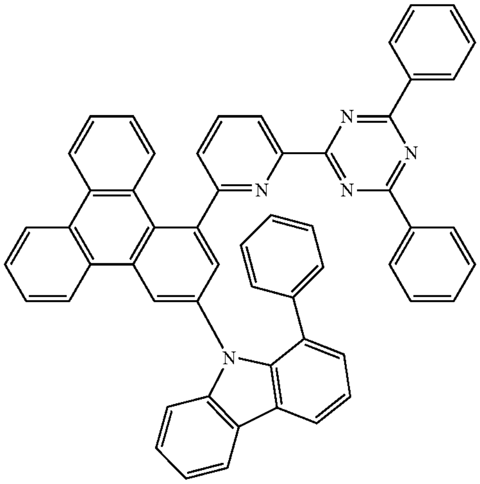
1-78
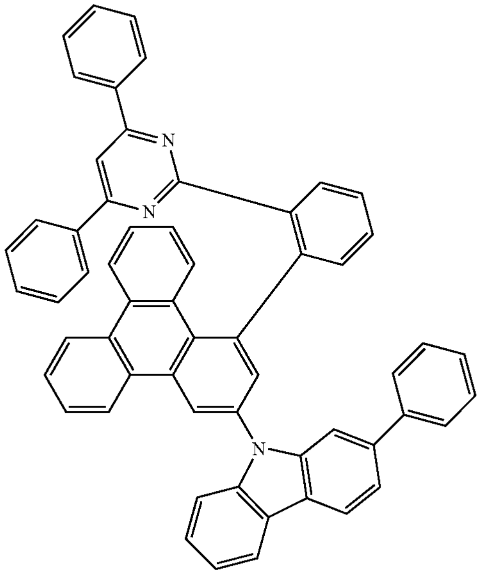

-continued
1-79
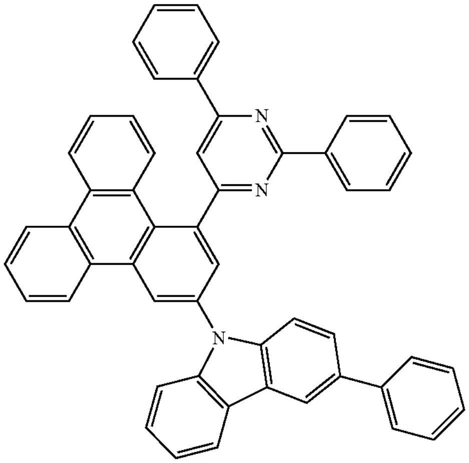
1-80
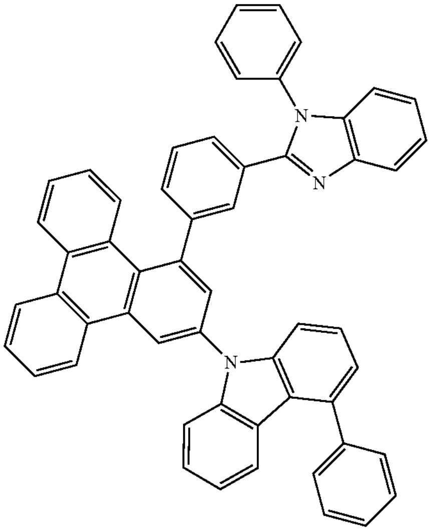
1-81
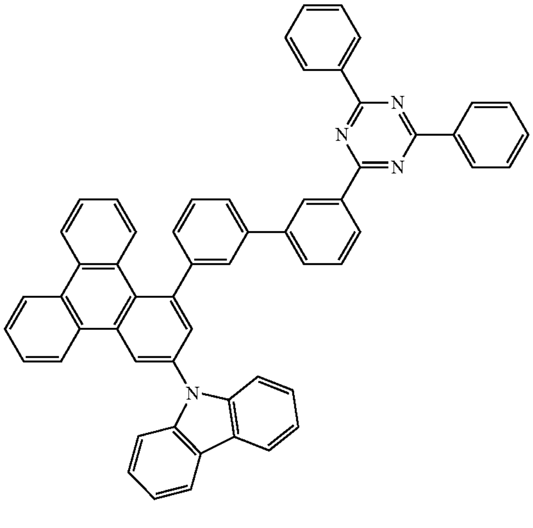
1-82
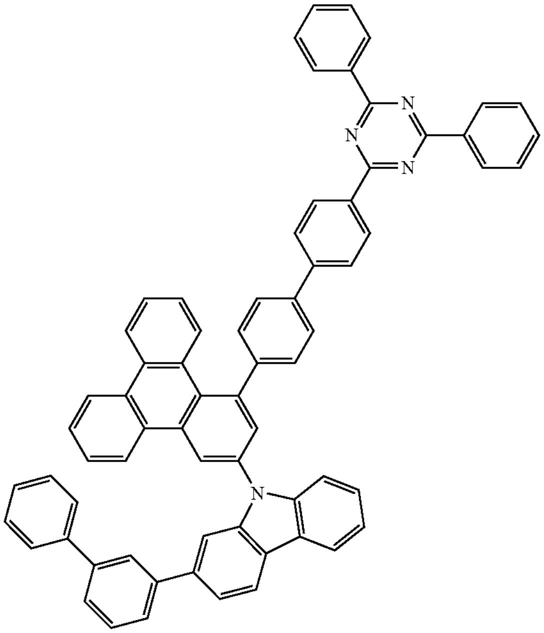

-continued
1-83
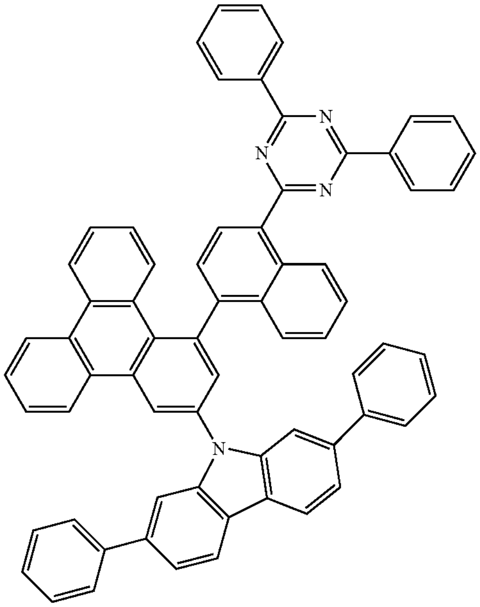
1-84
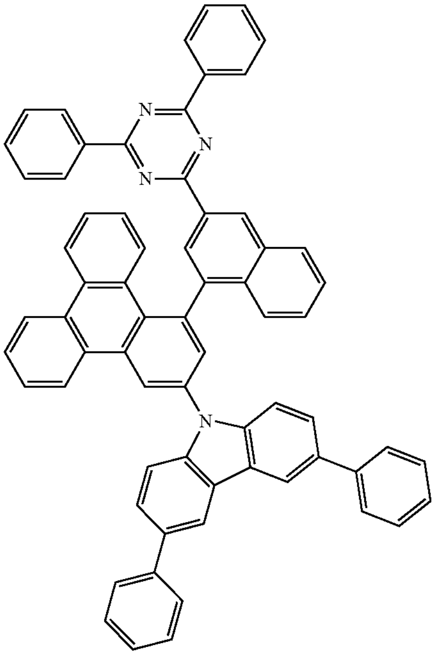
1-85
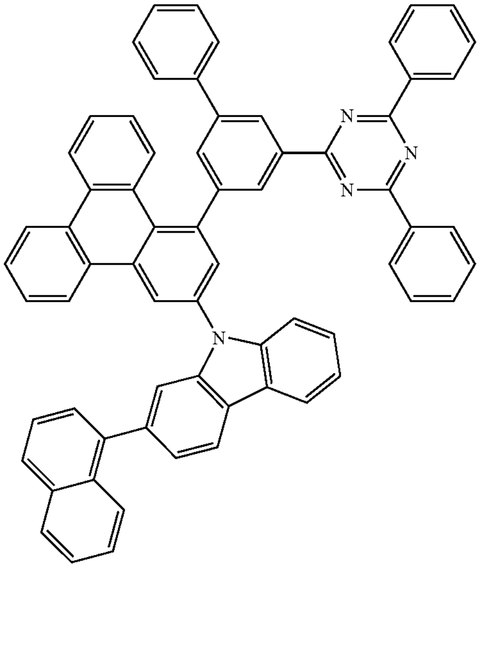
1-86
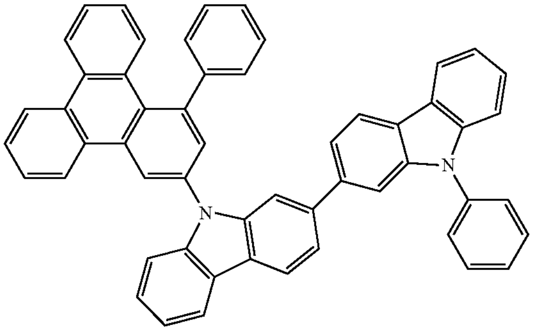

-continued
1-87
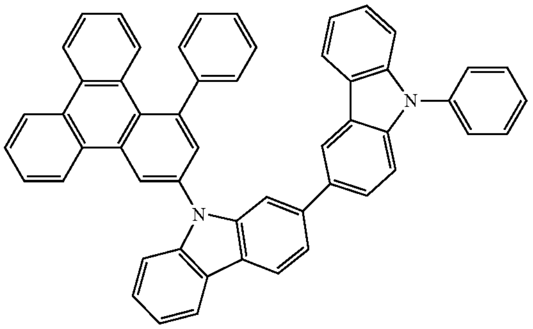
1-88
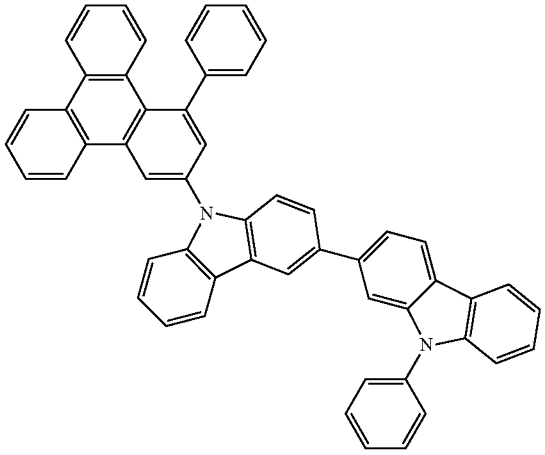
1-89
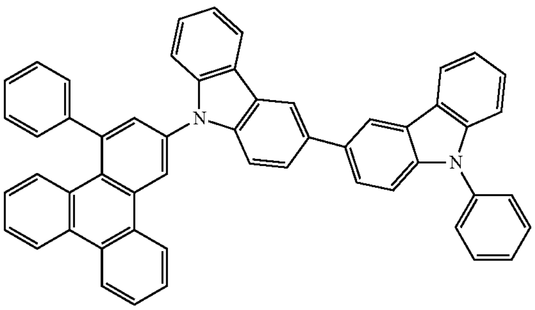
1-90
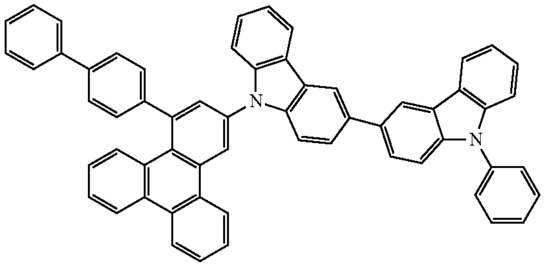
1-91
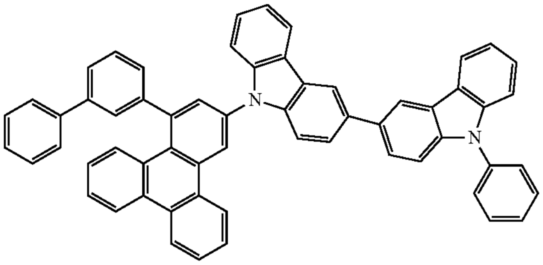
1-92
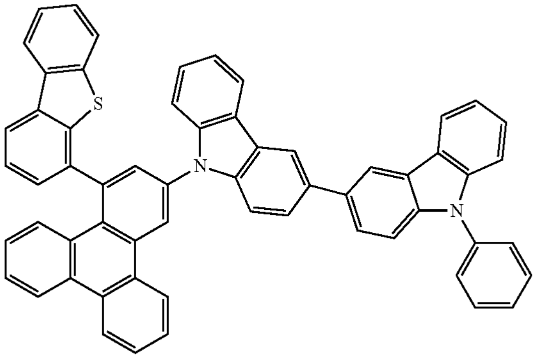
1-93
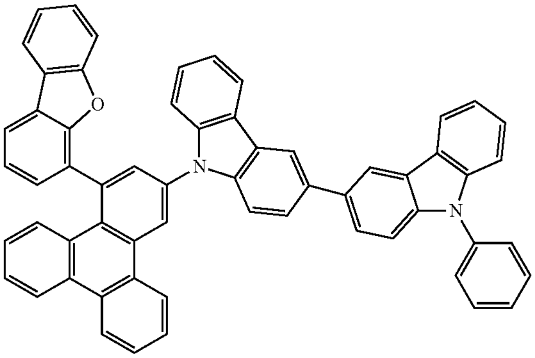
1-94
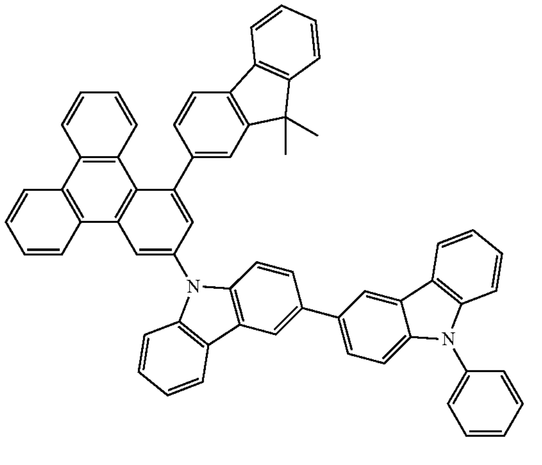

-continued
1-95
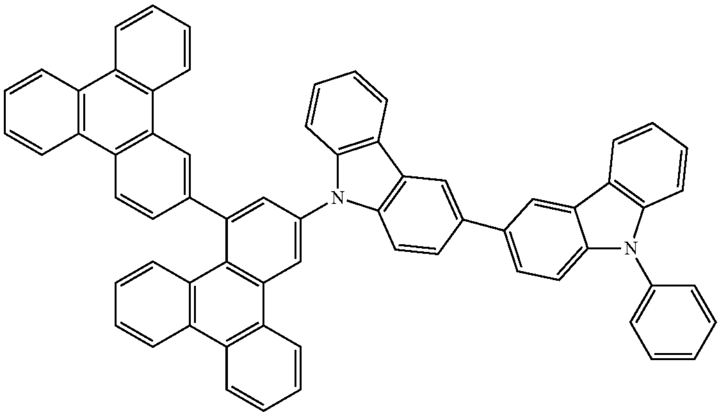
1-96
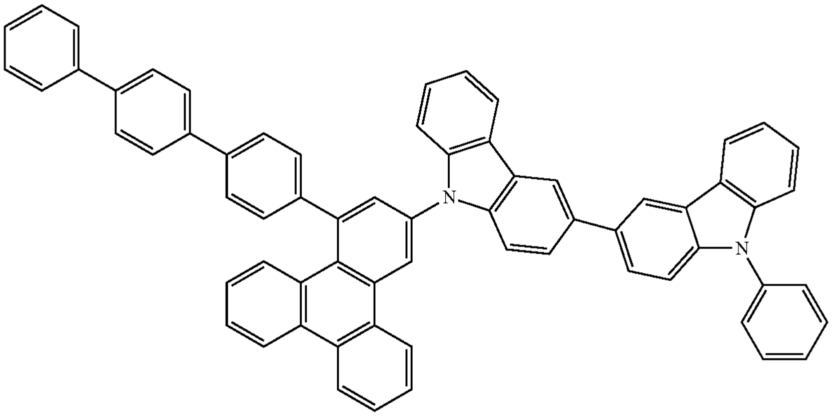
1-97
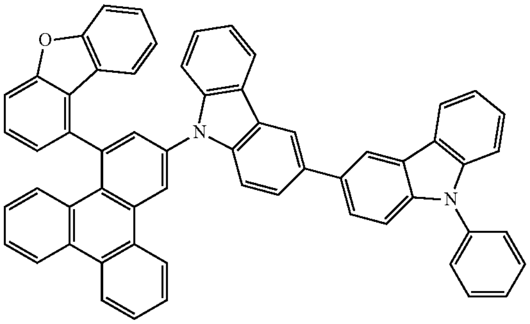
1-98
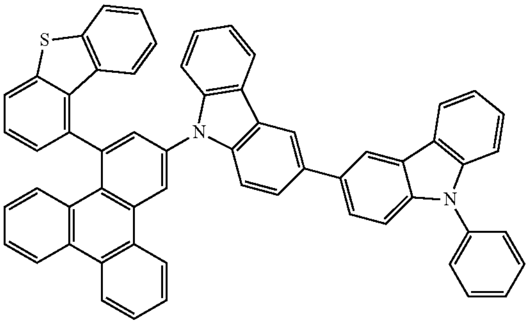
1-99
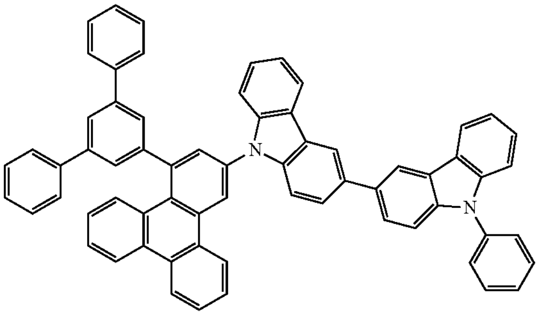
1-100
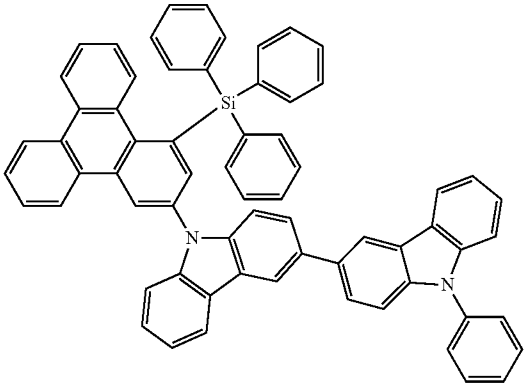

-continued
1-101
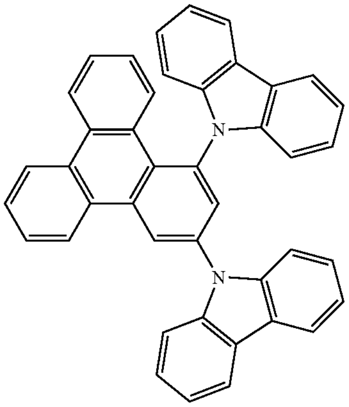
1-102
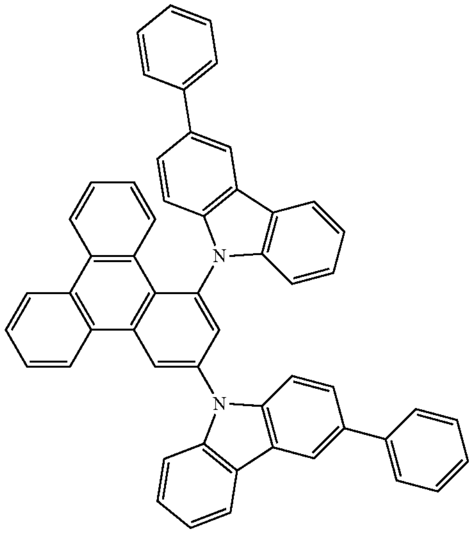
1-103
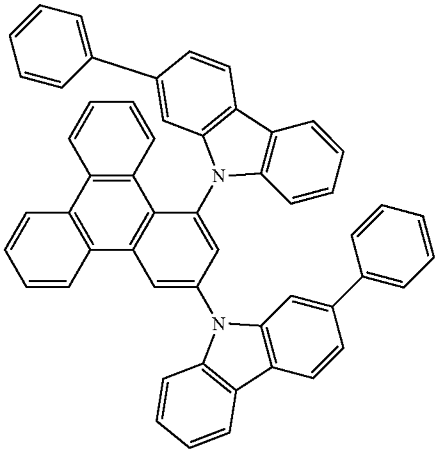
1-104
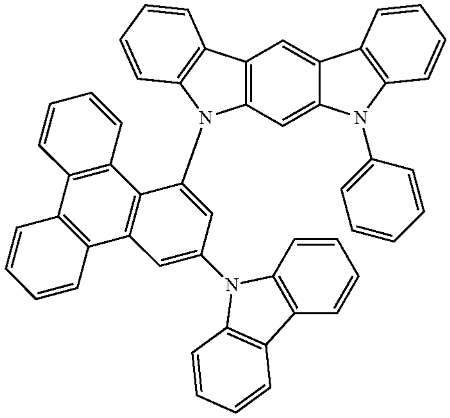
1-105
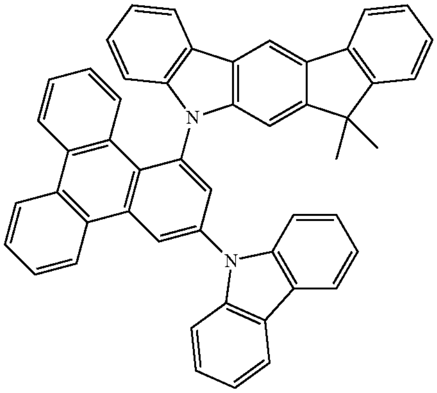
1-106
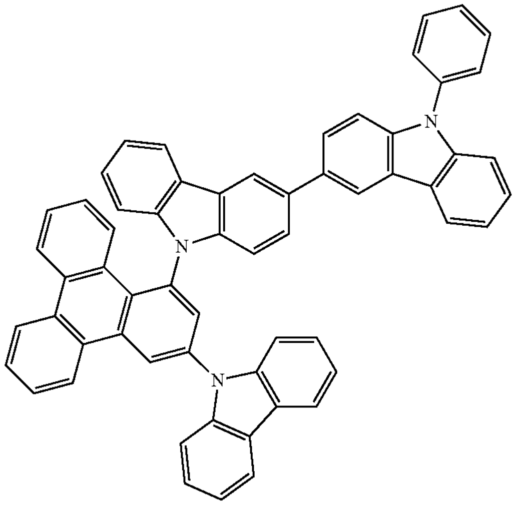

-continued
1-107
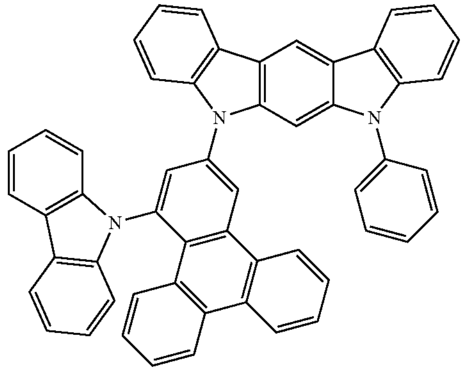
1-108
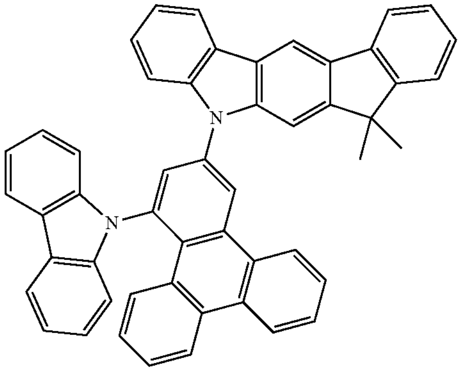
1-109
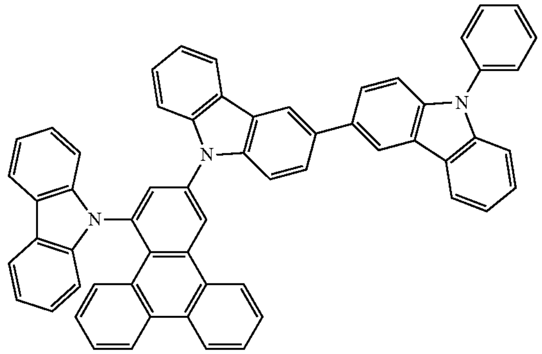
1-110
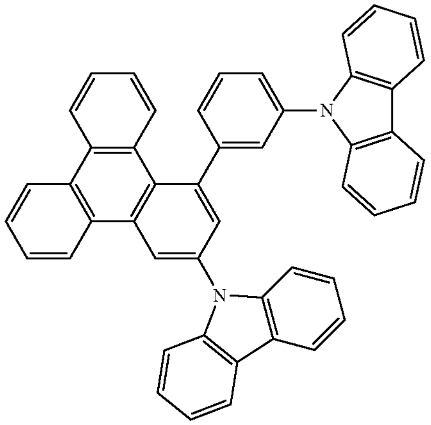
1-111
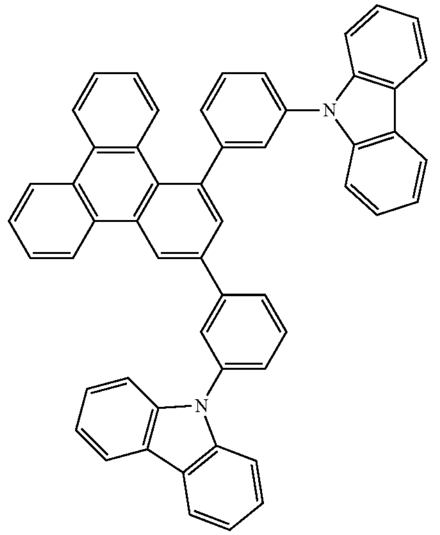
1-112
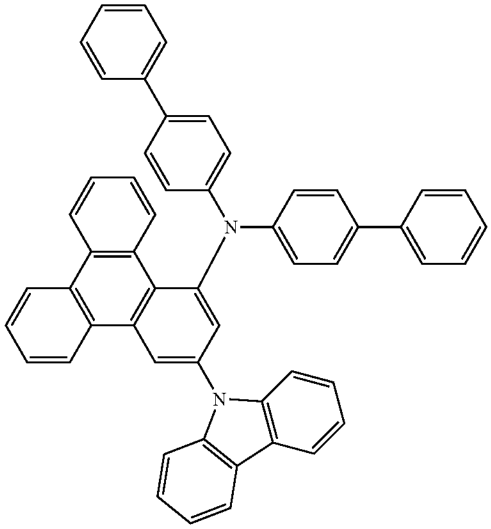

-continued
1-113
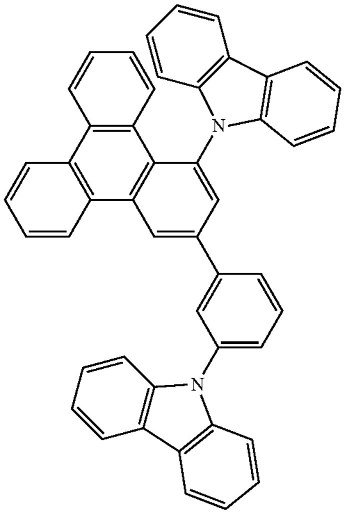
1-114
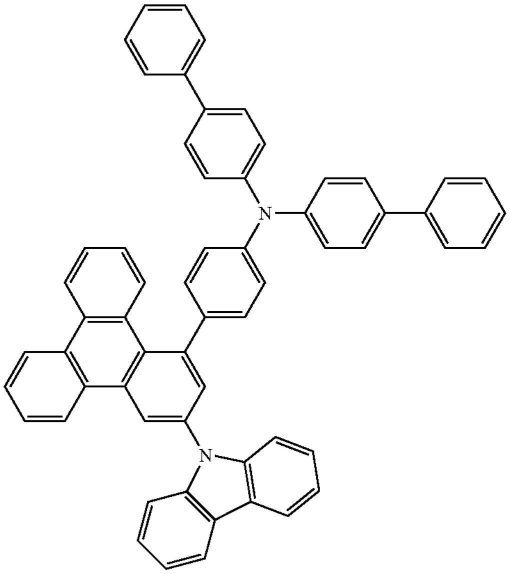
1-115
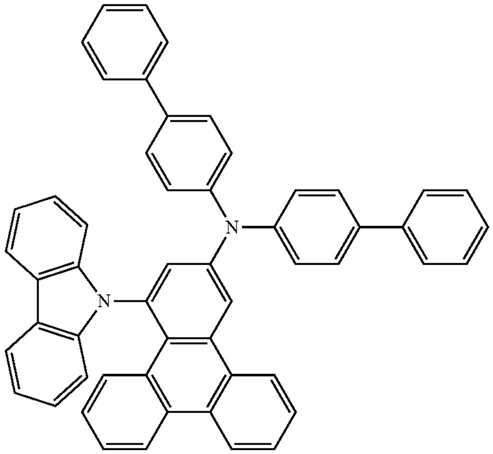
1-116
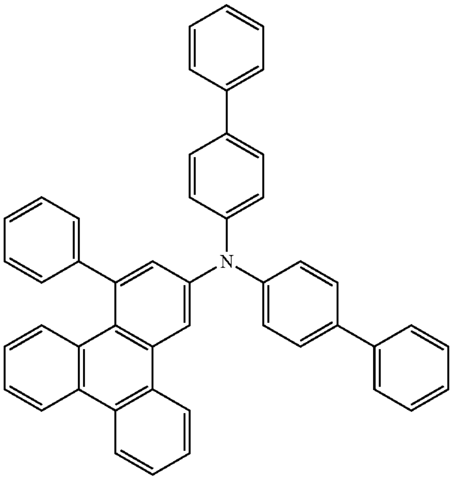
1-117
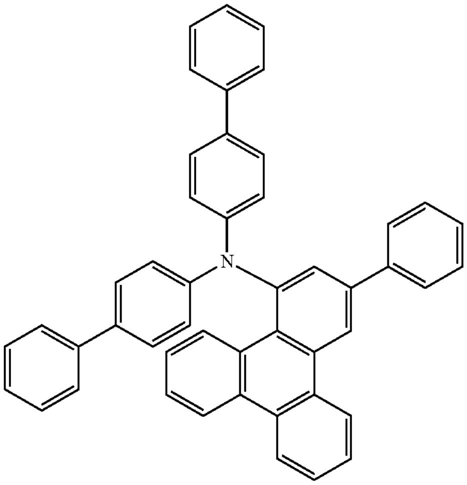
1-118
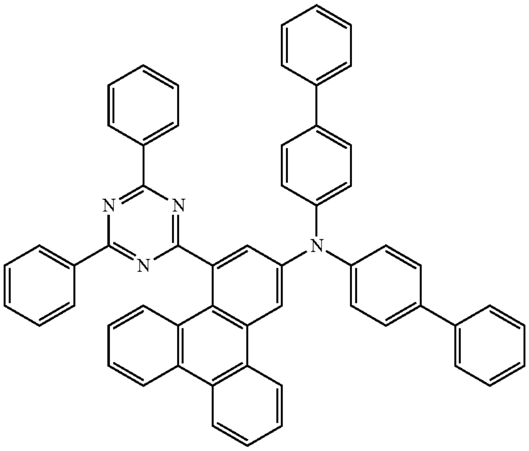

-continued
1-119
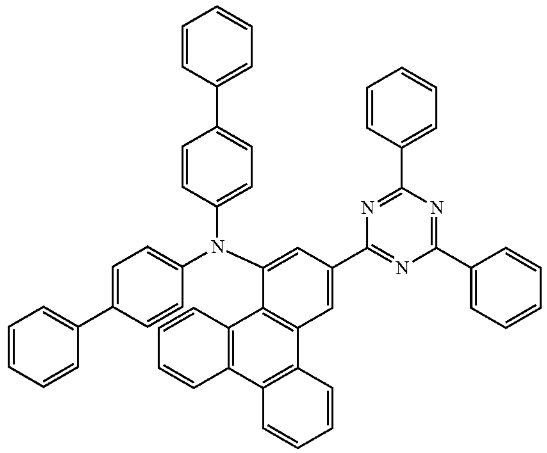
2-1
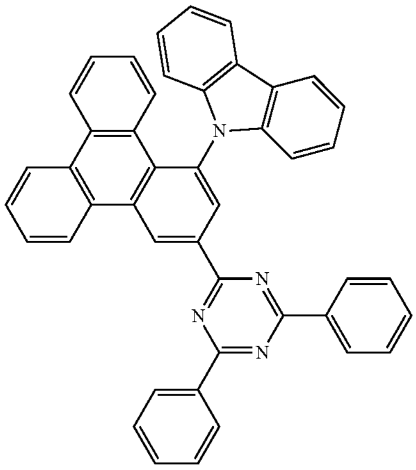
2-2
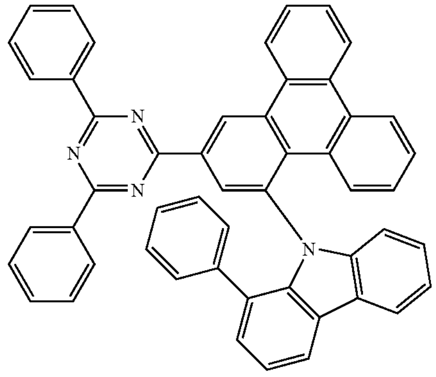
2-3
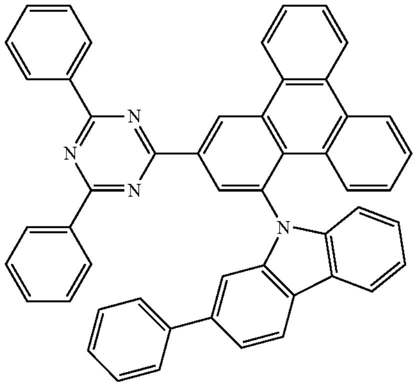
2-4
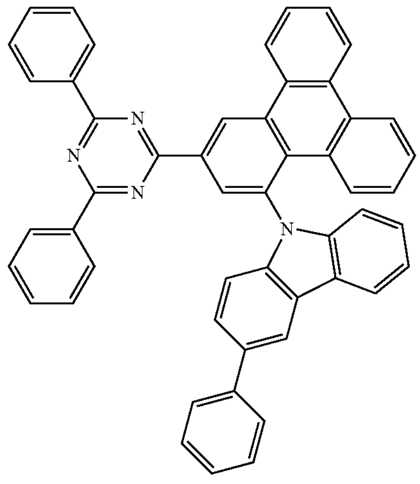
2-5
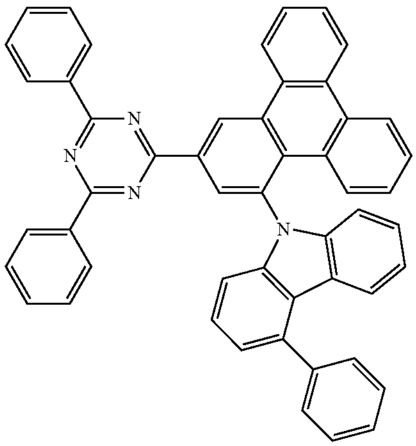

-continued
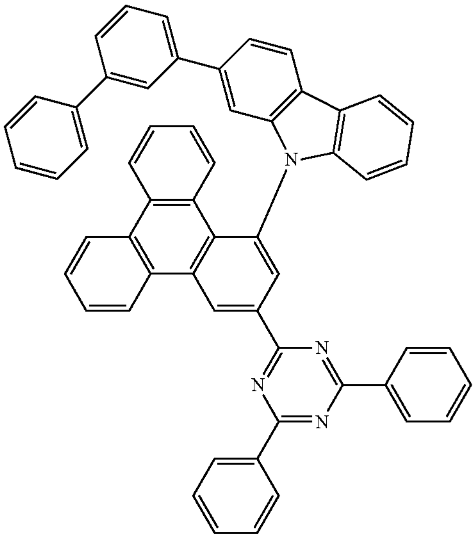
2-6
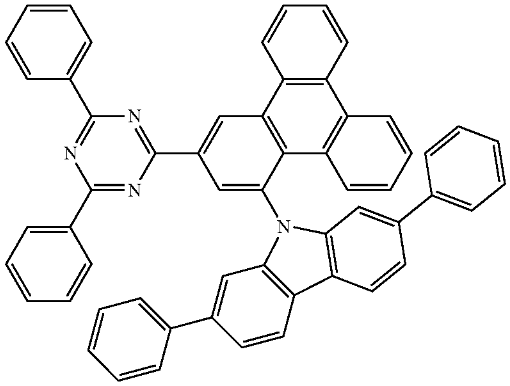
2-7
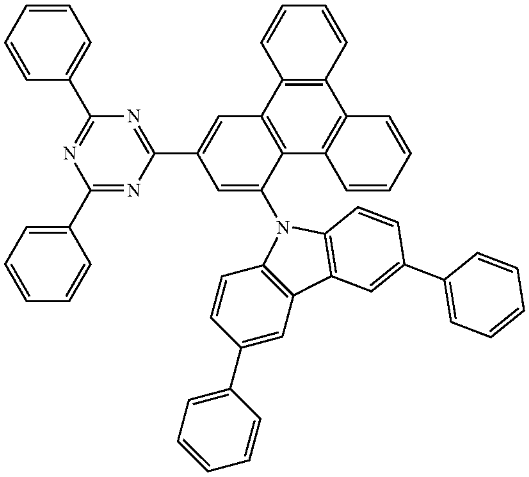
2-8
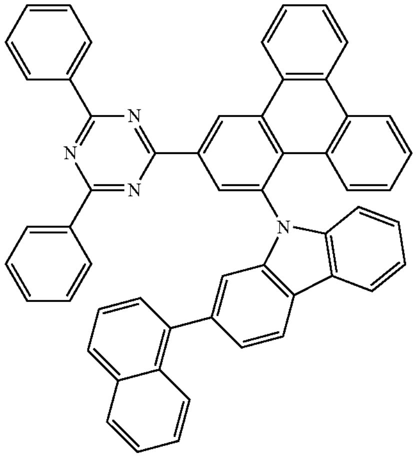
2-9
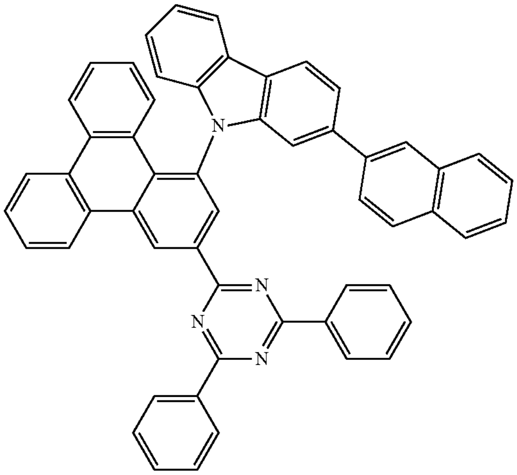
2-10
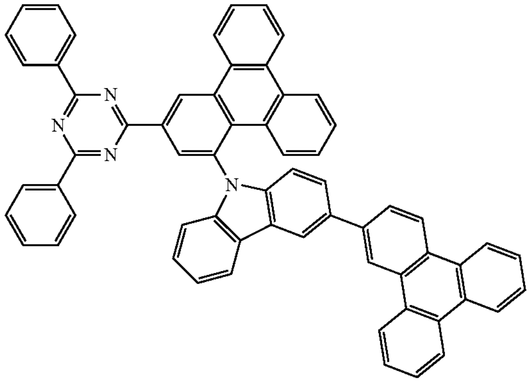
2-11

-continued
2-12
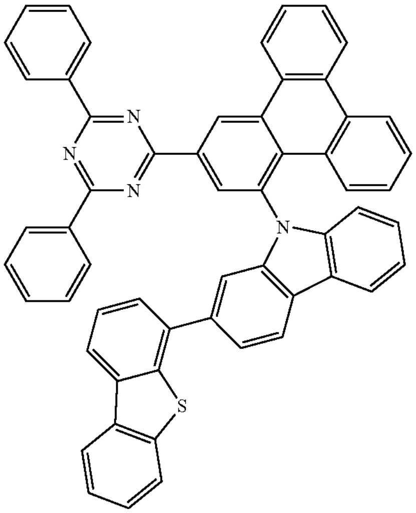
2-13
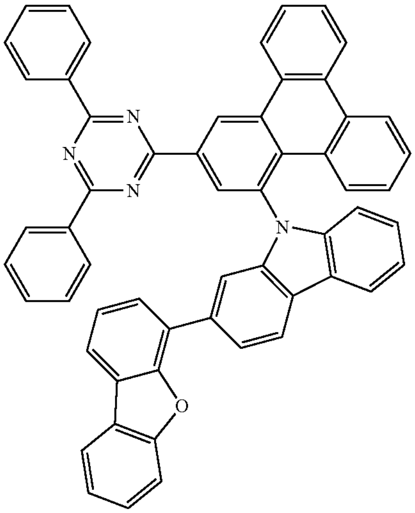
2-14
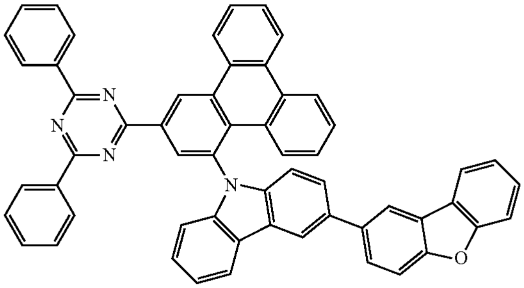
2-15
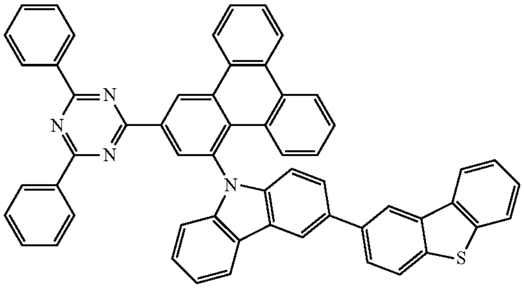
2-16
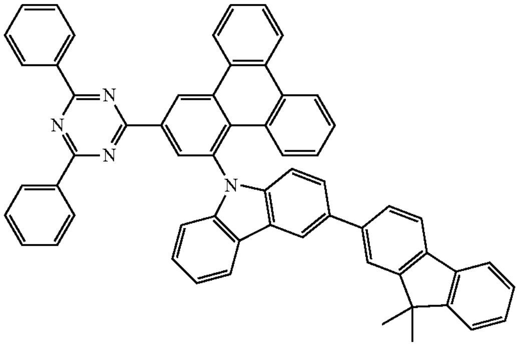
2-17
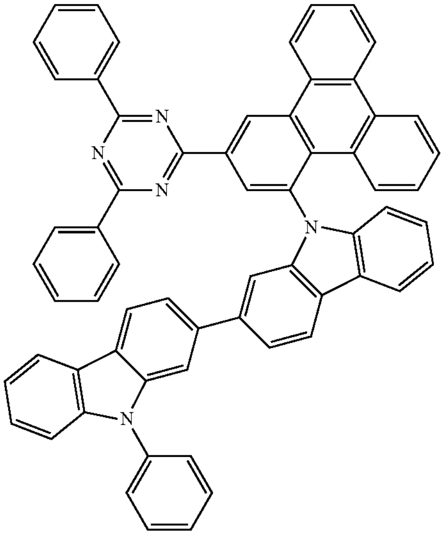

-continued
2-18
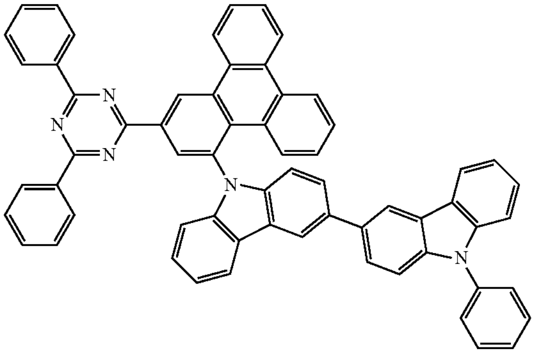
2-19
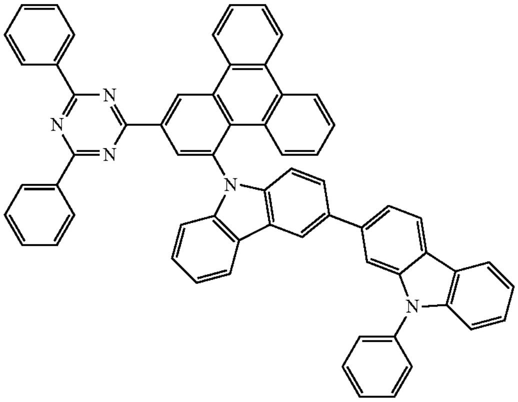
2-20
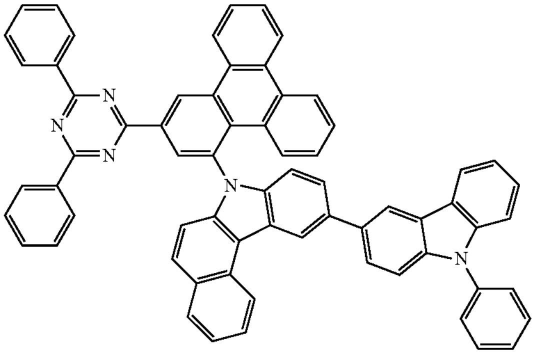
2-21
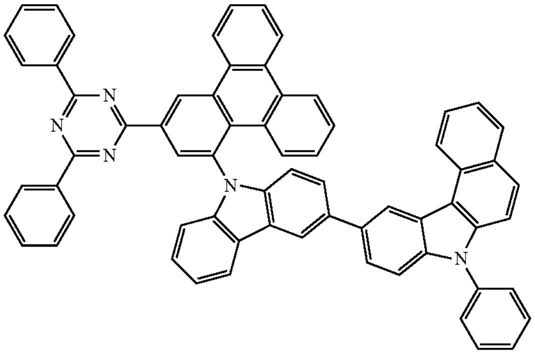
2-22
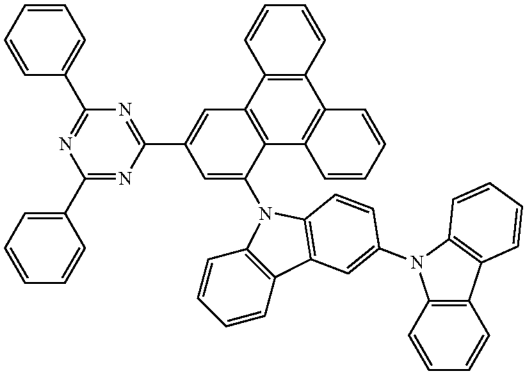
2-23
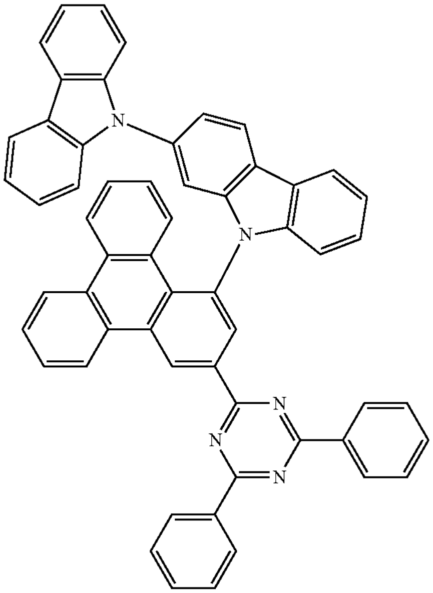

-continued
2-24
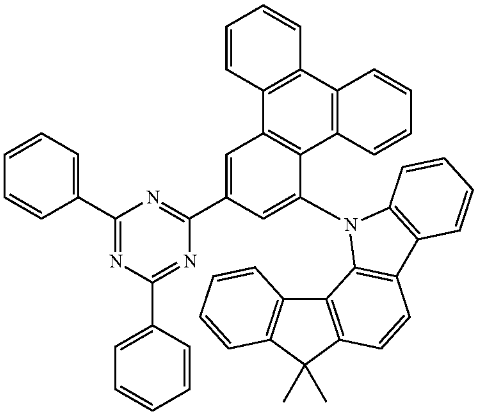
2-25
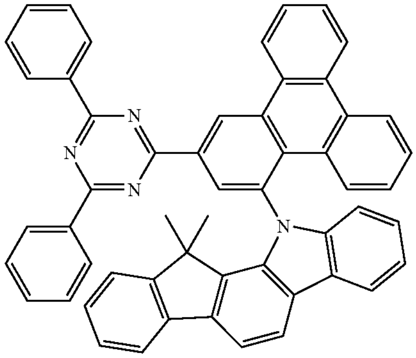
2-26
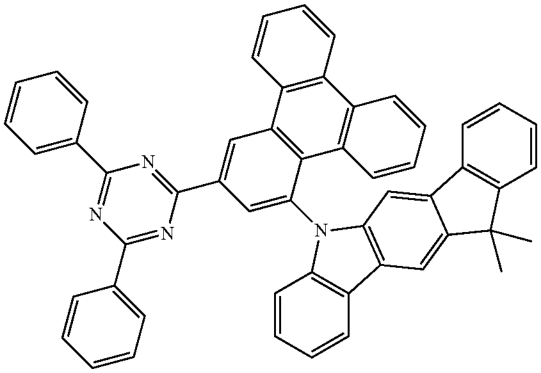
2-27
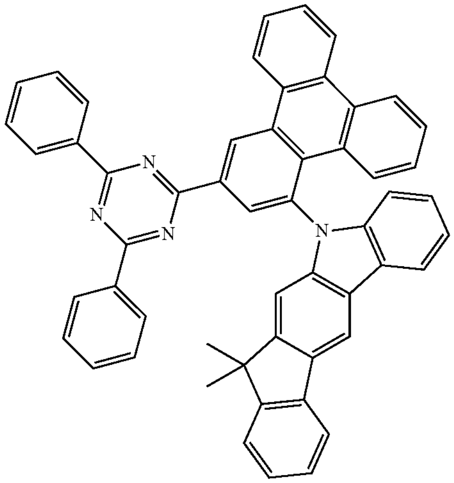
2-28
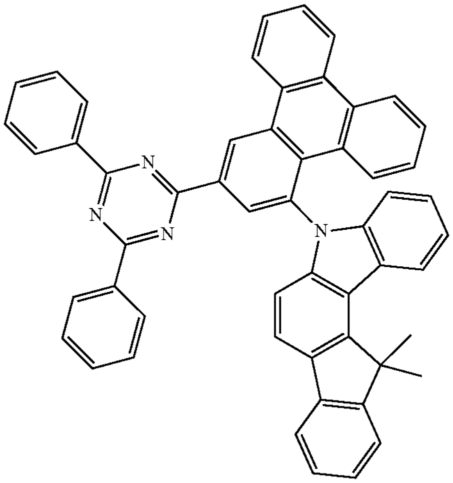
2-29
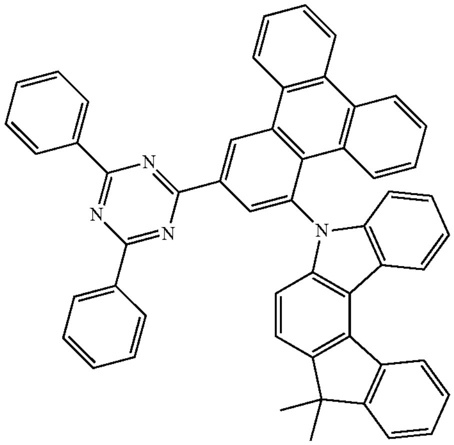

-continued
2-30
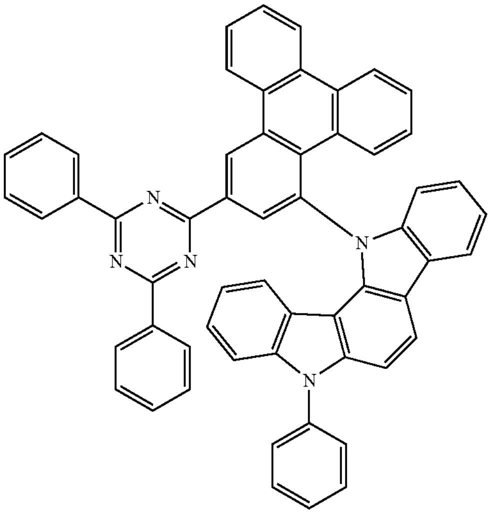
2-31
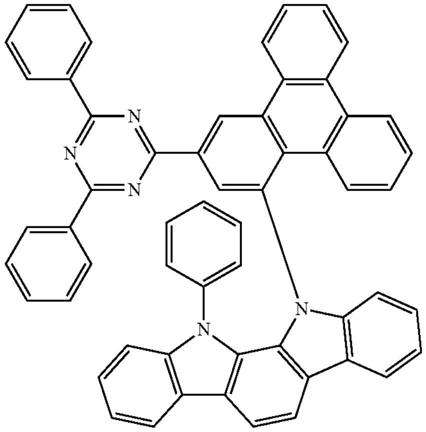
2-32
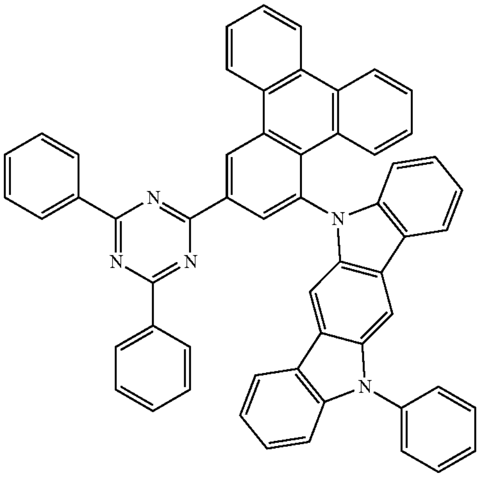
2-33
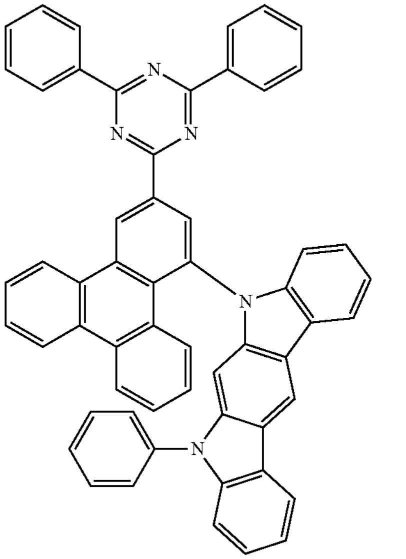
2-34
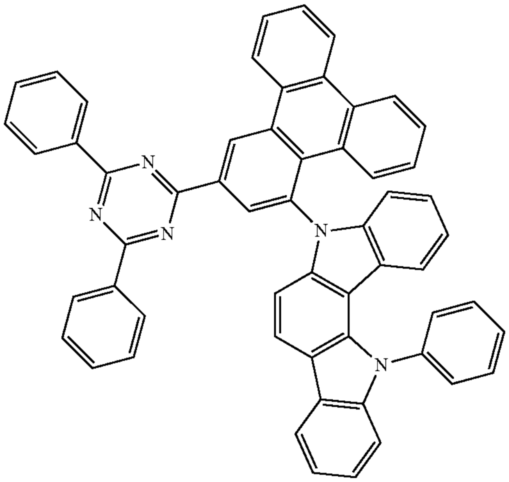
2-35
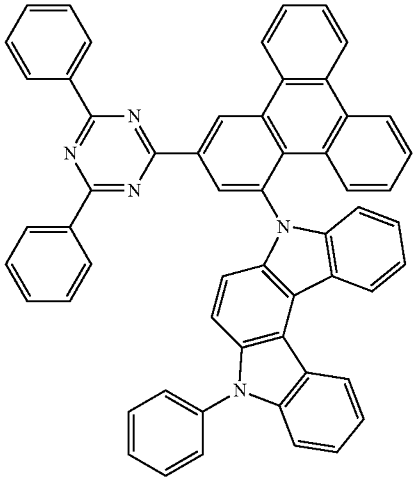

-continued
2-36
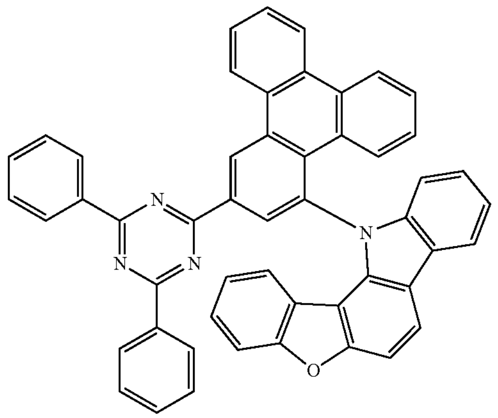
2-37
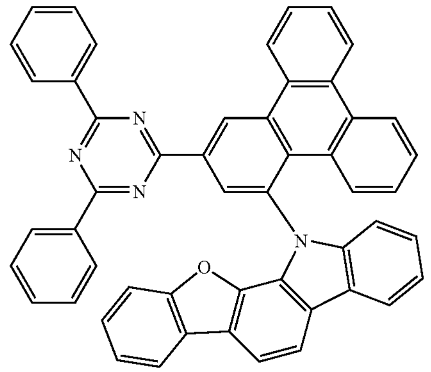
2-38
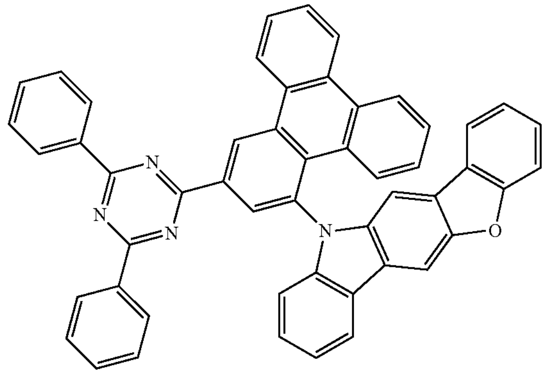
2-39
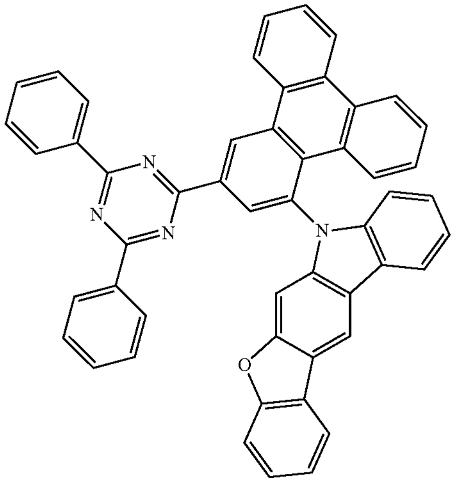
2-40
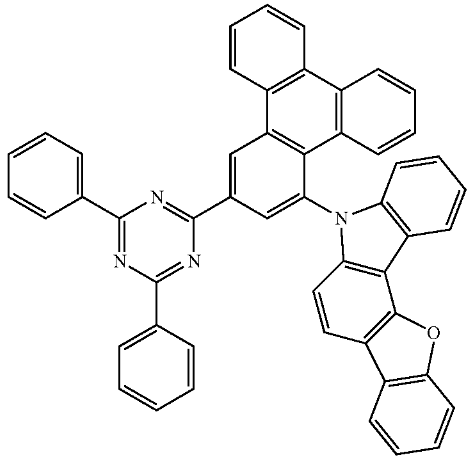
2-41
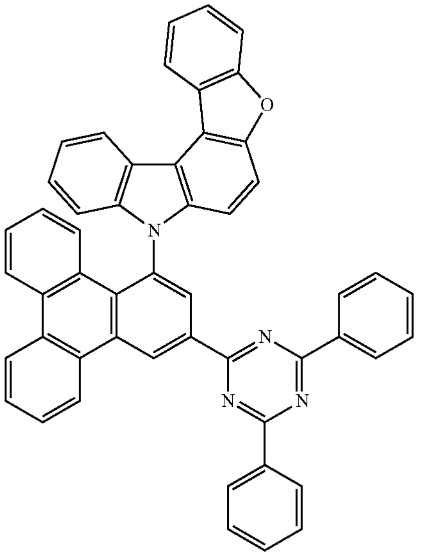

-continued
2-42
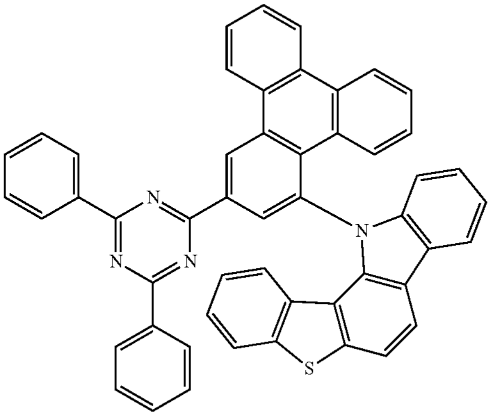
2-43
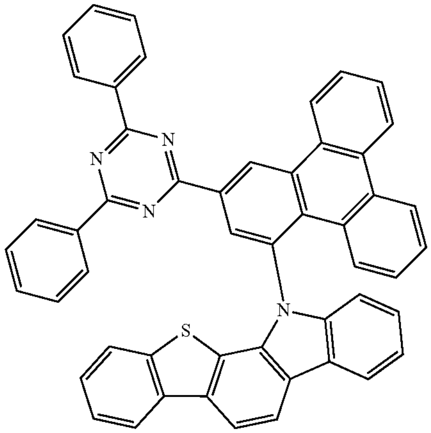
2-44
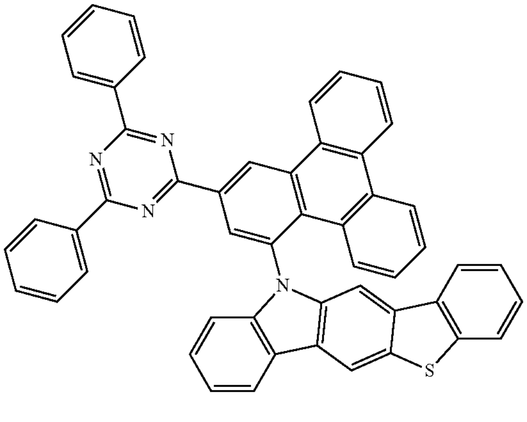
2-45
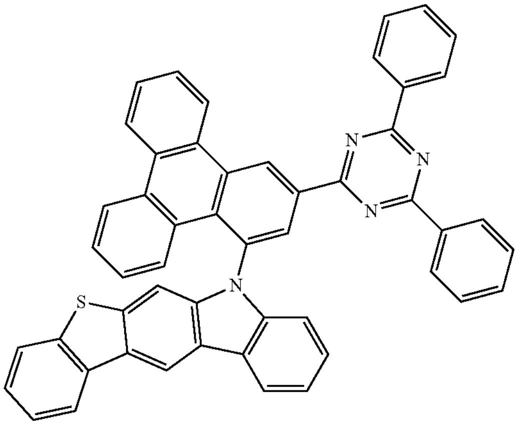
2-46
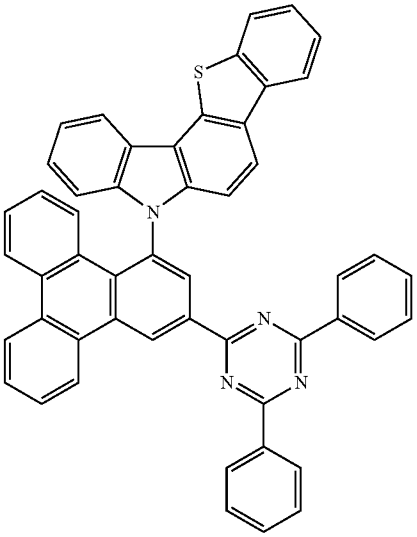
2-47
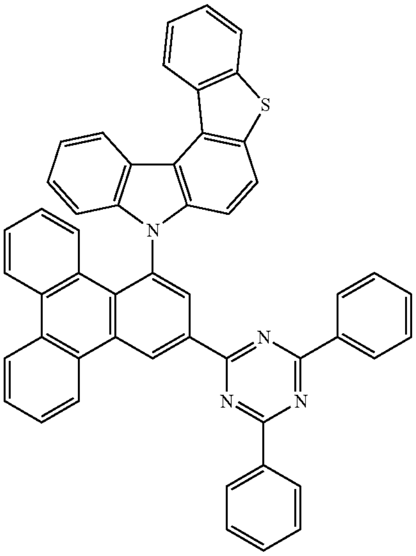

-continued
2-48
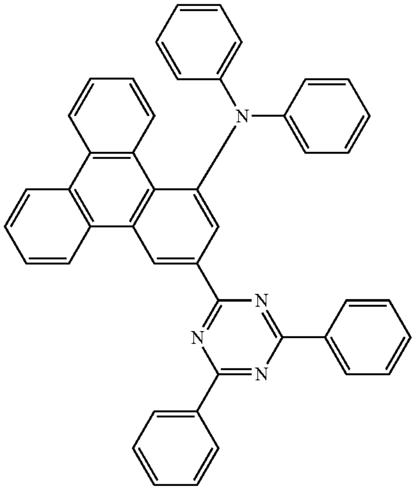
2-49
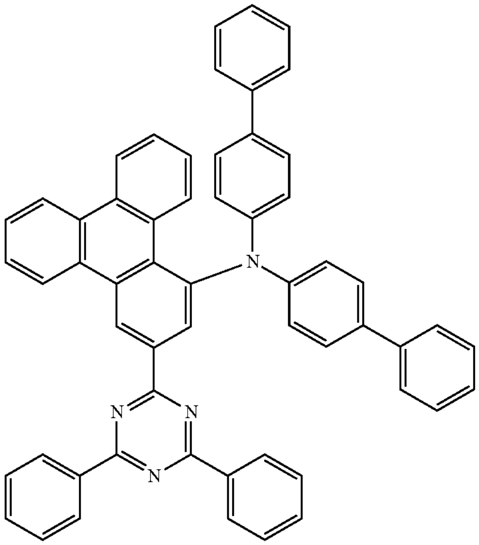
2-50
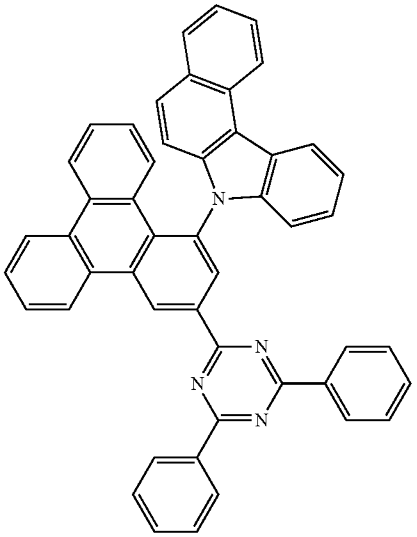
2-51
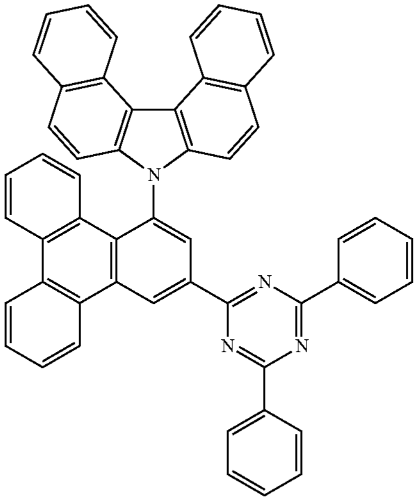
2-52
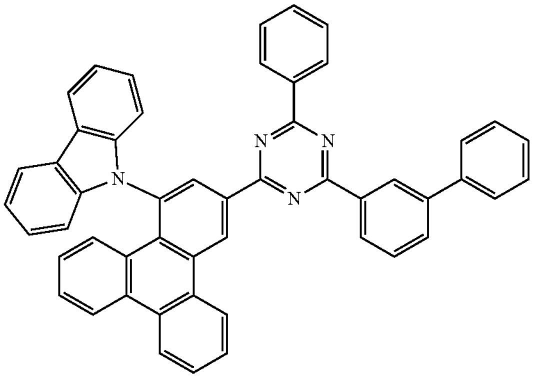
2-53
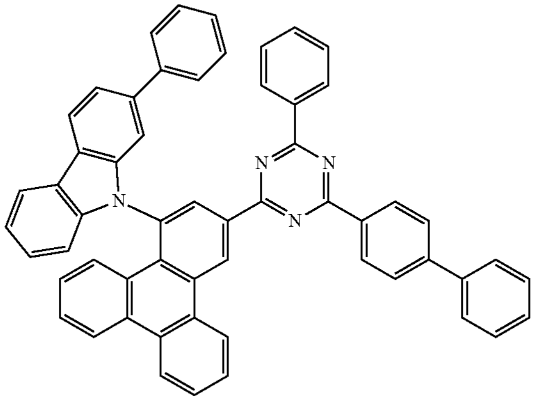

-continued
2-54
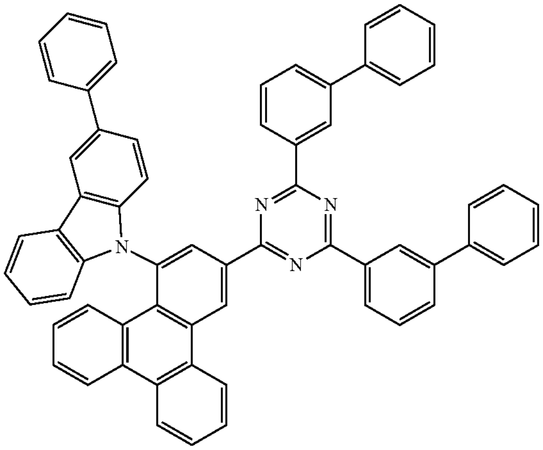
2-55
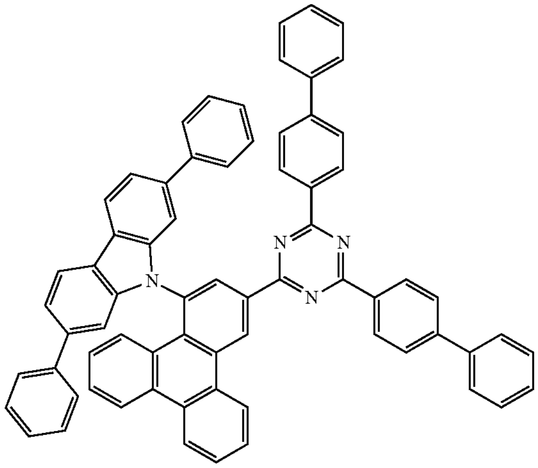
2-56
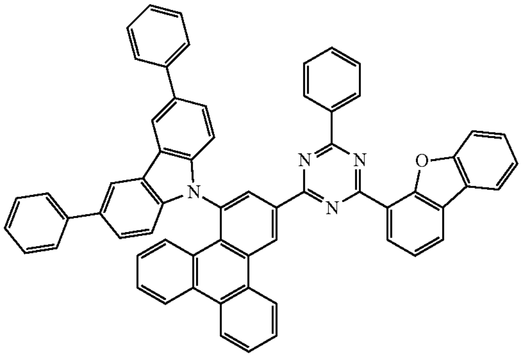
2-57
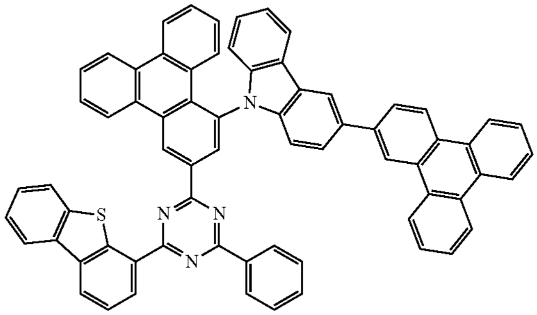
2-58
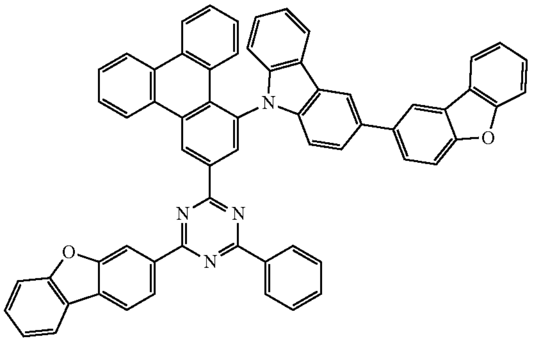
2-59
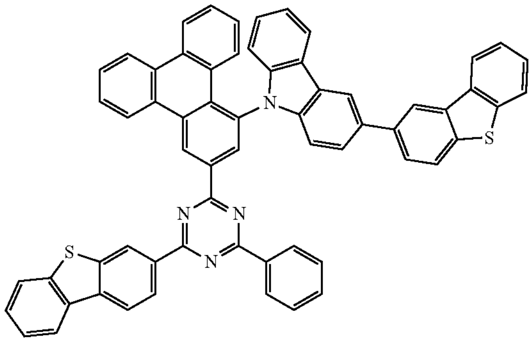
2-60
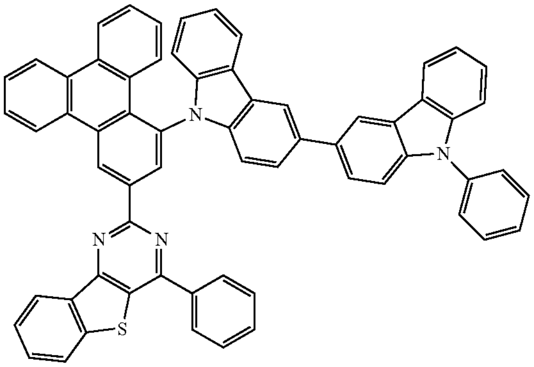
2-61
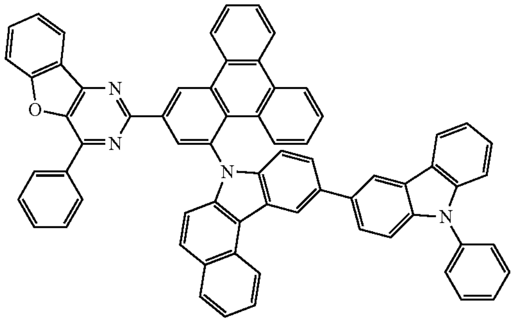

-continued
2-62
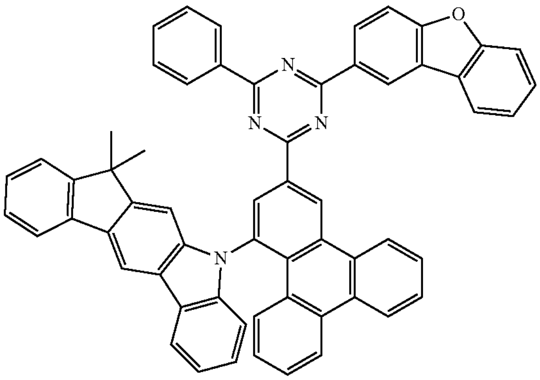
2-63
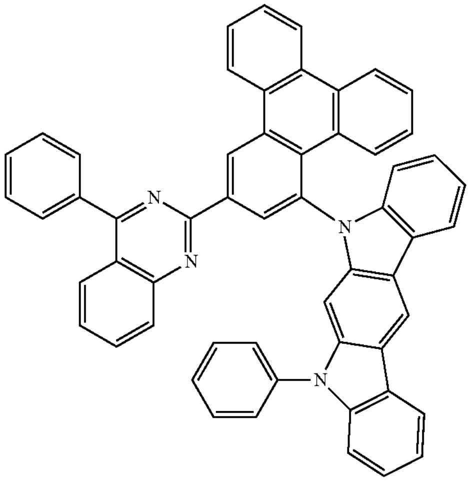
2-64
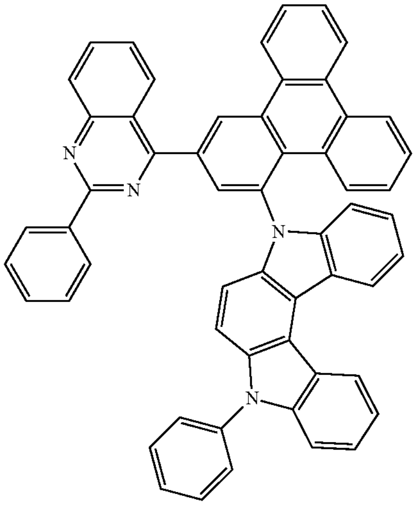
2-65
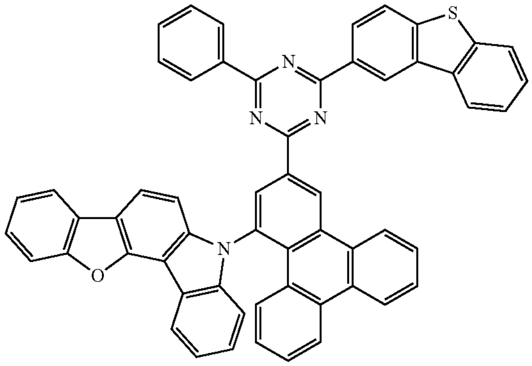
2-66
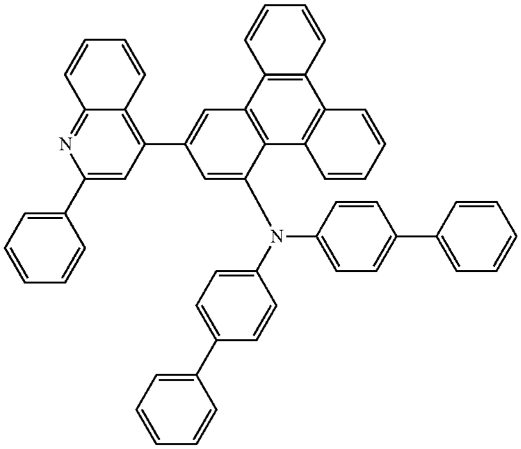
2-67
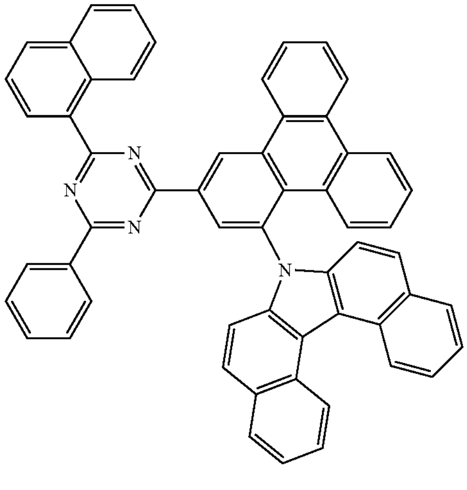

-continued
2-68
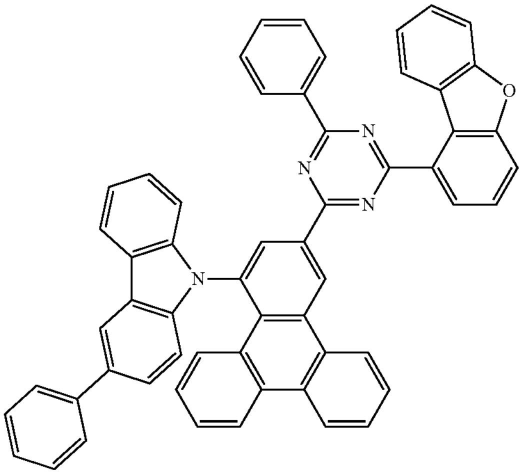
2-69
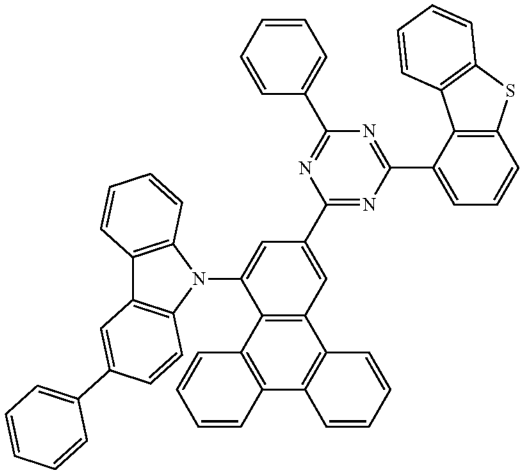
2-70
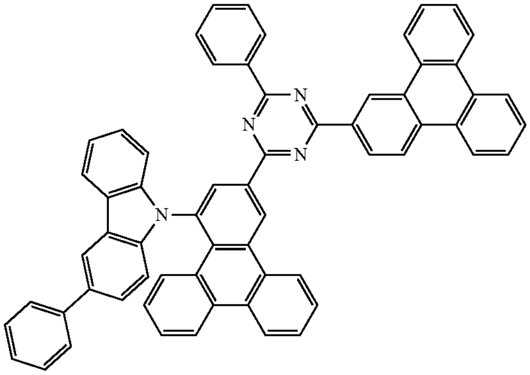
2-71
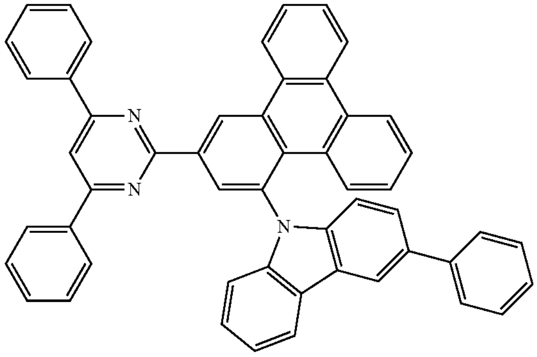
2-72
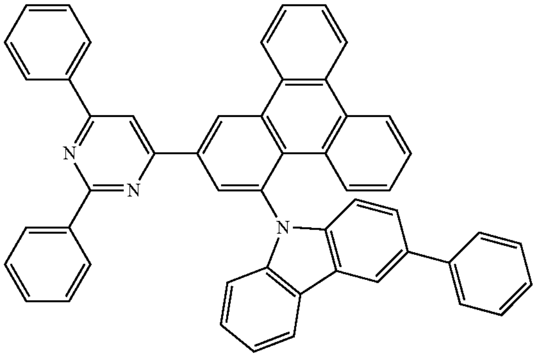
2-73
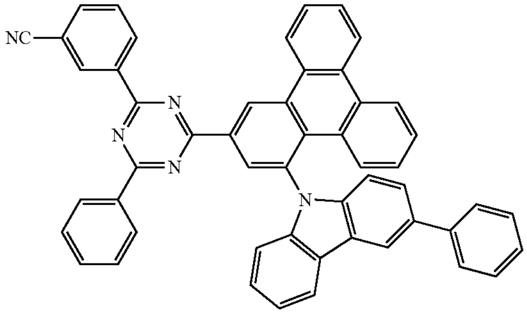
2-74
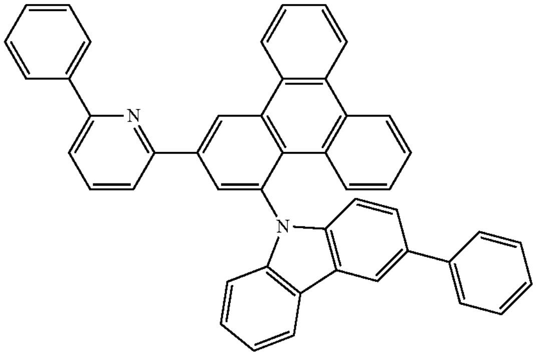
2-75
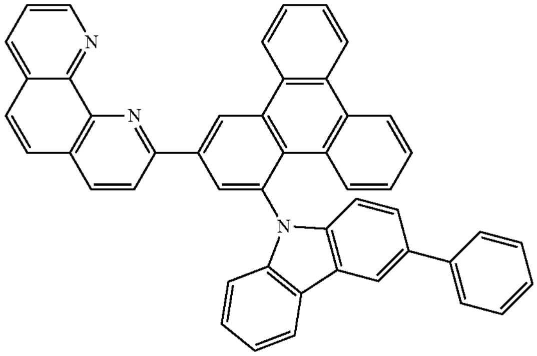

-continued
2-76
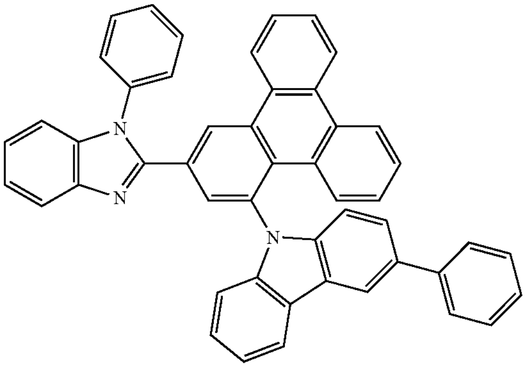
2-77
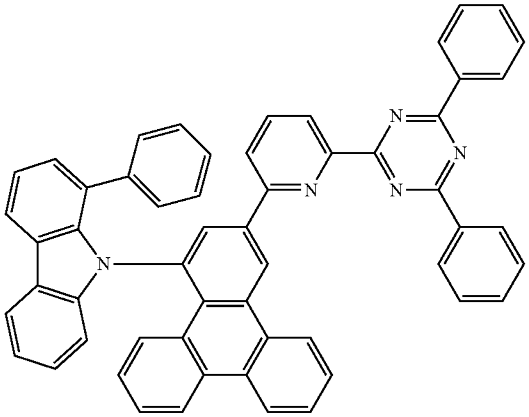
2-78
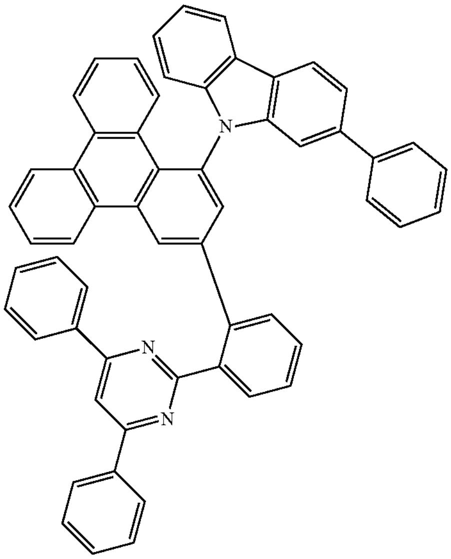
2-79
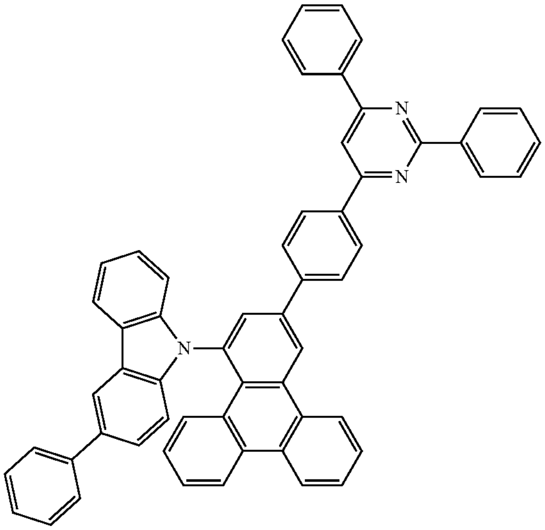
2-80
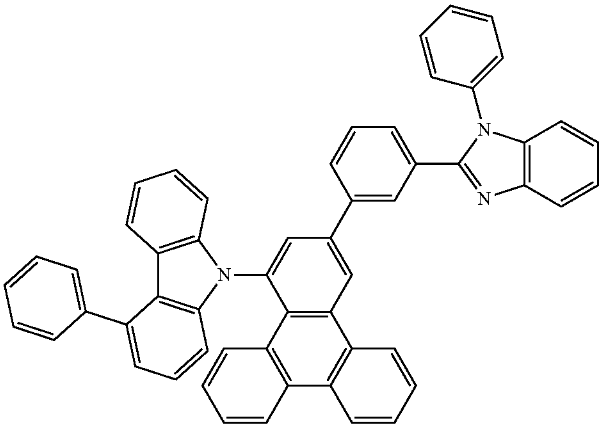

-continued
2-81
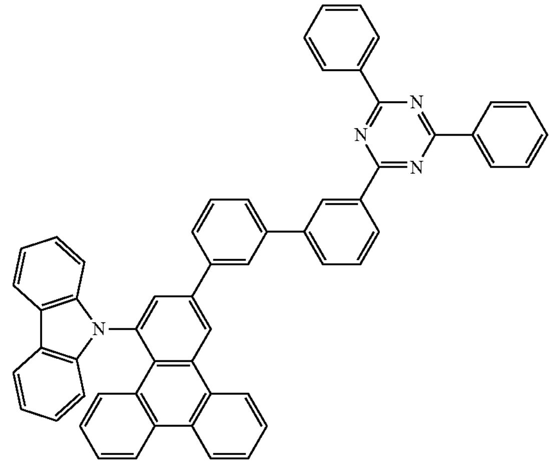
2-82
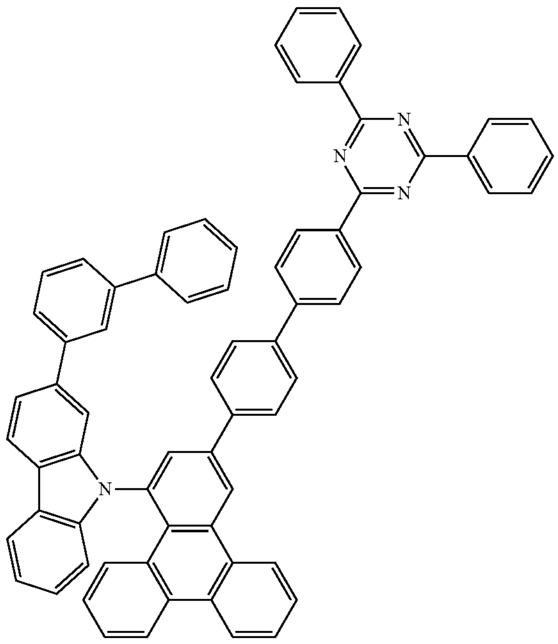
2-83
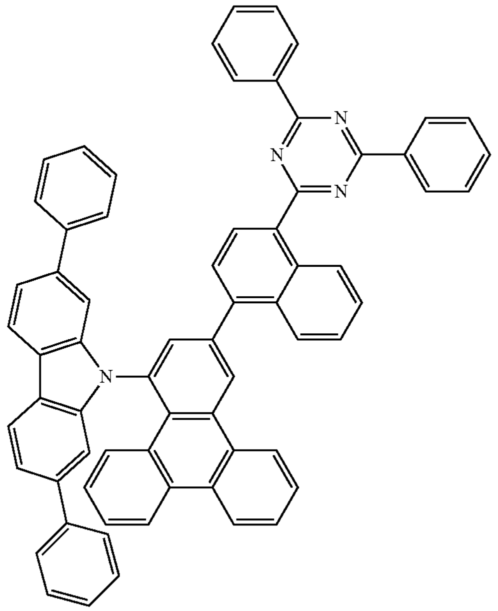
2-84
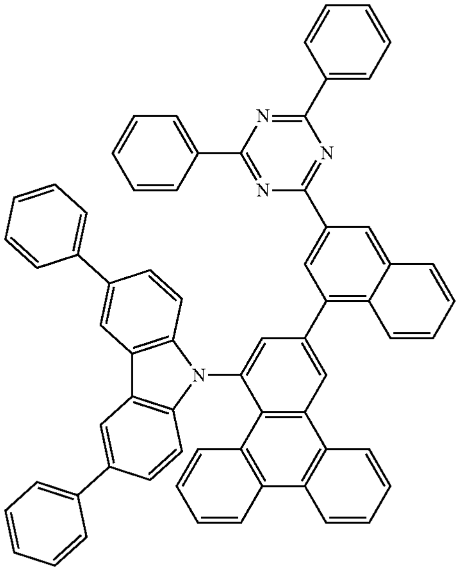
2-85
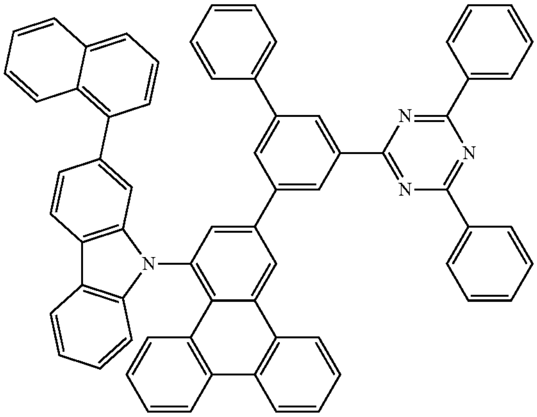

-continued
2-86
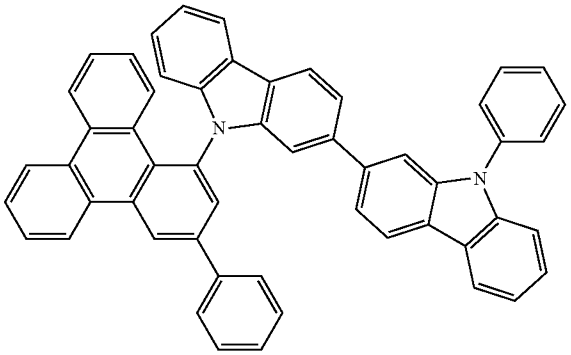
2-87
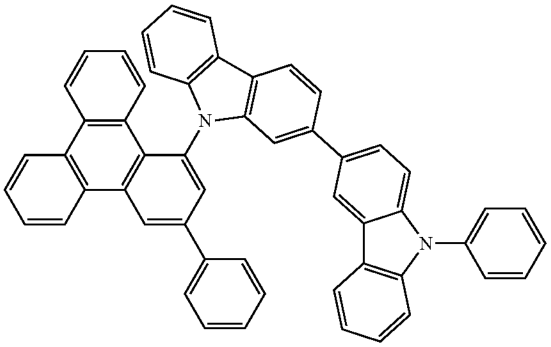
2-88
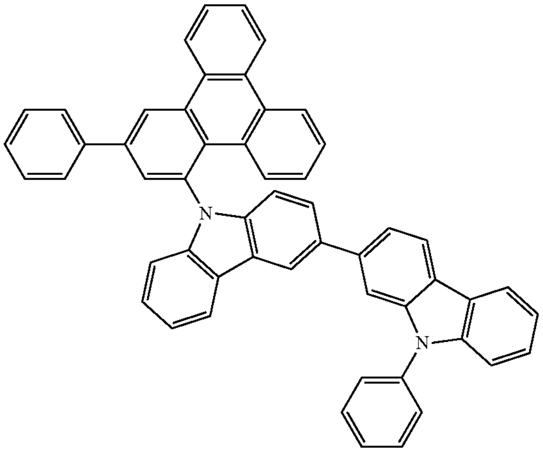
-continued
2-89
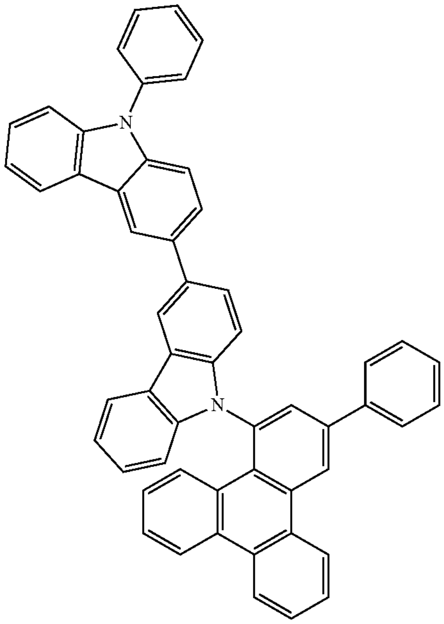
2-90
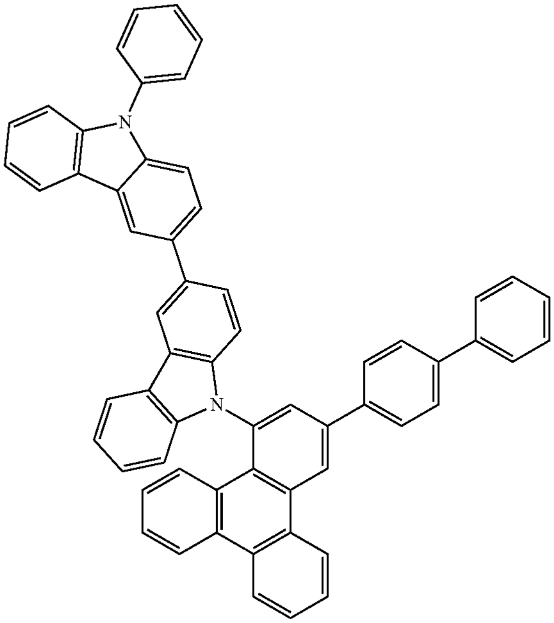

-continued
2-91
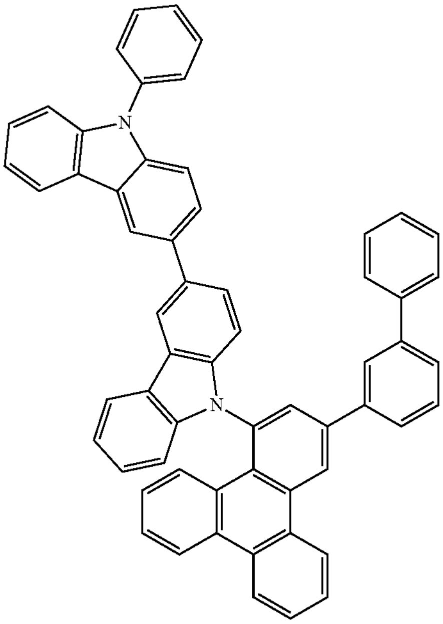
2-92
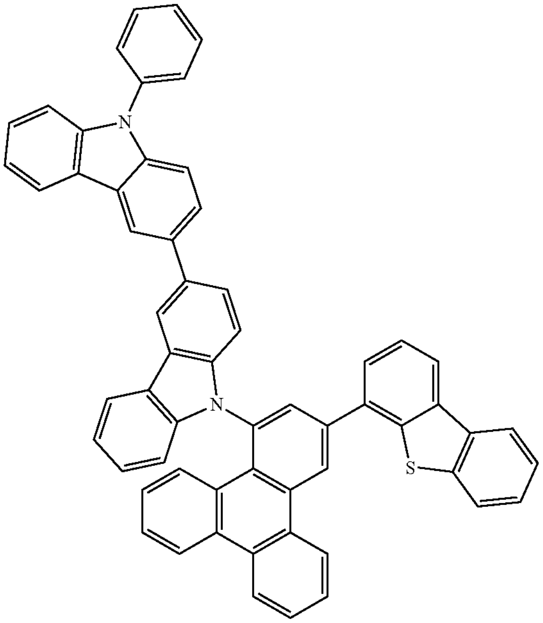
-continued
2-93
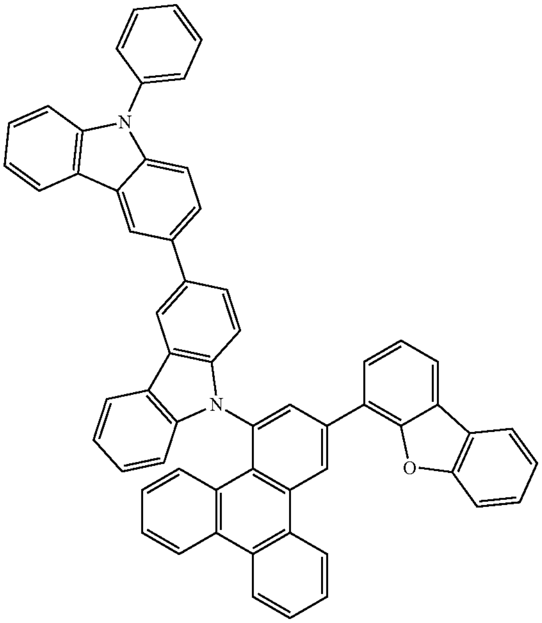
2-94
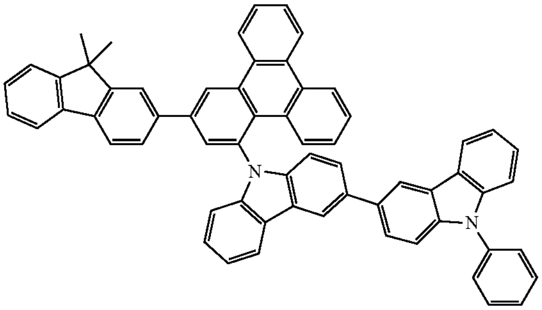
2-95
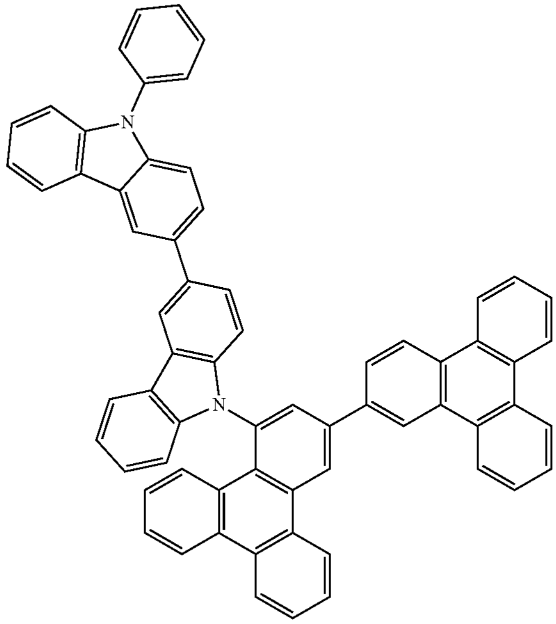

-continued
2-96
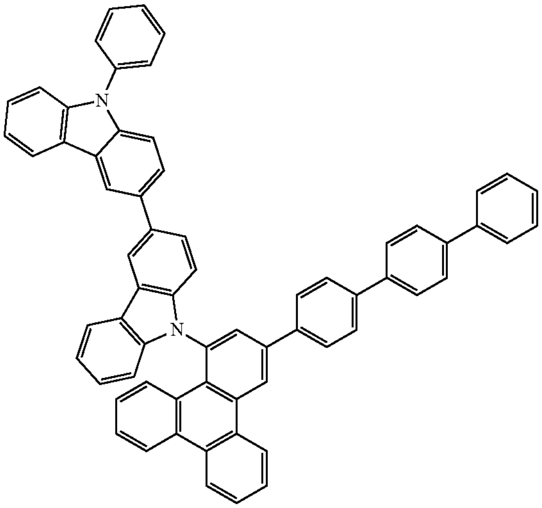
2-97
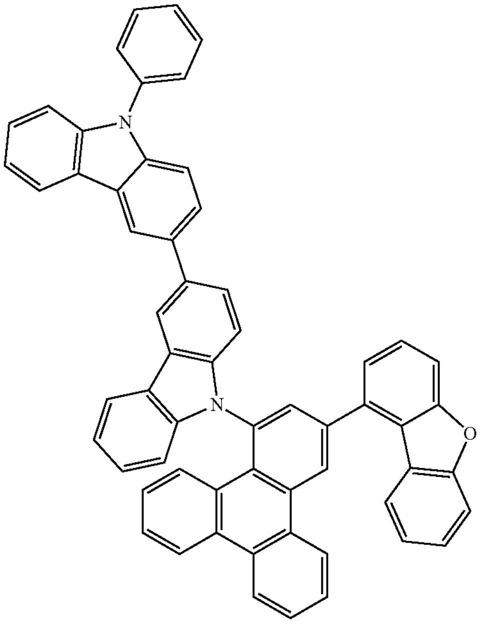
-continued
2-98
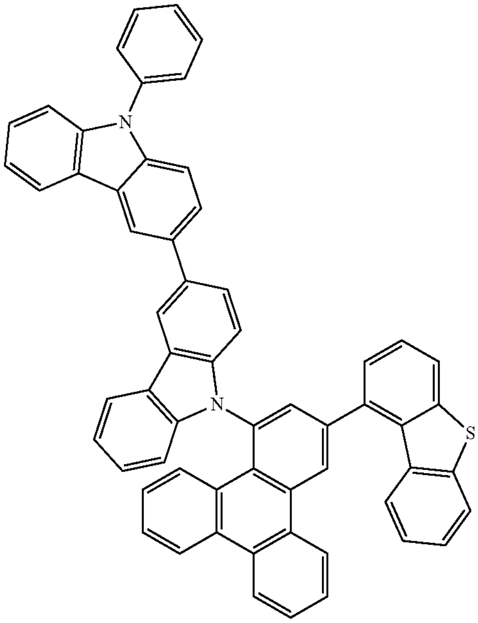
2-99
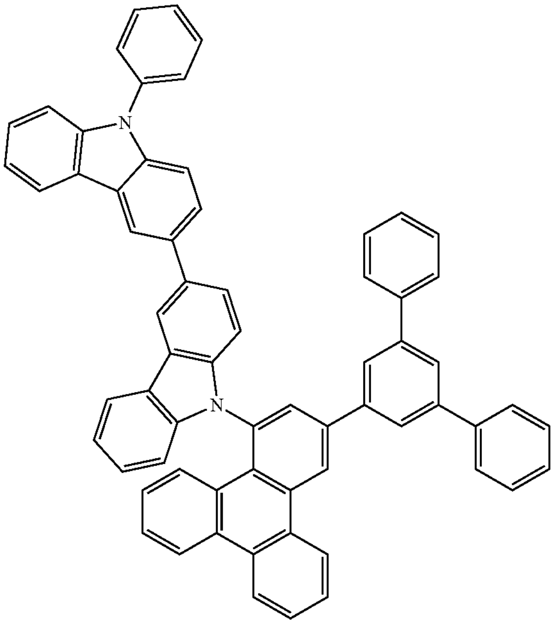

-continued 2-100

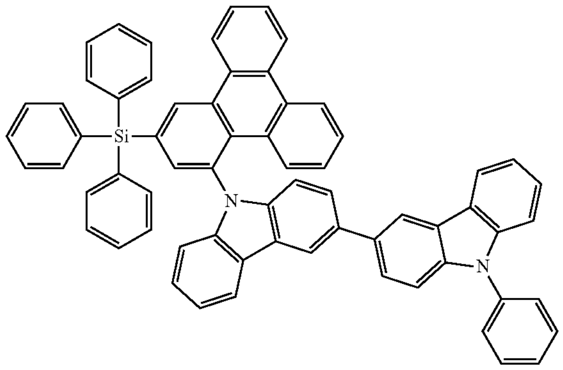

In addition, by introducing various substituents to the structure of Chemical Formula 1, compounds having unique properties of the introduced substituents may be synthesized. For example, by introducing substituents normally used as hole injection layer materials, hole transfer layer materials, light emitting layer materials, electron transfer layer materials and charge generation layer materials used for manufacturing an organic light emitting device to the core structure, materials satisfying conditions required for each organic material layer may be synthesized.

In addition, by introducing various substituents to the structure of Chemical Formula 1, the energy band gap may be finely controlled, and meanwhile, properties at interfaces between organic materials are enhanced, and material applications may become diverse.

Meanwhile, the compound has a high glass transition temperature (Tg), and has excellent thermal stability. Such an increase in the thermal stability becomes an important factor providing driving stability to a device.

Another embodiment of the present application provides an organic light emitting device comprising a first electrode; a second electrode provided opposite to the first electrode; and one or more organic material layers provided between the first electrode and the second electrode, wherein one or more layers of the organic material layers comprise the heterocyclic compound represented by Chemical Formula 1.

In one embodiment of the present application, the first electrode may be an anode, and the second electrode may be a cathode.

In another embodiment, the first electrode may be a cathode, and the second electrode may be an anode.

Specific details on the heterocyclic compound represented by Chemical Formula 1 are the same as the descriptions provided above.

The organic light emitting device of the present disclosure may be manufactured using common organic light emitting device manufacturing methods and materials except that one or more organic material layers are formed using the heterocyclic compound described above.

The heterocyclic compound may be formed into an organic material layer through a solution coating method as well as a vacuum deposition method when manufacturing the organic light emitting device. Herein, the solution coating method means spin coating, dip coating, inkjet printing, screen printing, a spray method, roll coating and the like, but is not limited thereto.

The organic material layer of the organic light emitting device of the present disclosure may be formed in a single layer structure, or may also be formed in a multilayer structure in which two or more organic material layers are laminated. For example, the organic light emitting device according to one embodiment of the present disclosure may have a structure comprising a hole injection layer, a hole transfer layer, a light emitting layer, an electron transfer layer, an electron injection layer and the like as the organic material layer. However, the structure of the organic light emitting device is not limited thereto, and may comprise a smaller number of organic material layers.

In the organic light emitting device according to one embodiment of the present application, the organic material layer comprising the heterocyclic compound represented by Chemical Formula 1 further comprises a heterocyclic compound represented by the following Chemical Formula 2.

[Chemical Formula 2]

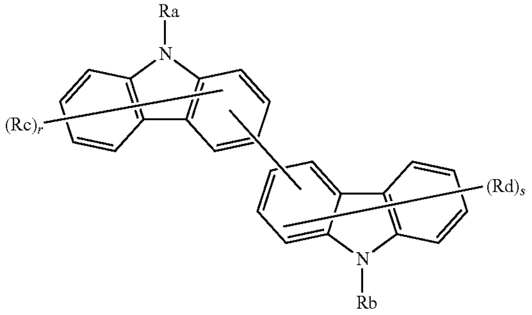

In Chemical Formula 2,

Rc and Rd are the same as or different from each other, and each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; $—SiR_{101}R_{102}R_{103}$; $—P(=O)R_{101}R_{102}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring, $R_{101}$, $R_{102}$ and $R_{103}$ are the same as or different from each other, and each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group, Ra and Rb are the same as or different from each other, and each independently a substituted or unsubstituted aryl group; or a substituted or unsubstituted heteroaryl group, r and s are an integer of 0 to 7, and when r and s are each an integer of 2 or greater, substituents in the parentheses are the same as or different from each other.

In the organic light emitting device according to one embodiment of the present application, Rc and Rd of Chemical Formula 2 may be hydrogen.

In the organic light emitting device according to one embodiment of the present application, Ra and Rb of Chemical Formula 2 are the same as or different from each other, and may be each independently a substituted or unsubstituted aryl group; or a substituted or unsubstituted heteroaryl group.

In the organic light emitting device according to another embodiment, Ra and Rb of Chemical Formula 2 are the same as or different from each other, and may be each independently a substituted or unsubstituted C6 to C40 aryl group; or a substituted or unsubstituted C6 to C40 heteroaryl group.

In the organic light emitting device according to another embodiment, Ra and Rb of Chemical Formula 2 are the same as or different from each other, and may be each independently a C6 to C40 aryl group unsubstituted or substituted with one or more substituents selected from the group consisting of a C1 to C40 alkyl group, a C6 to C40 aryl group, —CN and —$SiR_{101}R_{102}R_{103}$; or a C2 to C40 heteroaryl group unsubstituted or substituted with one or more substituents selected from the group consisting of a C6 to C40 aryl group and a C2 to C40 heteroaryl group.

In the organic light emitting device according to another embodiment, Ra and Rb of Chemical Formula 2 are the same as or different from each other, and may be each independently a phenyl group unsubstituted or substituted with a phenyl group, —CN or —$SiR_{101}R_{102}R_{103}$; a biphenyl group unsubstituted or substituted with a phenyl group; a naphthyl group; a fluorene group unsubstituted or substituted with a methyl group or a phenyl group; a spirobifluorene group; a dibenzothiophene group unsubstituted or substituted with one or more substituents selected from the group consisting of a phenyl group, a biphenyl group, a naphthyl group, a dimethylfluorene group, a dibenzothiophene group and a dibenzofuran group; or a triphenylene group unsubstituted or substituted with a phenyl group.

In the organic light emitting device according to one embodiment of the present application, $R_{101}$, $R_{102}$ and $R_{103}$ of Chemical Formula 2 may be a phenyl group.

When including the compound of Chemical Formula 1 and the compound of Chemical Formula 2 in an organic material layer of an organic light emitting device, more superior efficiency and lifetime effects are obtained. Such results may lead to a forecast that an exciplex phenomenon occurs when comprising the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with enhancement in the lifetime.

In one embodiment of the present application, Chemical Formula 2 may be represented by any one of the following Chemical Formulae 13 to 20.

[Chemical Formula 13]

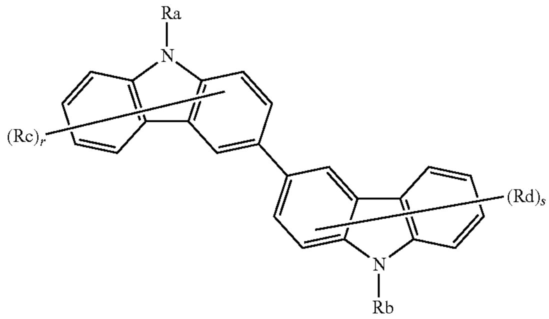

[Chemical Formula 14]

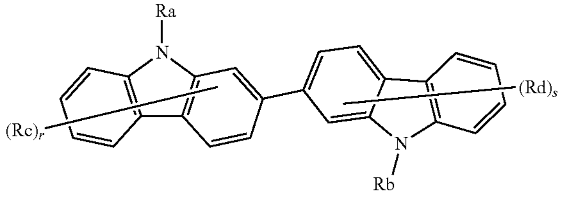

[Chemical Formula 15]

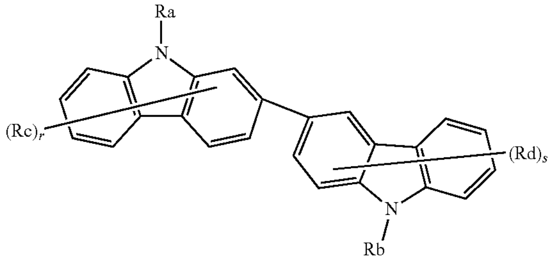

[Chemical Formula 16]

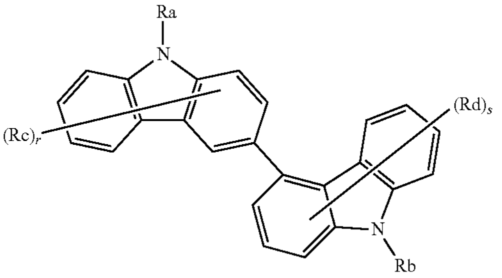

[Chemical Formula 17]

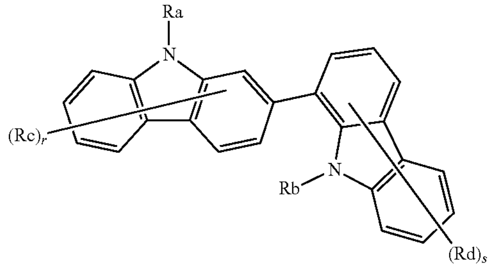

-continued
[Chemical Formula 18]
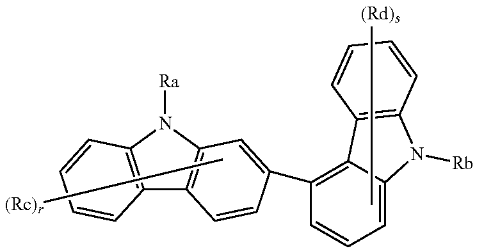
[Chemical Formula 19]
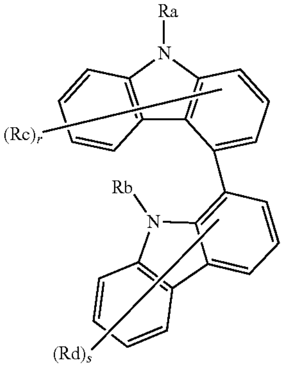
-continued
[Chemical Formula 20]
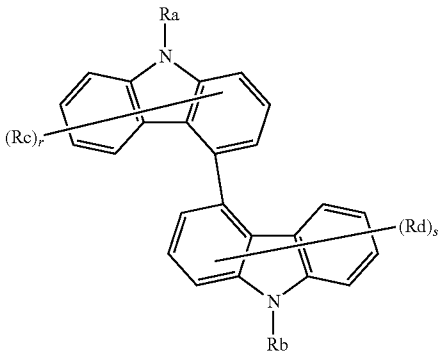
In Chemical Formulae 13 to 20,
Ra, Rb, Rc, Rd, r and s have the same definitions as in Chemical Formula 2.
In the organic light emitting device according to one embodiment of the present application, Chemical Formula 2 may be represented by any one of the following heterocyclic compounds.
3-1
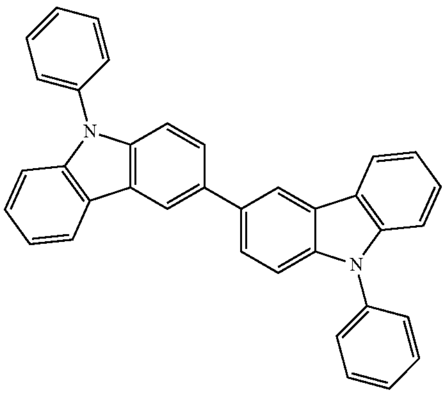
3-2
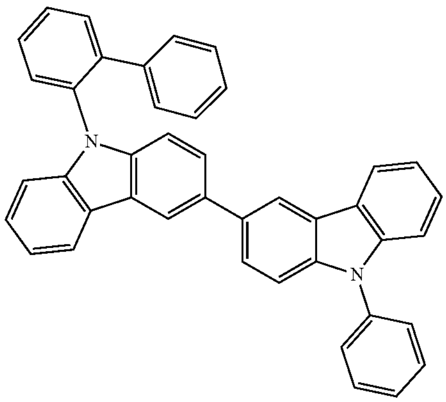
3-3
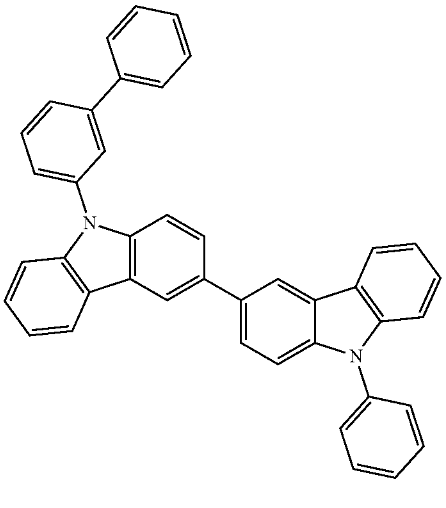
3-4
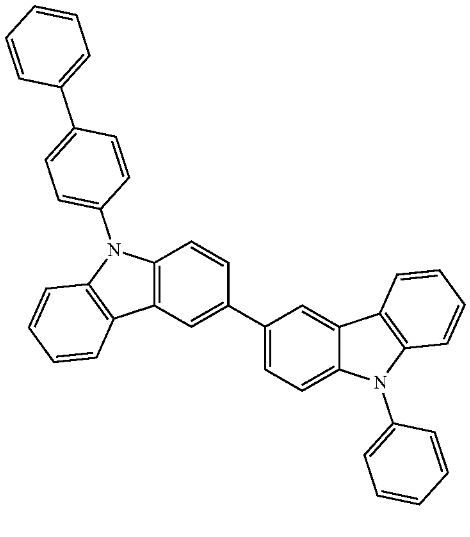

-continued
3-5
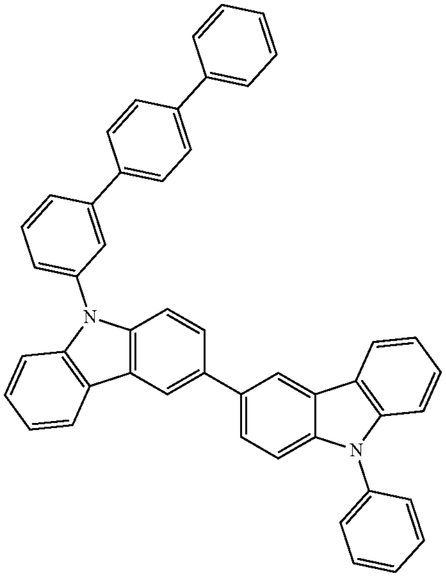
3-6
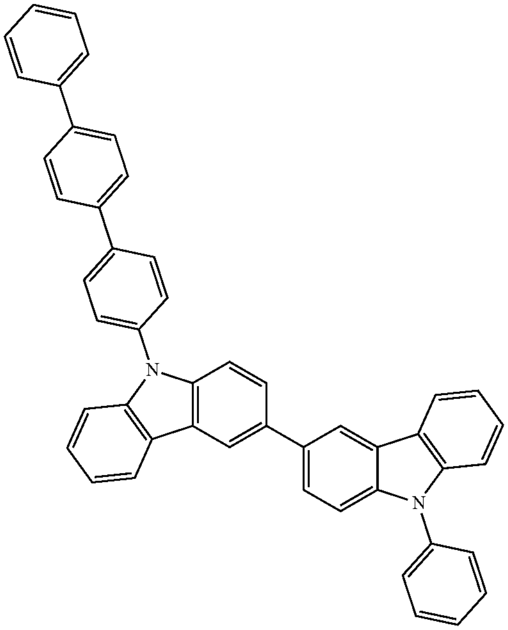
3-7
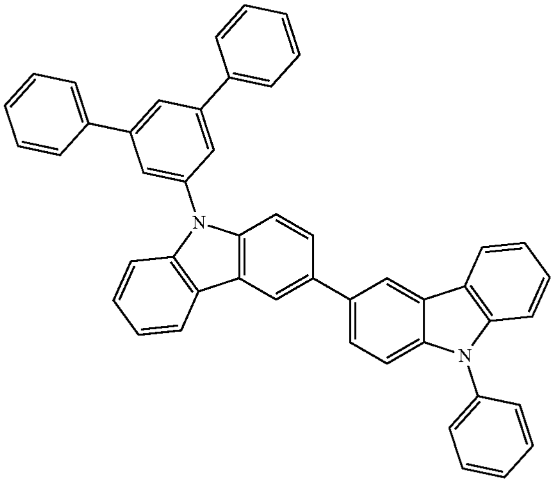
3-8
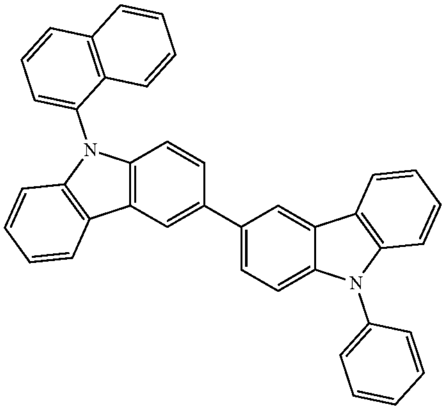
3-9
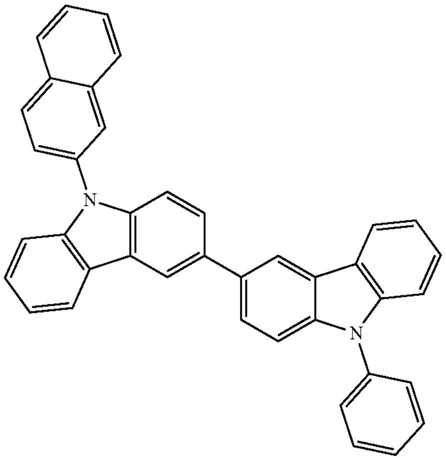
3-10
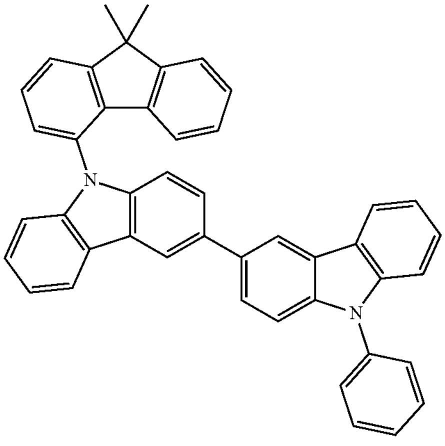

-continued
3-11
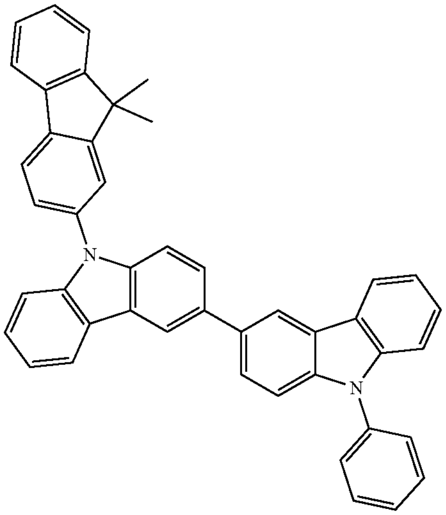
3-12
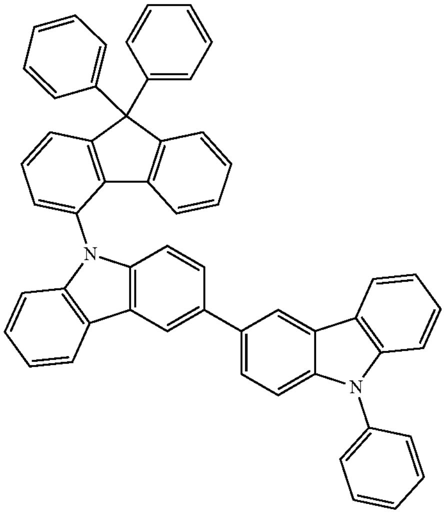
3-13
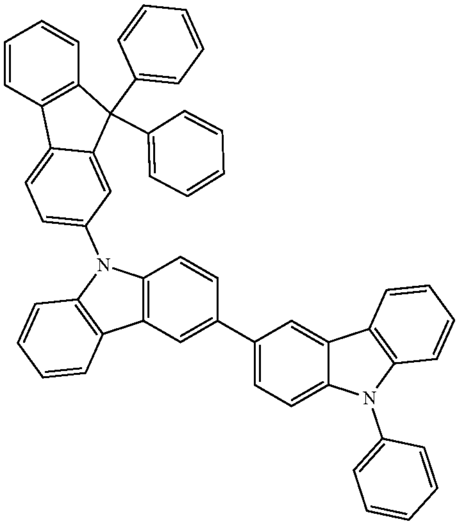
3-14
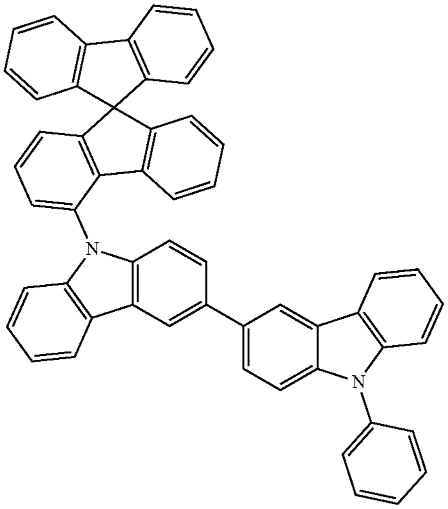
3-15
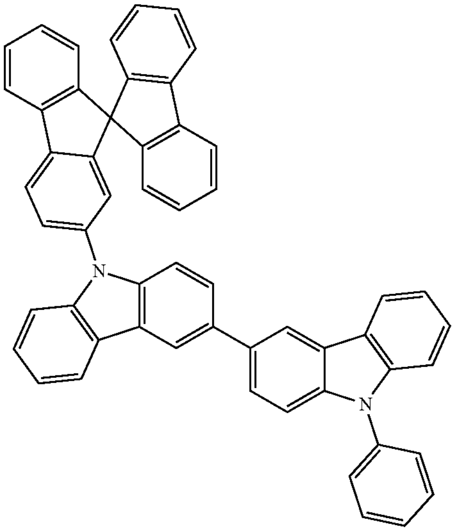
3-16
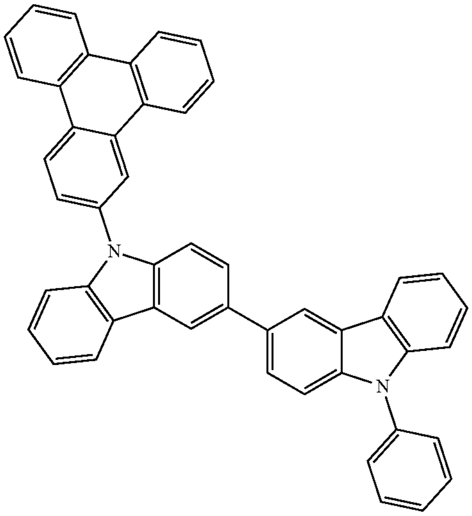

-continued
3-17
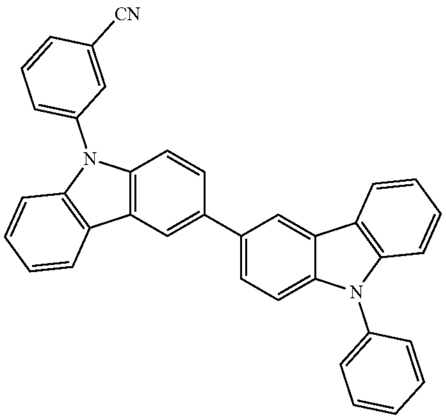
3-18
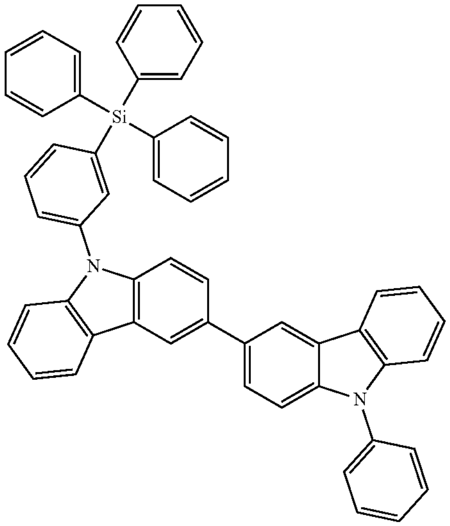
3-19
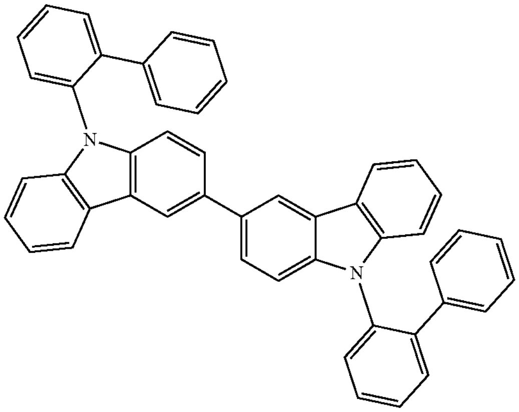
3-20
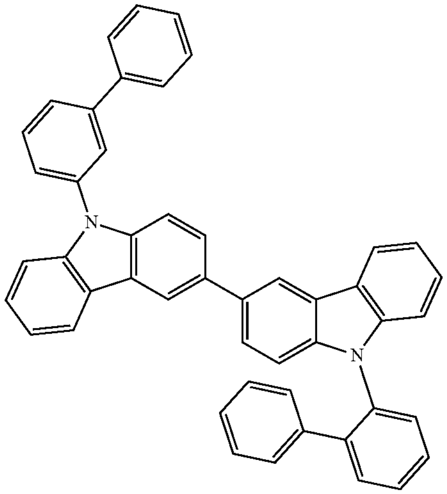
3-21
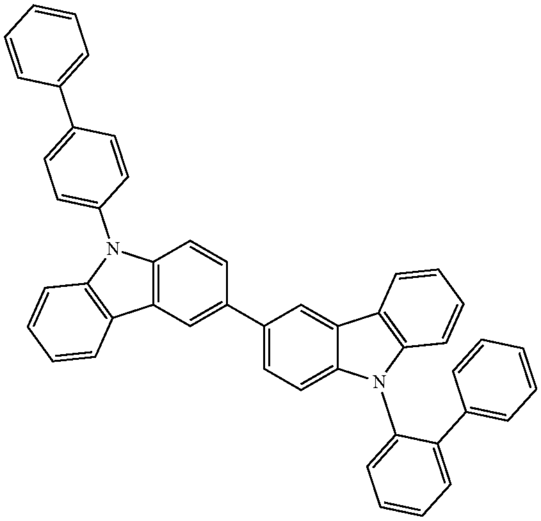
3-22
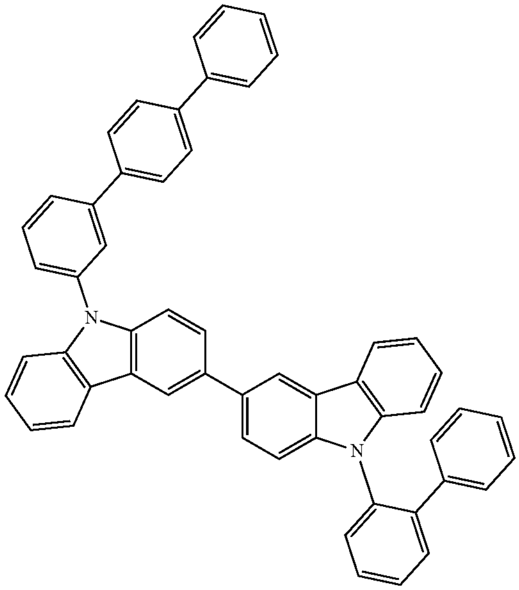

-continued
3-23
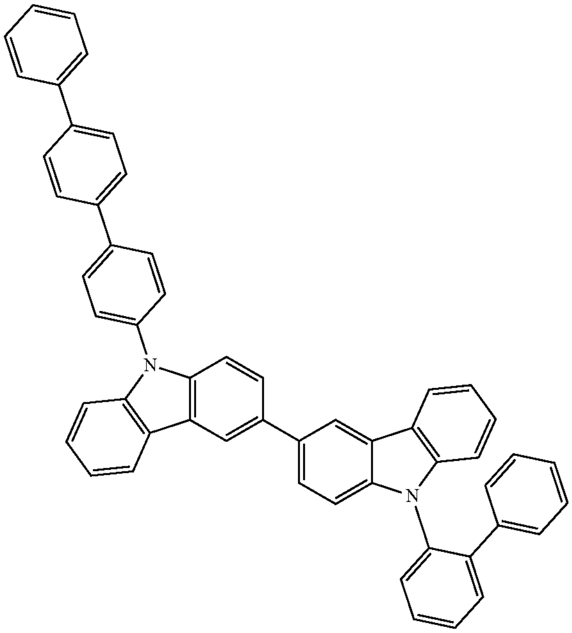
3-24
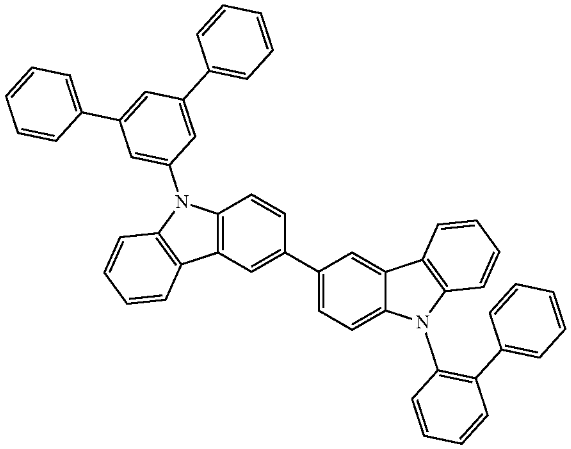
3-25
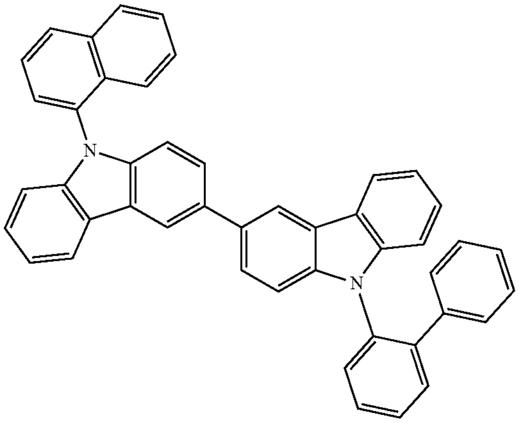
3-26
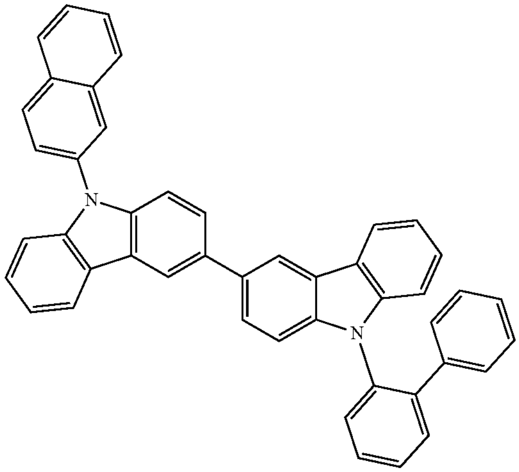
3-27
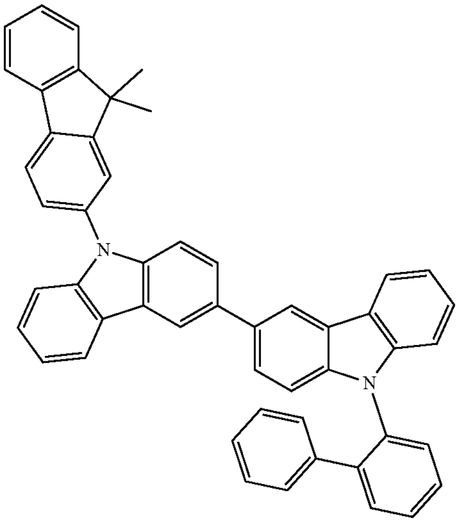
3-28
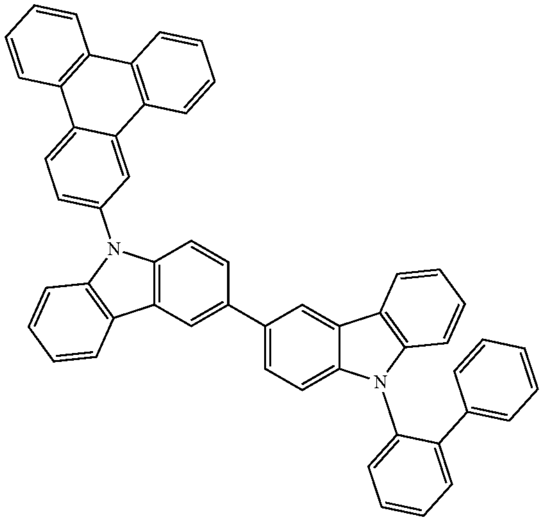

-continued
3-29
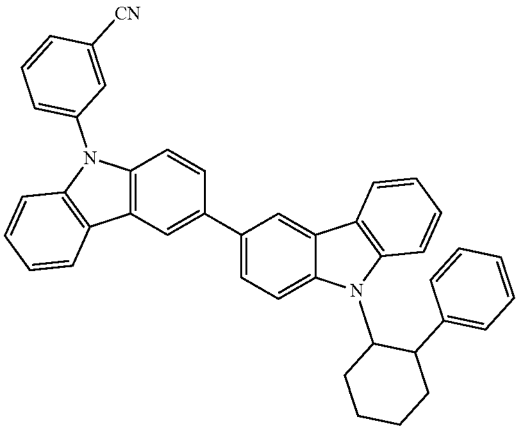
3-30
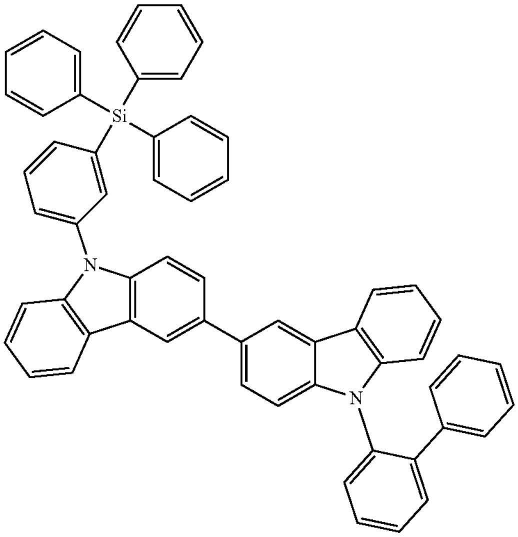
3-30
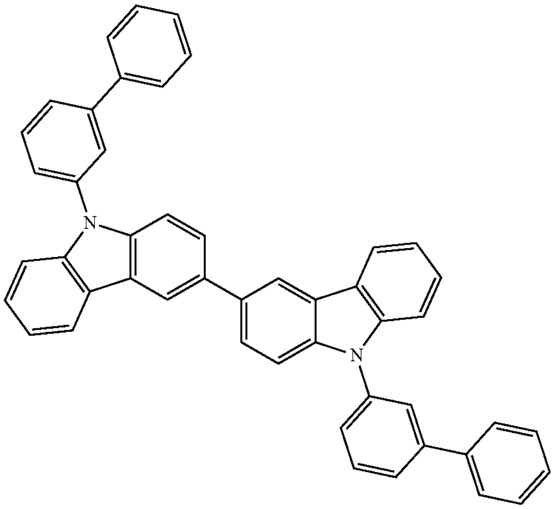
3-32
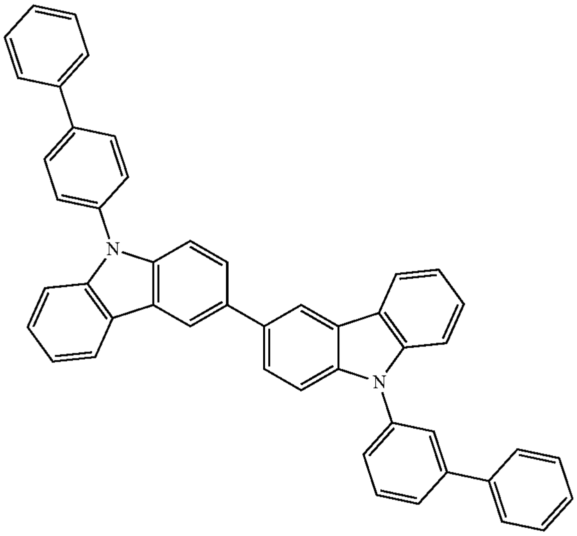

-continued
3-33
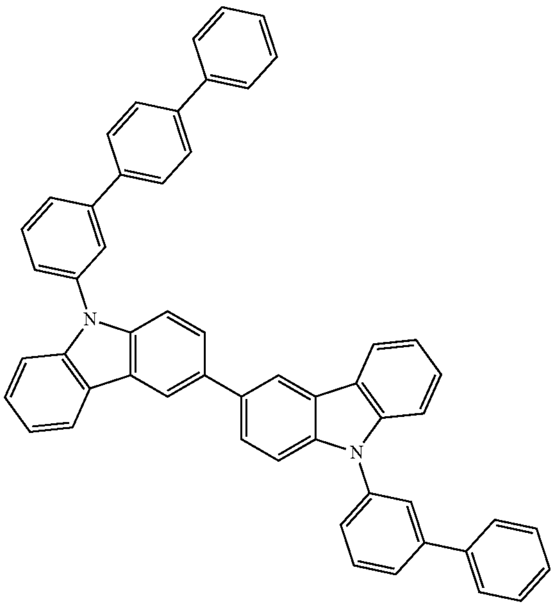
3-34
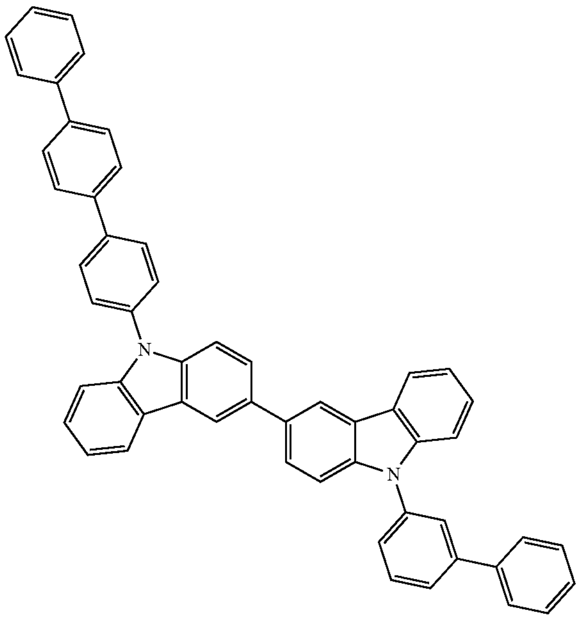
3-35
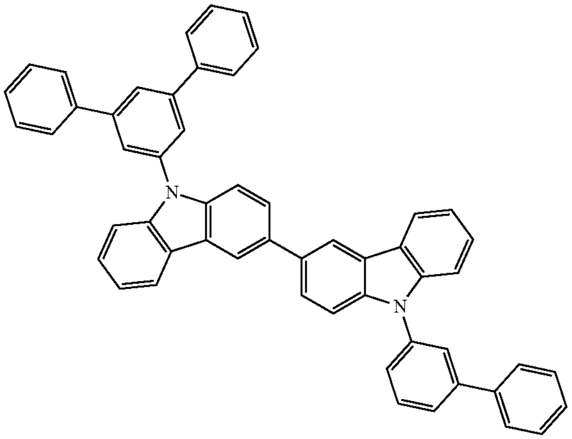
3-36
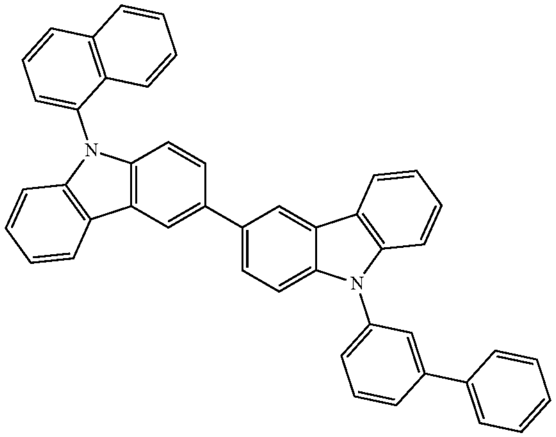
3-37
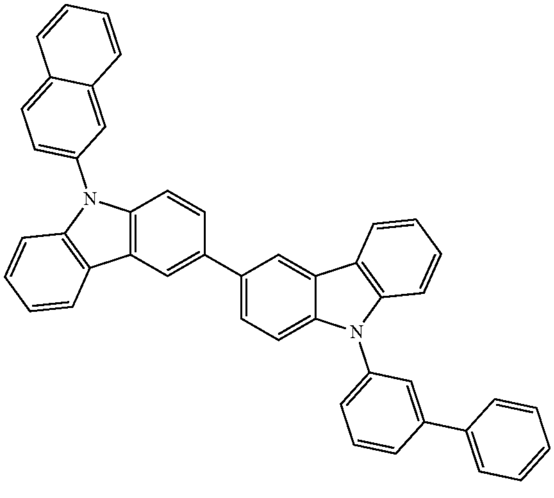
3-38
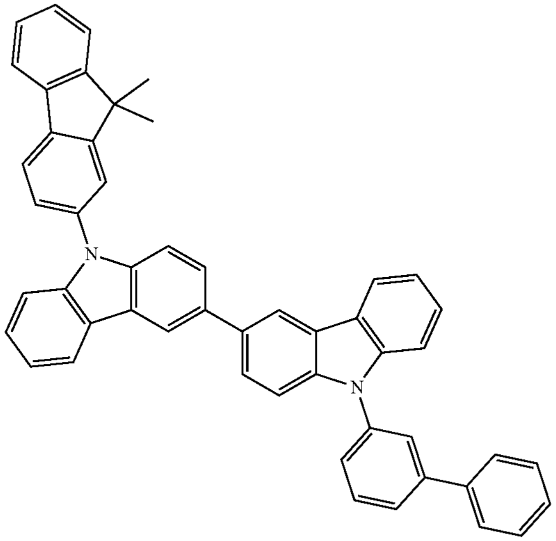

-continued
3-39
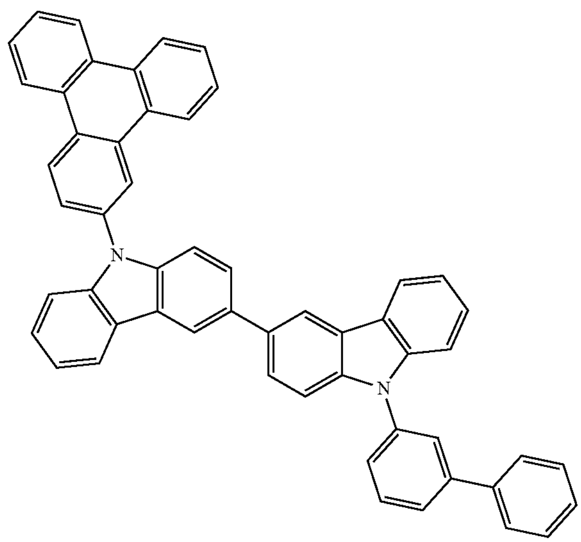
3-40
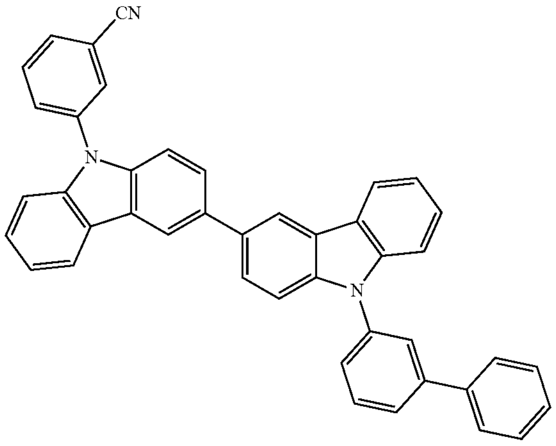
3-41
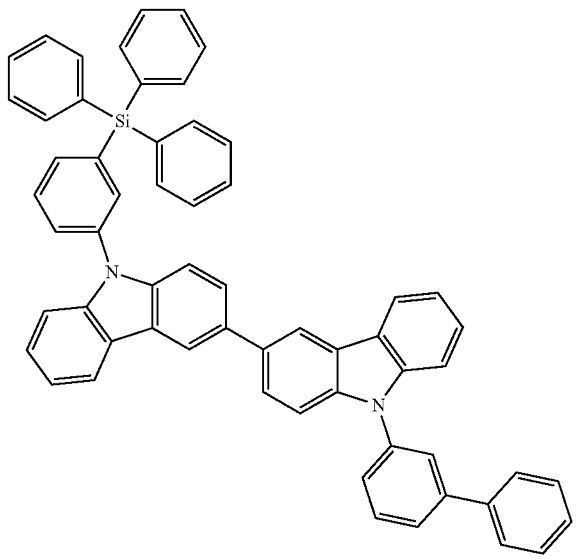
3-42
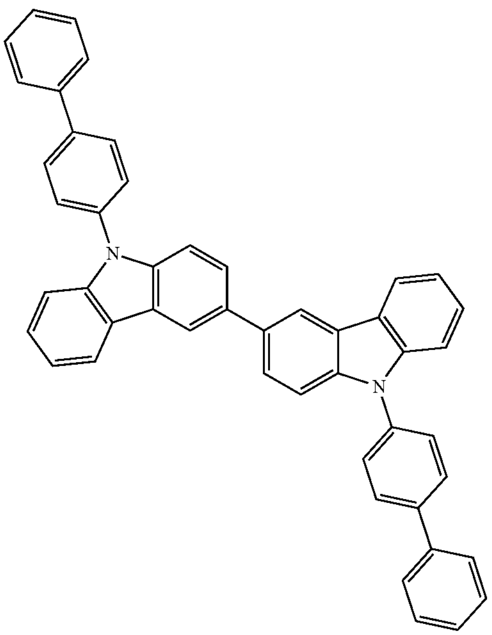

-continued
3-43
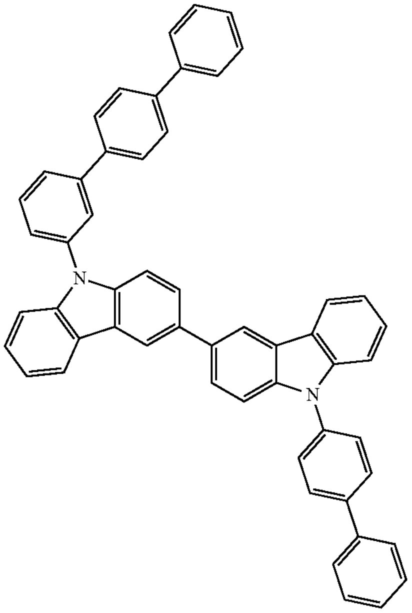
3-44
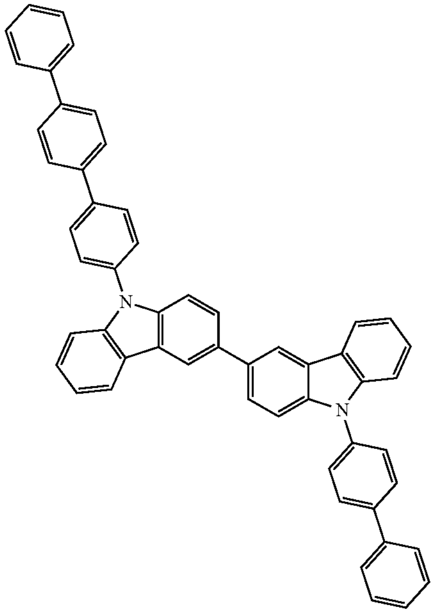
3-45
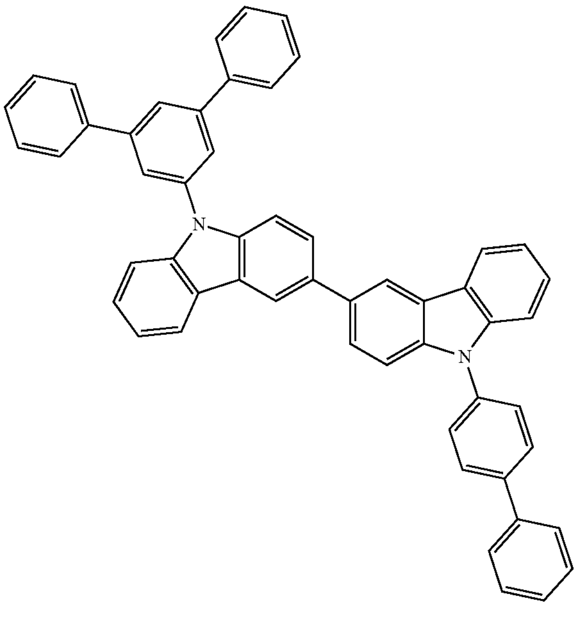
3-46
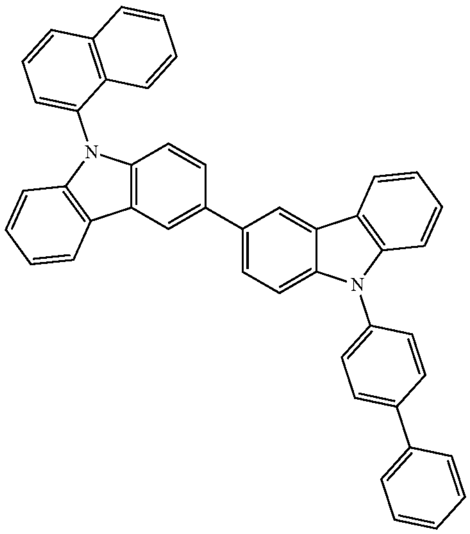

-continued
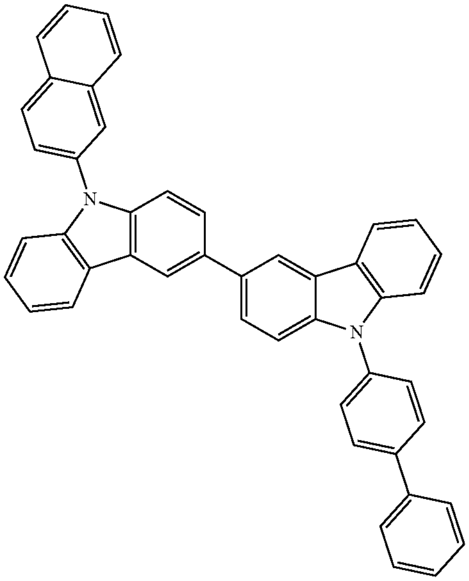
3-47
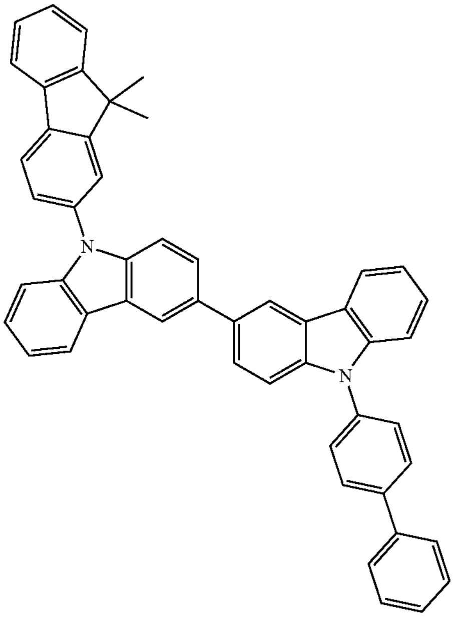
3-48
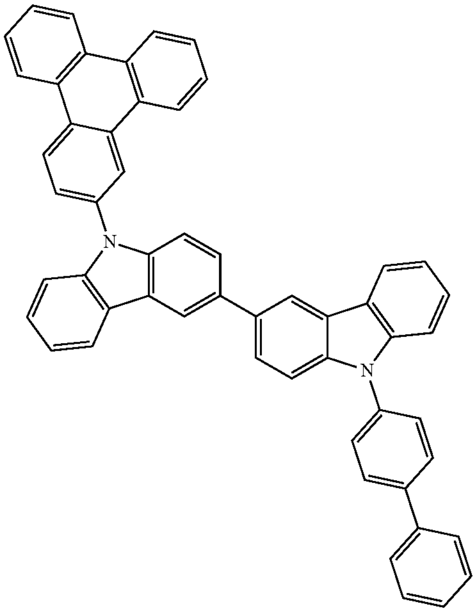
3-49
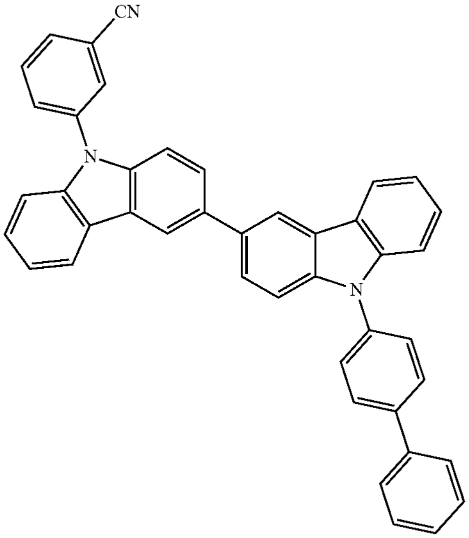
3-50

-continued
3-51
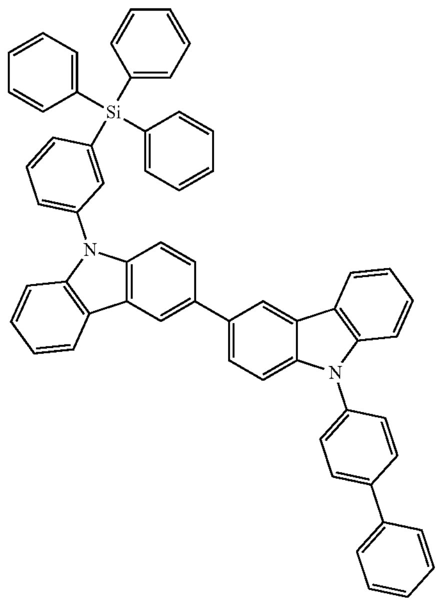
3-52
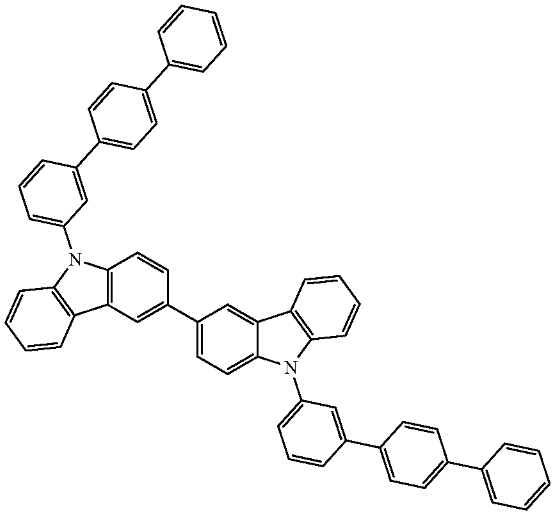
3-53
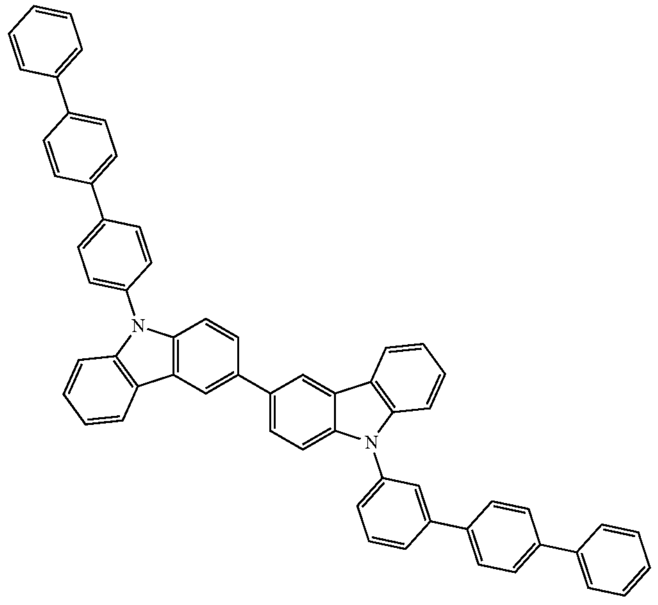

-continued
3-54
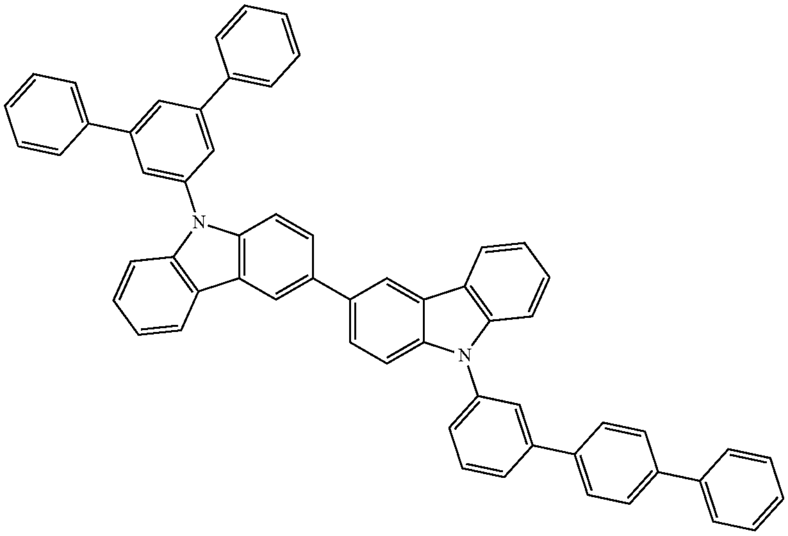
3-55
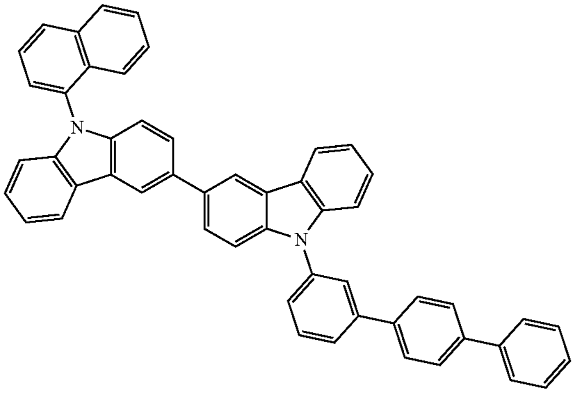
3-56
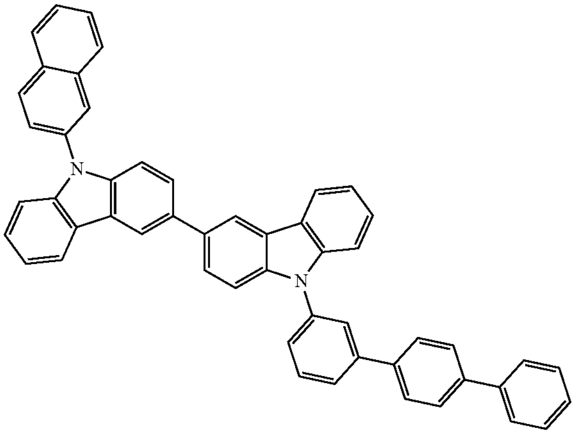
3-57
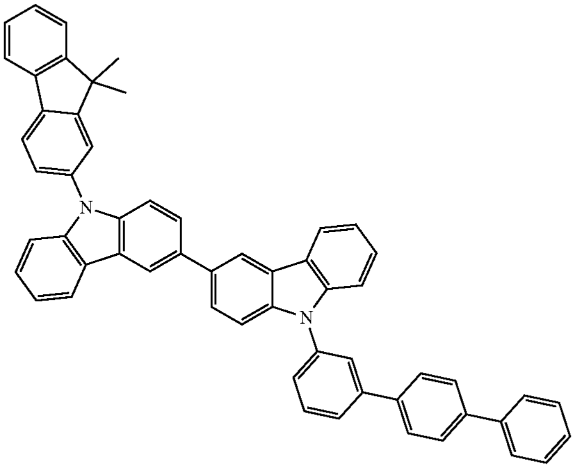
3-58
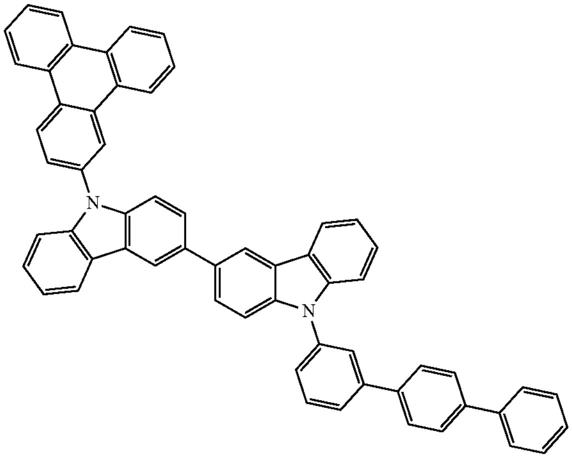

-continued
3-59
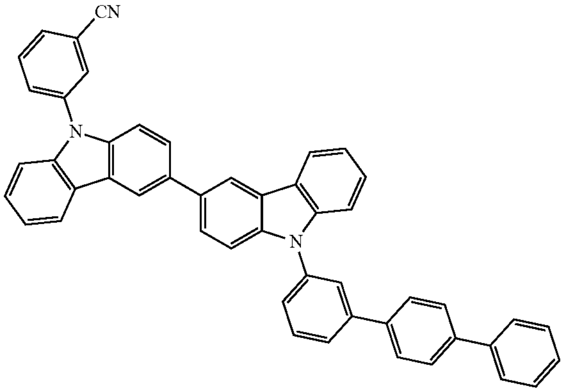
3-60
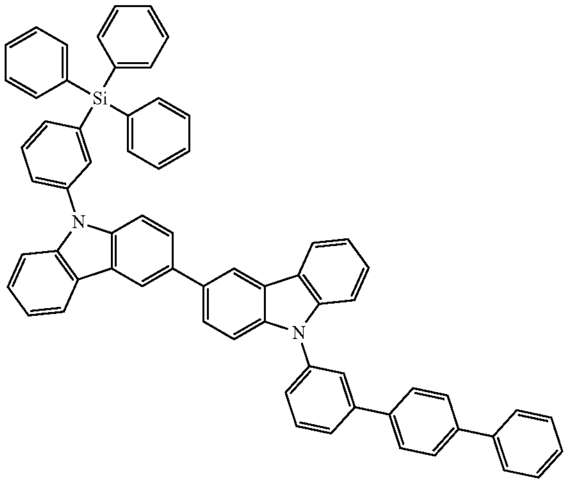
3-61
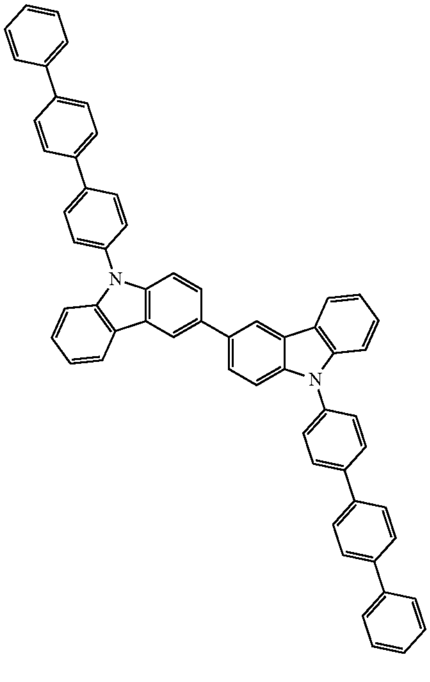
3-62
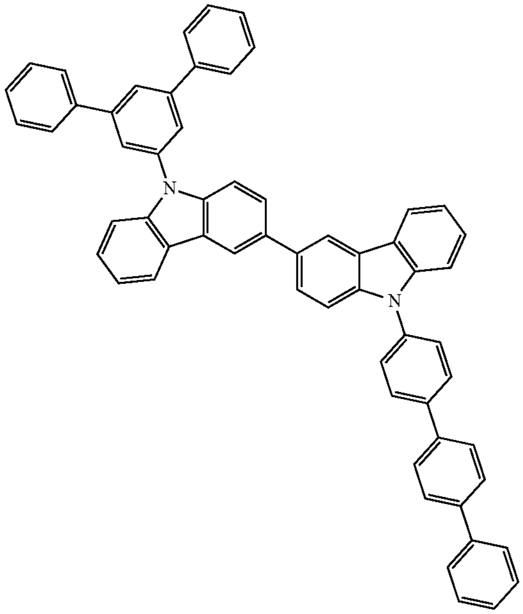

-continued
3-63
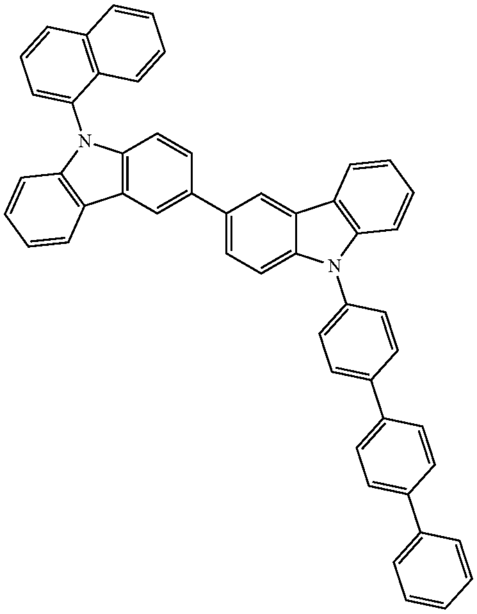
3-64
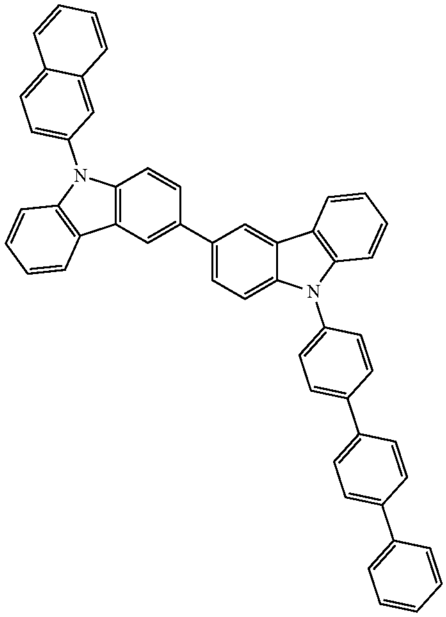
3-65
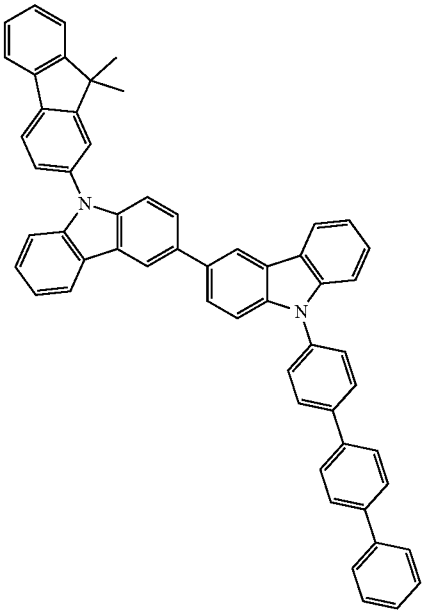
3-66
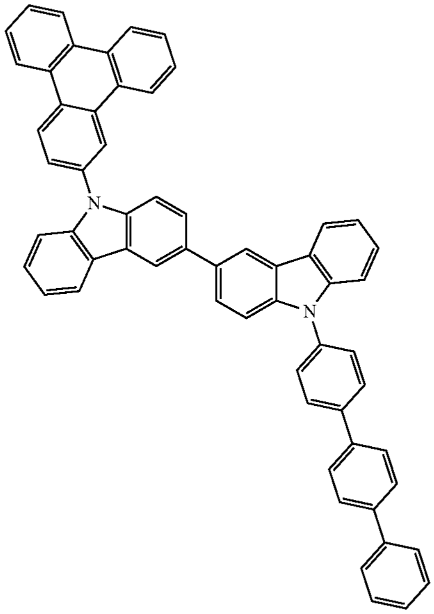

-continued
3-67
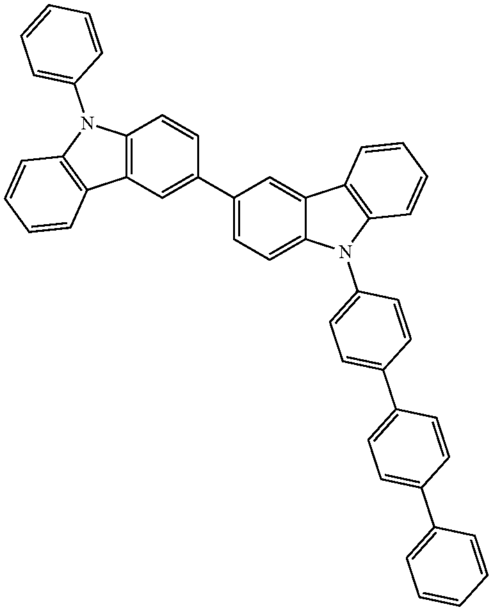
3-68
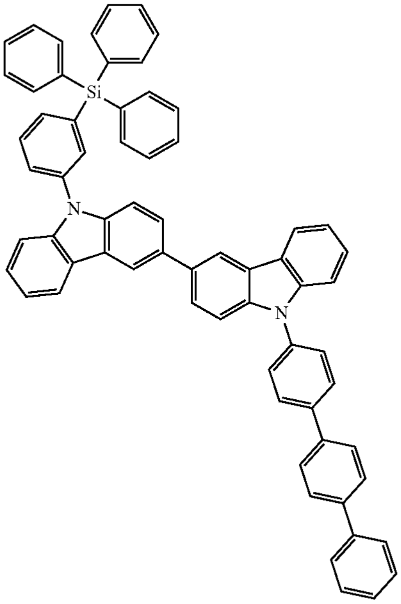
3-69
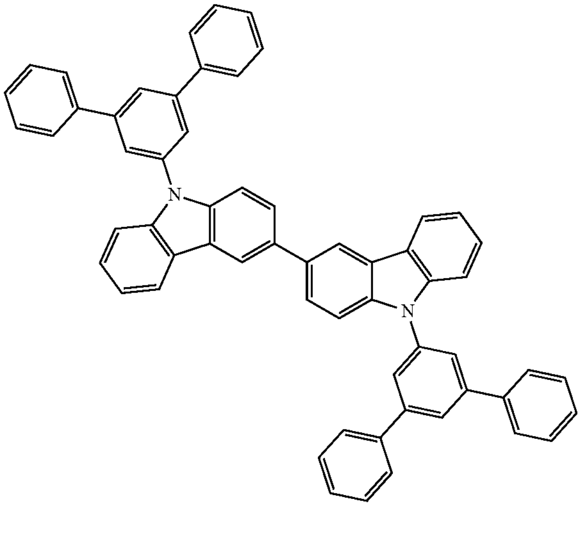
3-70
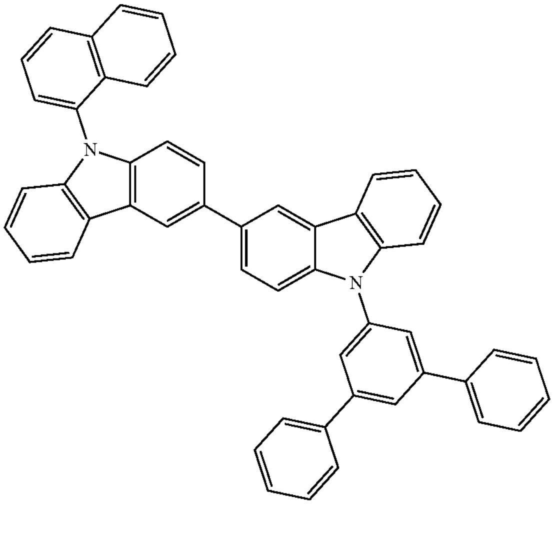

-continued
3-71
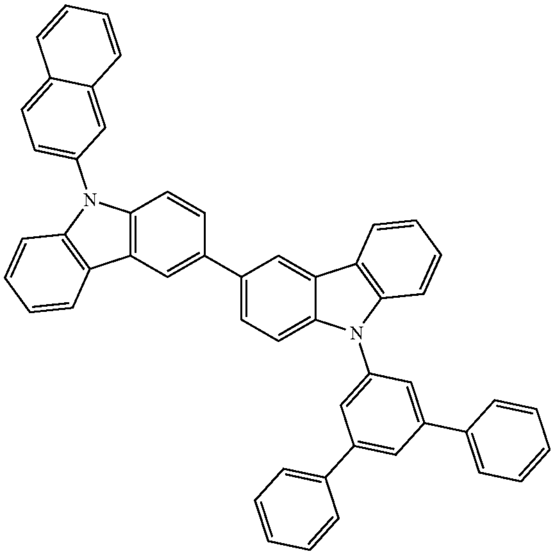
3-72
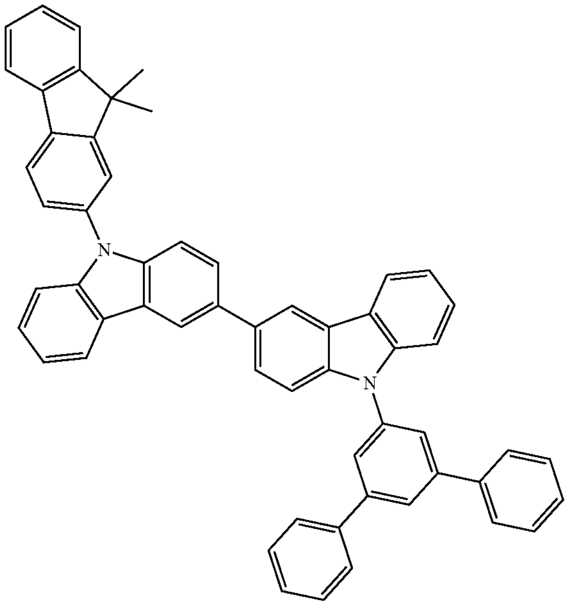
3-74
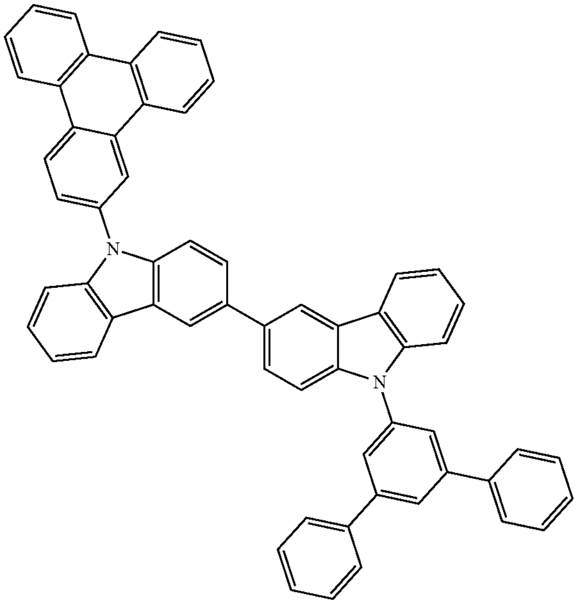
3-73
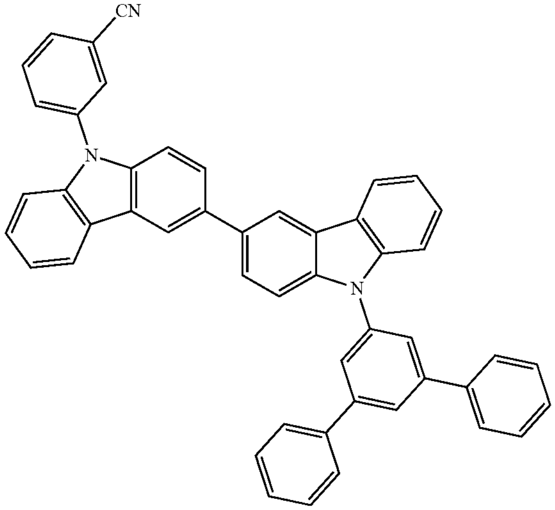

-continued
3-75
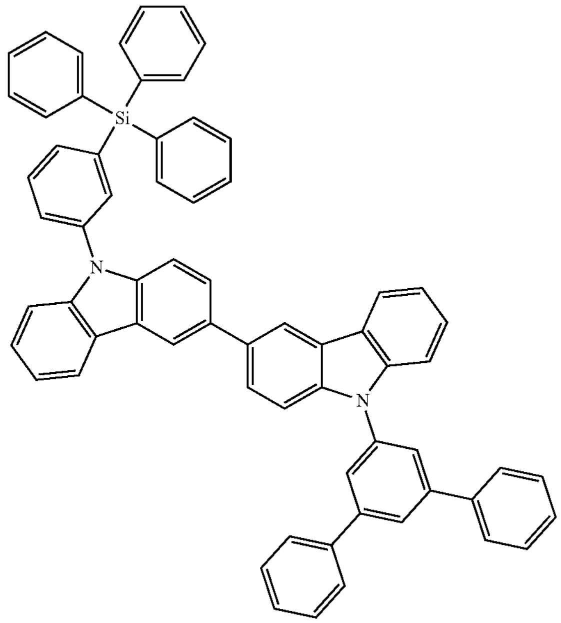
3-76
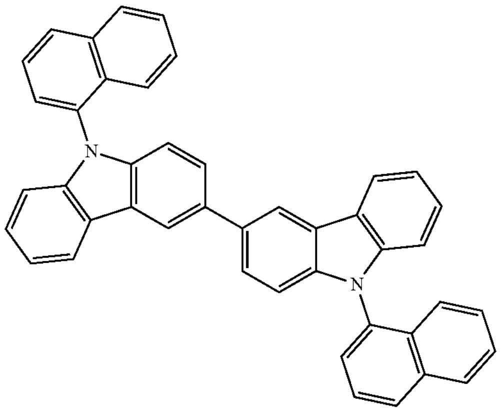
3-77
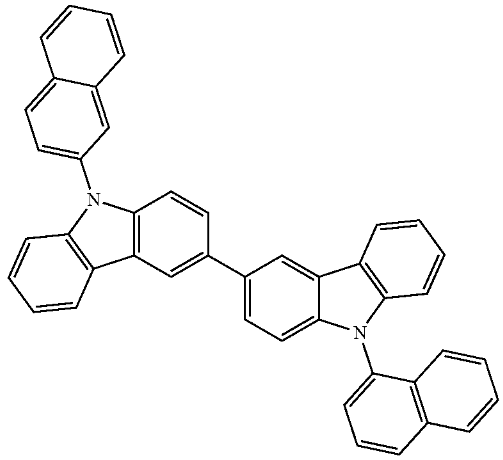
3-78
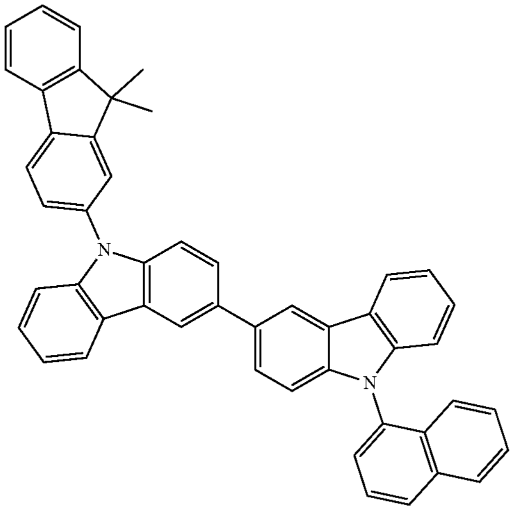
3-79
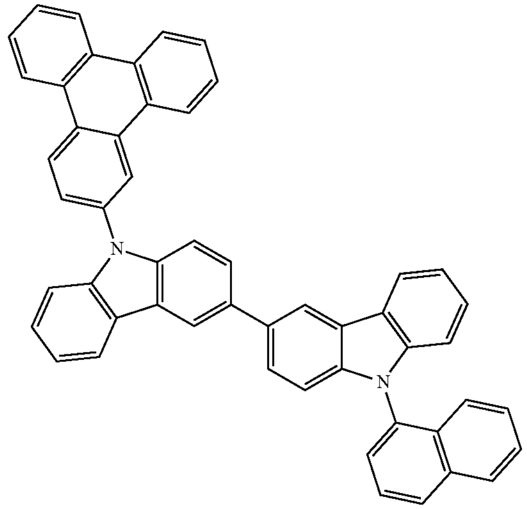
3-80
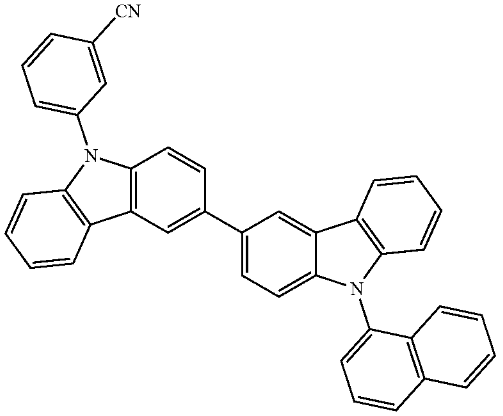

-continued
3-81
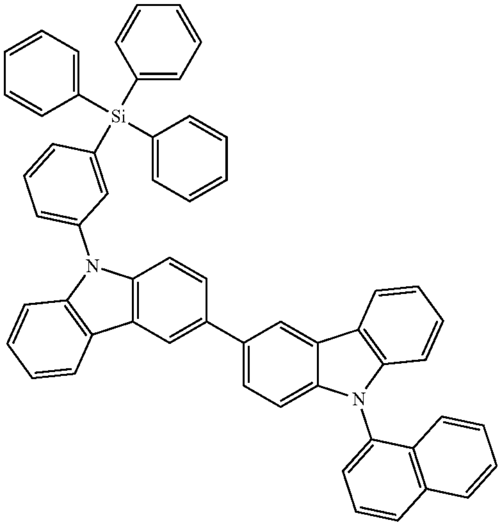
3-82
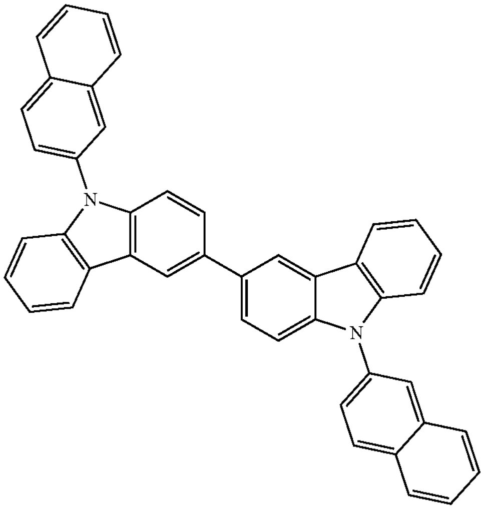
3-83
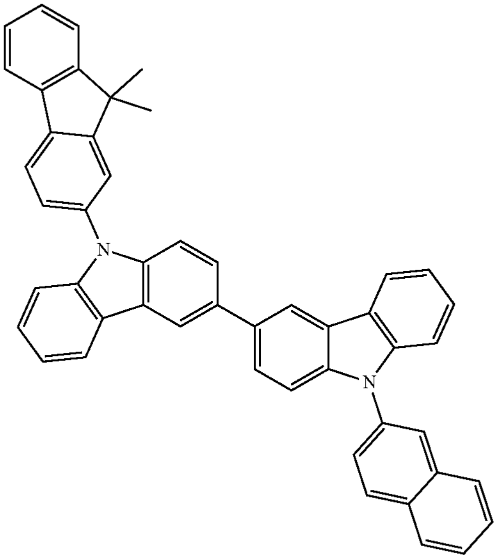
3-84
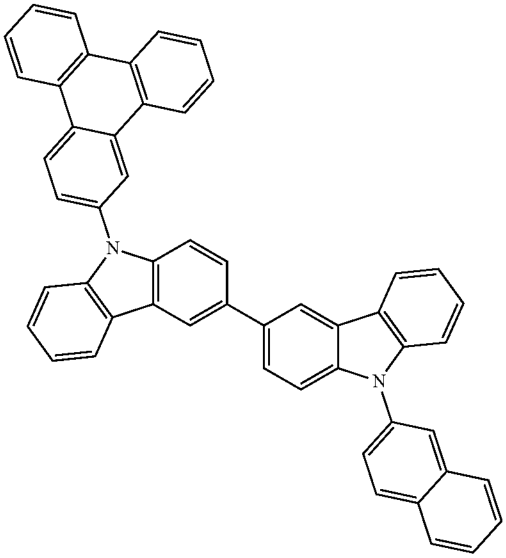
3-85
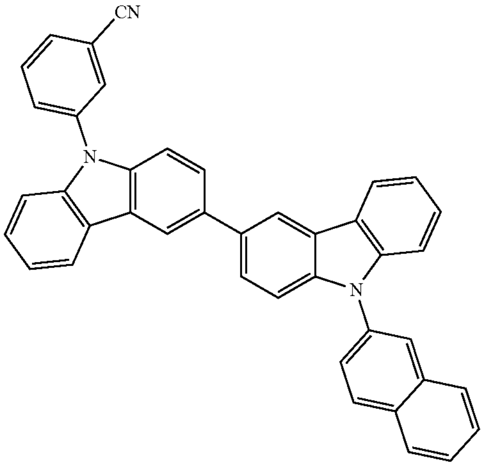
3-86
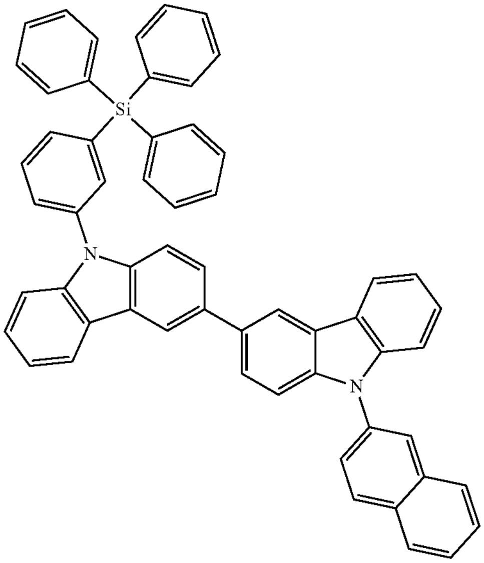

-continued
3-87
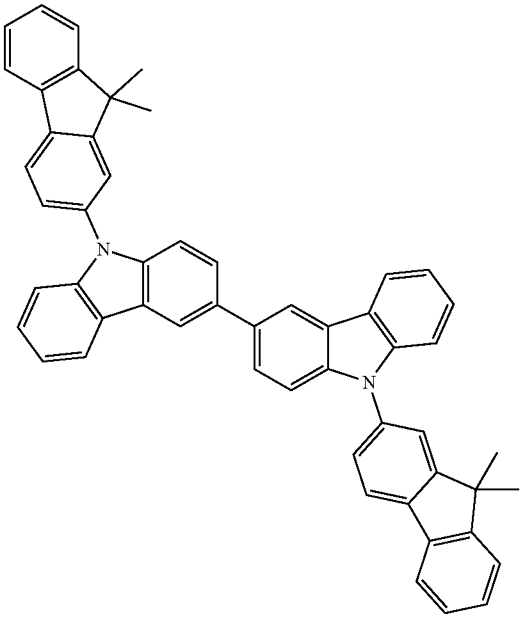
3-88
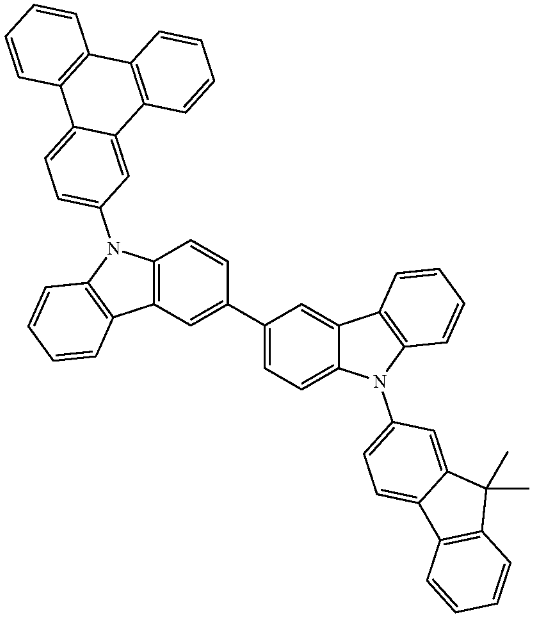
3-89
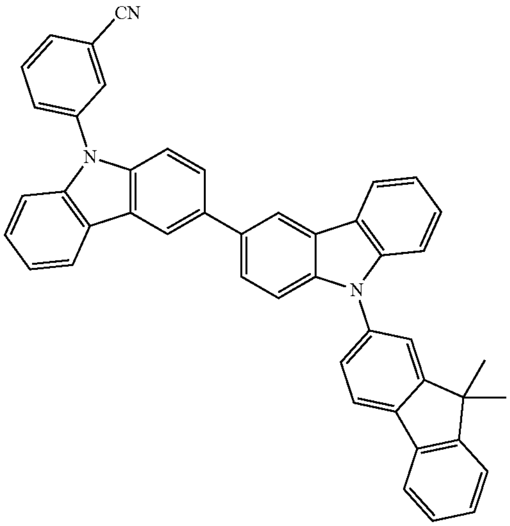
3-90
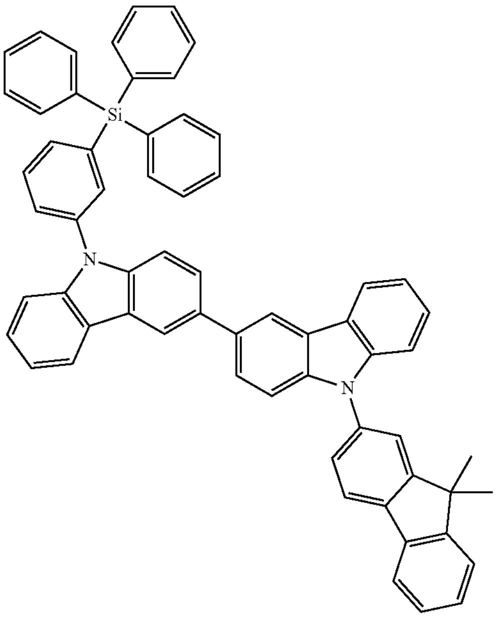

-continued
3-91
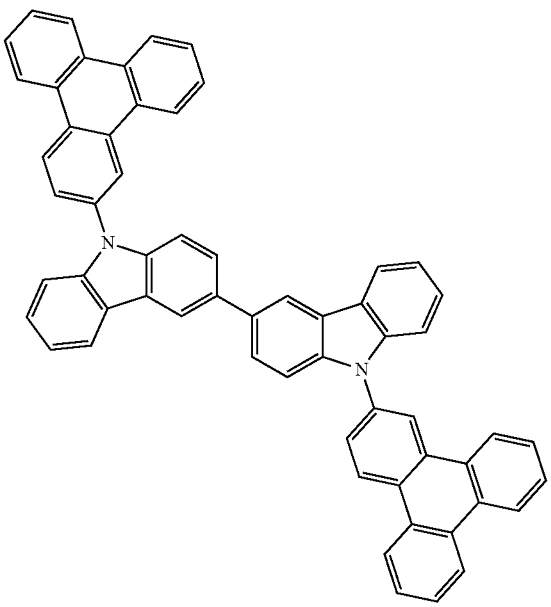
3-92
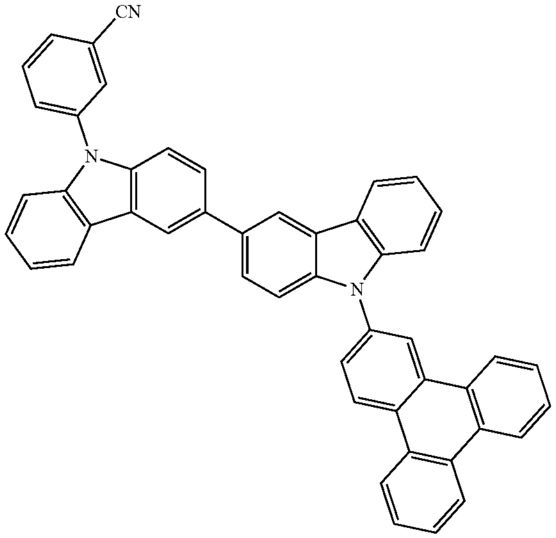
3-93
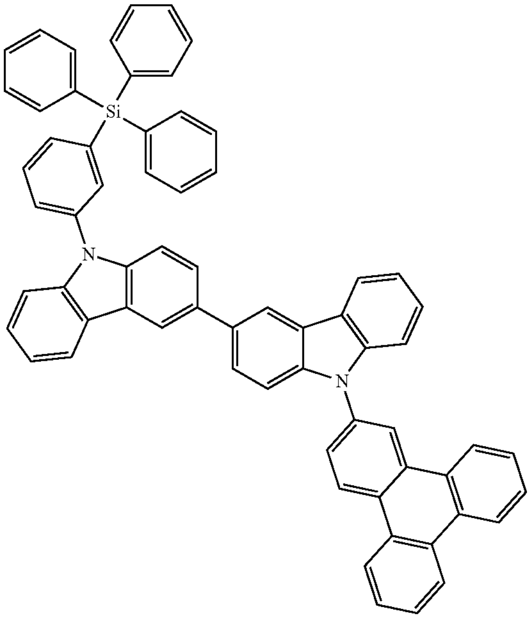
3-84
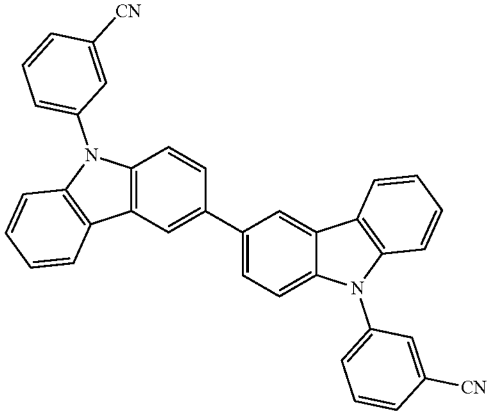

-continued
3-95
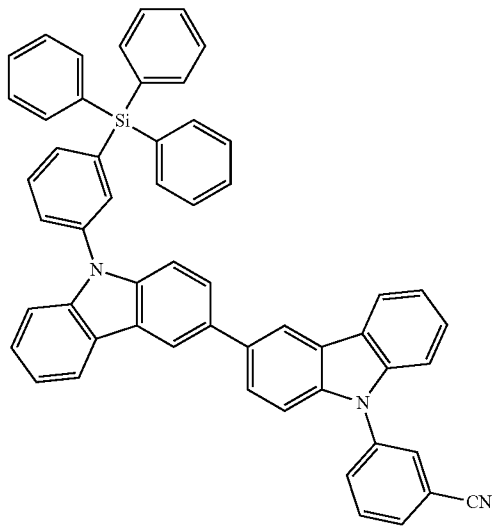
3-96
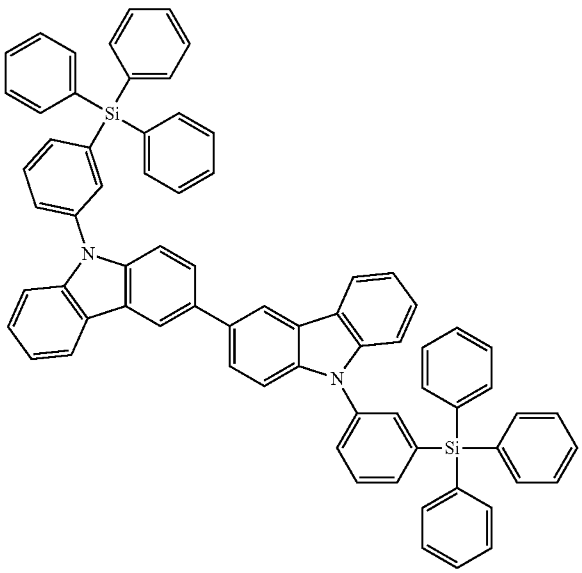
4-1
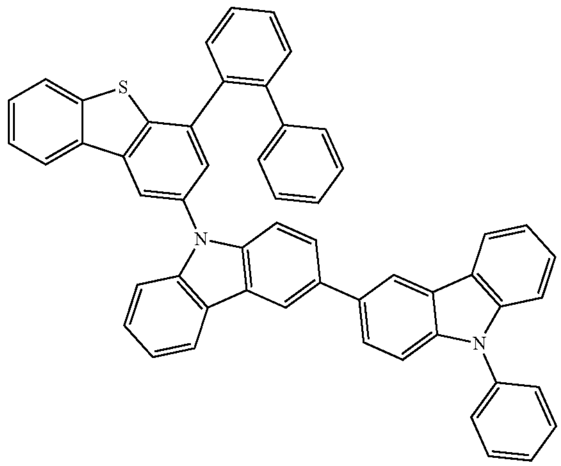
4-2
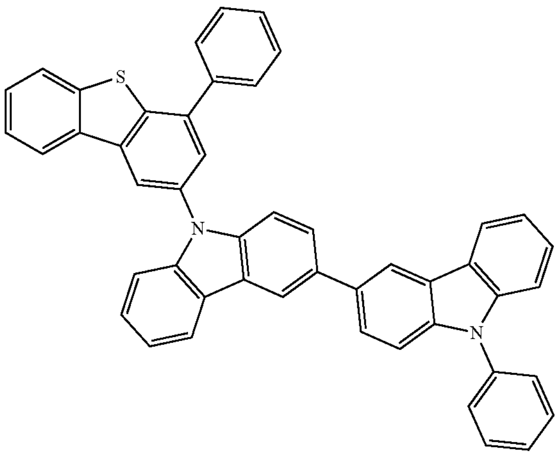
4-3
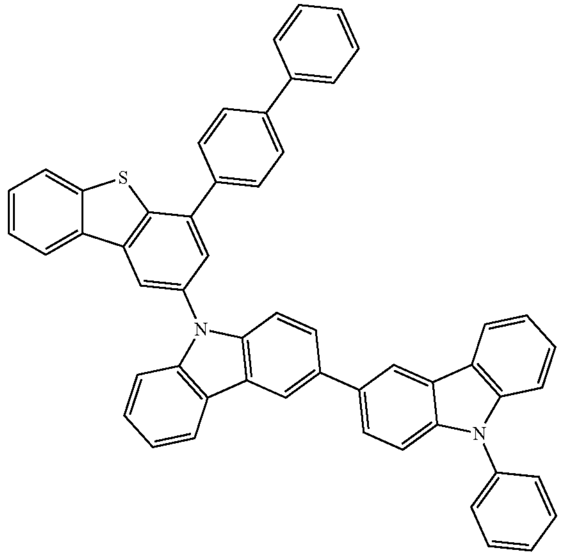
4-4
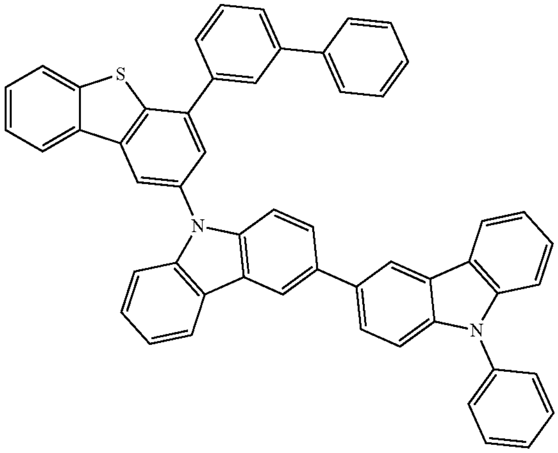

-continued
4-5
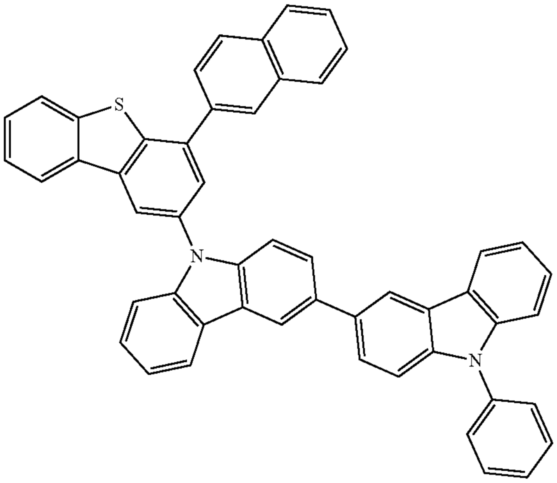
4-6
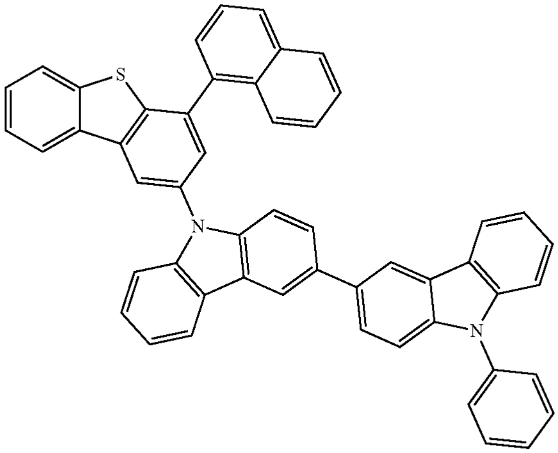
4-7
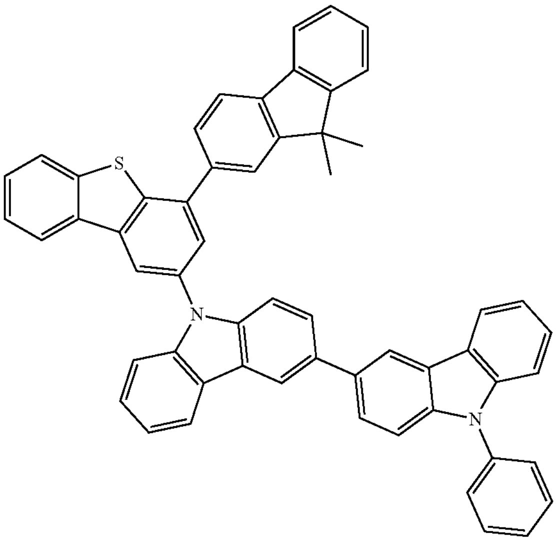
4-8
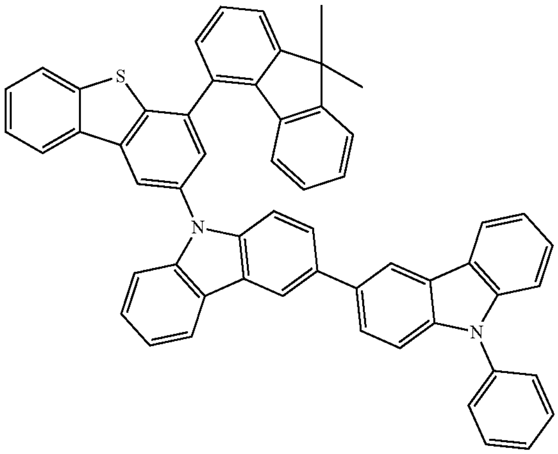
4-9
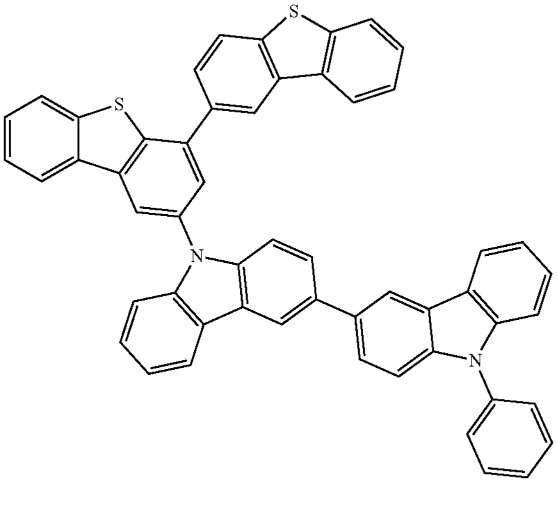
4-10
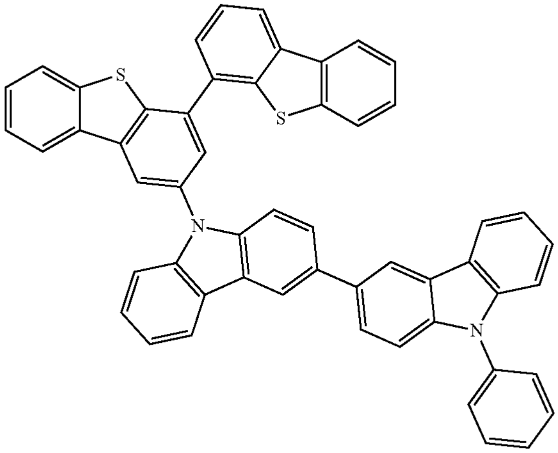

-continued
4-11
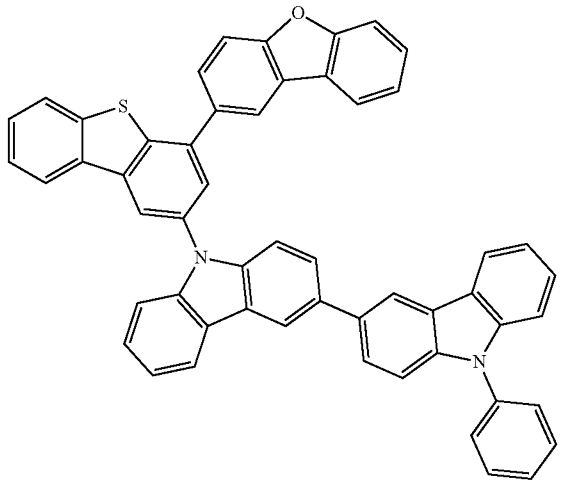
4-12
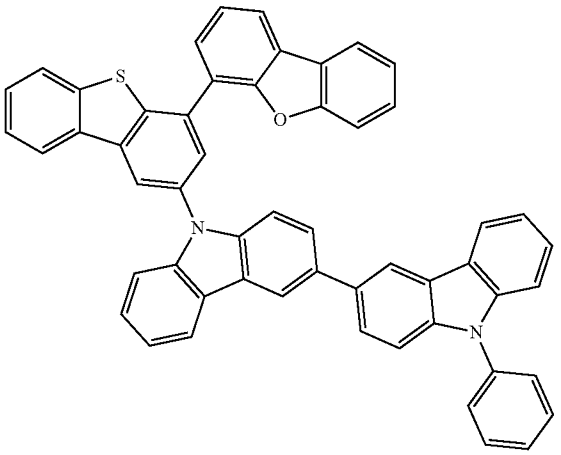
4-13
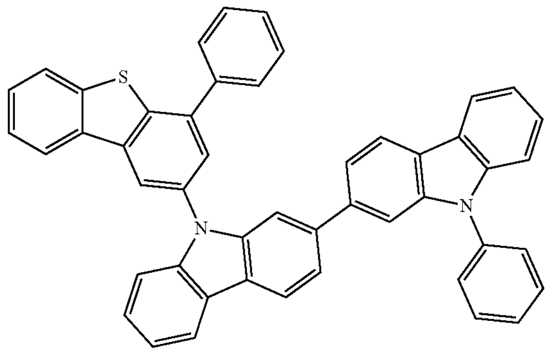
4-14
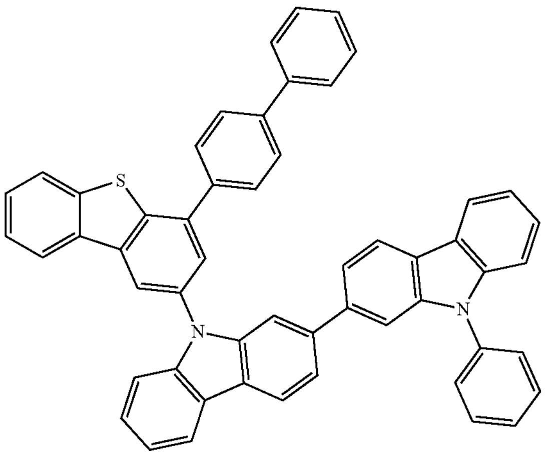
4-15
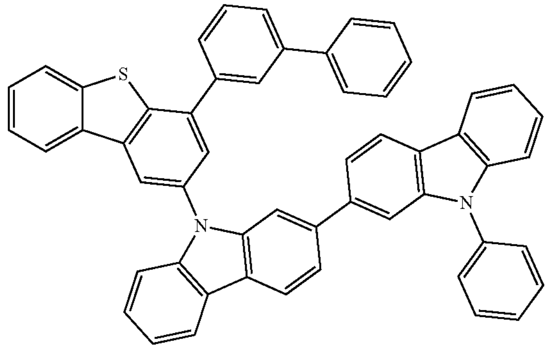
4-16
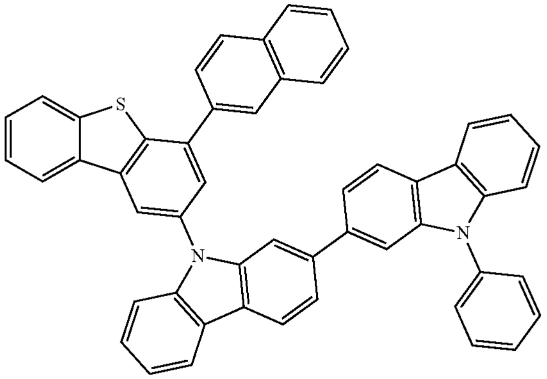

-continued
4-17
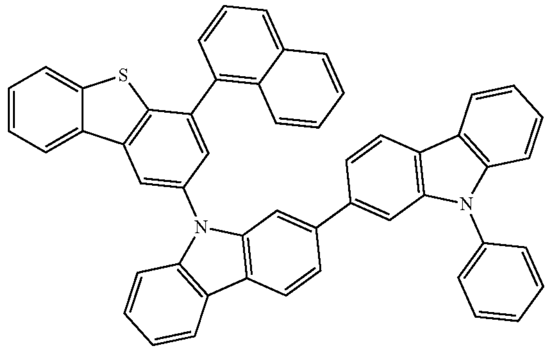
4-18
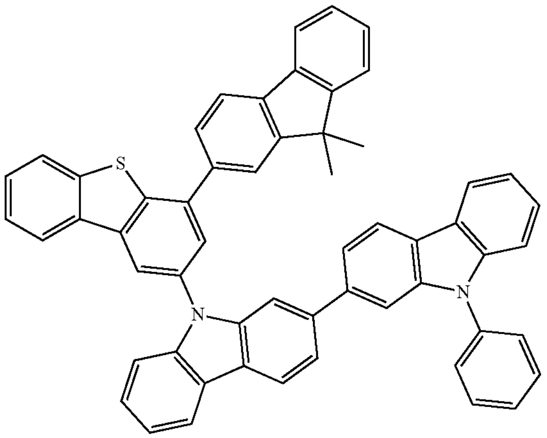
4-20
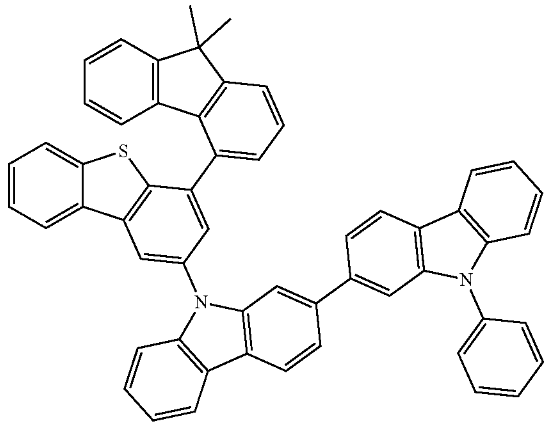
4-19
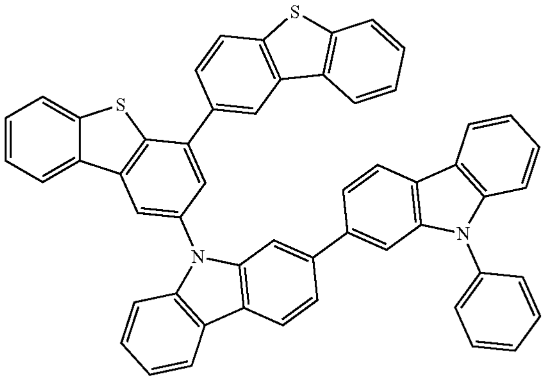
4-21
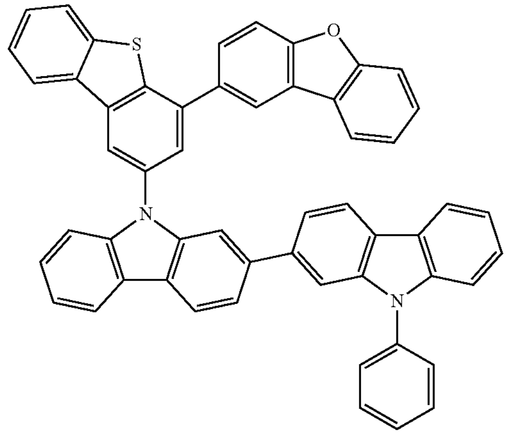
4-22
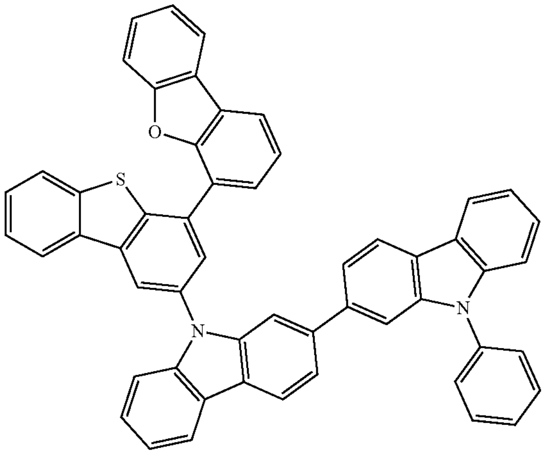

-continued
4-23
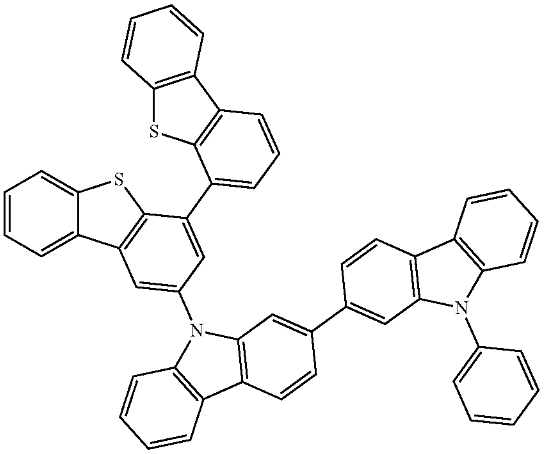
4-24
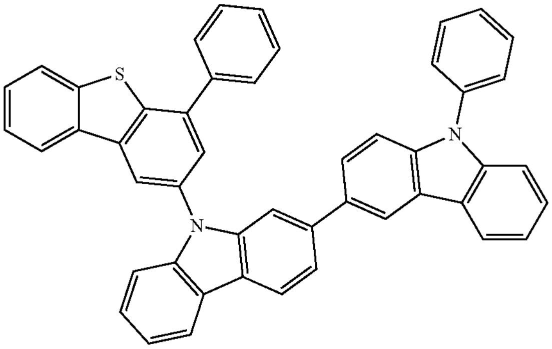
4-25
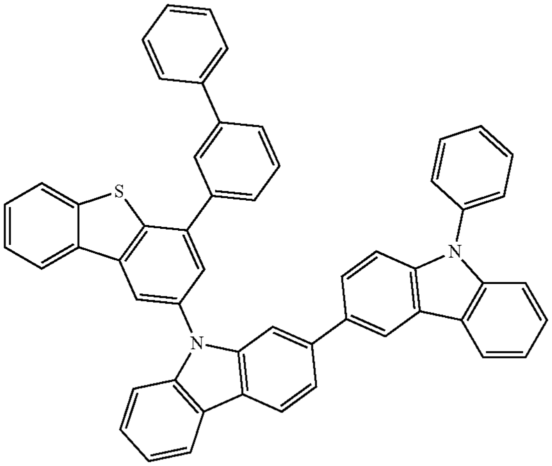
4-26
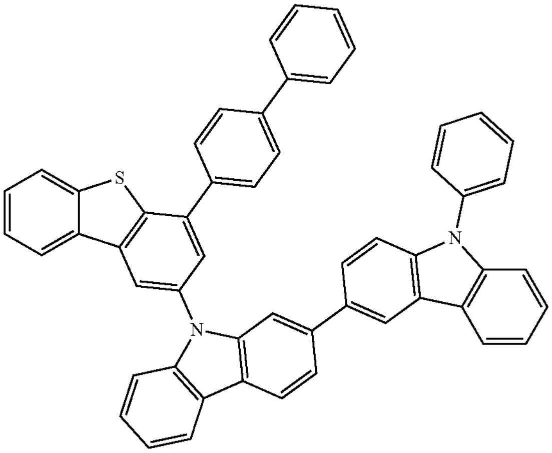
4-27
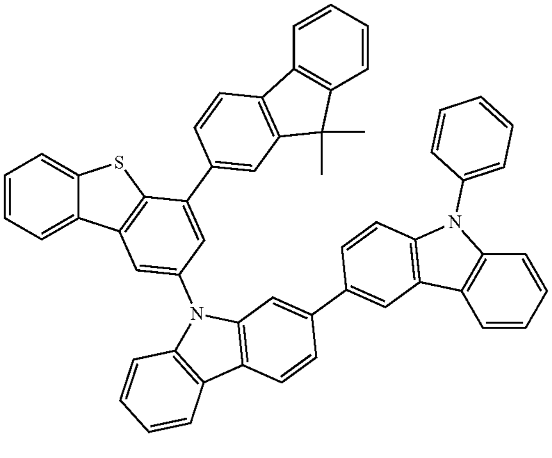
4-28
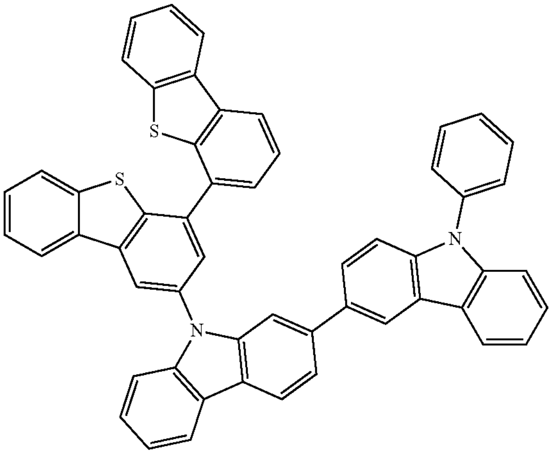

-continued
4-29
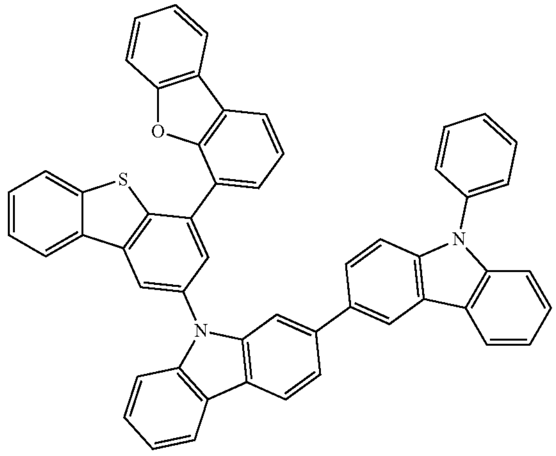
4-30
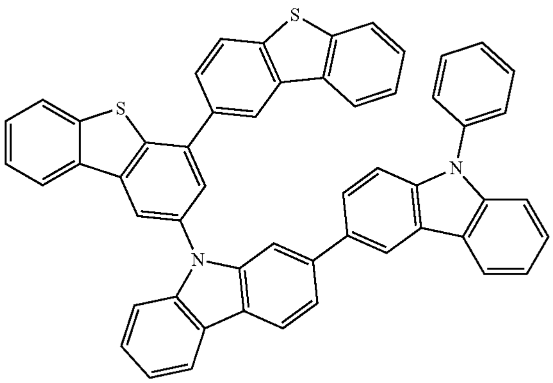
4-31
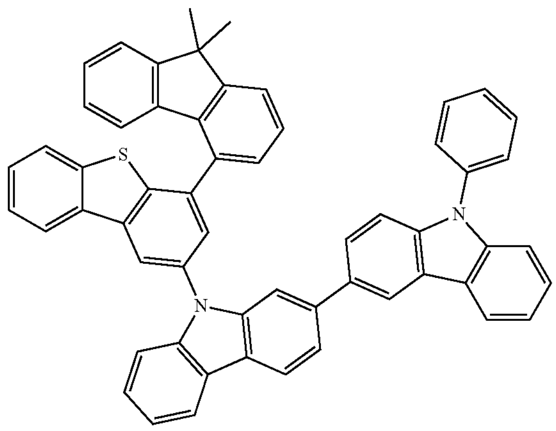
4-32
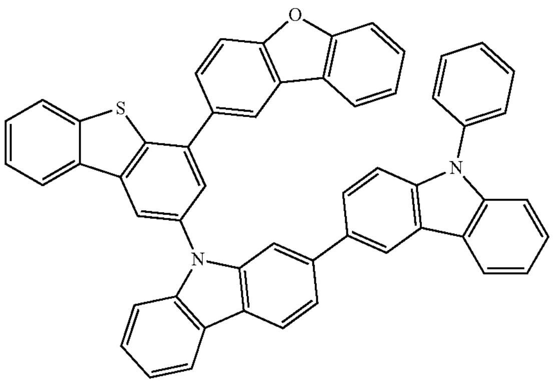
4-33
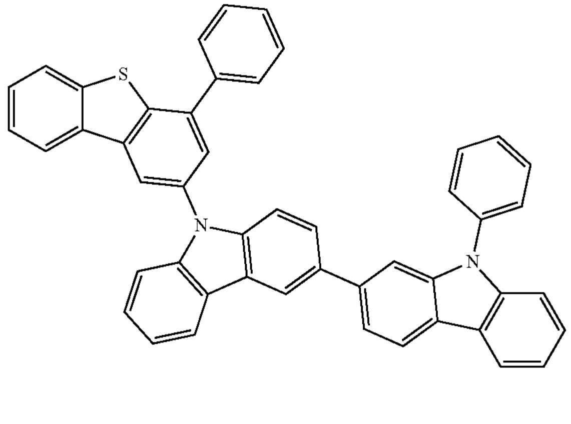
4-34
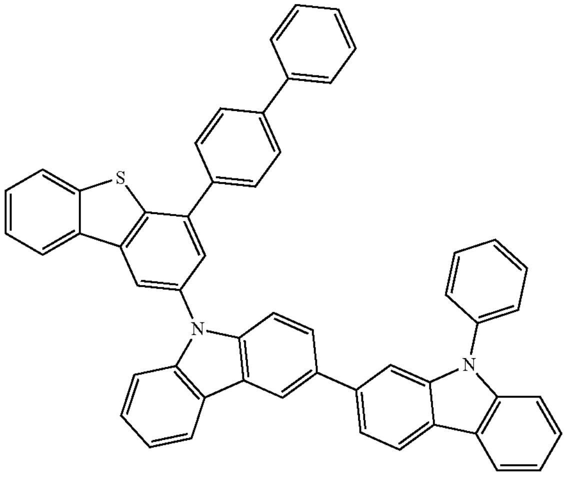

-continued
4-35
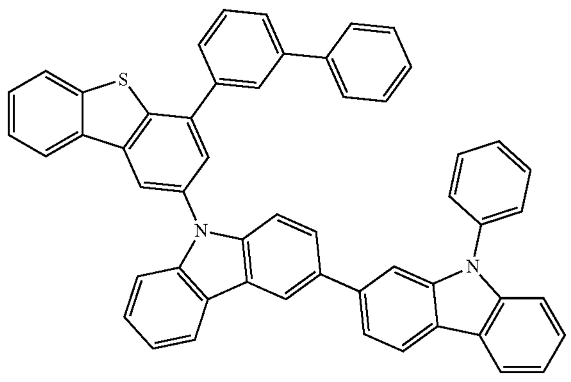
4-36
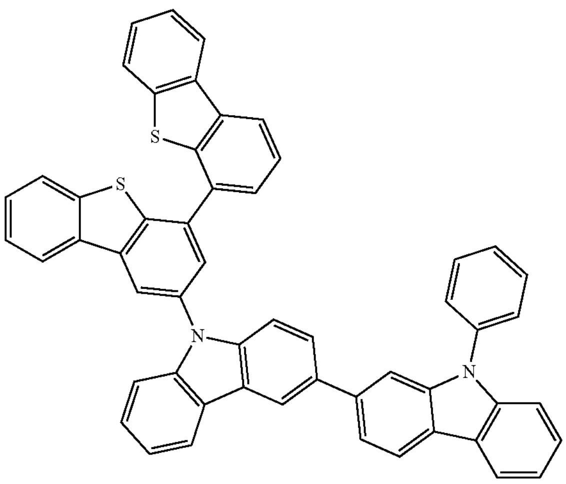
4-37
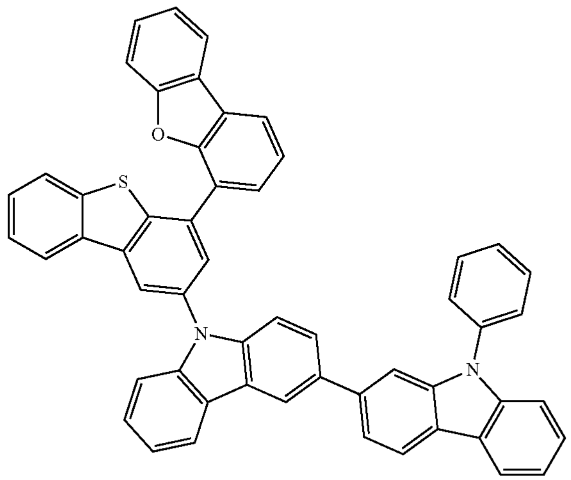
4-38
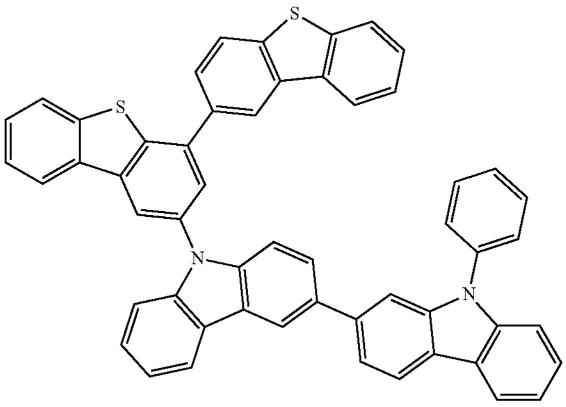
4-39
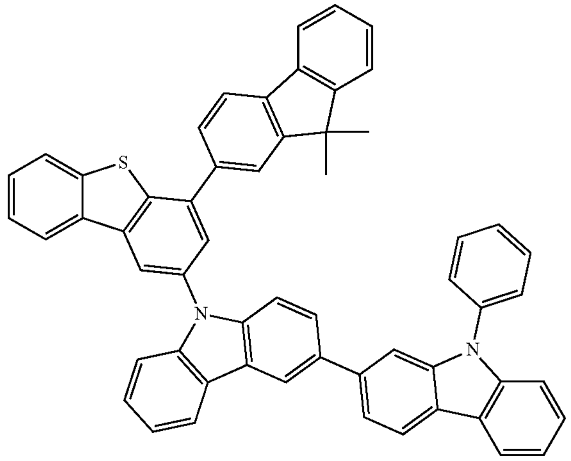
4-40
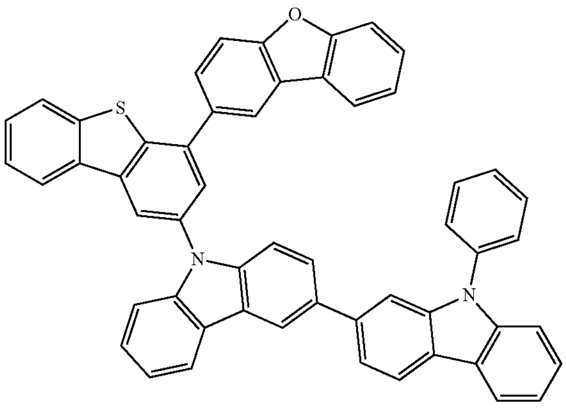

-continued
4-41
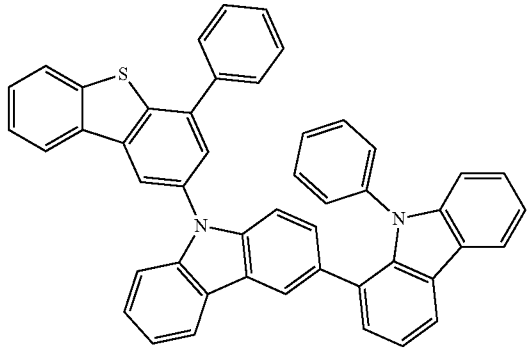
4-42
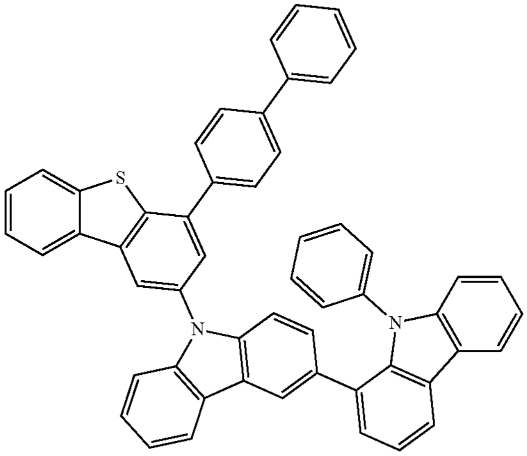
4-43
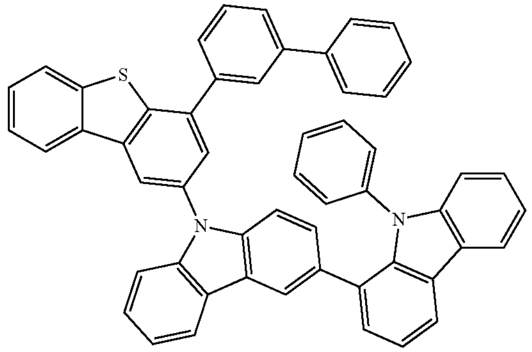
4-44
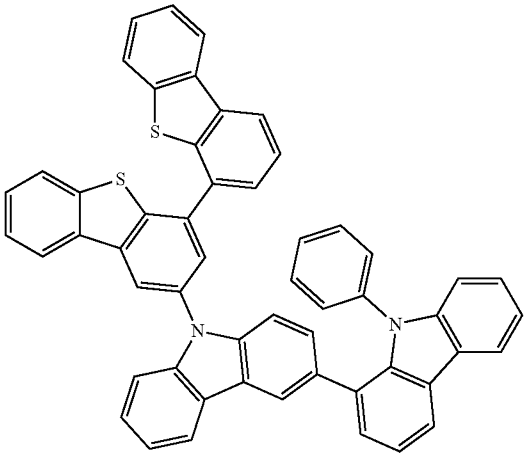
4-45
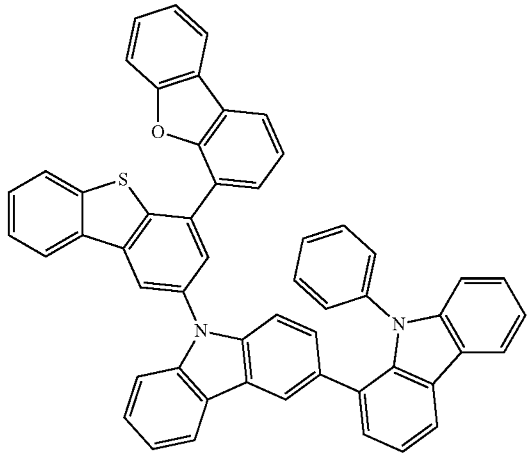
4-46
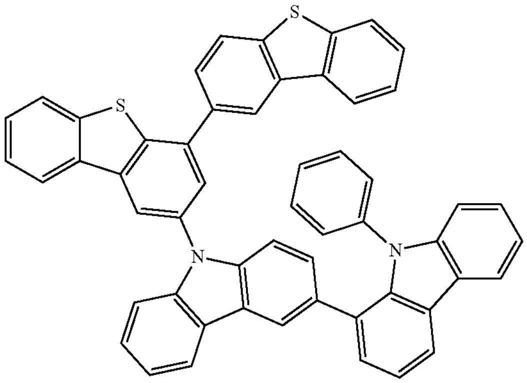

-continued
4-47
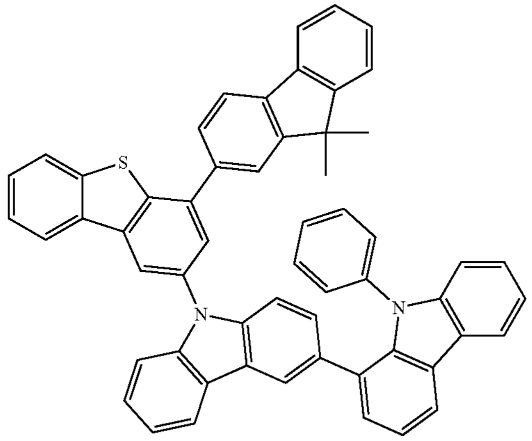
4-48
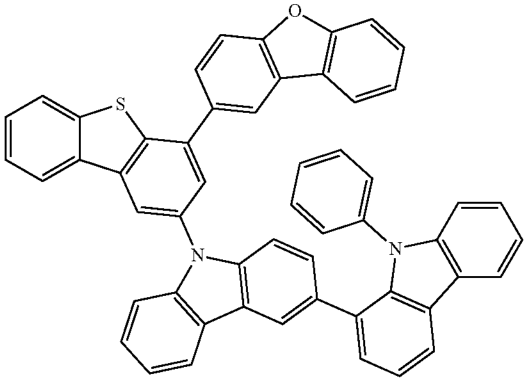
4-49
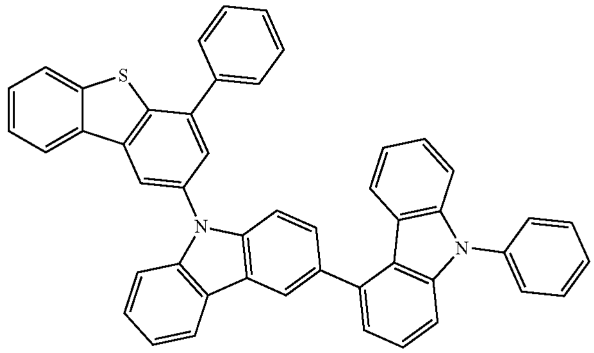
4-50
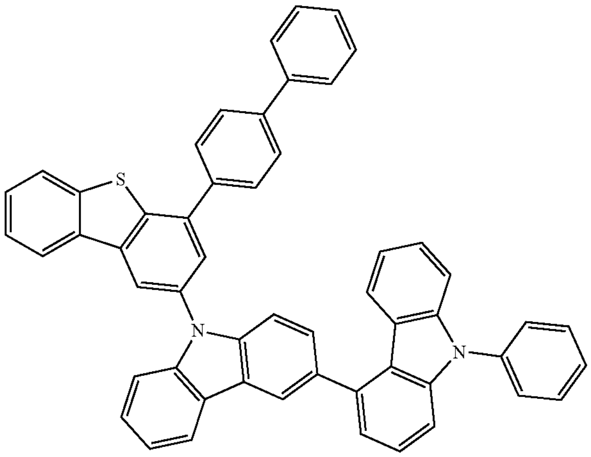
4-51
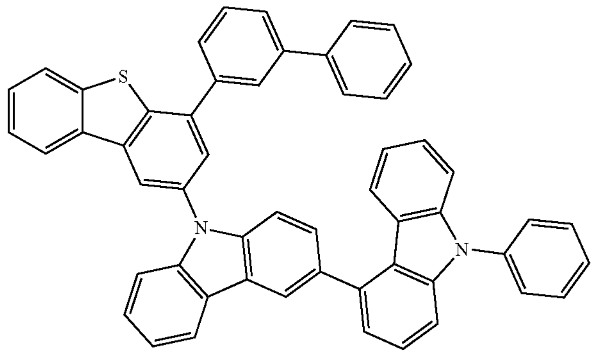
4-52
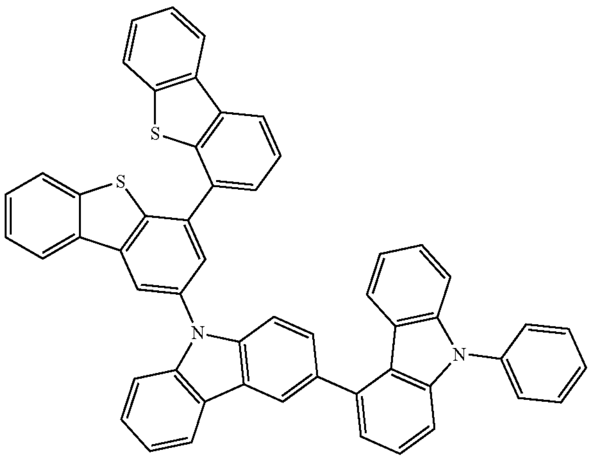

-continued
4-53
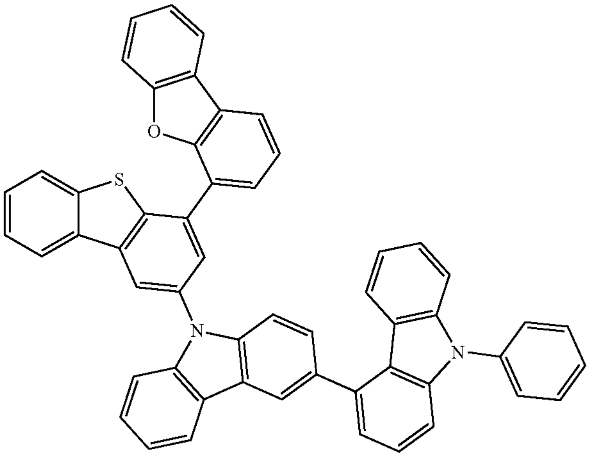
4-54
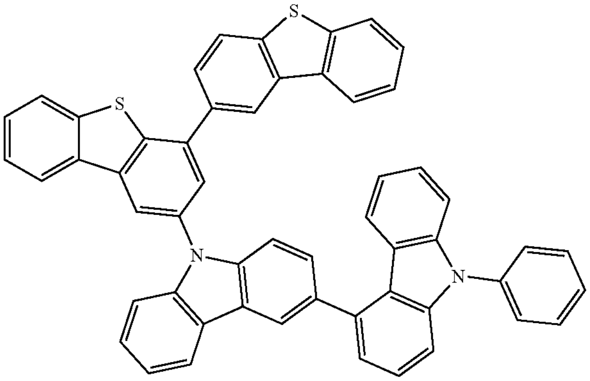
4-55
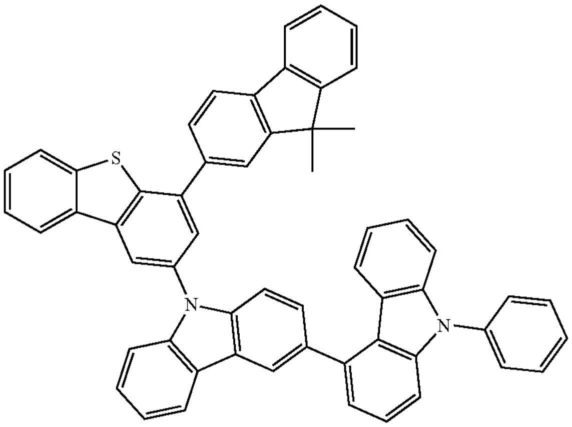
4-56
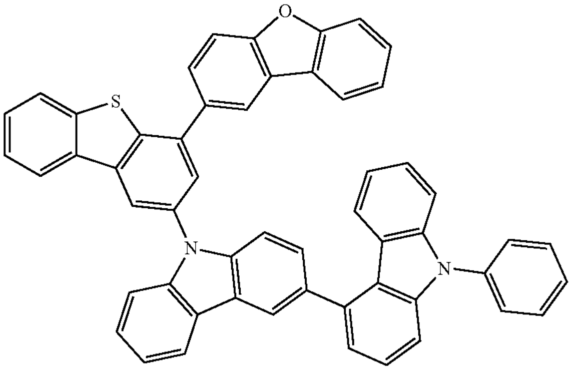
4-57
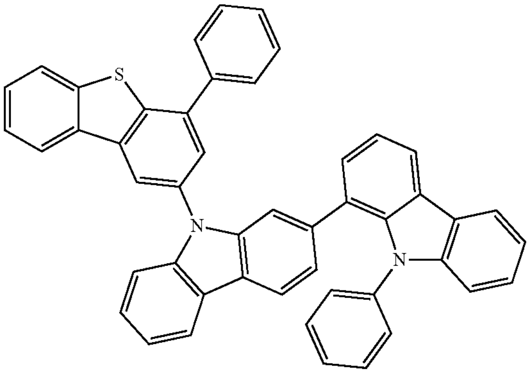
4-58
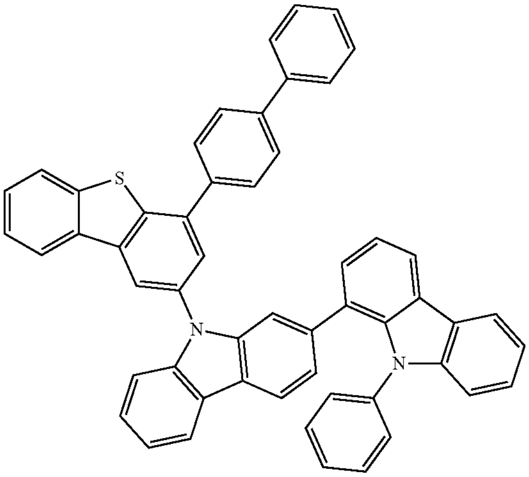

-continued
4-59
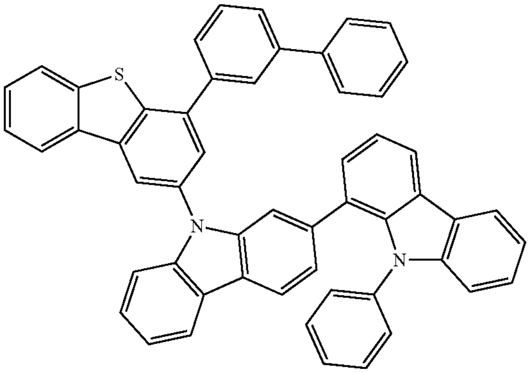
4-60
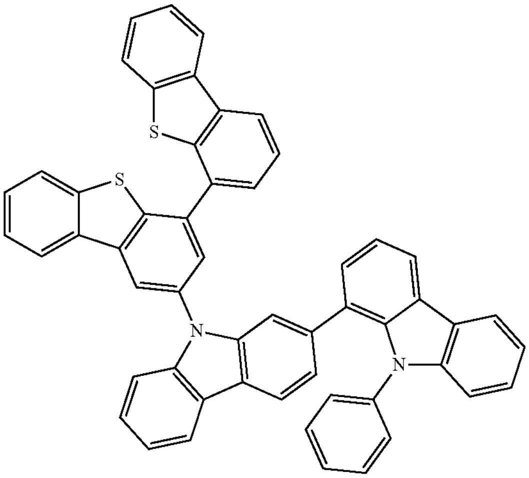
4-61
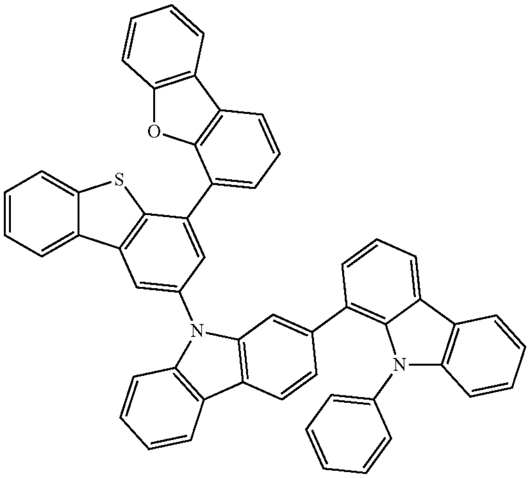
4-62
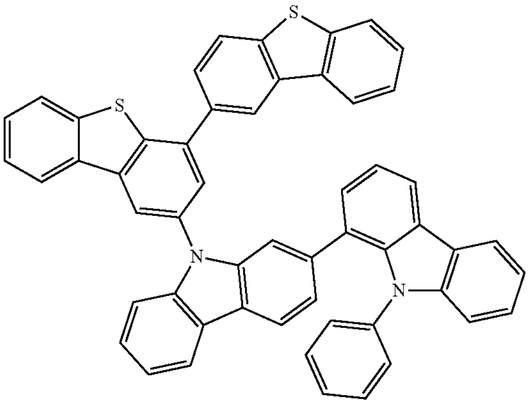
4-63
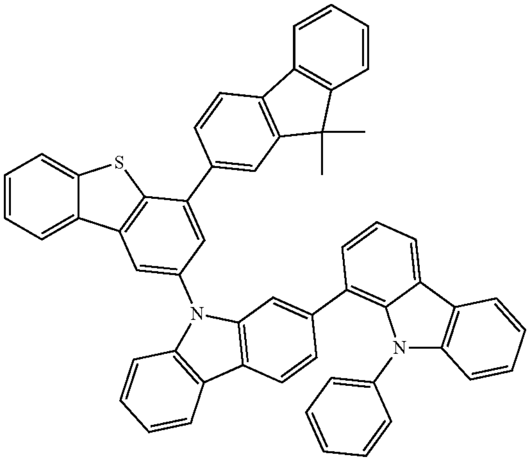
4-64
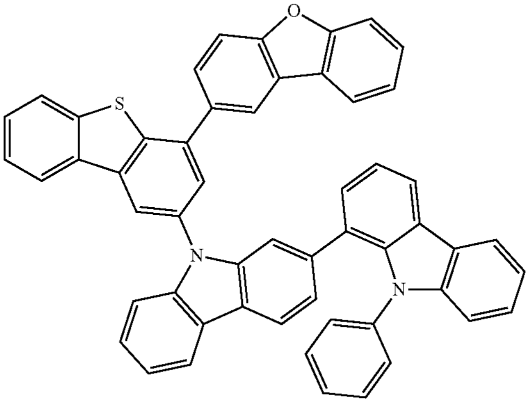

-continued
4-65
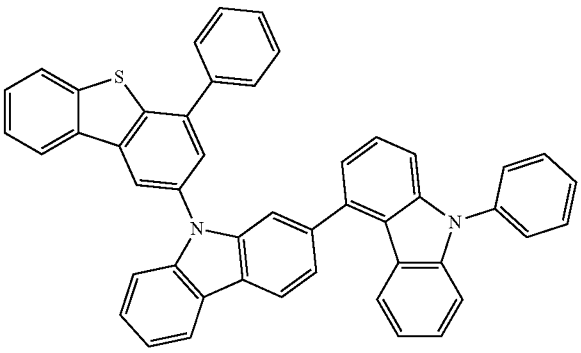
4-66
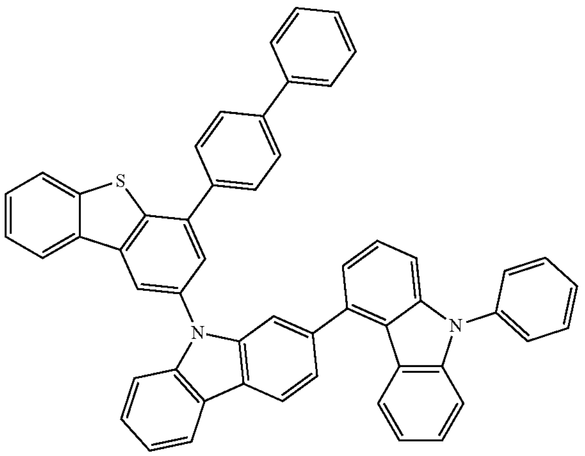
4-67
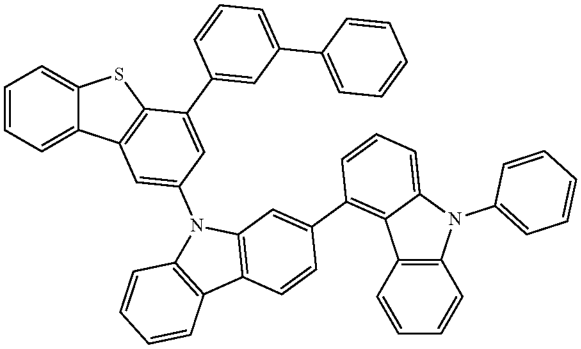
4-68
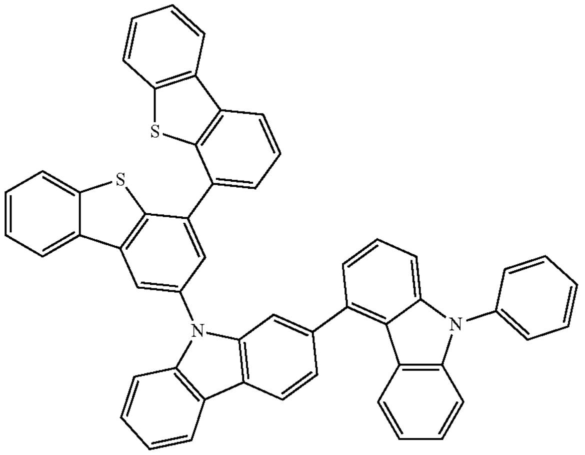
4-69
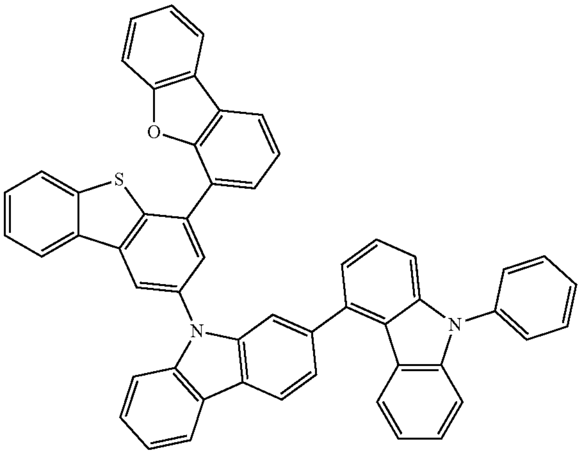
4-70
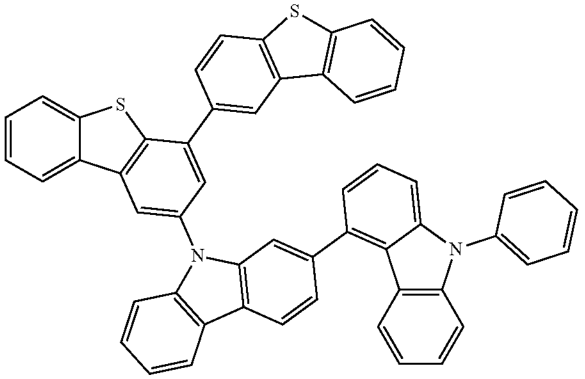

-continued
4-71
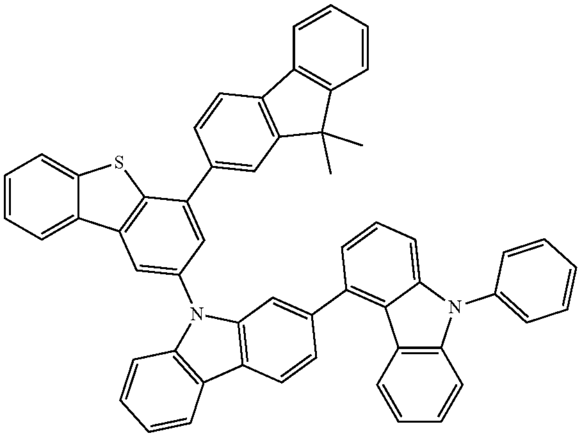
4-72
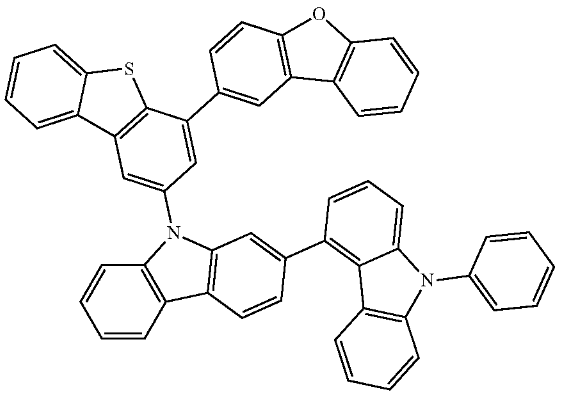
4-73
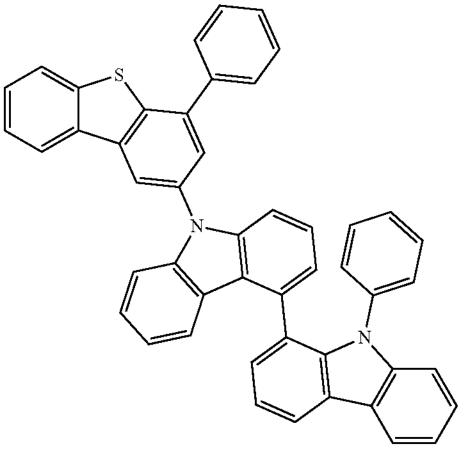
4-74
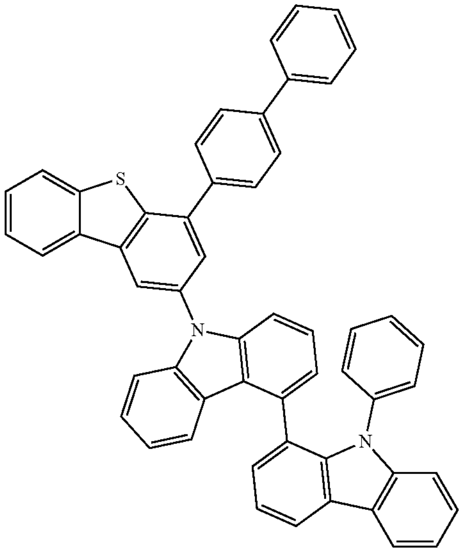
4-75
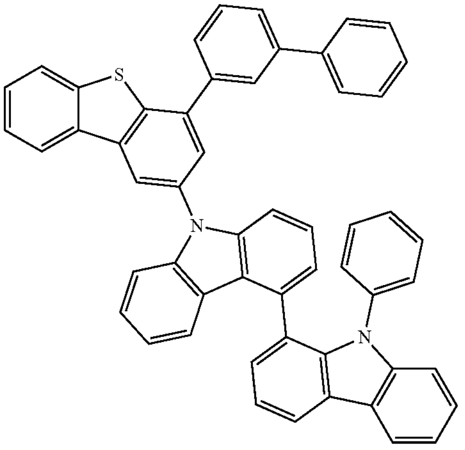
4-76
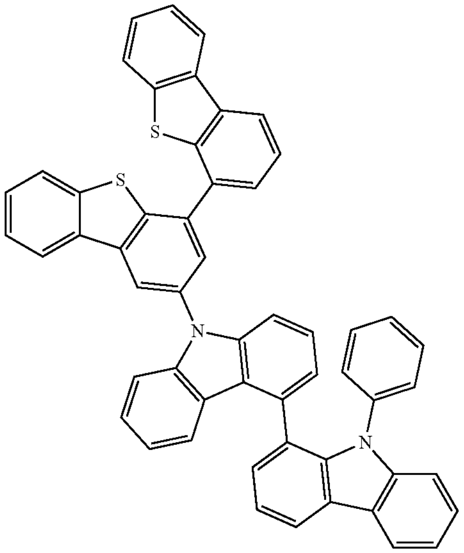

-continued
4-77
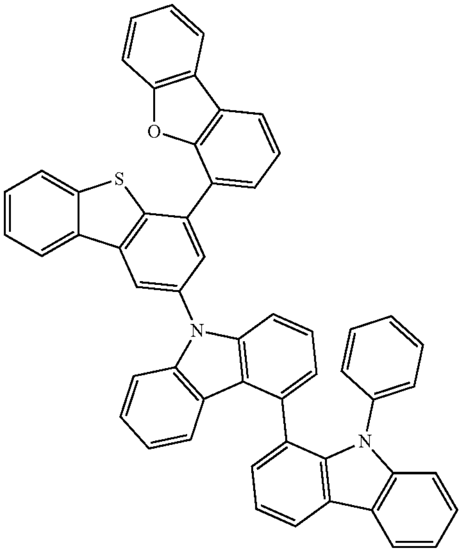
4-78
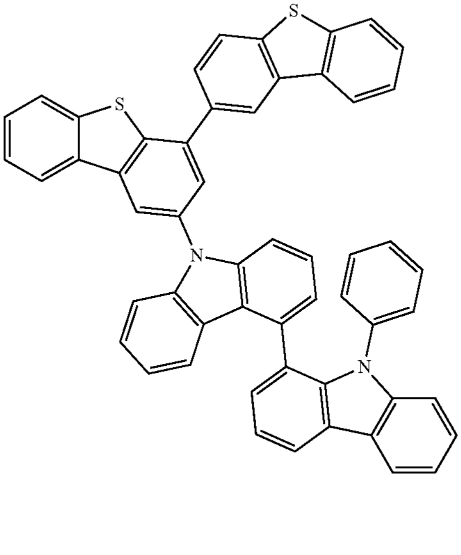
4-79
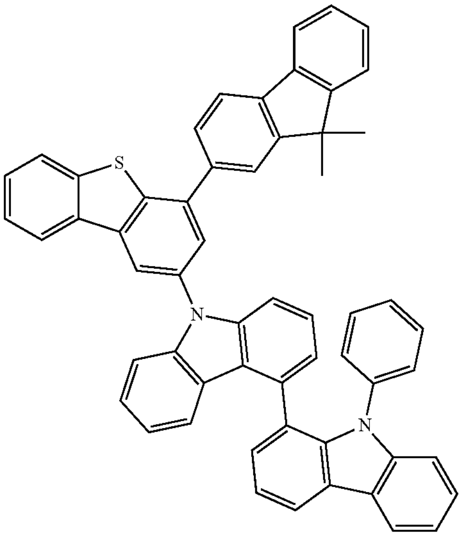
4-80
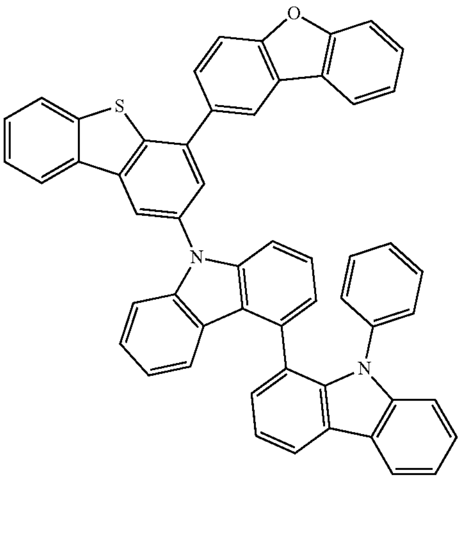

-continued
4-81
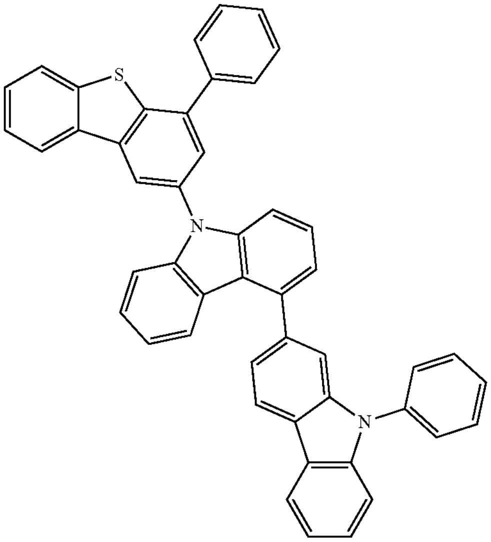
4-82
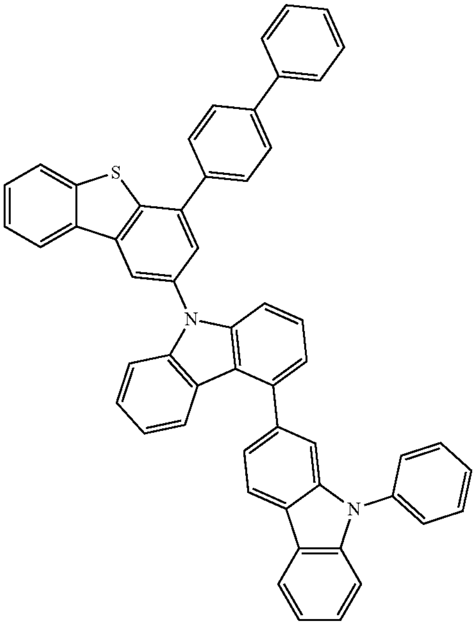
4-83
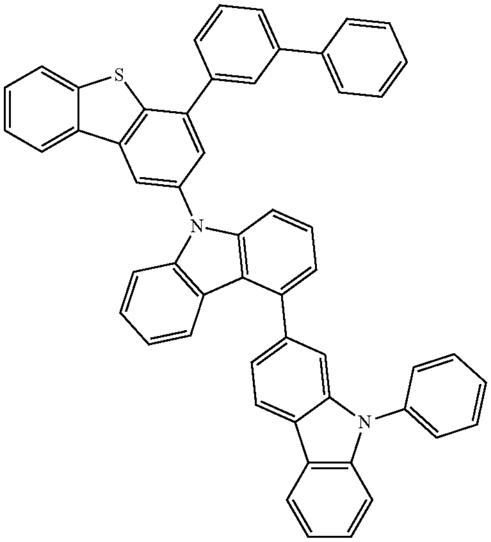
4-84
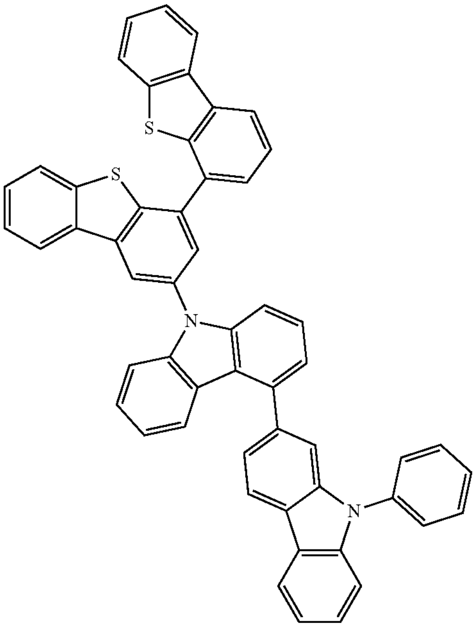

-continued
4-85
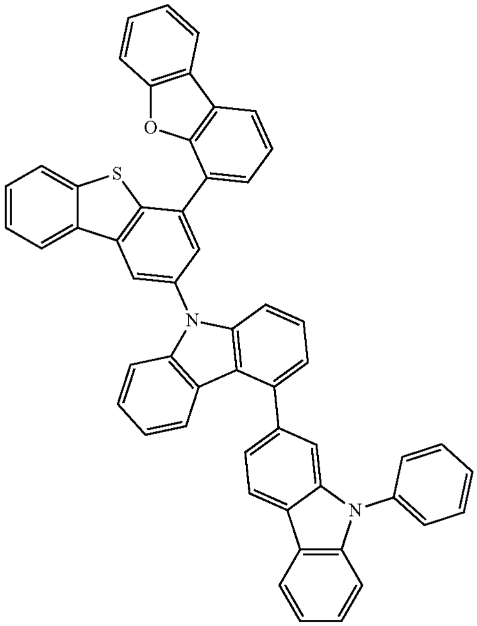
4-86
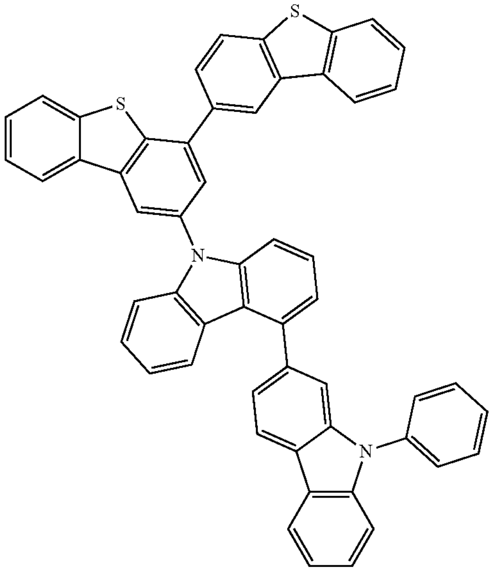
4-87
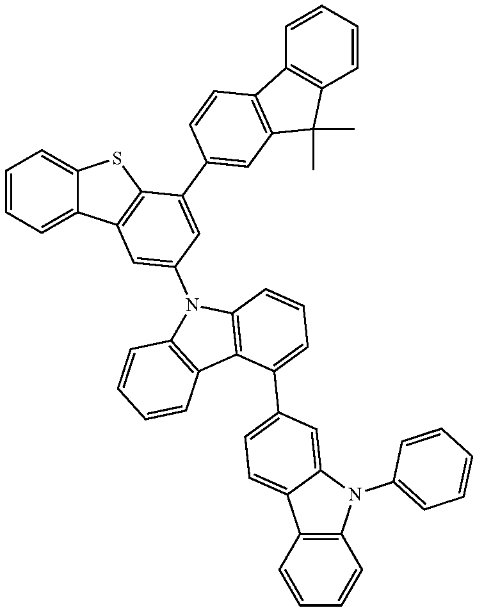
4-88
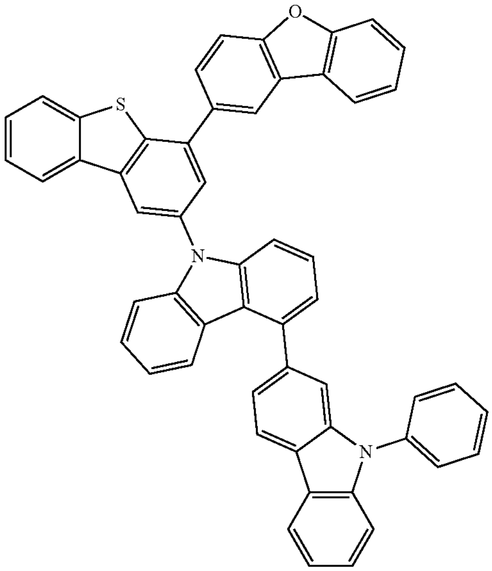

-continued
4-89
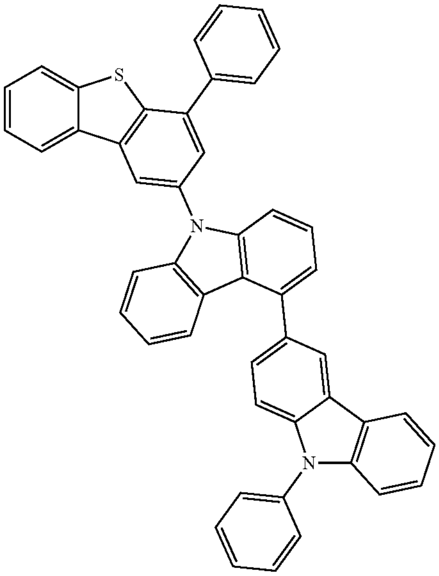
4-90
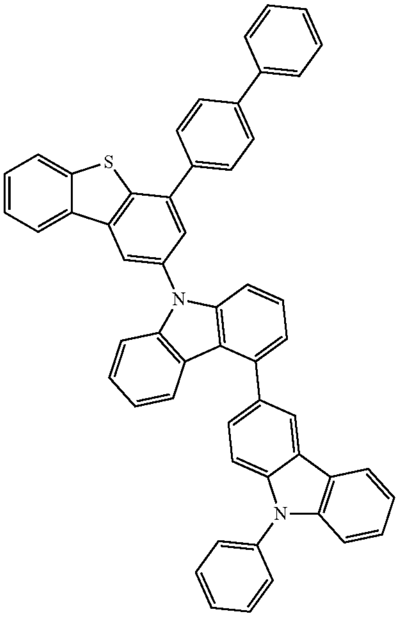
4-91
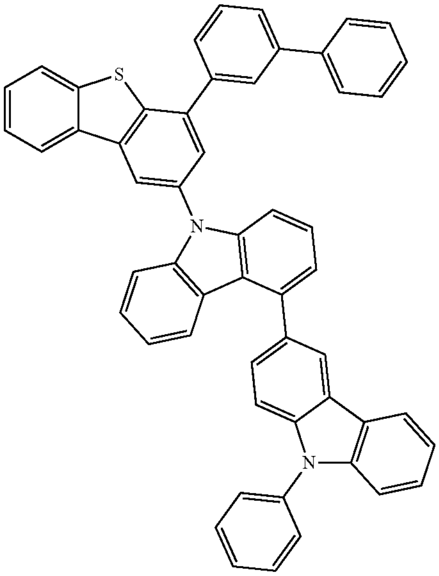
4-92
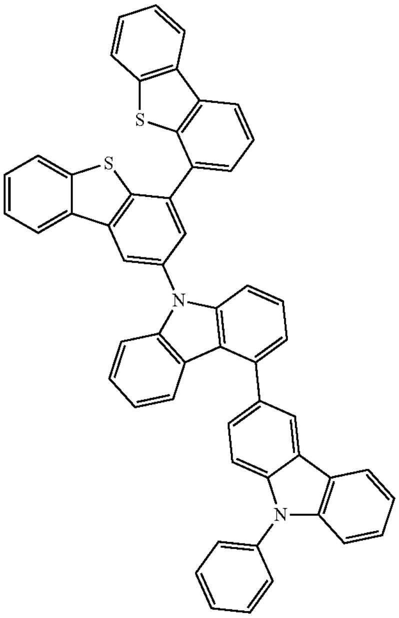

-continued
4-94
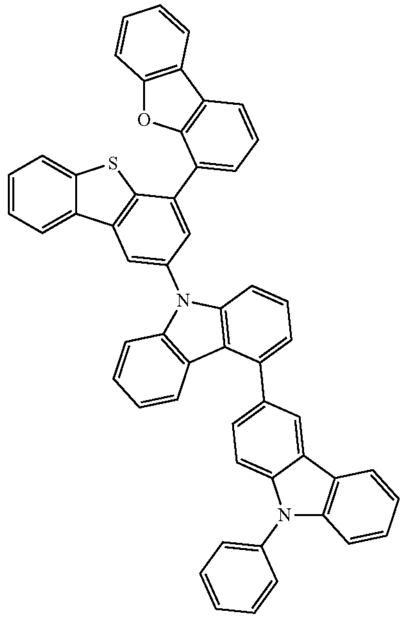
4-93
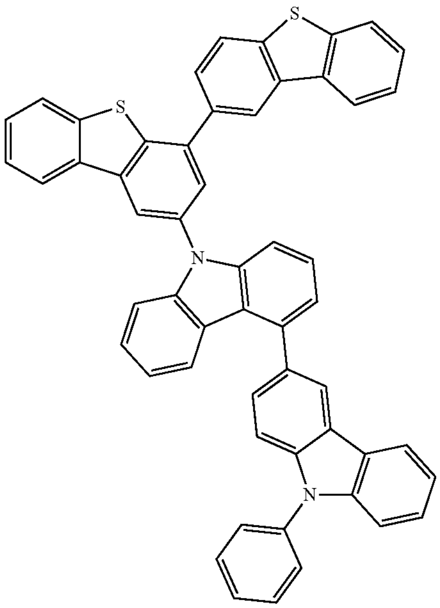
4-95
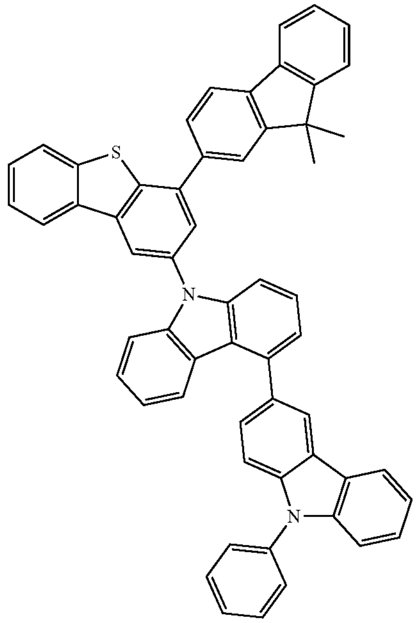
4-96
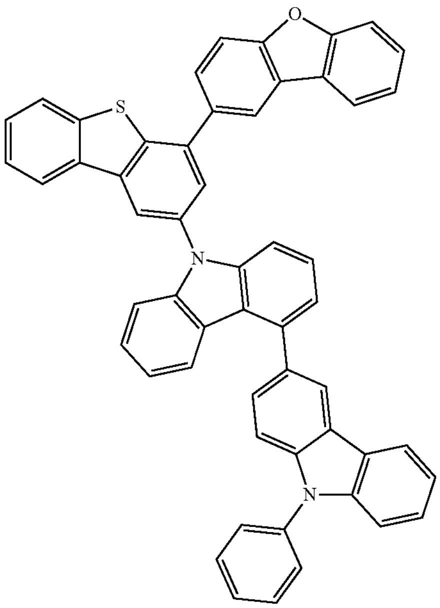

-continued
4-97
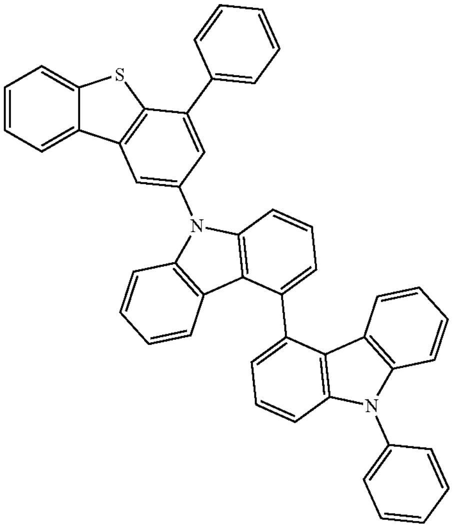
4-98
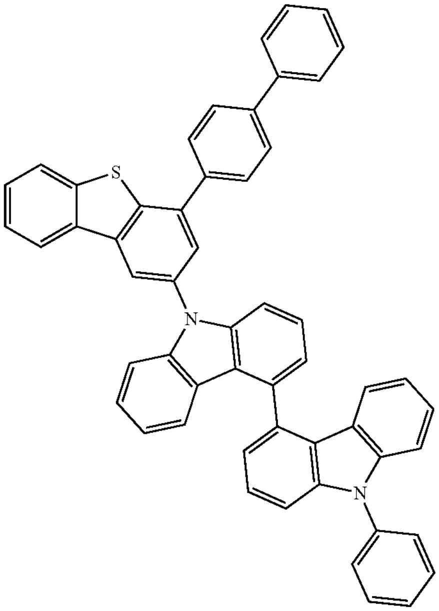
4-99
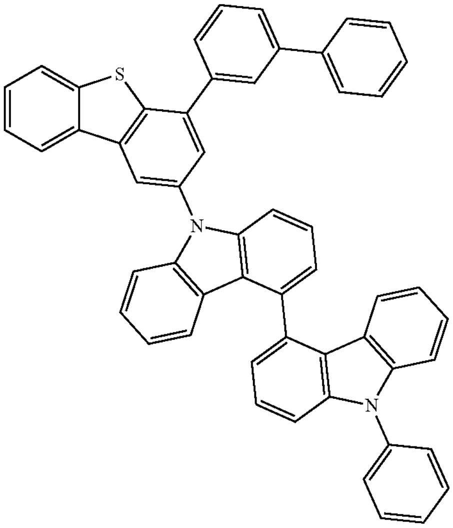
4-100
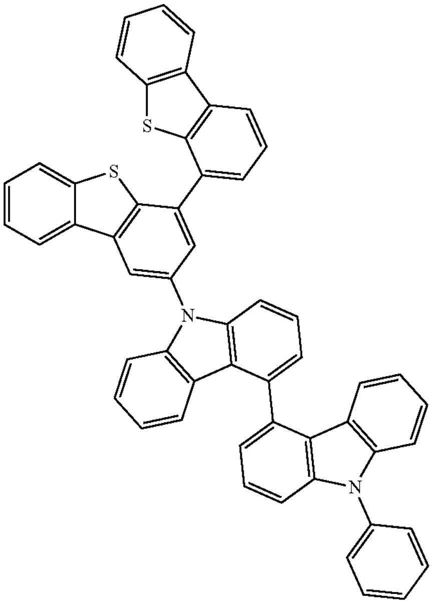
4-101
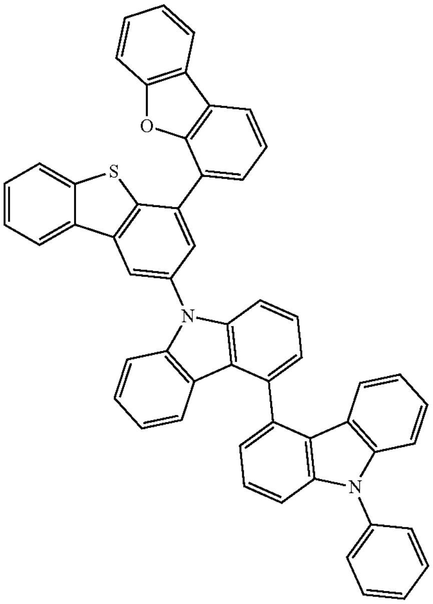

-continued
4-102
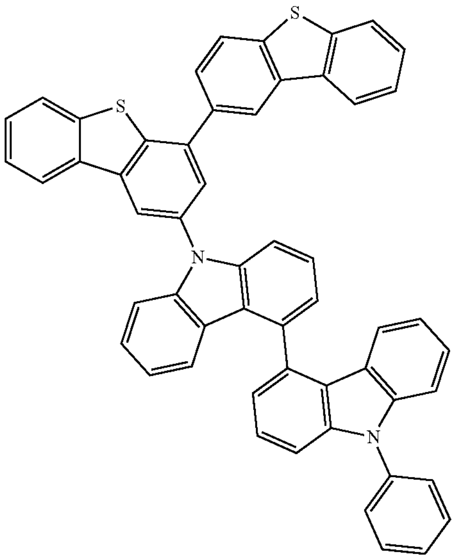
4-103
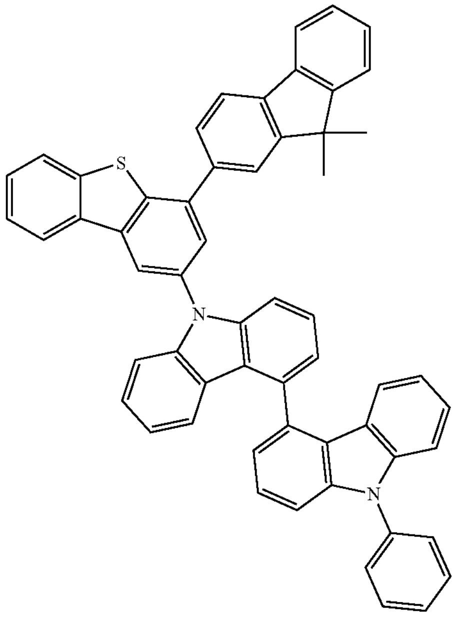
-continued
4-104
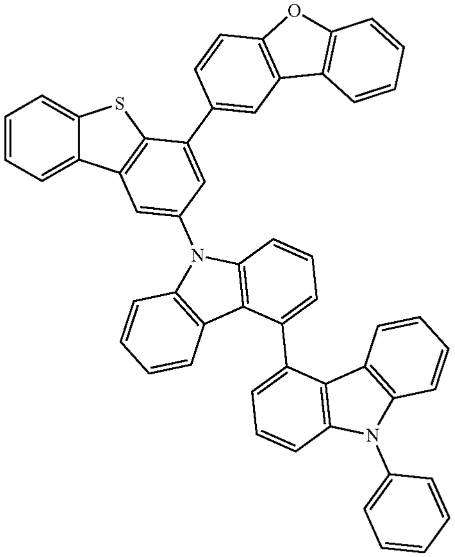
4-105
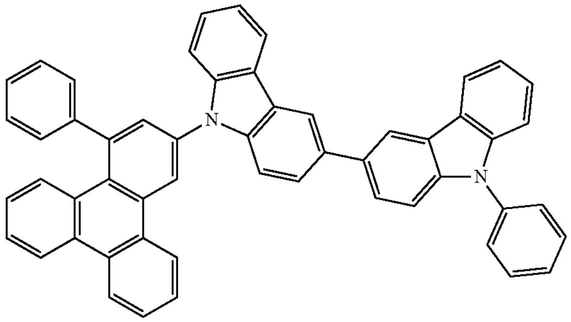
4-106
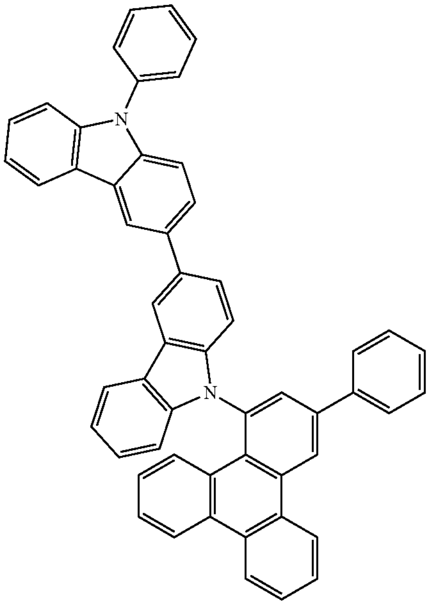
In addition, another embodiment of the present application provides a composition for an organic material layer of an organic light emitting device comprising the heterocyclic compound represented by Chemical Formula 1 and the heterocyclic compound represented by Chemical Formula 2.

Specific details on the heterocyclic compound represented by Chemical Formula 1 and the heterocyclic compound represented by Chemical Formula 2 are the same as the descriptions provided above.

In the composition, the heterocyclic compound represented by Chemical Formula 1:the heterocyclic compound represented by Chemical Formula 2 may have a weight ratio of 1:10 to 10:1, 1:8 to 8:1, 1:5 to 5:1, or 1:2 to 2:1, however, the weight ratio is not limited thereto.

The composition may be used when forming an organic material of an organic light emitting device, and particularly, may be more preferably used when forming a host of a light emitting layer.

In one embodiment of the present application, the organic material layer comprises the heterocyclic compound represented by Chemical Formula 1 and the heterocyclic compound represented by Chemical Formula 2, and a phosphorescent dopant may be used therewith.

In one embodiment of the present application, the organic material layer comprises the heterocyclic compound represented by Chemical Formula 1 and the heterocyclic compound represented by Chemical Formula 2, and an iridium-based dopant may be used therewith.

As a material of the phosphorescent dopant, those known in the art may be used.

For example, phosphorescent dopant materials represented by LL'MX', LL'L"M, LMX'X", L2MX' and L3M may be used, however, the scope of the present disclosure is not limited to these examples.

Herein, L, L', L", X' and X" are bidentate ligands different from each other, and M is a metal forming an octahedral complex.

M may include iridium, platinum, osmium and the like.

L is an anionic bidentate ligand coordinated to M as the iridium-based dopant by sp2 carbon and heteroatom, and X may function to trap electrons or holes. Nonlimiting examples of L may include 2-(1-naphthyl)benzoxazole, (2-phenylbenzoxazole), (2-phenylbenzothiazole), (2-phenylbenzothiazole), (7,8-benzoquinoline), (thiophene group pyrizine), phenylpyridine, benzothiophene group pyrizine, 3-methoxy-2-phenylpyridine, thiophene group pyrizine, tolylpyridine and the like. Nonlimiting examples of X' and X" may include acetylacetonate (acac), hexafluoroacetylacetonate, salicylidene, picolinate, 8-hydroxyquinolinate and the like.

More specific examples are described below, however, the phosphorescent dopant is not limited to these examples.

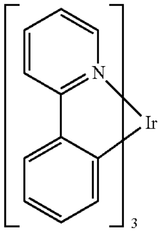
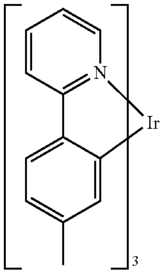
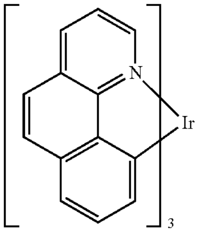

-continued

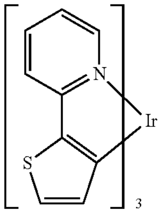
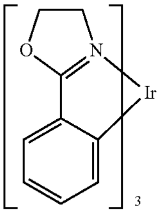
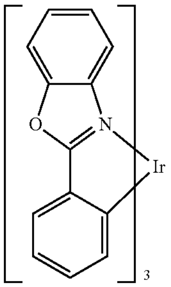
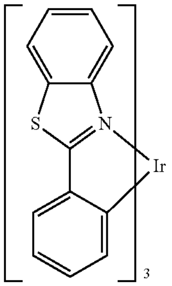
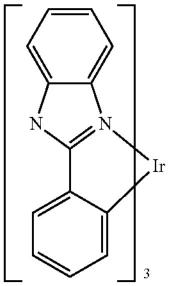
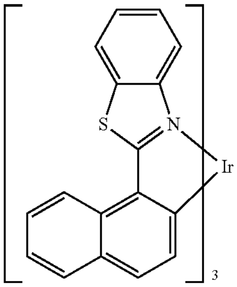
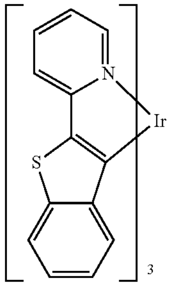
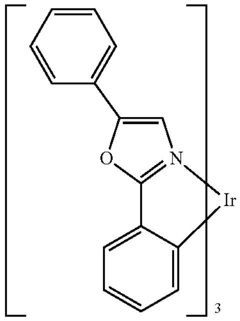
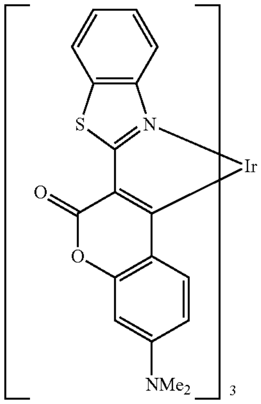
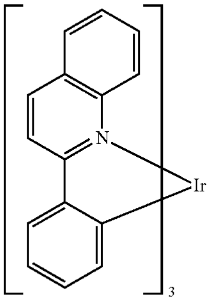
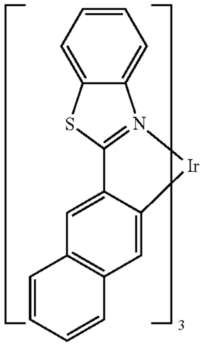

-continued

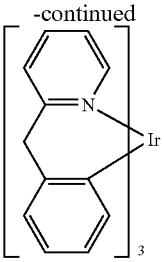

In one embodiment of the present application, as the iridium-based dopant, $Ir(ppy)_3$ may be used as a green phosphorescent dopant.

In one embodiment of the present application, the content of the dopant may be from 1% to 15%, preferably from 3% to 10% and more preferably from 5% to 10% based on the whole light emitting layer.

In the organic light emitting device of the present disclosure, the organic material layer comprises an electron injection layer or an electron transfer layer, and the electron injection layer or the electron transfer layer may comprise the heterocyclic compound.

In another organic light emitting device, the organic material layer comprises an electron blocking layer or a hole blocking layer, and the electron blocking layer or the hole blocking layer may comprise the heterocyclic compound.

In another organic light emitting device, the organic material layer comprises an electron transfer layer, a light emitting layer or a hole blocking layer, and the electron transfer layer, the light emitting layer or the hole blocking layer may comprise the heterocyclic compound.

The organic light emitting device of the present disclosure may further comprise one, two or more layers selected from the group consisting of a light emitting layer, a hole injection layer, a hole transfer layer, an electron injection layer, an electron transfer layer, an electron blocking layer and a hole blocking layer.

FIGS. 1 to 3 illustrate a lamination order of electrodes and organic material layers of an organic light emitting device according to one embodiment of the present application. However, the scope of the present application is not limited to these diagrams, and structures of organic light emitting devices known in the art may also be used in the present application.

FIG. 1 illustrates an organic light emitting device in which an anode (200), an organic material layer (300) and a cathode (400) are consecutively laminated on a substrate (100). However, the structure is not limited to such a structure, and as illustrated in FIG. 2, an organic light emitting device in which a cathode, an organic material layer and an anode are consecutively laminated on a substrate may also be obtained.

FIG. 3 illustrates a case of the organic material layer being a multilayer. The organic light emitting device according to FIG. 3 comprises a hole injection layer (301), a hole transfer layer (302), a light emitting layer (303), a hole blocking layer (304), an electron transfer layer (305) and an electron injection layer (306). However, the scope of the present application is not limited to such a lamination structure, and as necessary, other layers except the light emitting layer may not be included, and other necessary functional layers may be further included.

One embodiment of the present application provides a method for manufacturing an organic light emitting device, the method comprising preparing a substrate; forming a first electrode on the substrate; forming one or more organic material layers on the first electrode; and forming a second electrode on the organic material layer, wherein the forming of organic material layers comprises forming one or more organic material layers using the composition for an organic material layer according to one embodiment of the present application.

In the method for manufacturing an organic light emitting device according to one embodiment of the present application, the forming of organic material layers is forming using a method of thermal vacuum deposition after premixing the heterocyclic compound of Chemical Formula 1 and the heterocyclic compound of Chemical Formula 2.

The premixing means mixing materials of the heterocyclic compound of Chemical Formula 1 and the heterocyclic compound of Chemical Formula 2 in advance in one source of supply before depositing on an organic material layer.

The pre-mixed material may be referred to as the composition for an organic material layer according to one embodiment of the present application.

The organic material layer comprising Chemical Formula 1 may further comprise other materials as necessary.

The organic material layer comprising both Chemical Formula 1 and Chemical Formula 2 may further comprise other materials as necessary.

In the organic light emitting device according to one embodiment of the present application, materials other than the compound of Chemical Formula 1 or Chemical Formula 2 are illustrated below, however, these are for illustrative purposes only and not for limiting the scope of the present application, and may be replaced by materials known in the art.

As the anode material, materials having relatively large work function may be used, and transparent conductive oxides, metals, conductive polymers or the like may be used. Specific examples of the anode material comprise metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

As the cathode material, materials having relatively small work function may be used, and metals, metal oxides, conductive polymers or the like may be used. Specific examples of the cathode material comprise metals such as magnesium, calcium, sodium, potassium, titanium, indium, yttrium, lithium, gadolinium, aluminum, silver, tin and lead, or alloys thereof; multilayer structure materials such as LiF/Al or $LiO_2$/Al, and the like, but are not limited thereto.

As the hole injection material, known hole injection materials may be used, and for example, phthalocyanine compounds such as copper phthalocyanine disclosed in U.S. Pat. No. 4,356,429, or starburst-type amine derivatives such as tris(4-carbazoyl-9-ylphenyl)amine (TCTA), 4,4',4"-tri[phenyl(m-tolyl)amino]triphenylamine (m-MTDATA) or 1,3,5-tris[4-(3-methylphenylphenylamino)phenyl]benzene (m-MTDAPB) described in the literature [Advanced Material, 6, p. 677 (1994)], polyaniline/dodecylbenzene sulfonic acid, poly(3,4-ethylenedioxythiophene)/poly(4-styrenesulfonate), polyaniline/camphor sulfonic acid or polyaniline/poly(4-styrene-sulfonate) that are conductive polymers having solubility, and the like, may be used.

As the hole transfer material, pyrazoline derivatives, arylamine-based derivatives, stilbene derivatives, triphenyldiamine derivatives and the like may be used, and low molecular or high molecular materials may also be used.

As the electron transfer material, metal complexes of oxadiazole derivatives, anthraquinodimethane and derivatives thereof, benzoquinone and derivatives thereof, naphthoquinone and derivatives thereof, anthraquinone and derivatives thereof, tetracyanoanthraquinodimethane and derivatives thereof, fluorenone derivatives, diphenyldicyanoethylene and derivatives thereof, diphenoquinone derivatives, 8-hydroxyquinoline and derivatives thereof, and the like, may be used, and high molecular materials may also be used as well as low molecular materials.

As examples of the electron injection material, LiF is typically used in the art, however, the present application is not limited thereto.

As the light emitting material, red, green or blue light emitting materials may be used, and as necessary, two or more light emitting materials may be mixed and used. Herein, two or more light emitting materials may be used by being deposited as individual sources of supply or by being premixed and deposited as one source of supply. In addition, fluorescent materials may also be used as the light emitting material, however, phosphorescent materials may also be used. As the light emitting material, materials emitting light by bonding electrons and holes injected from an anode and a cathode, respectively, may be used alone, however, materials having a host material and a dopant material involving in light emission together may also be used.

When mixing light emitting material hosts, same series hosts may be mixed, or different series hosts may be mixed. For example, any two or more types of materials among n-type host materials or p-type host materials may be selected, and used as a host material of a light emitting layer.

The organic light emitting device according to one embodiment of the present application may be a top-emission type, a bottom-emission type or a dual-emission type depending on the materials used.

The heterocyclic compound according to one embodiment of the present application may also be used in an organic electronic device comprising an organic solar cell, an organic photo conductor, an organic transistor and the like under a similar principle used in the organic light emitting device.

Hereinafter, the present specification will be described in more detail with reference to examples, however, these are for illustrative purposes only, and the scope of the present application is not limited thereto.

PREPARATION EXAMPLE

<Preparation Example 1> Preparation of Compound 1-1

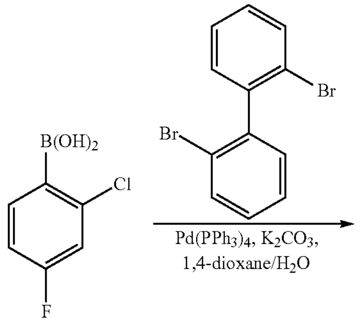

-continued

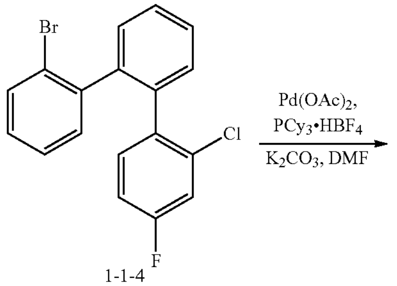

1-1-4

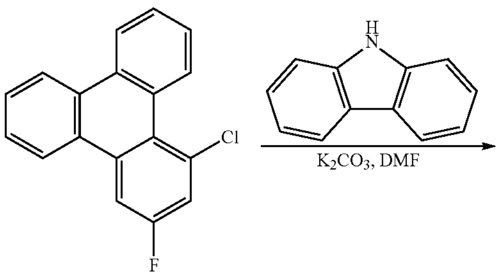

1-1-3

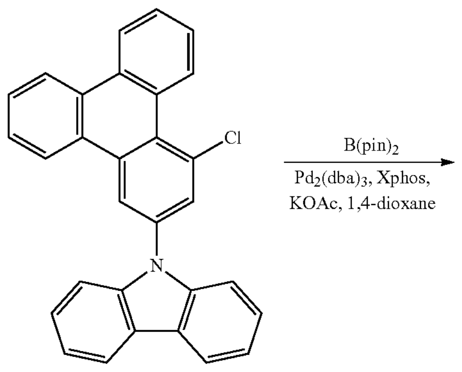

1-1-2

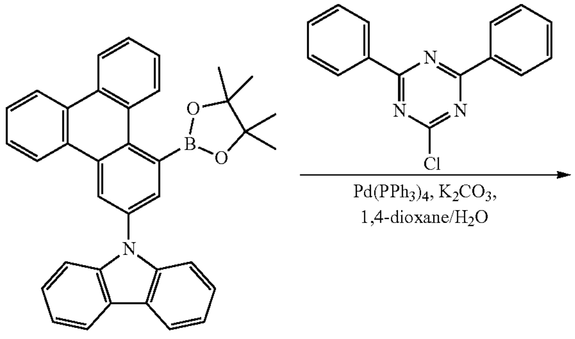

1-1-1

-continued

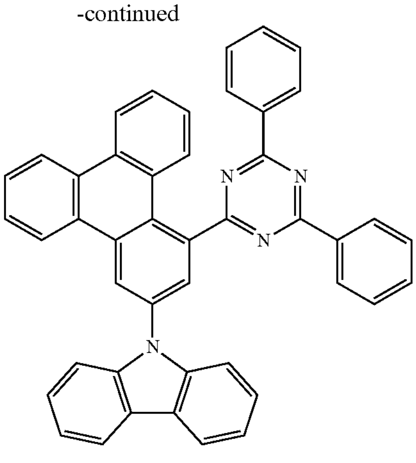

1-1

1) Preparation of Compound 1-1-4

After dissolving (2-chloro-4-fluorophenyl)boronic acid (10.0 g, 57.4 mM), 2,2'-dibromo-1,1'-biphenyl (19.7 g, 63.1 mM), $Pd(PPh)_4$ (3.3 g, 2.9 mM) and $K_2CO_3$ (15.9 g, 114.8 mM) in 1,4-dioxane/$H_2O$ (200 mL/40 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:10) to obtain target Compound 1-1-4 (16.6 g, 80%).

2) Preparation of Compound 1-1-3

After dissolving Compound 1-1-4 (10 g, 27.7 mM), $Pd(OAc)_2$ (622 mg, 2.8 mM), $PCy_3 \cdot HBF_4$ (2.0 g, 5.5 mM) and $K_2CO_3$ (7.7 g, 55.4 mM) in DMA (100 mL), the result was refluxed for 12 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:10) to obtain target Compound 1-1-3 (6.5 g, 83%).

3) Preparation of Compound 1-1-2

After dissolving Compound 1-1-3 (6.0 g, 21.4 mM), 9H-carbazole (3.6 g, 21.4 mM) and $K_2CO_3$ (5.9 g, 42.8 mM) in DMF (100 mL), the result was refluxed for 12 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 1-1-2 (8.2 g, 90%).

4) Preparation of Compound 1-1-1

After dissolving Compound 1-1-2 (8.2 g, 19.2 mM), bis(pinacolato)diboron (7.3 g, 28.8 mM), $PdCl_2(dppf)$ (0.7 g, 0.9 mM) and KOAc (5.6 g, 57.3 mM) in 1,4-dioxane (100 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 1-1-1 (8.5 g, 85%).

5) Preparation of Compound 1-1

After dissolving Compound 1-1-1 (8.4 g, 16.1 mM), 2-chloro-4,6-diphenyl-1,3,5-triazine (4.7 g, 17.7 mM), $Pd(PPh)_4$ (0.9 g, 0.8 mM) and $K_2CO_3$ (4.5 g, 32.3 mM) in 1,4-dioxane/$H_2O$ (200/40 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 1-1 (8.2 g, 82%).

Target Compound A was synthesized in the same manner as in the preparation of Preparation Example 1 except that Intermediate A of the following Table 1 was used instead of 9H-carbazole and Intermediate B of the following Table 1 was used instead of 2-chloro-4,6-diphenyl-1,3,5-triazine.

TABLE 1

| Compound Number | Intermediate A | Intermediate B |
|---|---|---|
| 1-3 | 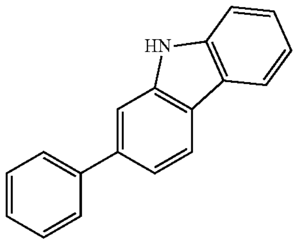 [SMILES: c1ccc(-c2ccc3c(c2)[nH]c2ccccc23)cc1] | 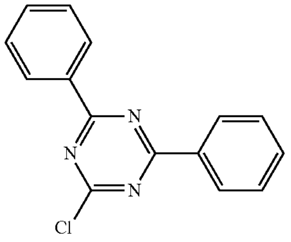 [SMILES: Clc1nc(-c2ccccc2)nc(-c2ccccc2)n1] |

TABLE 1-continued
1-4
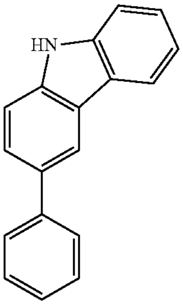 [SMILES: c1ccc(-c2ccc3[nH]c4ccccc4c3c2)cc1]
1-7
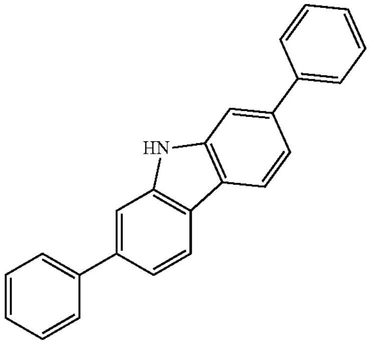 [SMILES: c1ccc(-c2ccc3c(c2)[nH]c2cc(-c4ccccc4)ccc23)cc1]
1-8
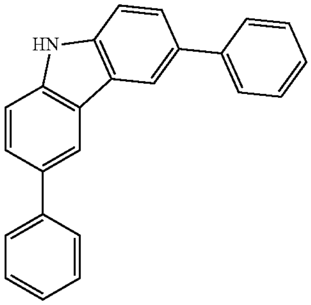 [SMILES: c1ccc(-c2ccc3[nH]c4ccc(-c5ccccc5)cc4c3c2)cc1]
1-11
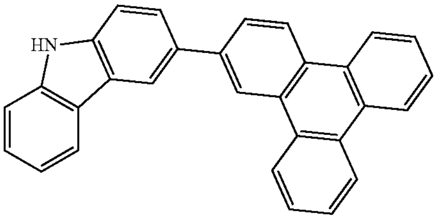 [SMILES: c1ccc2c(c1)[nH]c1ccc(-c3ccc4c5ccccc5c5ccccc5c4c3)cc12]
1-14
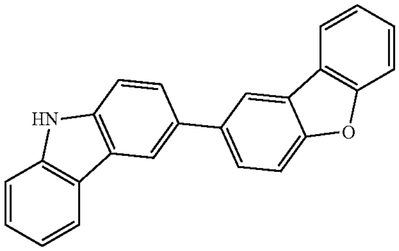 [SMILES: c1ccc2c(c1)[nH]c1ccc(-c3ccc4oc5ccccc5c4c3)cc12]

TABLE 1-continued
1-18
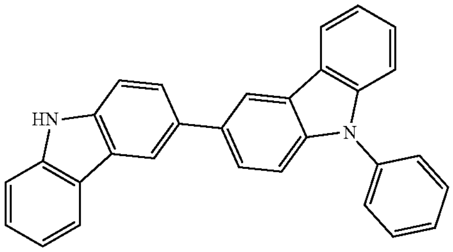 [SMILES: c1ccc(-n2c3ccccc3c3cc(-c4ccc5[nH]c6ccccc6c5c4)ccc32)cc1]
1-20
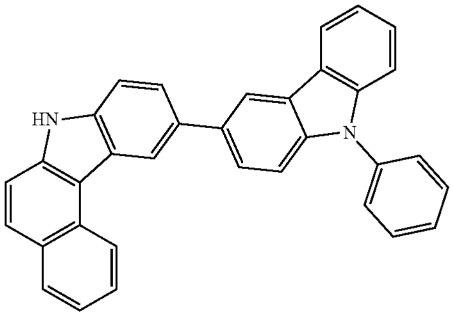 [SMILES: c1ccc(-n2c3ccccc3c3cc(-c4ccc5[nH]c6ccc7ccccc7c6c5c4)ccc32)cc1]
1-27
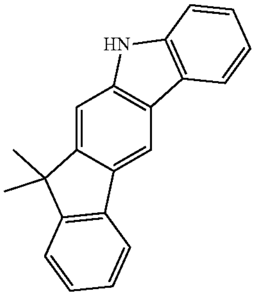 [SMILES: CC1(C)c2ccccc2-c2cc3c(cc21)[nH]c1ccccc13]
1-31
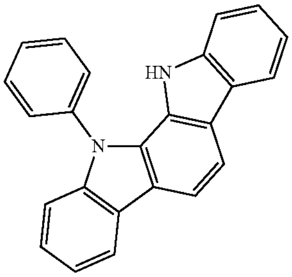 [SMILES: c1ccc(-n2c3ccccc3c3ccc4c5ccccc5[nH]c4c32)cc1]
1-33
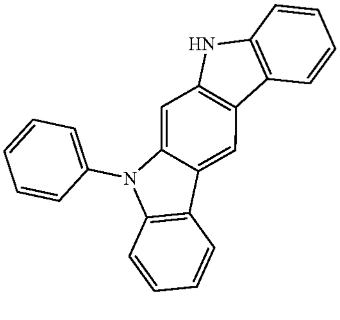 [SMILES: c1ccc(-n2c3ccccc3c3cc4c(cc32)[nH]c2ccccc24)cc1]

TABLE 1-continued
1-35
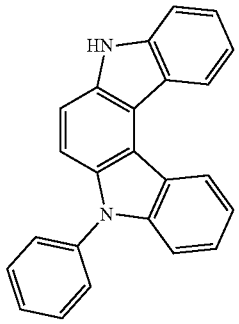 [SMILES: c1ccc(-n2c3ccccc3c3c4c(ccc32)[nH]c2ccccc24)cc1]
1-40
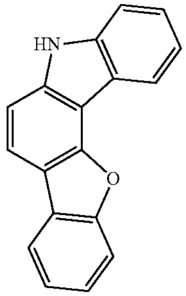 [SMILES: c1ccc2c(c1)[nH]c1ccc3c4ccccc4oc3c12]
1-46
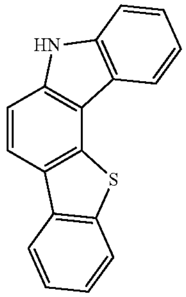 [SMILES: c1ccc2c(c1)[nH]c1ccc3c4ccccc4sc3c12]
1-49
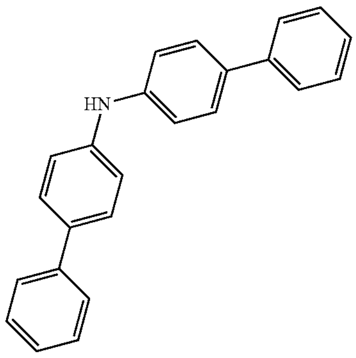 [SMILES: c1ccc(-c2ccc(Nc3ccc(-c4ccccc4)cc3)cc2)cc1]
1-51
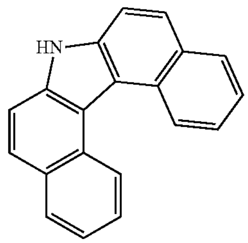 [SMILES: c1ccc2c(c1)ccc1[nH]c3ccc4ccccc4c3c12]

TABLE 1-continued
1-54
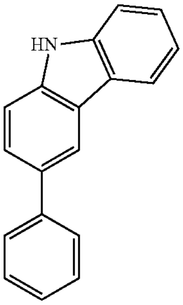 [SMILES: c1ccc(-c2ccc3[nH]c4ccccc4c3c2)cc1] 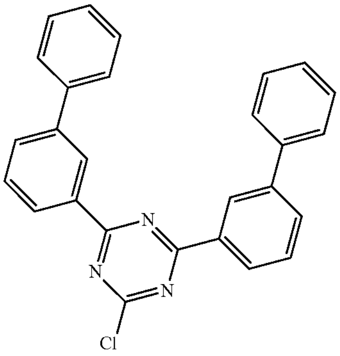 [SMILES: Clc1nc(-c2cccc(-c3ccccc3)c2)nc(-c2cccc(-c3ccccc3)c2)n1]
1-60
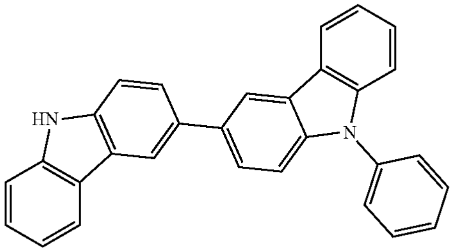 [SMILES: c1ccc(-n2c3ccccc3c3cc(-c4ccc5[nH]c6ccccc6c5c4)ccc32)cc1] 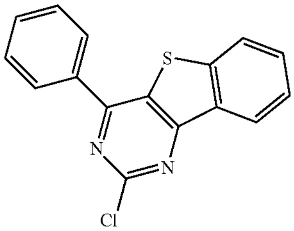 [SMILES: Clc1nc(-c2ccccc2)c2sc3ccccc3c2n1]
1-63
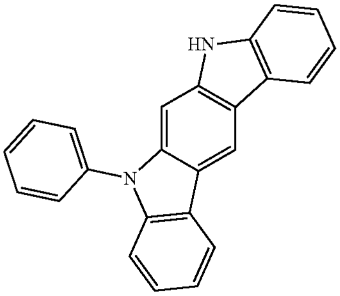 [SMILES: c1ccc(-n2c3ccccc3c3cc4c(cc32)[nH]c2ccccc24)cc1] 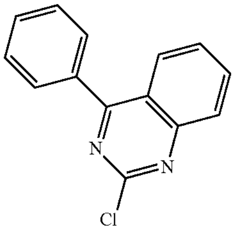 [SMILES: Clc1nc(-c2ccccc2)c2ccccc2n1]
1-68
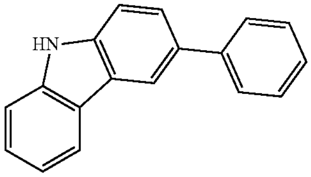 [SMILES: c1ccc(-c2ccc3[nH]c4ccccc4c3c2)cc1] 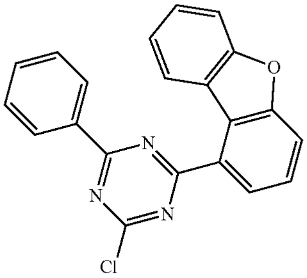 [SMILES: Clc1nc(-c2ccccc2)nc(-c2cccc3oc4ccccc4c23)n1]
1-70
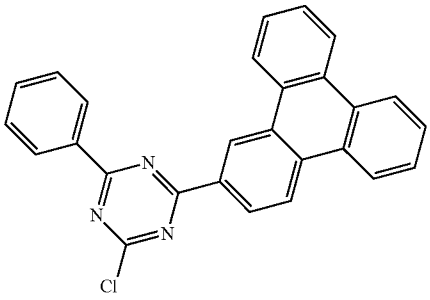 [SMILES: Clc1nc(-c2ccccc2)nc(-c2ccc3c4ccccc4c4ccccc4c3c2)n1]

TABLE 1-continued
| | | |
|---|---|---|
| 1-71 | | 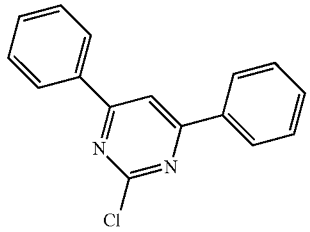 [SMILES: Clc1nc(-c2ccccc2)cc(-c2ccccc2)n1] |
| 1-80 | 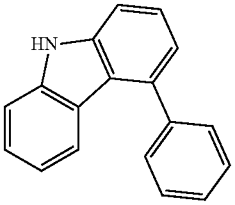 [SMILES: c1ccc(-c2cccc3[nH]c4ccccc4c23)cc1] | 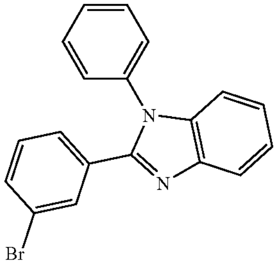 [SMILES: Brc1cccc(-c2nc3ccccc3n2-c2ccccc2)c1] |
| Compound Number | Target Compound A | Yield |
|---|---|---|
| 1-3 | 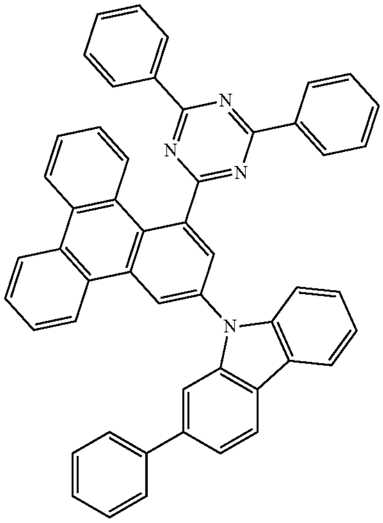 [SMILES: c1ccc(-c2ccc3c4ccccc4n(-c4cc(-c5nc(-c6ccccc6)nc(-c6ccccc6)n5)c5c6ccccc6c6ccccc6c5c4)c3c2)cc1] | 44% |
| 1-4 | 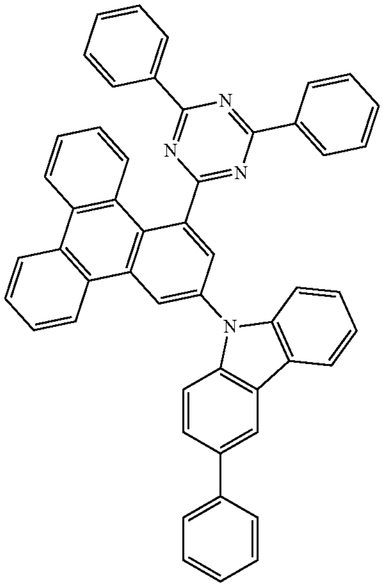 [SMILES: c1ccc(-c2ccc3c(c2)c2ccccc2n3-c2cc(-c3nc(-c4ccccc4)nc(-c4ccccc4)n3)c3c4ccccc4c4ccccc4c3c2)cc1] | 42% |

TABLE 1-continued
| | | |
|---|---|---|
| 1-7 | 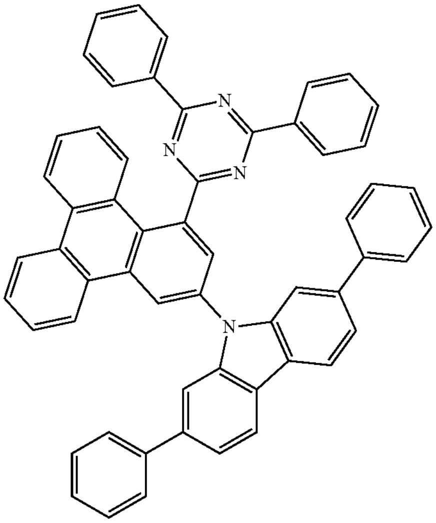 [SMILES: c1ccc(-c2ccc3c4ccc(-c5ccccc5)cc4n(-c4cc(-c5nc(-c6ccccc6)nc(-c6ccccc6)n5)c5c6ccccc6c6ccccc6c5c4)c3c2)cc1] | 46% |
| 1-8 | 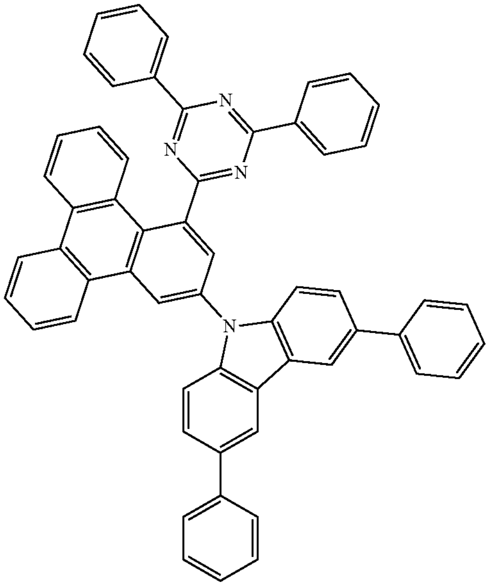 [SMILES: c1ccc(-c2ccc3c(c2)c2cc(-c4ccccc4)ccc2n3-c2cc(-c3nc(-c4ccccc4)nc(-c4ccccc4)n3)c3c4ccccc4c4ccccc4c3c2)cc1] | 43% |
| 1-11 | 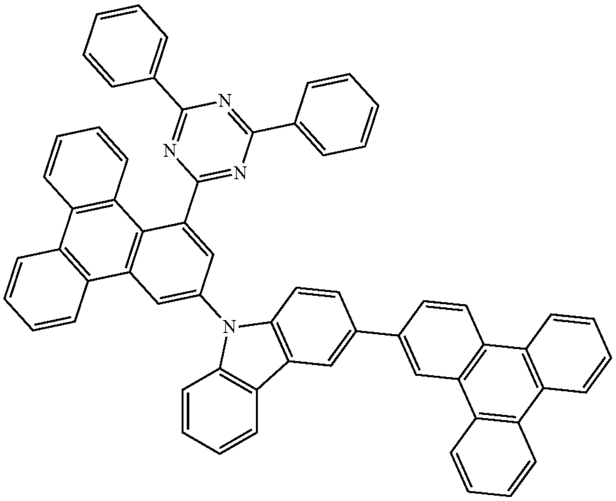 [SMILES: c1ccc(-c2nc(-c3ccccc3)nc(-c3cc(-n4c5ccccc5c5cc(-c6ccc7c8ccccc8c8ccccc8c7c6)ccc54)cc4c5ccccc5c5ccccc5c34)n2)cc1] | 45% |

TABLE 1-continued
| | | |
|---|---|---|
| 1-14 | 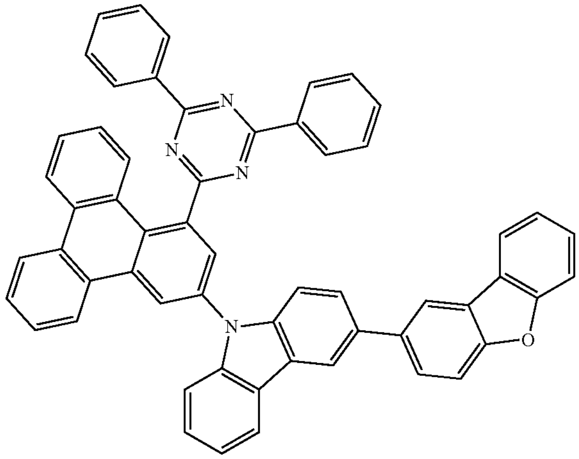 [SMILES: c1ccc(-c2nc(-c3ccccc3)nc(-c3cc(-n4c5ccccc5c5cc(-c6ccc7oc8ccccc8c7c6)ccc54)cc4c5ccccc5c5ccccc5c34)n2)cc1] | 44% |
| 1-18 | 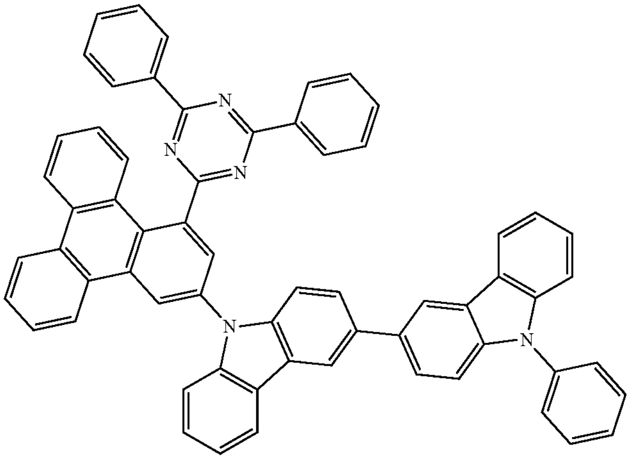 [SMILES: c1ccc(-c2nc(-c3ccccc3)nc(-c3cc(-n4c5ccccc5c5cc(-c6ccc7c(c6)c6ccccc6n7-c6ccccc6)ccc54)cc4c5ccccc5c5ccccc5c34)n2)cc1] | 42% |
| 1-20 | 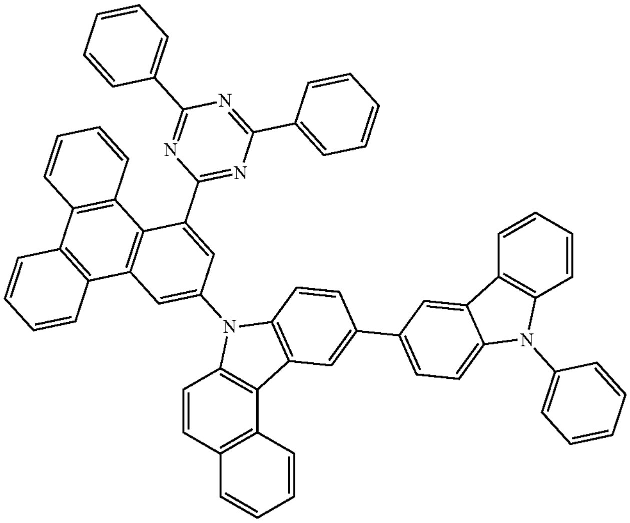 [SMILES: c1ccc(-c2nc(-c3ccccc3)nc(-c3cc(-n4c5ccc(-c6ccc7c(c6)c6ccccc6n7-c6ccccc6)cc5c5c6ccccc6ccc54)cc4c5ccccc5c5ccccc5c34)n2)cc1] | 46% |

TABLE 1-continued
| | | |
|---|---|---|
| 1-27 | 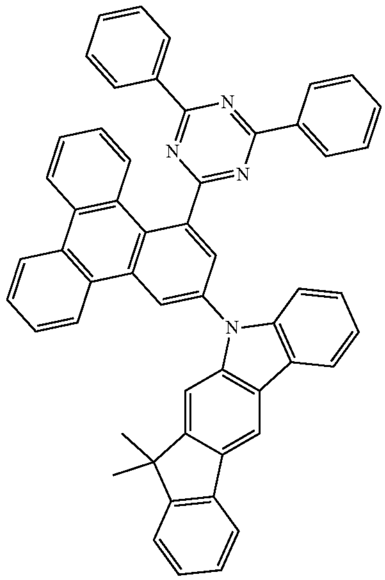 [SMILES: CC1(C)c2ccccc2-c2cc3c4ccccc4n(-c4cc(-c5nc(-c6ccccc6)nc(-c6ccccc6)n5)c5c6ccccc6c6ccccc6c5c4)c3cc21] | 43% |
| 1-31 | 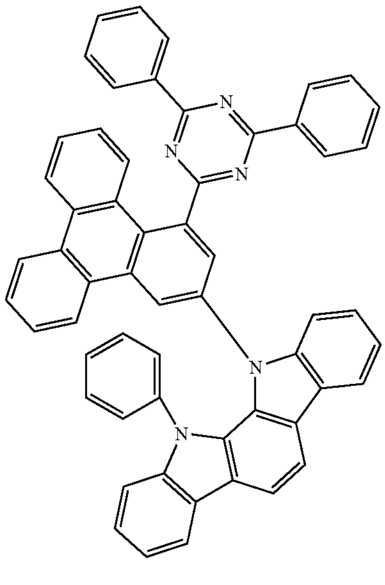 [SMILES: c1ccc(-c2nc(-c3ccccc3)nc(-c3cc(-n4c5ccccc5c5ccc6c7ccccc7n(-c7ccccc7)c6c54)cc4c5ccccc5c5ccccc5c34)n2)cc1] | 45% |

TABLE 1-continued
| | | |
|---|---|---|
| 1-33 | 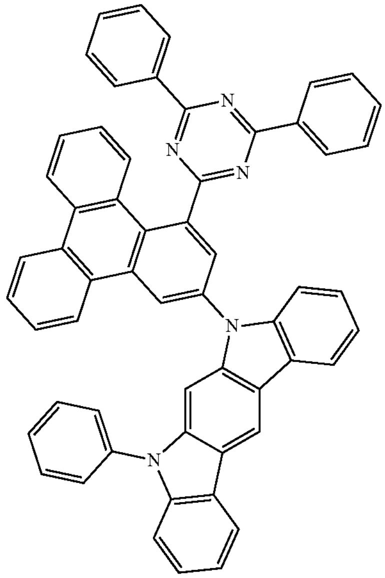 [SMILES: c1ccc(-c2nc(-c3ccccc3)nc(-c3cc(-n4c5ccccc5c5cc6c7ccccc7n(-c7ccccc7)c6cc54)cc4c5ccccc5c5ccccc5c34)n2)cc1] | 44% |
| 1-35 | 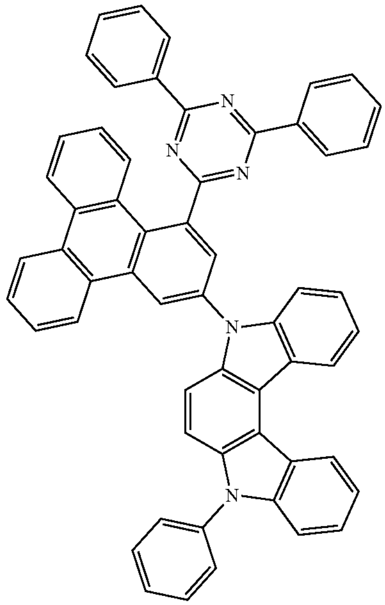 [SMILES: c1ccc(-c2nc(-c3ccccc3)nc(-c3cc(-n4c5ccccc5c5c6c7ccccc7n(-c7ccccc7)c6ccc54)cc4c5ccccc5c5ccccc5c34)n2)cc1] | 44% |

TABLE 1-continued
1-40 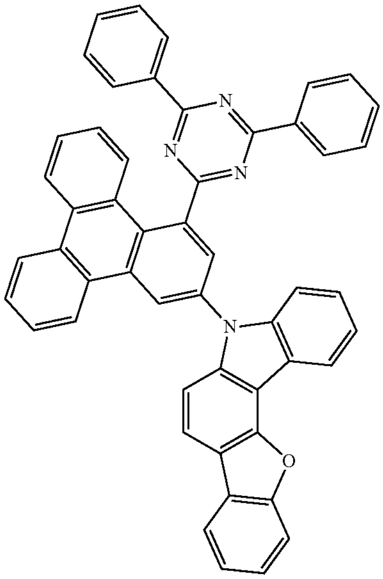 [SMILES: c1ccc(-c2nc(-c3ccccc3)nc(-c3cc(-n4c5ccccc5c5c6oc7ccccc7c6ccc54)cc4c5ccccc5c5ccccc5c34)n2)cc1] 42%
1-46 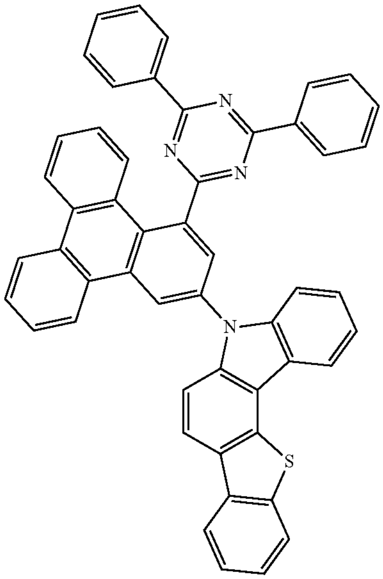 [SMILES: c1ccc(-c2nc(-c3ccccc3)nc(-c3cc(-n4c5ccccc5c5c6sc7ccccc7c6ccc54)cc4c5ccccc5c5ccccc5c34)n2)cc1] 46%

TABLE 1-continued
| | | |
|---|---|---|
| 1-49 | 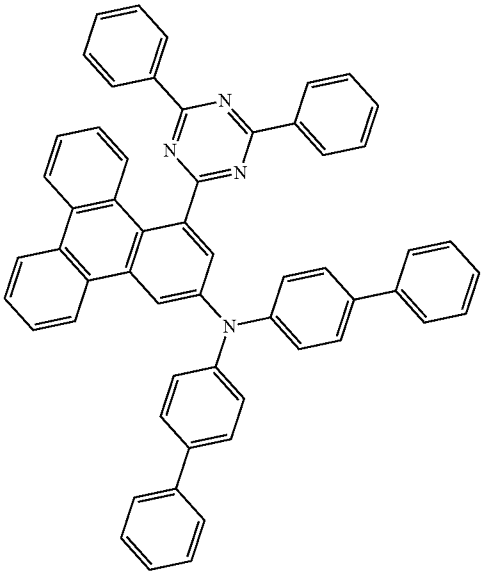 [SMILES: c1ccc(-c2ccc(N(c3ccc(-c4ccccc4)cc3)c3cc(-c4nc(-c5ccccc5)nc(-c5ccccc5)n4)c4c5ccccc5c5ccccc5c4c3)cc2)cc1] | 43% |
| 1-51 | 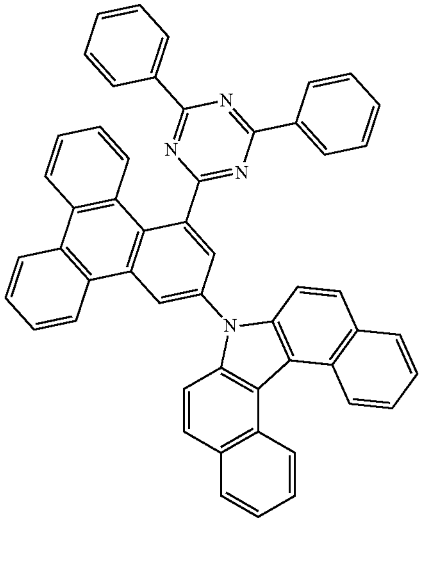 [SMILES: c1ccc(-c2nc(-c3ccccc3)nc(-c3cc(-n4c5ccc6ccccc6c5c5c6ccccc6ccc54)cc4c5ccccc5c5ccccc5c34)n2)cc1] | 45% |

TABLE 1-continued
| | | |
|---|---|---|
| 1-54 | 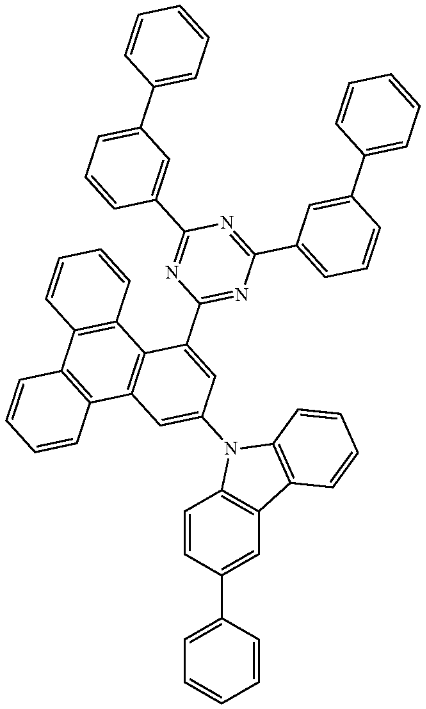 [SMILES: c1ccc(-c2cccc(-c3nc(-c4cccc(-c5ccccc5)c4)nc(-c4cc(-n5c6ccccc6c6cc(-c7ccccc7)ccc65)cc5c6ccccc6c6ccccc6c45)n3)c2)cc1] | 44% |
| 1-60 | 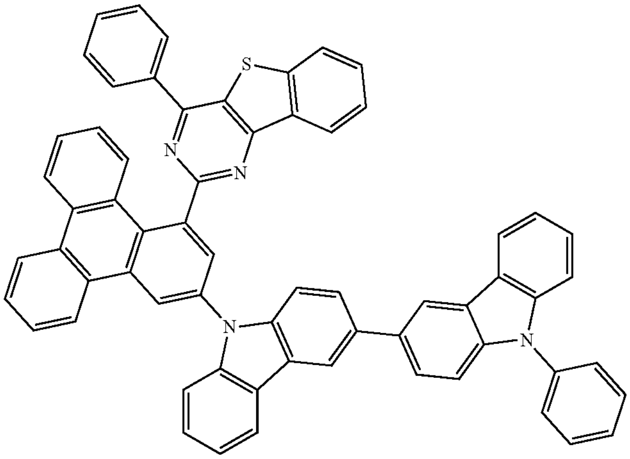 [SMILES: c1ccc(-c2nc(-c3cc(-n4c5ccccc5c5cc(-c6ccc7c(c6)c6ccccc6n7-c6ccccc6)ccc54)cc4c5ccccc5c5ccccc5c34)nc3c2sc2ccccc23)cc1] | 42% |

TABLE 1-continued
| | | |
|---|---|---|
| 1-63 | 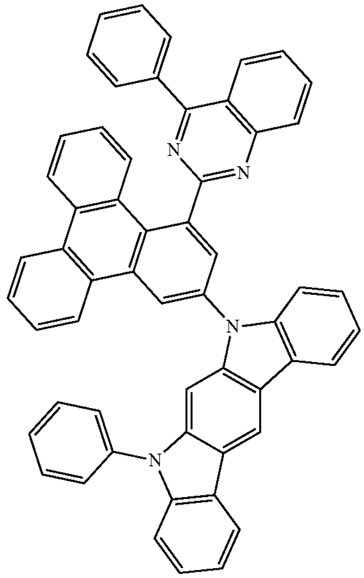 [SMILES: c1ccc(-c2nc(-c3cc(-n4c5ccccc5c5cc6c7ccccc7n(-c7ccccc7)c6cc54)cc4c5ccccc5c5ccccc5c34)nc3ccccc23)cc1] | 46% |
| 1-68 | 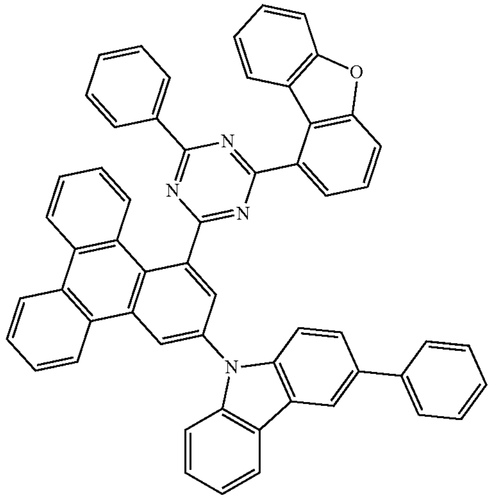 [SMILES: c1ccc(-c2ccc3c(c2)c2ccccc2n3-c2cc(-c3nc(-c4ccccc4)nc(-c4cccc5oc6ccccc6c45)n3)c3c4ccccc4c4ccccc4c3c2)cc1] | 43% |
| 1-70 | 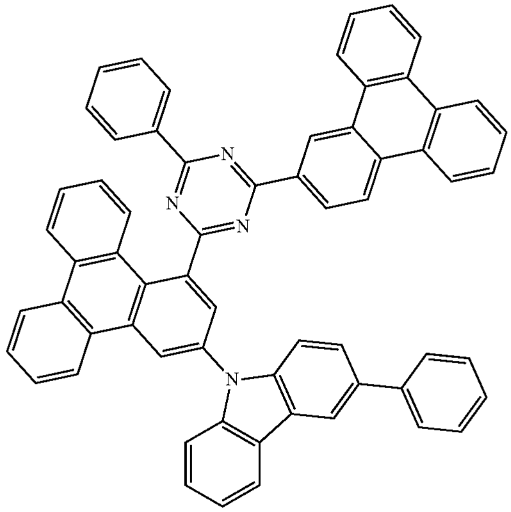 [SMILES: c1ccc(-c2ccc3c(c2)c2ccccc2n3-c2cc(-c3nc(-c4ccccc4)nc(-c4ccc5c6ccccc6c6ccccc6c5c4)n3)c3c4ccccc4c4ccccc4c3c2)cc1] | 45% |

TABLE 1-continued

| | | |
|---|---|---|
| 1-71 | 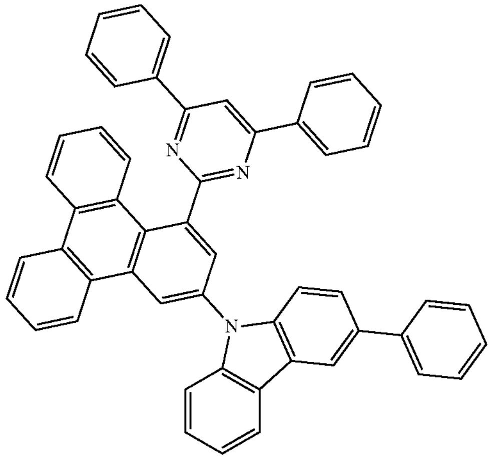 [SMILES: c1ccc(-c2ccc3c(c2)c2ccccc2n3-c2cc(-c3nc(-c4ccccc4)cc(-c4ccccc4)n3)c3c4ccccc4c4ccccc4c3c2)cc1] | 42% |
| 1-80 | 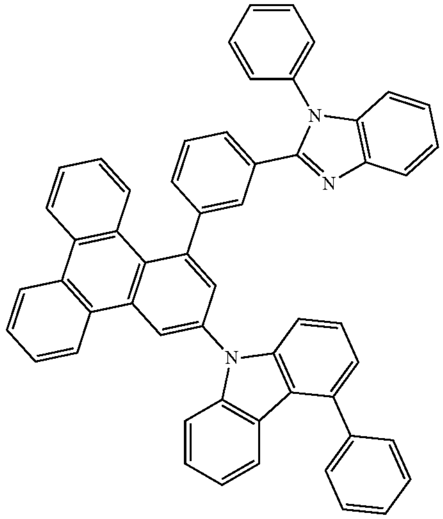 [SMILES: c1ccc(-c2cccc3c2c2ccccc2n3-c2cc(-c3cccc(-c4nc5ccccc5n4-c4ccccc4)c3)c3c4ccccc4c4ccccc4c3c2)cc1] | 49% |

Target Compound A was synthesized in the same manner as in the preparation of Preparation Example 1 except that (4-chloro-2-fluorophenyl)boronic acid was used instead of (2-chloro-4-fluorophenyl)boronic acid, Intermediate A of the following Table 2 was used instead of 9H-carbazole, and Intermediate B of the following Table 2 was used instead of 2-chloro-4,6-diphenyl-1,3,5-triazine.

TABLE 2

| Compound Number | Intermediate A | Intermediate B |
|---|---|---|
| 2-4 | 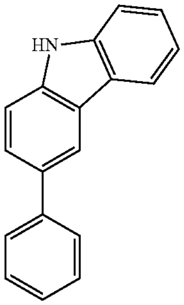 [SMILES: c1ccc(-c2ccc3[nH]c4ccccc4c3c2)cc1] | 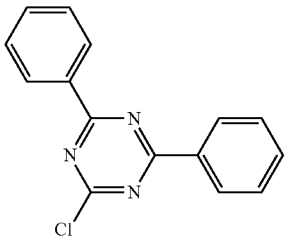 [SMILES: Clc1nc(-c2ccccc2)nc(-c2ccccc2)n1] |

TABLE 2-continued
2-11
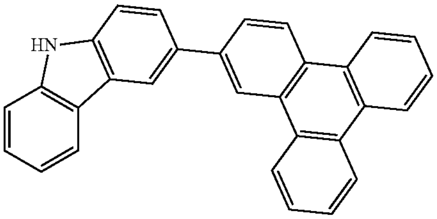 [SMILES: c1ccc2c(c1)[nH]c1ccc(-c3ccc4c5ccccc5c5ccccc5c4c3)cc12]
2-14
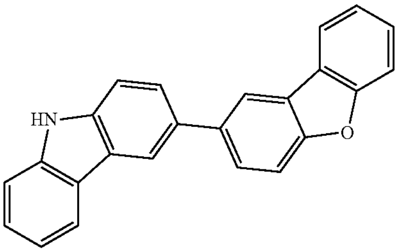 [SMILES: c1ccc2c(c1)[nH]c1ccc(-c3ccc4oc5ccccc5c4c3)cc12]
2-18
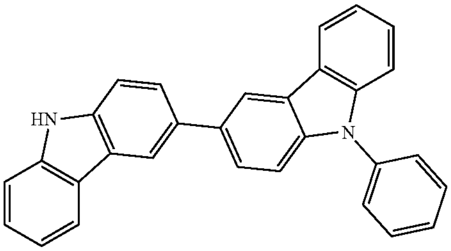 [SMILES: c1ccc(-n2c3ccccc3c3cc(-c4ccc5[nH]c6ccccc6c5c4)ccc32)cc1]
2-27
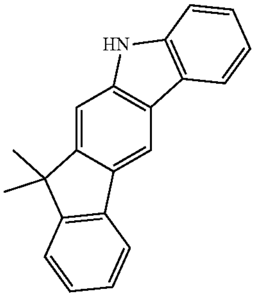 [SMILES: CC1(C)c2ccccc2-c2cc3c(cc21)[nH]c1ccccc13]
2-33
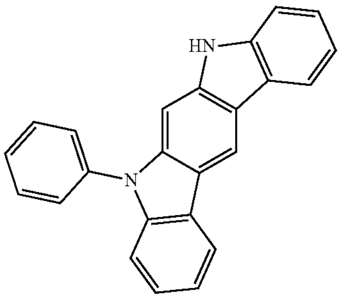 [SMILES: c1ccc(-n2c3ccccc3c3cc4c(cc32)[nH]c2ccccc24)cc1]

TABLE 2-continued
| | | |
|---|---|---|
| 2-54 | 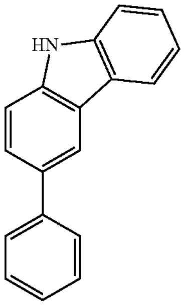 [SMILES: c1ccc(-c2ccc3[nH]c4ccccc4c3c2)cc1] | 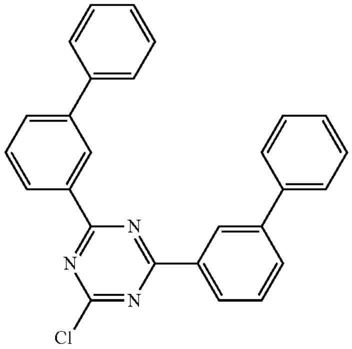 [SMILES: Clc1nc(-c2cccc(-c3ccccc3)c2)nc(-c2cccc(-c3ccccc3)c2)n1] |
| Compound Number | Target Compound A | Yield |
|---|---|---|
| 2-4 | 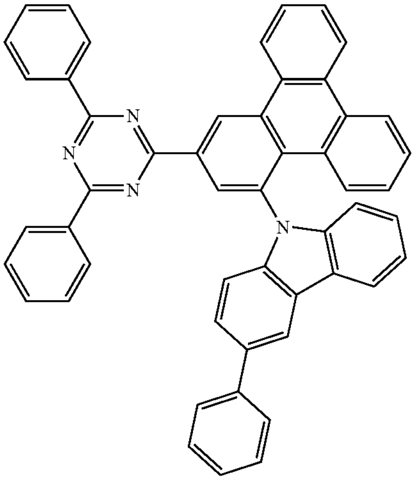 [SMILES: c1ccc(-c2ccc3c(c2)c2ccccc2n3-c2cc(-c3nc(-c4ccccc4)nc(-c4ccccc4)n3)cc3c4ccccc4c4ccccc4c23)cc1] | 44% |
| 2-11 | 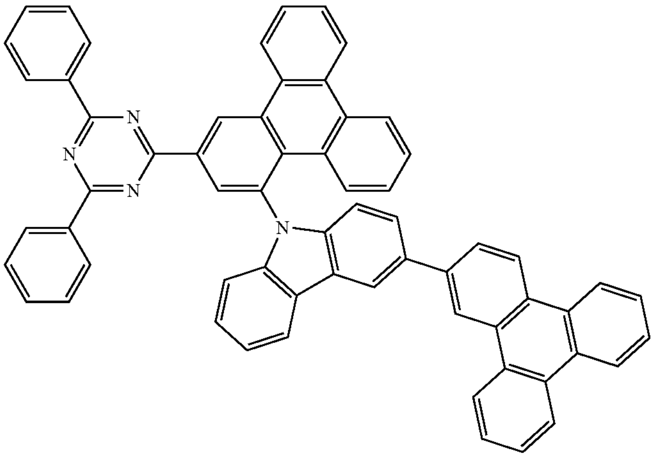 [SMILES: c1ccc(-c2nc(-c3ccccc3)nc(-c3cc(-n4c5ccccc5c5cc(-c6ccc7c8ccccc8c8ccccc8c7c6)ccc54)c4c5ccccc5c5ccccc5c4c3)n2)cc1] | 42% |

TABLE 2-continued
| | | |
|---|---|---|
| 2-14 | 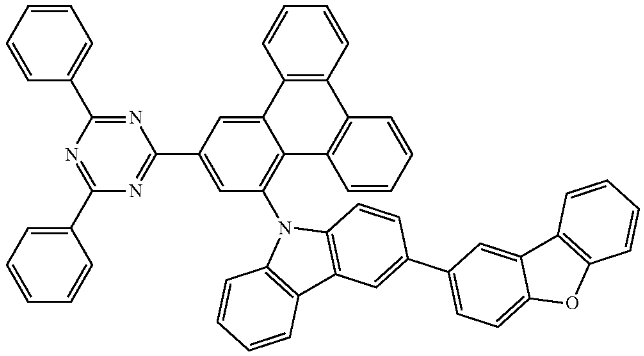 [SMILES: c1ccc(-c2nc(-c3ccccc3)nc(-c3cc(-n4c5ccccc5c5cc(-c6ccc7oc8ccccc8c7c6)ccc54)c4c5ccccc5c5ccccc5c4c3)n2)cc1] | 46% |
| 2-18 | 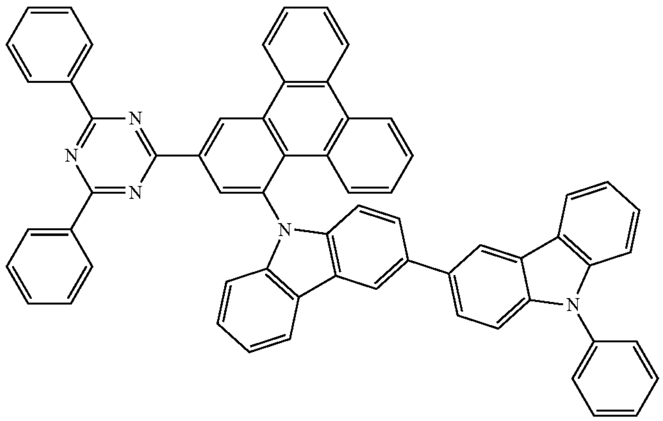 [SMILES: c1ccc(-c2nc(-c3ccccc3)nc(-c3cc(-n4c5ccccc5c5cc(-c6ccc7c(c6)c6ccccc6n7-c6ccccc6)ccc54)c4c5ccccc5c5ccccc5c4c3)n2)cc1] | 43% |
| 2-27 | 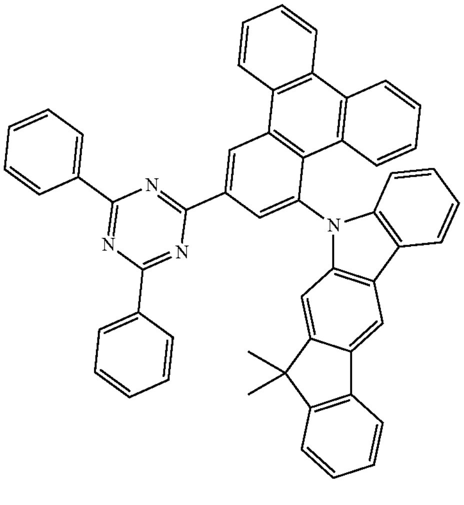 [SMILES: CC1(C)c2ccccc2-c2cc3c4ccccc4n(-c4cc(-c5nc(-c6ccccc6)nc(-c6ccccc6)n5)cc5c6ccccc6c6ccccc6c45)c3cc21] | 45% |

TABLE 2-continued
| | | |
|---|---|---|
| 2-33 | 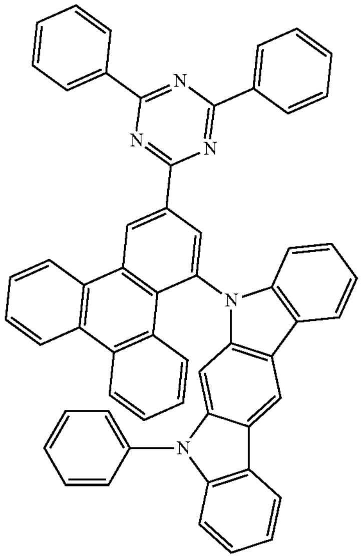 [SMILES: c1ccc(-c2nc(-c3ccccc3)nc(-c3cc(-n4c5ccccc5c5cc6c7ccccc7n(-c7ccccc7)c6cc54)c4c5ccccc5c5ccccc5c4c3)n2)cc1] | 44% |
| 2-54 | 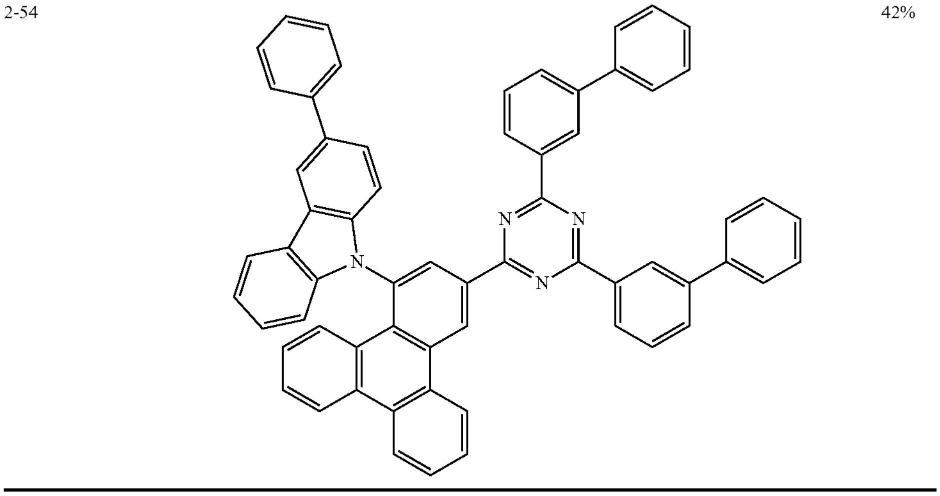 | 42% |
<Preparation Example 2> Synthesis of Compound 3-3
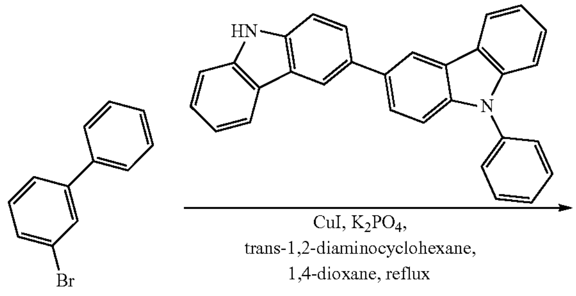
-continued
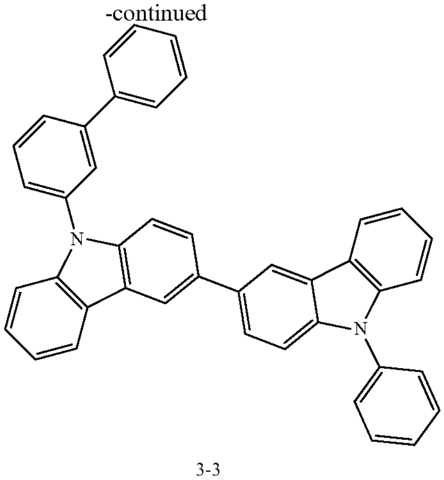
3-3

1) Preparation of Compound 3-3

After dissolving 3-bromo-1,1'-biphenyl (3.7 g, 15.8 mM), 9-phenyl-9H,9'H-3,3'-bicarbazole (6.5 g, 15.8 mM), CuI (3.0 g, 15.8 mM), trans-1,2-diaminocyclohexane (1.9 mL, 15.8 mM) and $K_3PO_4$ (3.3 g, 31.6 mM) in 1,4-oxane (100 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 3-3 (7.5 g, 85%).

Target Compound A was synthesized in the same manner as in the preparation of Preparation Example 2 except that Intermediate A of the following Table 3 was used instead of 3-bromo-1,1'-biphenyl and Intermediate B of the following Table 3 was used instead of 9-phenyl-9H,9'H-3,3'-bicarbazole.

TABLE 3

| Compound Number | Intermediate A | Intermediate B |
|---|---|---|
| 3-4 | 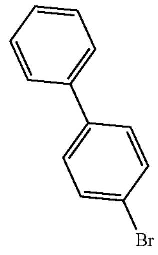 [SMILES: Brc1ccc(-c2ccccc2)cc1] | 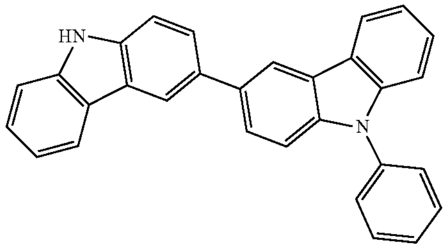 [SMILES: c1ccc(-n2c3ccccc3c3cc(-c4ccc5[nH]c6ccccc6c5c4)ccc32)cc1] |
| 3-7 | 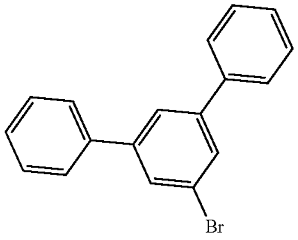 [SMILES: Brc1cc(-c2ccccc2)cc(-c2ccccc2)c1] | |
| 3-31 | 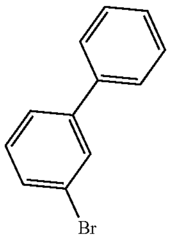 [SMILES: Brc1cccc(-c2ccccc2)c1] | 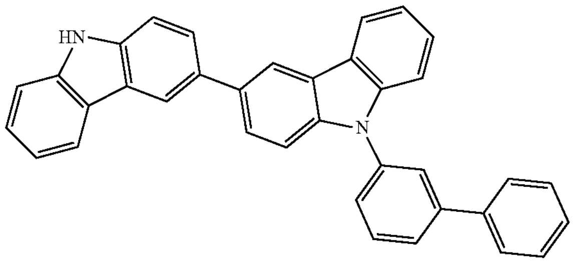 [SMILES: c1ccc(-c2cccc(-n3c4ccccc4c4cc(-c5ccc6[nH]c7ccccc7c6c5)ccc43)c2)cc1] |
| 3-32 | 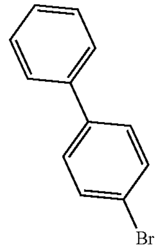 [SMILES: Brc1ccc(-c2ccccc2)cc1] | |

TABLE 3-continued
| | | |
|---|---|---|
| 3-42 | 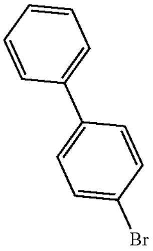 | 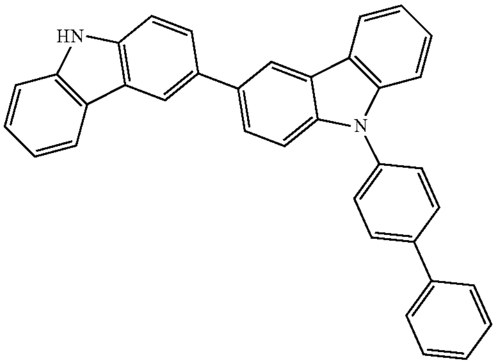 [SMILES: c1ccc(-c2ccc(-n3c4ccccc4c4cc(-c5ccc6[nH]c7ccccc7c6c5)ccc43)cc2)cc1] |
| Compound Number | Target Compound A | Total Yield |
|---|---|---|
| 3-4 | 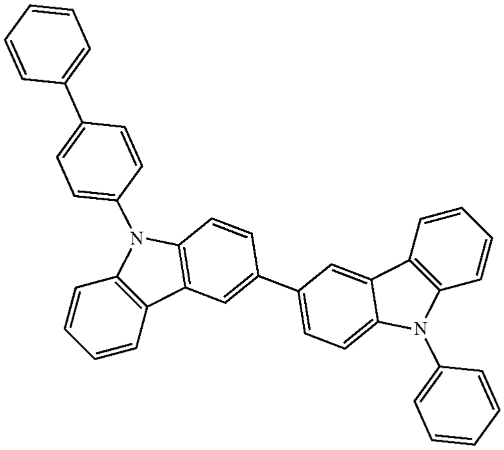 [SMILES: c1ccc(-c2ccc(-n3c4ccccc4c4cc(-c5ccc6c(c5)c5ccccc5n6-c5ccccc5)ccc43)cc2)cc1] | 83% |
| 3-7 | 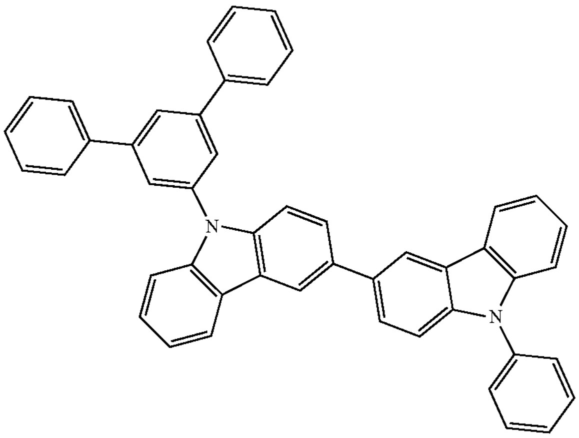 [SMILES: c1ccc(-c2cc(-c3ccccc3)cc(-n3c4ccccc4c4cc(-c5ccc6c(c5)c5ccccc5n6-c5ccccc5)ccc43)c2)cc1] | 84% |

TABLE 3-continued
| | | |
|---|---|---|
| 3-31 | 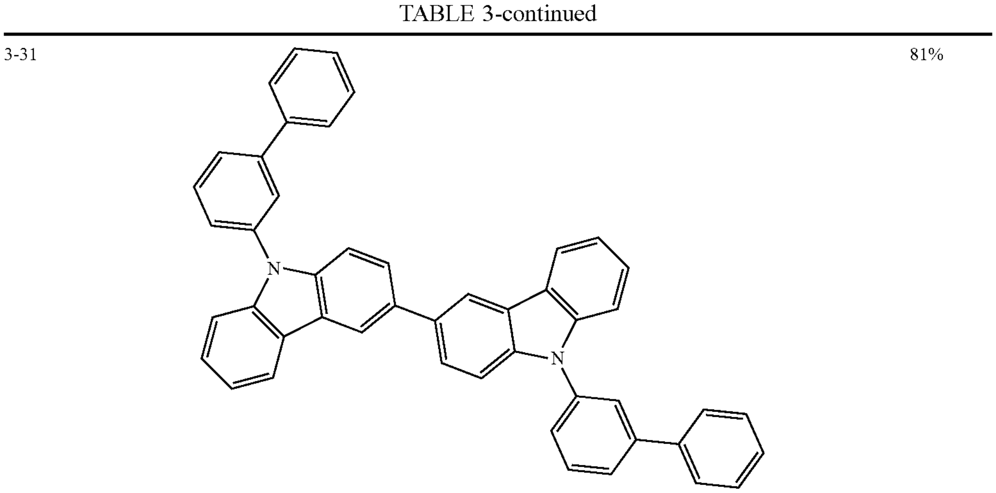 | 81% |
| 3-32 | 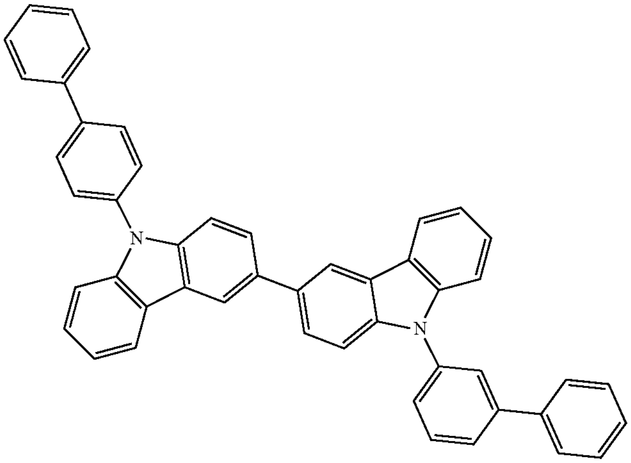 [SMILES: c1ccc(-c2ccc(-n3c4ccccc4c4cc(-c5ccc6c(c5)c5ccccc5n6-c5cccc(-c6ccccc6)c5)ccc43)cc2)cc1] | 80% |
| 3-42 | 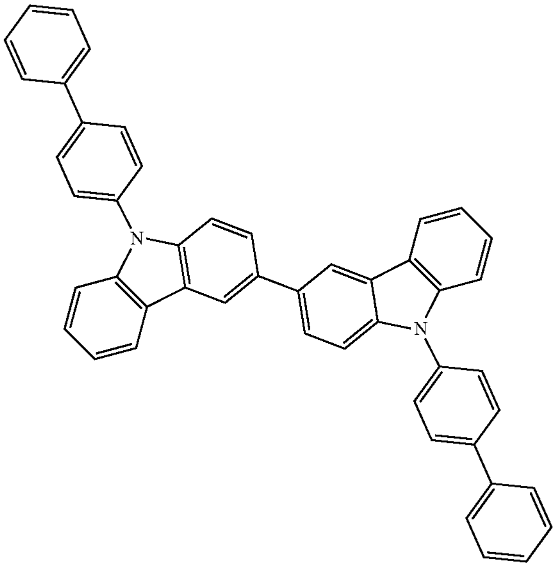 [SMILES: c1ccc(-c2ccc(-n3c4ccccc4c4cc(-c5ccc6c(c5)c5ccccc5n6-c5ccc(-c6ccccc6)cc5)ccc43)cc2)cc1] | 82% |

<Preparation Example 3> Synthesis of Compound 4-2

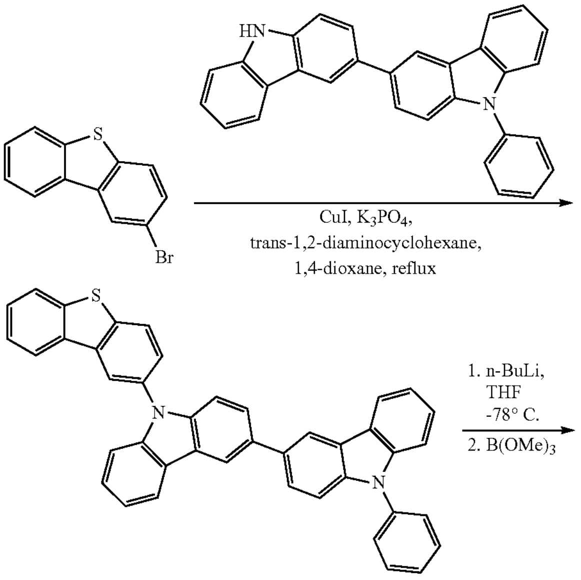

4-2-2

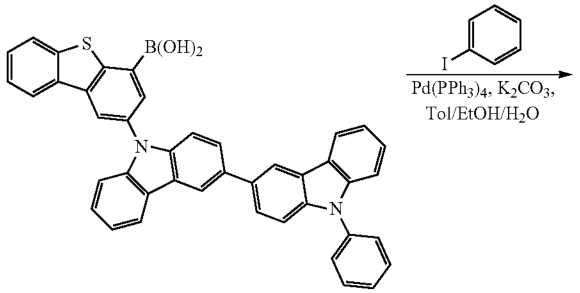

4-2-1

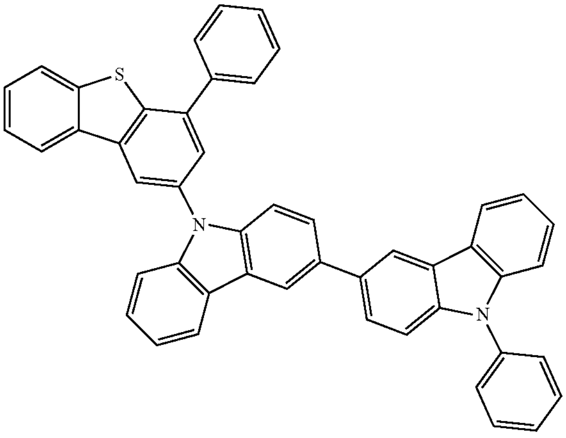

4-2

1) Preparation of Compound 4-2-2

After dissolving 2-bromodibenzo[b,d]thiophene (4.2 g, 15.8 mM), 9-phenyl-9H,9'H-3,3'-bicarbazole (6.5 g, 15.8 mM), CuI (3.0 g, 15.8 mM), trans-1,2-diaminocyclohexane (1.9 mL, 15.8 mM) and $K_3PO_4$ (3.3 g, 31.6 mM) in 1,4-oxane (100 mL), the result was refluxed for 24 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 4-2-2 (7.9 g, 85%).

2) Preparation of Compound 4-2-1

To a mixed solution of Compound 4-2-2 (8.4 g, 14.3 mmol) and THF (100 mL), 2.5 M n-BuLi (7.4 mL, 18.6 mmol) was added dropwise at −78° C., and the result was stirred for 1 hour at room temperature. To the reaction mixture, trimethyl borate (4.8 mL, 42.9 mmol) was added dropwise, and the result was stirred for 2 hours at room temperature. After the reaction was completed, the result was extracted using distilled water and DCM at room temperature, the organic layer was dried with $MgSO_4$, and then the solvent was removed using a rotary evaporator. The reaction material was purified using column chromatography (DCM:MeOH=100:3) and recrystallized with DCM to obtain target Compound 4-2-1 (3.9 g, 70%).

3) Preparation of Compound 4-2

After dissolving Compound 4-2-1 (6.7 g, 10.5 mM), iodobenzene (2.1 g, 10.5 mM), $Pd(PPh_3)_4$ (606 mg, 0.52 mM) and $K_2CO_3$ (2.9 g, 21.0 mM) in toluene/EtOH/$H_2O$ (100/20/20 mL), the result was refluxed for 12 hours. After the reaction was completed, the result was extracted using distilled water and DCM at room temperature, the organic layer was dried with $MgSO_4$, and then the solvent was removed using a rotary evaporator. The reaction material was purified using column chromatography (DCM:Hex=1:3) and recrystallized with methanol to obtain target Compound 4-2 (4.9 g, 70%).

<Preparation Example 4> Synthesis of Compound 4-3

Target Compound 4-3 (83%) was obtained in the same manner as in the preparation of Compound 2 of Preparation Example 3 except that 4-iodo-1,1'-biphenyl was used instead of iodobenzene.

Compounds other than the compounds described in Preparation Example 1 to Preparation Example 4 and Tables 1 to 3 were also prepared in the same manner as in the methods described in the preparation examples provided above.

The following Table 4 and Table 5 present 1H NMR data and FD-MS data of the synthesized compounds, and through the following data, syntheses of target compounds may be identified.

TABLE 4

| Compound Number | $^1H$ NMR ($CDCl_3$, 200 Mz) |
|---|---|
| 1-1 | δ = 9.08 (1H, d), 8.98 (1H, d), 8.55 (1H, d), 8.27-8.36 (7H, m), 8.19 (1H, d), 7.94 (1H, d), 7.50-7.70 (13H, m), 7.35 (1H, t), 7.16-7.20 (2H, m) |
| 1-3 | δ = 9.08 (1H, d), 8.98 (1H, d), 8.55 (1H, d), 8.27-8.36 (8H, m), 7.91-7.94 (2H, t), 7.91-7.94 (2H, t), 7.64-7.75 (7H, m), 7.35-7.50 (11H, m), 7.16 (1H, t) |
| 1-4 | δ = 9.08 (1H, d), 8.98 (1H, d), 8.55 (1H, d), 8.27-8.36 (7H, m), 7.89-7.99 (3H, m), 7.64-7.77 (7H, m), 7.35-7.52 (11H, m), 7.16 (1H, t) |
| 1-7 | δ = 9.08 (1H, d), 8.98 (1H, d), 8.62 (1H, d), 8.22-8.36 (9H, m), 7.91 (1H, d), 7.64-7.75 (10H, m), 7.41-7.52 (13H, m) |

TABLE 4-continued

| Compound Number | $^1$H NMR ($CDCl_3$, 200 Mz) |
|---|---|
| 1-8 | δ = 9.08 (1H, d), 8.98 (1H, d), 8.27-8.36 (8H, m), 8.13 (1H, d), 7.99 (1H, d), 7.89 (2H, s), 7.64-7.77 (9H, m), 7.41-7.52 (13H, m) |
| 1-11 | δ = 9.60 (1H, d), 9.27 (1H, s), 9.08 (1H, d), 8.98 (1H, d), 8.55 (1H, d), 8.27-8.37 (10H, m), 7.94-7.99 (3H, m), 7.64-7.77 (9H, m), 7.50-7.52 (9H, m), 7.35 (1H, t), 7.16 (1H, t) |
| 1-14 | δ = 8.98 (1H, d), 8.55 (1H, d), 8.27-8.36 (9H, m), 7.64-7.99 (12H, m), 7.50-7.54 (7H, m), 7.31-7.39 (2H, m), 7.16 (1H, t) |
| 1-18 | δ = 9.08 (1H, d), 8.98 (1H, d), 8.55 (1H, d), 8.27-8.36 (8H, m), 8.13-8.19 (2H, m), 7.89-7.99 (4H, m), 7.50-7.70 (19H, m), 7.35 (1H, t), 7.16-7.20 (2H, m) |
| 1-20 | δ = 9.8 (1H, d), 8.98 (1H, d), 8.54 (1H, d), 8.27-8.36 (9H, m), 8.13-8.19 (3H, m), 7.99 (1H, d), 7.89 (2H, s), 7.50-7.70 (22H, m), 7.20 (1H, t) |
| 1-27 | δ = 9.08 (1H, d), 8.98 (1H, d), 8.55 (1H, d), 8.27-8.36 (8H, m), 7.94 (1H, d), 7.88 (1H, s), 7.49-7.74 (14H, m), 7.35-7.38 (2H, m), 7.16 (1H, t), 1.69 (2H, s) |
| 1-31 | δ = 9.08 (1H, d), 8.98 (1H, d), 8.55 (2H, d), 8.27-8.36 (7H, m), 8.12 (1H, d), 7.94 (2H, d), 7.50-8.34 (17H, m), 7.35 (2H, t), 7.16 (2H, t) |
| 1-33 | δ = 9.08 (1H, d), 8.98 (1H, d), 8.55 (1H, d), 8.34-8.36 (6H, m), 8.27 (1H, d), 8.19 (1H, d), 7.94 (1H, d), 7.50-7.70 (19H, m), 7.35-7.40 (2H, m), 7.16-7.20 (2H, m) |
| 1-35 | δ = 9.08 (1H, d), 8.98 (1H, d), 8.55 (2H, d), 8.27-8.36 (7H, m), 7.94 (2H, d), 7.50-7.70 (17H, m), 7.35 (2H, t), 7.26 (1H, d), 7.16 (2H, t) |
| 1-40 | δ = 9.08 (1H, d), 8.98 (1H, d), 8.55 (1H, d), 8.27-8.36 (7H, m), 7.94-7.98 (2H, t), 7.84 (1H, d), 7.64-7.70 (4H, m), 7.50-7.54 (8H, m), 7.31-7.39 (3H, m), 7.13-7.16 (2H, m) |
| 1-46 | δ = 9.08 (1H, d), 8.98 (1H, d), 8.55 (1H, d), 8.45 (1H, d), 8.27-8.36 (7H, m), 8.05 (1H, d), 7.93-7.94 (2H, d), 7.49-7.70 (13H, m), 7.33-7.35 (2H, m), 7.16 (1H, t) |
| 1-49 | δ = 9.08 (1H, d), 8.98 (1H, d), 8.36 (4H, s), 8.27 (1H, d), 8.00 (2H, s), 7.37-7.75 (29H, m) |
| 1-51 | δ = 9.08 (1H, d), 8.98 (1H, d), 8.54 (2H, d), 8.27-8.36 (7H, m), 7.94-7.99 (4H, m), 7.50-7.70 (17H, m) |
| 1-54 | δ = 9.08 (1H, d), 8.98 (1H, d), 8.55 (1H, d), 8.34-8.38 (4H, t), 8.27 (1H, d), 7.89-7.99 (5H, m), 7.61-7.77 (15H, m), 7.35-7.52 (11H, m), 7.16 (1H, t) |
| 1-60 | δ = 9.08 (1H, d), 8.98 (1H, d), 8.55 (1H, d), 8.27-8.8.34 (4H, m), 8.13-8.19 (2H, m), 7.35-8.05 (27H, m), 7.16-7.20 (2H, t) |
| 1-63 | δ = 9.08 (1H, d), 8.98 (1H, d), 8.55 (1H, d), 8.27-8.34 (3H, m), 8.13-8.19 (2H, m), 7.94 (1H, d), 7.80-7.84 (4H, m), 7.49-7.70 (17H, m), 7.35-7.40 (2H, m), 7.16-7.20 (2H, m) |
| 1-68 | δ = 9.08 (1H, d), 8.98 (1H, d), 8.55 (1H, d), 8.34-8.36 (5H, m), 7.89-7.99 (4H, m), 7.31-7.77 (21H, m), 7.16 (1H, t) |
| 1-70 | δ = 9.27 (1H, s), 9.08 (1H, d), 8.98 (1H, d), 8.79 (1H, d), 8.55 (1H, d), 8.27-8.36 (8H, m), 8.15 (1H, d), 7.89-7.99 (3H, m), 7.64-7.77 (11H, m), 7.35-7.52 (9H, m), 7.16 (1H, t) |
| 1-71 | δ = 9.08 (1H, d), 8.98 (1H, d), (1H, d), 8.23-8.34 (4H, m), 7.89-7.99 (7H, m), 7.35-7.77 (18H, m), 7.16 (1H, t) |
| 1-80 | δ = 9.08 (1H, d), 8.98 (1H, d), 8.55-8.56 (2H, d), 8.27-8.38 (4H, m), 7.91-7.94 (3H, m), 7.38-7.81 (23H, m), 7.16 (1H, t) |
| 1-89 | δ = 9.08 (1H, d), 8.98 (1H, d), 8.55 (1H, d), 8.13-8.34 (6H, m), 7.89-7.99 (4H, m), 7.35-7.79 (19H, m), 7.16-7.20 (2H, t) |
| 2-4 | δ = 9.08 (1H, d), 8.98 (1H, d), 8.55 (1H, d), 8.34-8.42 (6H, m), 8.27 (1H, d), 7.89-7.99 (3H, m), 7.64-7.77 (7H, m), 7.35-7.52 (11H, m), 7.16 (1H, t) |
| 2-11 | δ = 9.60 (1H, d), 9.27 (1H, s), 9.08 (1H, d), 8.98 (1H, d), 8.55 (1H, d), 8.27-8.42 (10H, m), 7.89-7.99 (3H, m), 7.64-7.77 (9H, m), 7.50-7.52 (9H, m), 7.35 (1H, t), 7.16 (1H, t) |
| 2-14 | δ = 8.98 (1H, d), 8.55 (1H, d), 8.27-8.42 (9H, m), 7.64-7.99 (12H, m), 7.50-7.54 (7H, m), 7.31-7.39 (3H, m), 7.16 (1H, t) |
| 2-18 | δ = 9.08 (1H, d), 8.98 (1H, d), 8.55 (1H, d), 8.27-8.8.42 (8H, m), 8.13-8.19 (2H, m), 7.89-7.99 (4H, m), 7.50-7.77 (19H, m), 7.35 (1H, t), 7.16-7.20 (2H, t) |
| 2-27 | δ = 9.08 (1H, d), 8.98 (1H, d), 8.55 (1H, d), 8.27-8.42 (8H, m), 7.94 (1H, d), 7.88 (1H, s), 7.50-7.70 (14H, m), 7.35-7.38 (2H, m), 7.16 (1H, t), 1.69 (2H, s) |
| 2-33 | δ = 9.08 (1H, d), 8.98 (1H, d), 8.55 (1H, d), 8.34-8.42 (6H, m), 8.27 (1H, d), 8.19 (1H, d), 7.94 (1H, d), 7.50-7.70 (19H, m), 7.35-7.40 (2H, m), 7.16-7.20 (2H, t) |
| 2-54 | δ = 9.08 (1H, d), 8.98 (1H, d), 8.55 (1H, d), 8.34-8.42 (4H, m), 8.27 (1H, d), 7.89-7.99 (5H, m), 7.61-7.77 (15H, m), 7.35-7.52 (11H, m), 7.16 (1H, t) |
| 2-89 | δ = 9.08 (1H, d), 8.98 (1H, d), 8.55 (1H, d), 8.42 (1H, s), 8.30-8.47 (3H, m), 8.13-8.19 (2H, m), 7.89-7.99 (4H, m), 7.35-7.77 (19H, m), 7.16-7.20 (2H, m) |
| 7-89 | δ = 8.55 (1H, d), 8.30 (1H, d), 8.21-8.13 (3H, m), 7.99-(4H, m), 7.77-7.35 (17H, m), 7.20-7.16 (2H, m) |
| 3-4 | δ = 8.55 (1H, d), 8.30(1H, d), 8.19-8.13 (2H, m), 7.99-7.89 (8H, m), 7.77-7.75 (3H, m), 7.62-7.35 (11H, m), 7.20-7.16 (2H, m) |
| 3-7 | δ = 8.55 (1H, d), 8.31-8.30 (3H, d), 8.19-8.13 (2H, m), 7.99-7.89 (5H, m), 7.77-7.75 (5H, m), 7.62-7.35 (14H, m), 7.20-7.16 (2H, m) |
| 3-31 | δ = 8.55 (1H, d), 8.30 (1H, d), 8.21-8.13 (4H, m), 7.99-7.89 (4H, m), 7.77-7.35 (20H, m), 7.20-7.16 (2H, m) |
| 3-32 | δ = 8.55 (1H, d), 8.30 (1H, d), 8.21-8.13 (3H, m), 7.99-7.89 (8H, m), 7.77-7.35 (17H, m), 7.20-7.16 (2H, m) |
| 4-2 | δ = 8.55 (1H, d), 8.45 (1H, d), 8.30 (1H, d), 8.19 (1H, d), 8.13 (1H, d), 8.00-7.89 (6H, m), 7.77 (2H, m), 7.62-7.35 (15H, m), 7.20-7.16 (2H, m) |

TABLE 5

| Compound | FD-MS |
|---|---|
| 1-1 | m/z = 624.23 ($C_{45}H_{28}N_4$ = 624.75) |
| 1-3 | m/z = 700.26 ($C_{51}H_{32}N_4$ = 700.85) |
| 1-4 | m/z = 700.26 ($C_{51}H_{32}N_4$ = 700.85) |
| 1-7 | m/z = 776.29 ($C_{57}H_{36}N_4$ = 776.94) |
| 1-8 | m/z = 776.29 ($C_{57}H_{36}N_4$ = 776.94) |
| 1-11 | m/z = 850.31 ($C_{63}H_{38}N_4$ = 851.03) |
| 1-14 | m/z = 776.29 ($C_{57}H_{36}N_4O$ = 776.94) |
| 1-18 | m/z = 865.32 ($C_{63}H_{39}N_5$ = 866.04) |
| 1-20 | m/z = 915.34 ($C_{67}H_{41}N_5$ = 916.10) |
| 1-27 | m/z = 740.29 ($C_{54}H_{36}N_4$ = 740.91) |
| 1-31 | m/z = 789.29 ($C_{57}H_{35}N_5$ = 789.94) |
| 1-33 | m/z = 789.29 ($C_{57}H_{35}N_5$ = 789.94) |
| 1-35 | m/z = 789.29 ($C_{57}H_{35}N_5$ = 789.94) |
| 1-40 | m/z = 714.24 ($C_{51}H_{30}N_4O$ = 714 .83) |
| 1-46 | m/z = 730.89 ($C_{51}H_{30}N_4S$ = 730.89) |
| 1-49 | m/z = 778.31 ($C_{57}H_{38}N_4$ = 778.96) |
| 1-51 | m/z = 724.26 ($C_{53}H_{32}N_4$ = 724.87) |
| 1-54 | m/z = 852.33 ($C_{63}H_{40}N_4$ = 853.04) |
| 1-60 | m/z = 894.28 ($C_{64}H_{38}N_4S$ = 895.10) |

TABLE 5-continued

| Compound | FD-MS |
|---|---|
| 1-63 | m/z = 762.28 ($C_{56}H_{34}N_4$ = 762.92) |
| 1-68 | m/z = 790.27 ($C_{57}H_{34}N_{40}$ = 790. 93) |
| 1-70 | m/z = 850.31 ($C_{63}H_{38}N_4$ = 851.03) |
| 1-71 | m/z = 699.27 ($C_{52}H_{33}N_4S$ = 699.86) |
| 1-80 | m/z = 737.28 ($C_{55}H_{35}N_3$ = 737.91) |
| 1-89 | m/z = 710.27 ($C_{54}H_{34}N_2$ = 710.88) |
| 2-4 | m/z = 700.26 ($C_{51}H_{32}N_4$ = 700.85) |
| 2-11 | m/z = 850.31 ($C_{63}H_{38}N_4$ = 851.03) |
| 2-14 | m/z = 790.27 ($C_{57}H_{34}N_4$ = 790.93) |
| 2-18 | m/z = 865.32 ($C_{63}H_{39}N_5$ = 866.04) |
| 2-27 | m/z = 740.29 ($C_{54}H_{36}N_4$ = 740.91) |
| 2-33 | m/z = 789.29 ($C_{57}H_{35}N_5$ = 789.94) |
| 2-54 | m/z = 852.33 ($C_{63}H_{40}N_4$ = 853.04) |
| 2-89 | m/z = 710.27 ($C_{54}H_{34}N_2$ = 710.88) |
| 3-3 | m/z = 560.23 ($C_{42}H_{28}N_2$ = 560.70) |
| 3-4 | m/z = 560.23 ($C_{42}H_{28}N_2$ = 560.70) |
| 3-7 | m/z = 636.26 ($C_{48}H_{32}N_2$ = 636.80) |
| 3-31 | m/z = 636.26 ($C_{48}H_{32}N_2$ = 636.80) |
| 3-32 | m/z = 636.26 ($C_{48}H_{32}N_2$ = 636.80) |
| 4-2 | m/z = 666.84 ($C_{48}H_{30}N_2$ = 666.21) |

<Experimental Example 1>—Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treatment was conducted for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was deposited to 400 Å using the compound of Chemical Formula 1 described in the following Table 6 as a host, and $Ir(ppy)_3$ was deposited as a green phosphorescent dopant by 7% doping with respect to the deposited thickness of the light emitting layer. After that, bathocuproine (BCP) was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent light emission (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 6.

TABLE 6

| | Light Emitting Layer Compound | Driving Voltage (V) | Efficiency (cd/A) | Color Coordinate (x, y) | Lifetime ($T_{90}$) |
|---|---|---|---|---|---|
| Example 1 | 1-1 | 4.66 | 71.1 | (0.248, 0.711) | 271 |
| Example 2 | 1-3 | 4.31 | 79.2 | (0.246, 0.717) | 297 |
| Example 3 | 1-4 | 4.45 | 72.8 | (0.251, 0.718) | 315 |
| Example 4 | 1-7 | 4.67 | 71.2 | (0.251, 0.714) | 288 |
| Example 5 | 1-8 | 4.66 | 71.2 | (0.251, 0.714) | 302 |
| Example 6 | 1-11 | 4.35 | 79.2 | (0.241, 0.714) | 261 |
| Example 7 | 1-14 | 4.33 | 74.2 | (0.241, 0.714) | 221 |
| Example 8 | 1-18 | 4.69 | 69.2 | (0.231, 0.712) | 179 |
| Example 9 | 1-20 | 4.41 | 68.4 | (0.246, 0.717) | 176 |
| Example 10 | 1-27 | 4.11 | 72.2 | (0.231, 0.711) | 211 |
| Example 11 | 1-31 | 4.45 | 72.8 | (0.251, 0.714) | 189 |
| Example 12 | 1-33 | 4.66 | 71.1 | (0.248, 0.711) | 196 |
| Example 13 | 1-35 | 4.32 | 71.5 | (0.251, 0.713) | 199 |
| Example 14 | 1-40 | 4.67 | 71.2 | (0.251, 0.714) | 201 |
| Example 15 | 1-46 | 4.38 | 76.4 | (0.241, 0.711) | 200 |
| Example 16 | 1-49 | 4.66 | 71.1 | (0.241, 0.715) | 175 |
| Example 17 | 1-51 | 4.33 | 75.2 | (0.247, 0.727) | 227 |
| Example 18 | 1-54 | 4.13 | 79.2 | (0.247, 0.727) | 355 |
| Example 19 | 1-60 | 4.66 | 71.2 | (0.251, 0.714) | 187 |
| Example 20 | 1-63 | 4.38 | 76.4 | (0.241, 0.711) | 171 |
| Example 21 | 1-68 | 4.41 | 75.8 | (0.231, 0.711) | 332 |
| Example 22 | 1-70 | 4.67 | 71.2 | (0.251, 0.723) | 320 |
| Example 23 | 1-71 | 4.31 | 79.2 | (0.246, 0.717) | 243 |

TABLE 6-continued

| | Light Emitting Layer Compound | Driving Voltage (V) | Efficiency (cd/A) | Color Coordinate (x, y) | Lifetime ($T_{90}$) |
|---|---|---|---|---|---|
| Example 24 | 1-80 | 4.36 | 78.9 | (0.242, 0.713) | 239 |
| Example 25 | 1-89 | 4.69 | 66.2 | (0.231, 0.712) | 130 |
| Example 26 | 2-4 | 4.32 | 78.3 | (0.241, 0.711) | 310 |
| Example 27 | 2-11 | 4.41 | 75.8 | (0.231, 0.711) | 249 |
| Example 28 | 2-14 | 4.42 | 75.7 | (0.251, 0.714) | 221 |
| Example 29 | 2-18 | 4.45 | 72.8 | (0.251, 0.714) | 176 |
| Example 30 | 2-27 | 4.48 | 70.2 | (0.241, 0.714) | 206 |
| Example 31 | 2-33 | 4.69 | 77.2 | (0.243, 0.714) | 192 |
| Example 32 | 2-54 | 4.66 | 71.2 | (0.251, 0.724) | 340 |
| Example 33 | 2-89 | 4.83 | 65.9 | (0.233, 0.703) | 125 |
| Comparative Example 1 | 3-3 | 5.21 | 57.0 | (0.247, 0.727) | 85 |
| Comparative Example 2 | 3-4 | 4.75 | 51.2 | (0.254, 0.724) | 79 |
| Comparative Example 3 | 3-7 | 4.48 | 55.2 | (0.241, 0.714) | 86 |
| Comparative Example 4 | 3-31 | 4.75 | 51.2 | (0.264, 0.723) | 71 |
| Comparative Example 5 | 3-32 | 4.48 | 50.2 | (0.221, 0.712) | 89 |
| Comparative Example 6 | 4-2 | 4.83 | 61.9 | (0.233, 0.703) | 121 |
| Comparative Example 7 | Ref. 1 | 5.14 | 48.9 | (0.246, 0.717) | 40 |
| Comparative Example 8 | Ref. 2 | 5.26 | 47.6 | (0.255, 0.698) | 31 |
| Comparative Example 9 | Ref. 3 | 5.64 | 43.9 | (0.236, 0.696) | 20 |
| Comparative Example 10 | Ref. 4 | 5.54 | 45.9 | (0.246, 0.686) | 26 |
| Comparative Example 11 | Ref. 5 | 4.71 | 66.8 | (0.223, 0.693) | 135 |
| Comparative Example 12 | Ref. 6 | 4.96 | 64.1 | (0.231, 0.703) | 111 |

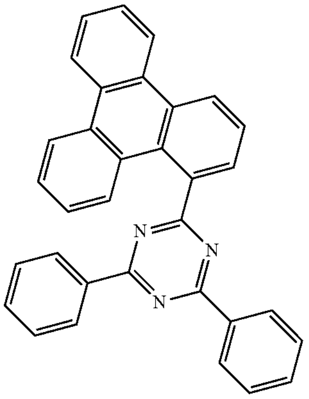

Ref. 1

TABLE 6-continued

| | Light Emitting Layer Compound | Driving Voltage (V) | Efficiency (cd/A) | Color Coordinate (x, y) | Lifetime ($T_{90}$) |
|---|---|---|---|---|---|

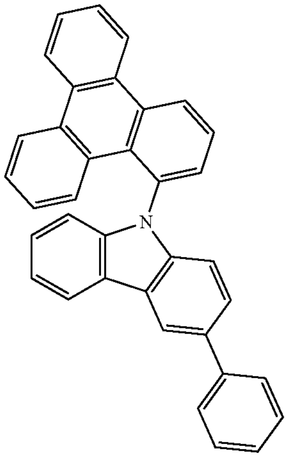

Ref. 2

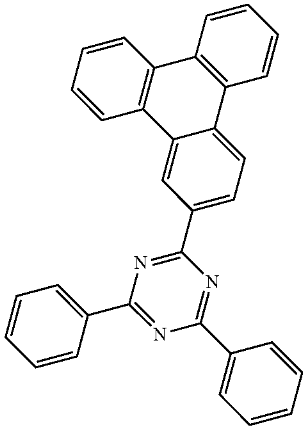

Ref. 3

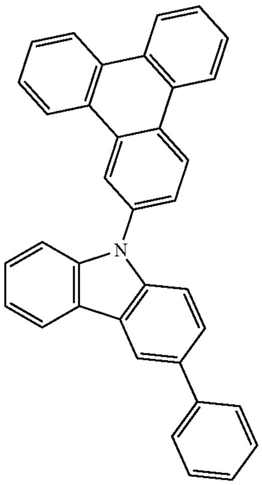

Ref. 4

TABLE 6-continued

| Light Emitting Layer Compound | Driving Voltage (V) | Efficiency (cd/A) | Color Coordinate (x, y) | Lifetime ($T_{90}$) |
|---|---|---|---|---|

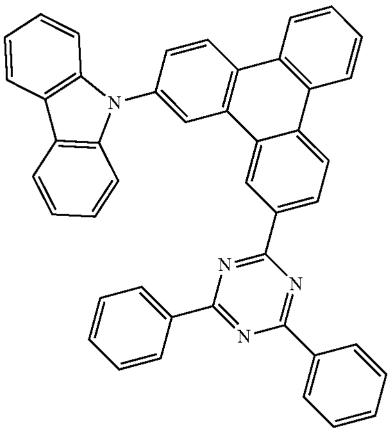

Ref. 5

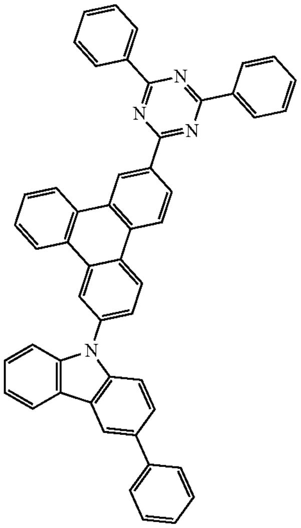

Ref. 6

<Experimental Example 2>—Manufacture of Organic Light Emitting Device

A glass substrate on which indium tin oxide (ITO) was coated as a thin film to a thickness of 1500 Å was cleaned with distilled water ultrasonic waves. After the cleaning with distilled water was finished, the substrate was ultrasonic cleaned with solvents such as acetone, methanol and isopropyl alcohol, then dried, and ultraviolet ozone (UVO) treatment was conducted for 5 minutes using UV in an ultraviolet (UV) cleaner. After that, the substrate was transferred to a plasma cleaner (PT), and after conducting plasma treatment under vacuum for ITO work function and residual film removal, the substrate was transferred to a thermal deposition apparatus for organic deposition.

On the transparent ITO electrode (anode), a hole injection layer 2-TNATA (4,4',4"-tris[2-naphthyl(phenyl)amino]triphenylamine) and a hole transfer layer NPB (N,N'-di(1-naphthyl)-N,N'-diphenyl-(1,1'-biphenyl)-4,4'-diamine), which are common layers, were formed.

A light emitting layer was thermal vacuum deposited thereon as follows. The light emitting layer was, as described in the following Table 7, deposited to 400 Å in one source of supply after pre-mixing one type of the compound of Chemical Formula 1 described in the following Table 7 and one type of the compound of Chemical Formula 2 described in the following Table 7 as a host, and $Ir(ppy)_3$ was deposited as a green phosphorescent dopant by doping in the amount of 7% respect to the deposited thickness of the light emitting layer. After that, bathocuproine (BCP) was deposited to 60 Å as a hole blocking layer, and $Alq_3$ was deposited to 200 Å thereon as an electron transfer layer. Lastly, an electron injection layer was formed on the electron transfer layer by depositing lithium fluoride (LiF) to a thickness of 10 Å, and then a cathode was formed on the electron injection layer by depositing an aluminum (Al) cathode to a thickness of 1,200 Å, and as a result, an organic electroluminescent device was manufactured.

Meanwhile, all the organic compounds required to manufacture the OLED were vacuum sublimation purified under $10^{-6}$ torr to $10^{-8}$ torr for each material to be used in the OLED manufacture.

For the organic electroluminescent devices manufactured as above, electroluminescent light emission (EL) properties were measured using M7000 manufactured by McScience Inc., and with the measurement results, $T_{90}$ was measured when standard luminance was 6,000 cd/m$^2$ using a lifetime measurement system (M6000) manufactured by McScience Inc.

Results of measuring driving voltage, light emission efficiency, color coordinate (CIE) and lifetime of the organic light emitting devices manufactured according to the present disclosure are as shown in the following Table 7.

TABLE 7

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 40 | 1-4:3-3 | 1:8 | 4.73 | 54.2 | (0.233, 0.714) | 338 |
| Example 41 | | 1:5 | 4.71 | 57.2 | (0.243, 0.714) | 344 |
| Example 42 | | 1:2 | 4.38 | 76.4 | (0.241, 0.711) | 428 |
| Example 43 | | 1:1 | 4.45 | 72.8 | (0.251, 0.714) | 411 |
| Example 44 | | 2:1 | 4.66 | 71.1 | (0.241, 0.711) | 389 |
| Example 45 | | 5:1 | 4.32 | 68.3 | (0.241, 0.711) | 333 |

TABLE 7-continued

| | Light Emitting Layer Compound | Ratio | Driving Voltage (V) | Efficiency (cd/A) | Color Coordinate (x, y) | Lifetime ($T_{90}$) |
|---|---|---|---|---|---|---|
| Example 46 | | 8:1 | 4.21 | 67.0 | (0.247, 0.727) | 325 |
| Example 47 | 1-70:3-4 | 1:2 | 4.38 | 76.4 | (0.241, 0.711) | 439 |
| Example 48 | | 1:1 | 4.45 | 72.8 | (0.251, 0.714) | 422 |
| Example 49 | | 2:1 | 4.66 | 71.1 | (0.241, 0.711) | 400 |
| Example 50 | 1-68:3-7 | 1:2 | 4.33 | 74.2 | (0.241, 0.714) | 462 |
| Example 51 | | 1:1 | 4.42 | 72.2 | (0.231, 0.711) | 453 |
| Example 52 | | 2:1 | 4.66 | 71.2 | (0.251, 0.714) | 428 |
| Example 53 | 1-54:3-31 | 1:2 | 4.31 | 79.2 | (0.246, 0.717) | 486 |
| Example 54 | | 1:1 | 4.42 | 75.7 | (0.251, 0.714) | 458 |
| Example 55 | | 2:1 | 4.66 | 71.1 | (0.241, 0.711) | 436 |
| Example 56 | 2-54:3-32 | 1:2 | 4.33 | 75.2 | (0.247, 0.727) | 469 |
| Example 57 | | 1:1 | 4.48 | 70.2 | (0.241, 0.714) | 443 |
| Example 58 | | 2:1 | 4.69 | 69.2 | (0.231, 0.711) | 418 |
| Example 59 | 1-54:4-105 | 1:2 | 4.33 | 75.2 | (0.247, 0.729) | 579 |
| Example 60 | | 1:1 | 4.48 | 70.2 | (0.241, 0.718) | 446 |
| Example 61 | | 2:1 | 4.69 | 69.2 | (0.231, 0.717) | 425 |
| Example 62 | 1-54:4-106 | 1:2 | 4.33 | 75.2 | (0.247, 0.723) | 520 |
| Example 63 | | 1:1 | 4.48 | 70.2 | (0.241, 0.712) | 482 |
| Example 64 | | 2:1 | 4.69 | 69.2 | (0.231, 0.716) | 443 |
| Example 65 | 1-54:4-2 | 1:2 | 4.35 | 79.2 | (0.241, 0.714) | 499 |
| Example 66 | | 1:1 | 4.41 | 75.8 | (0.231, 0.711) | 491 |
| Example 67 | | 2:1 | 4.67 | 71.2 | (0.251, 0.714) | 440 |

As can be seen from the results of Table 6, the organic electroluminescent device using the light emitting layer material of the organic electroluminescent device of the present disclosure had lower driving voltage, and significantly improved lifetime as well as having enhanced light emission efficiency compared to Comparative Examples 1 to 12.

Based on the results of Table 7, more superior efficiency and lifetime effects were obtained when including both the compound of Chemical Formula 1 and the compound of Chemical Formula 2. Such results may lead to a forecast that an exciplex phenomenon occurs when including the two compounds at the same time.

The exciplex phenomenon is a phenomenon of releasing energy having sizes of a donor (p-host) HOMO level and an acceptor (n-host) LUMO level due to electron exchanges between two molecules. When the exciplex phenomenon occurs between two molecules, reverse intersystem crossing (RISC) occurs, and as a result, internal quantum efficiency of fluorescence may increase up to 100%. When a donor (p-host) having favorable hole transfer capability and an acceptor (n-host) having favorable electron transfer capability are used as a host of a light emitting layer, holes are injected to the p-host and electrons are injected to the n-host, and therefore, a driving voltage may decrease, which resultantly helps with enhancement in the lifetime. In the present disclosure, it was identified that excellent device properties were obtained when using the heterocyclic compound of Chemical Formula 2 to have a donor role and the compound of Chemical Formula 1 to have an acceptor role as a light emitting layer host.

From the results of Table 6, it was identified that, when there was no carbazole-based substituent on the triphenylene group as in the compounds of Ref. 1 and 3, hole mobility decreased breaking a balance between holes and electrons in the light emitting layer, and as a result, the lifetime was reduced, and when there was no triazine on the triphenylene group as in the compounds of Ref. 2 and 4, electron mobility decreased breaking a balance between holes and electrons in the light emitting layer, and as a result, the lifetime was reduced.

The compounds of Ref. 5 and 6 have the same substituent as the compounds of the present disclosure, however, the position of substitution is different. In these compounds, the LUMO was delocalized from triazine to triphenylene. It was identified that this decreased electron stabilization and electron mobility compared to when the LUMO of Compounds 1-1 and 2-1 of the present application was localized to triphenylene, and as a result, the lifetime was reduced.

In Compounds 1-1 and 2-1 of the present disclosure, the substituents bond at a meta position to each other. In compounds having substituents bonding at an ortho position, molecular stability decreases due to a steric effect between the two substituents causing a decrease in the lifetime, and in compounds having substituents bonding at a para position, charge transfer between the two substituents becomes active narrowing a band gap and lowering a $T_1$ state, which resultantly causes a decrease in the efficiency.

Compounds 1-86 and 1-117, 2-86 and 2-100 of the present application are materials having a property of hole mobility, and has one or more carbazole and amine substituents on the triphenylene. In Compounds 1-86 and 1-100, 2-86 and 2-100, a biscarbazole substituent, and an aryl group, a heteroaryl group and —SiRR'R substitute around the triphenylene. This delocalizes the LUMO localized to the triphenylene to the aryl group, the heteroaryl group and the —SiRR'R, and increases electron stability. Compounds 1-101, 1-113, 1-114 and 1-115 of the present application enhance hole mobility by introducing substituents having a hole mobility property as both the two substituents, and, by using an amine substituent, Compounds 1-116 and 1-117 enhance hole mobility compared to when using a carbazole group.

The invention claimed is:

1. A heterocyclic compound represented by any one of the following Chemical Formulae 7 to 9, 11 or 12:

[Chemical Formula 7]

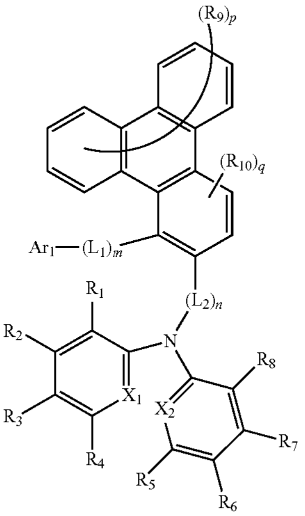

[Chemical Formula 8]

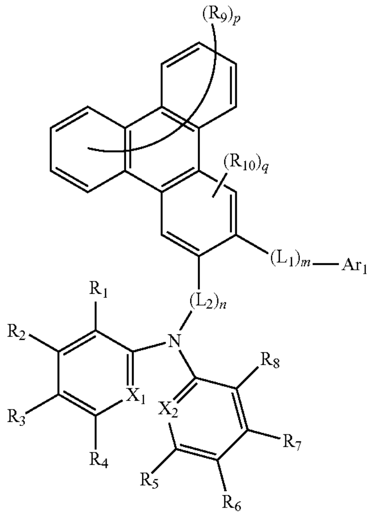

-continued

[Chemical Formula 9]

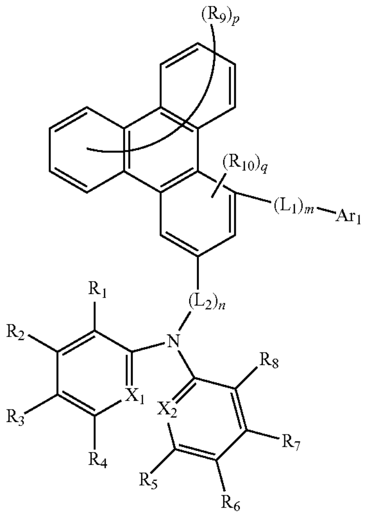

[Chemical Formula 11]

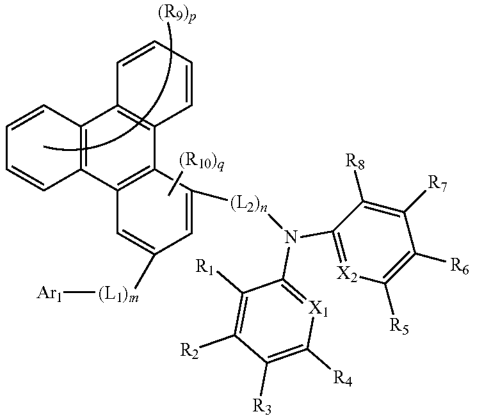

[Chemical Formula 12]

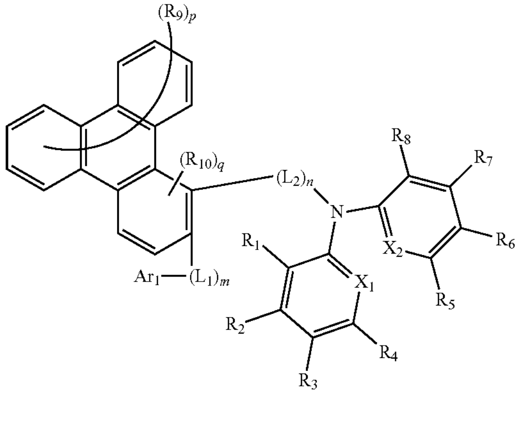

wherein, in Chemical Formulae 7 to 9, 11 and 12, $L_1$ and $L_2$ are a direct bond; a substituted or unsubstituted arylene group; or a substituted or unsubstituted heteroarylene group;

$Ar_1$ is a substituted or unsubstituted alkyl group; a substituted or unsubstituted aryl group; a substituted or unsubstituted heteroaryl group; —SiRR'R"; or —P(=O)RR';

$X_1$ is $CR_x$;

$X_2$ is $CR_y$;

$R_x$ and $R_y$ are the same as or different from each other, and are each independently hydrogen; a substituted or unsubstituted aryl group; or a substituted or unsubstituted heteroaryl group, or bond to each other to form a direct bond;

$R_1$ to $R_8$ are the same as or different from each other, and are each independently selected from the group consisting of hydrogen; a substituted or unsubstituted C6 to C40 aryl group; a substituted or unsubstituted C2 to C40 heteroaryl group; and an amine group unsubstituted or substituted with a substituted or unsubstituted C6 to C40 aryl group, or two or more groups adjacent to each other bond to each other to form a substituted or unsubstituted C6 to C40 aromatic hydrocarbon ring or a substituted or unsubstituted C2 to C40 heteroring, $R_{10}$ is hydrogen or deuterium;

$R_9$ is selected from the group consisting of hydrogen; deuterium; a halogen group; —CN;

a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; —SiRR'R"; —P(═O)RR'; and an amine group unsubstituted or substituted with a substituted or unsubstituted alkyl group, a substituted or unsubstituted aryl group or a substituted or unsubstituted heteroaryl group;

R, R' and R" are the same as or different from each other, and are each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;

p is an integer of 0 to 8;

q is an integer of 0 to 2;

m and n are an integer of 0 to 5; and when p, q, m and n are each an integer of 2 or greater, substituents in the parentheses are the same as or different from each other.

2. The heterocyclic compound of claim 1, wherein "substituted or unsubstituted" means being substituted with one or more substituents selected from the group consisting of C1 to C60 linear or branched alkyl; C2 to C60 linear or branched alkenyl; C2 to C60 linear or branched alkynyl; C3 to C60 monocyclic or polycyclic cycloalkyl; C2 to C60 monocyclic or polycyclic heterocycloalkyl; C6 to C60 monocyclic or polycyclic aryl; C2 to C60 monocyclic or polycyclic heteroaryl; —SiRR'R"; —P(═O)RR'; C1 to C20 alkylamine; C6 to C60 monocyclic or polycyclic arylamine; and C2 to C60 monocyclic or polycyclic heteroarylamine, or being substituted with a substituent linking two or more substituents selected from among the substituents illustrated above, or being unsubstituted; and R, R' and R" have the same definitions as in Chemical Formulae 7 to 9, 11 and 12.

3. The heterocyclic compound of claim 1, wherein $L_1$ and $L_2$ are a direct bond; a C6 to C40 arylene group; or a C2 to C40 heteroarylene group.

4. The heterocyclic compound of claim 1, wherein $Ar_1$ is a substituted or unsubstituted C6 to C40 aryl group; a substituted or unsubstituted C2 to C40 heteroaryl group; or —SiRR'R"; and R, R' and R" have the same definitions as in Chemical Formulae 7 to 9, 11 and 12.

5. The heterocyclic compound of claim 1, wherein any one of the Chemical Formulae 7 to 9, 11 or 12 is represented by any one of the following compounds:

1-1

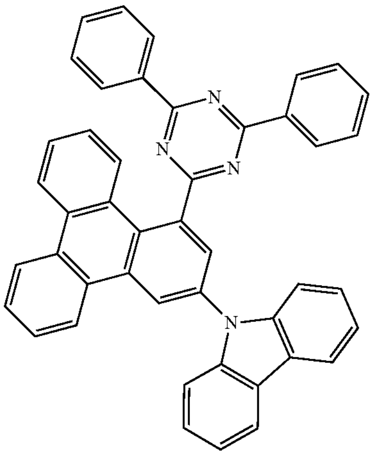

1-2

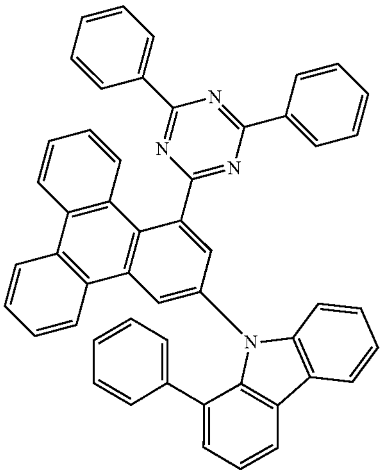

-continued
1-3
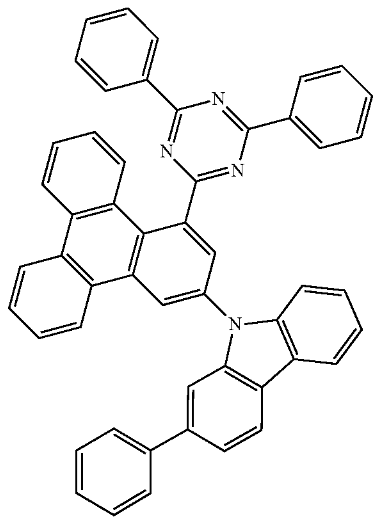
1-4
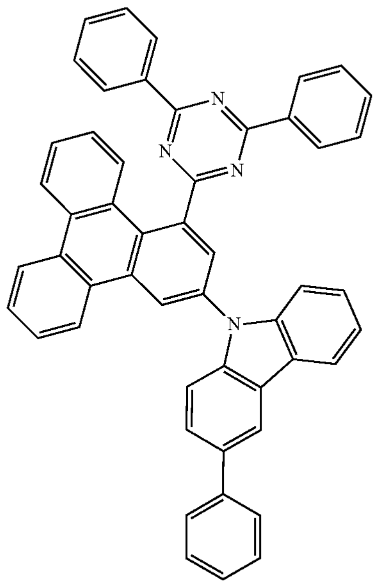
1-5
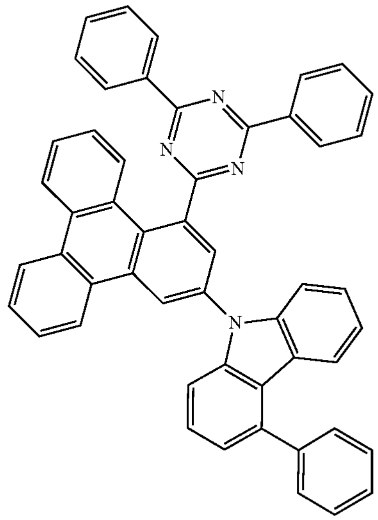
1-6
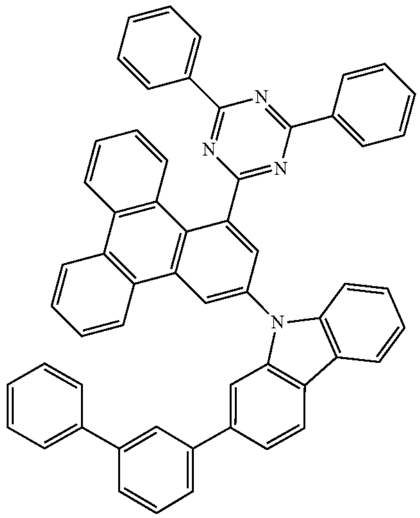

-continued
1-7
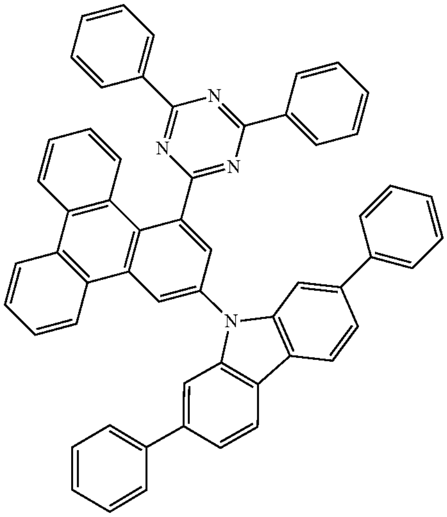
1-8
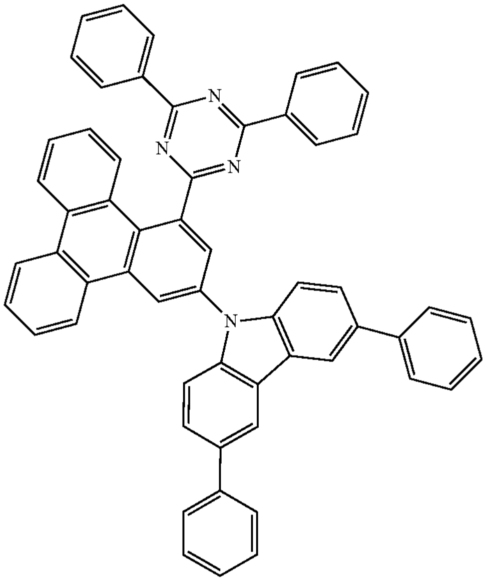
1-9
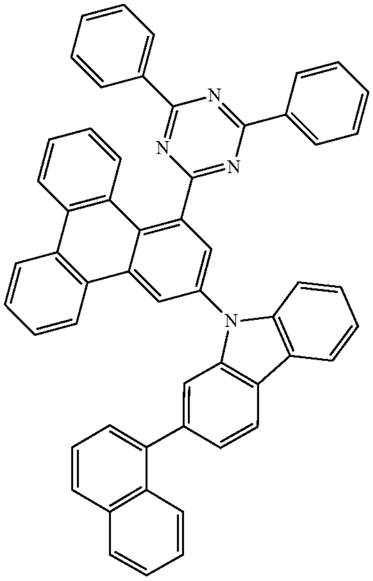
1-10
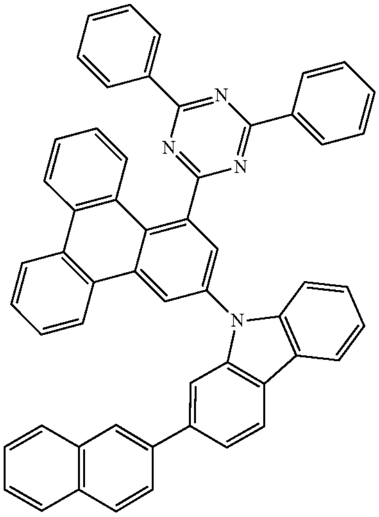

-continued
1-11
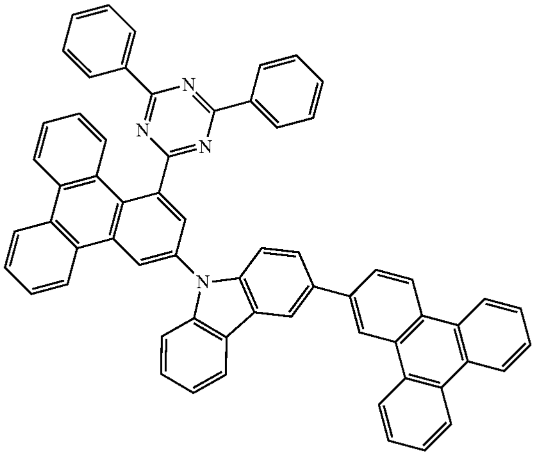
1-12
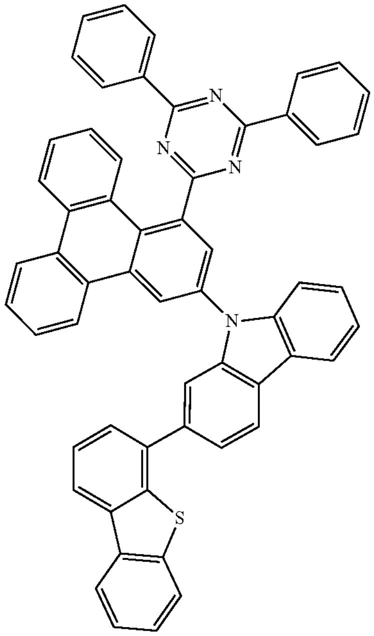
1-13
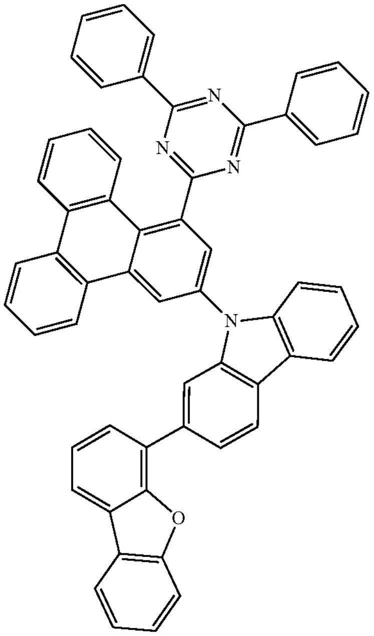
1-14
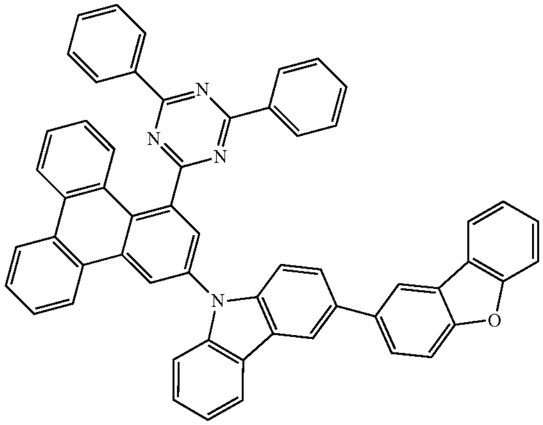

-continued
1-15
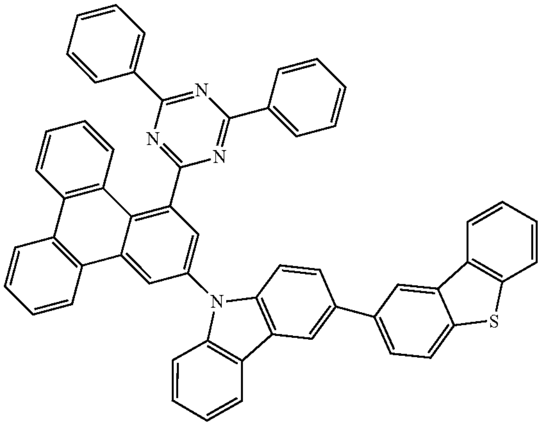
1-16
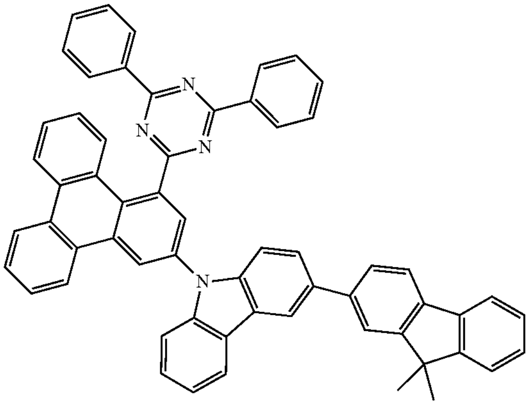
1-17
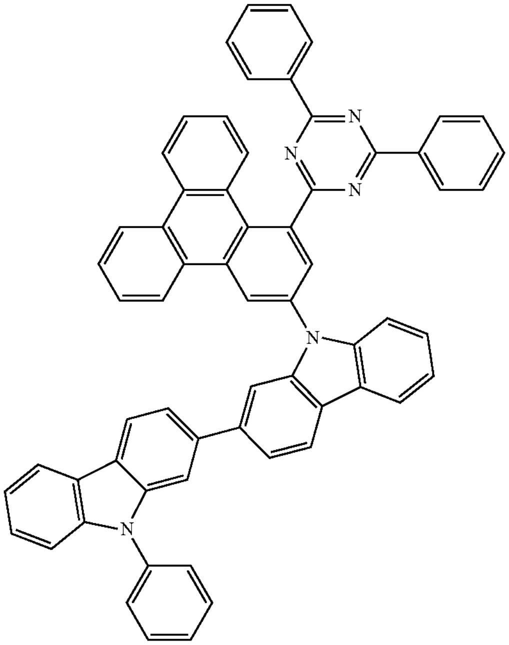
1-18
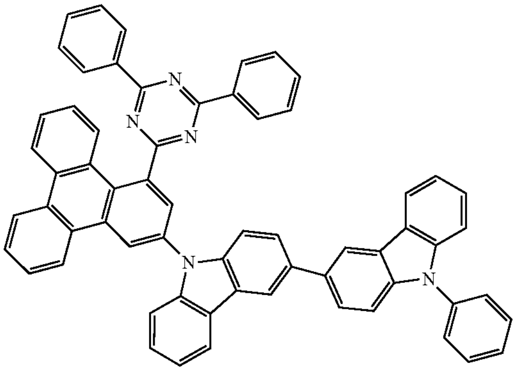
1-19
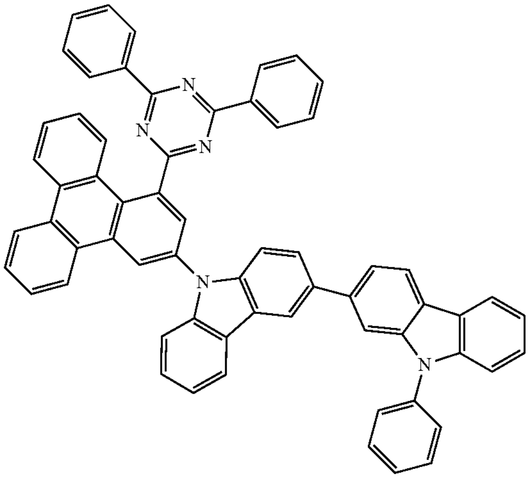
1-20
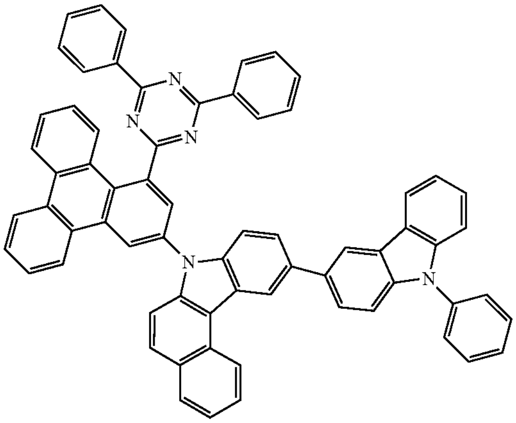

-continued
1-21
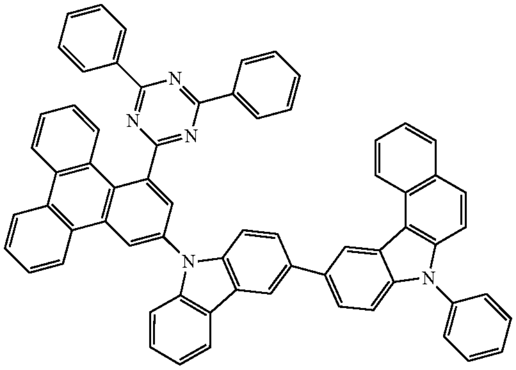
1-22
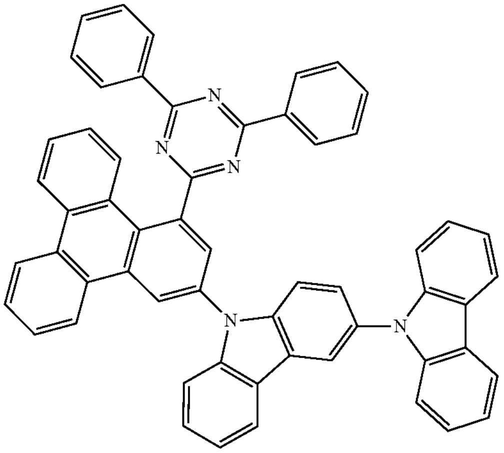
1-23
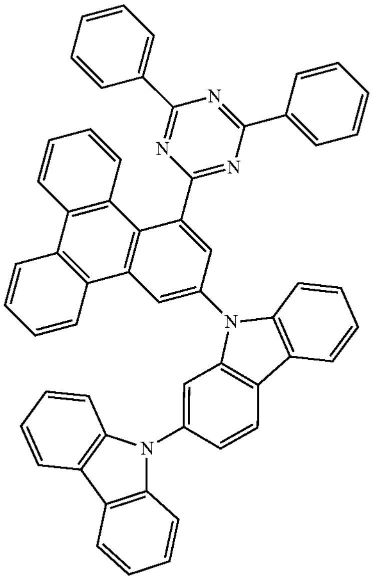
1-24
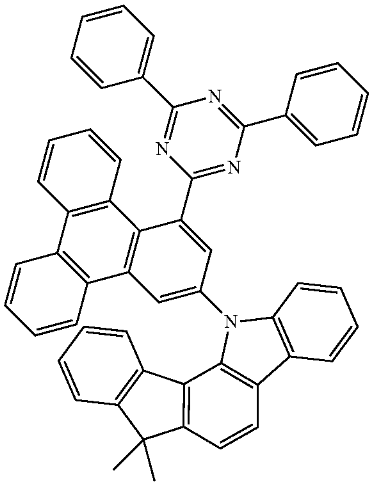
1-25
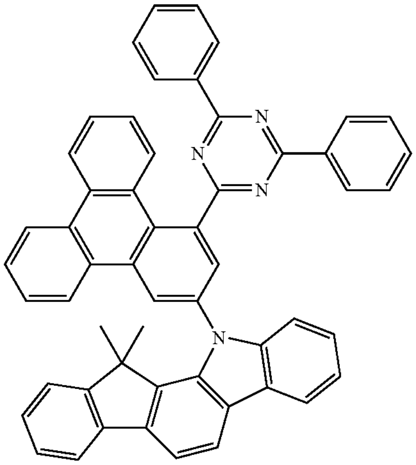
1-26
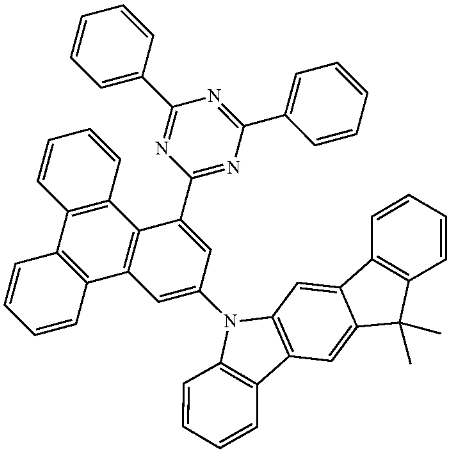

-continued
1-27
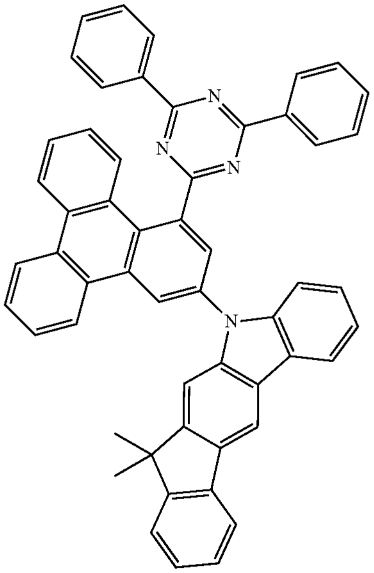
1-28
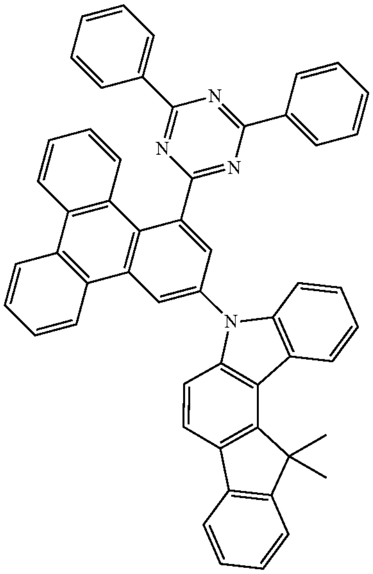
1-29
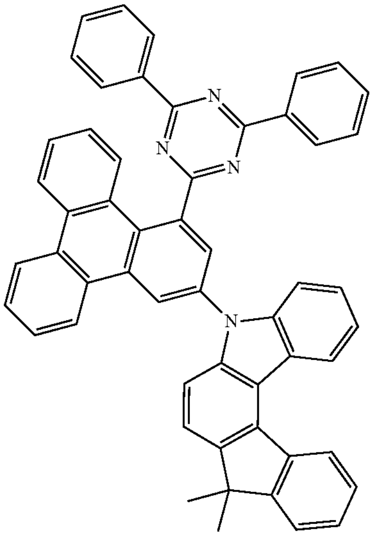
1-30
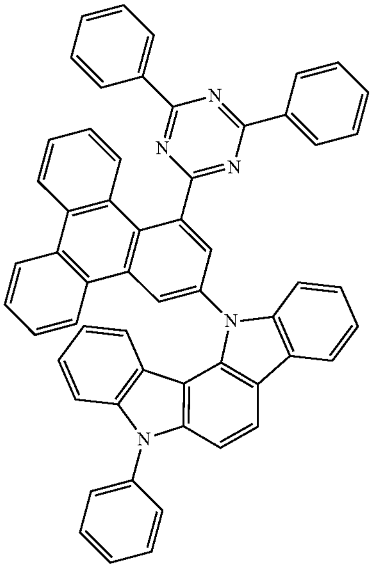

-continued
1-31
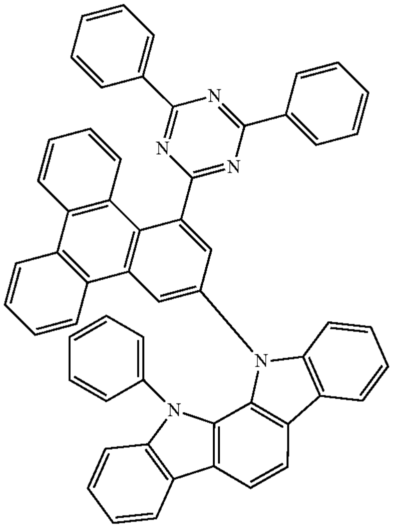
1-32
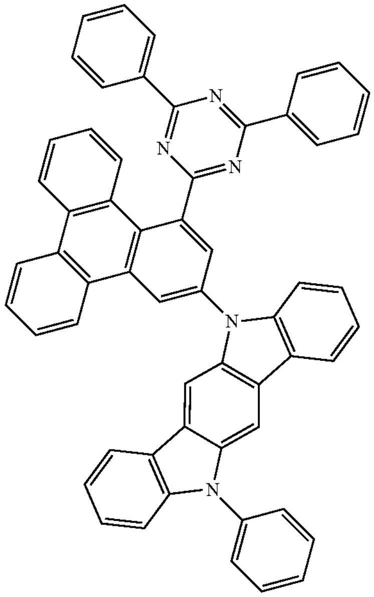
1-33
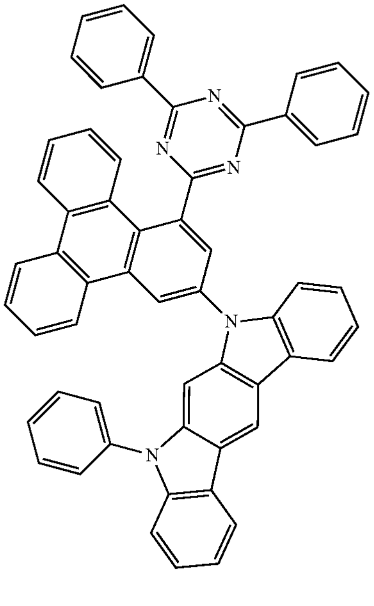
1-34
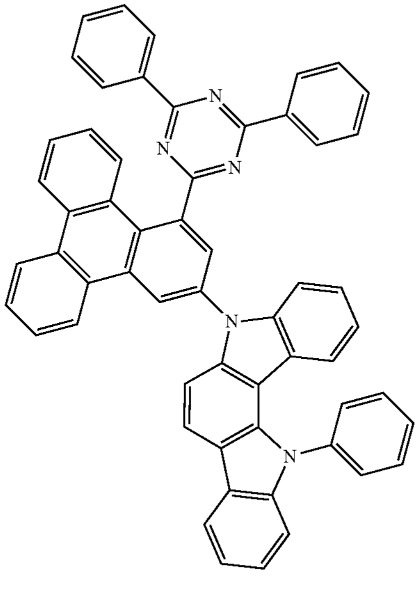

-continued
1-35
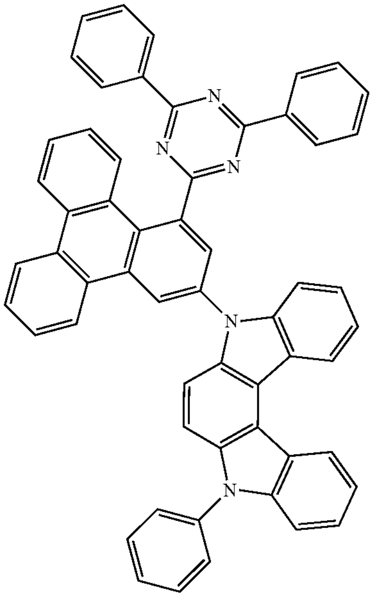
1-36
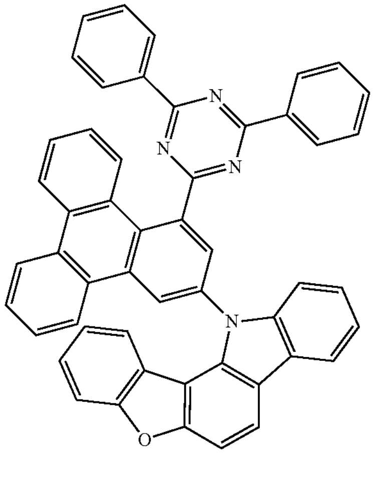
1-37
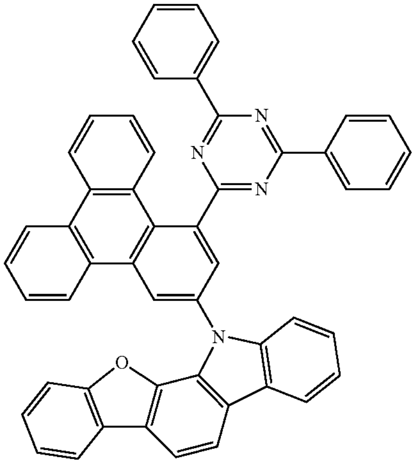
1-38
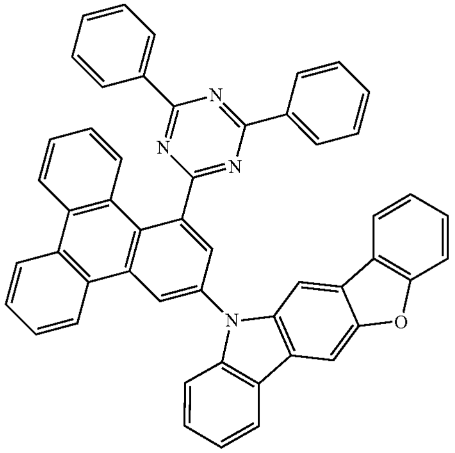
1-39
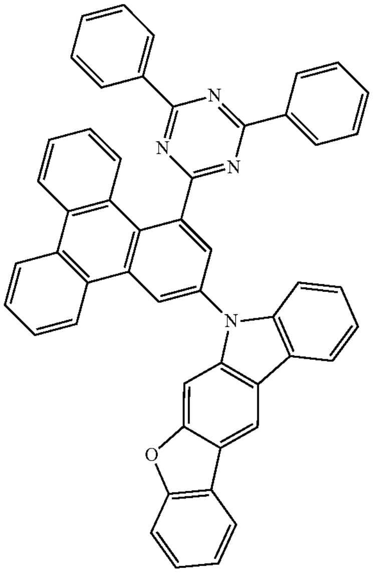
1-40
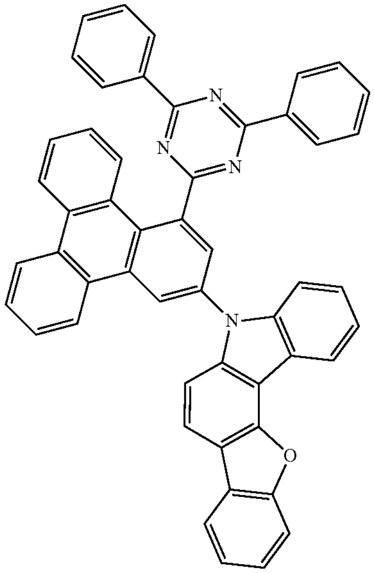

-continued
1-41
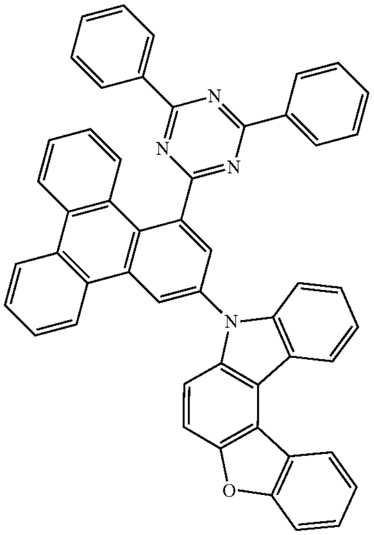
1-42
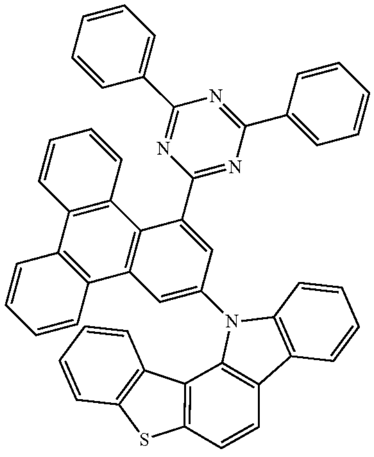
1-43
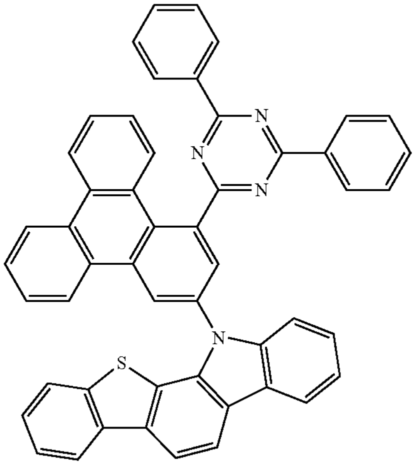
1-44
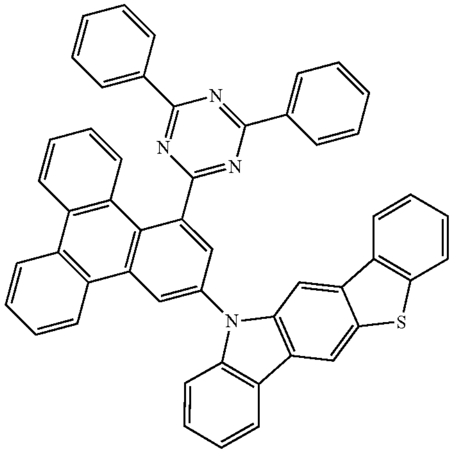
1-45
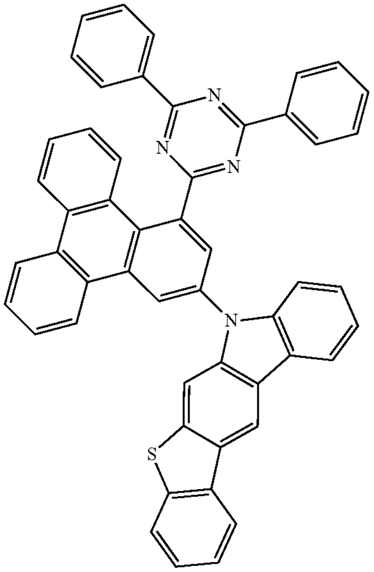
1-46
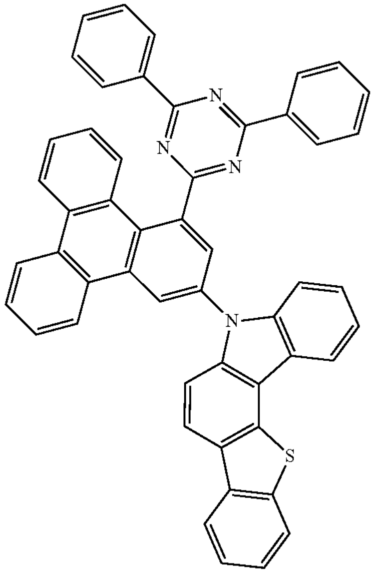

-continued
1-47
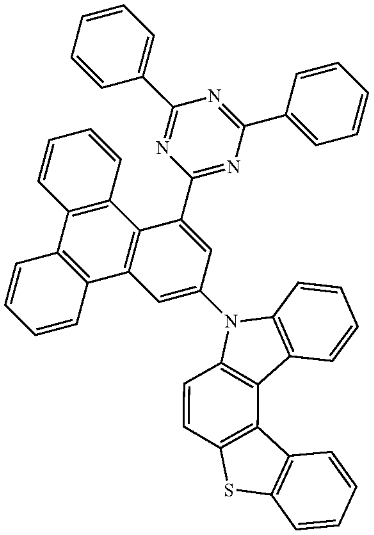
1-48
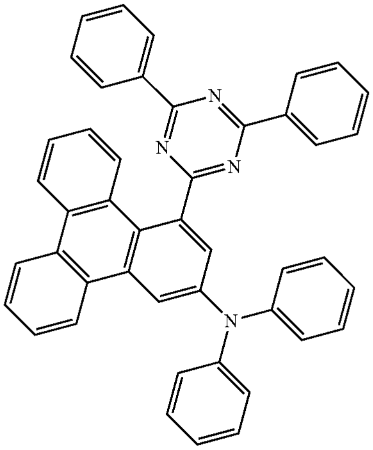
1-49
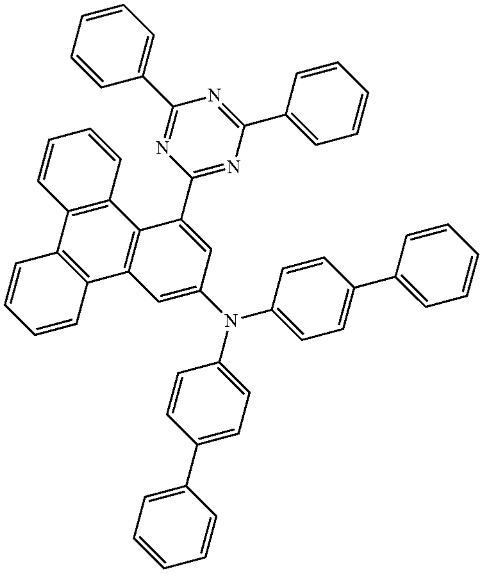
1-50
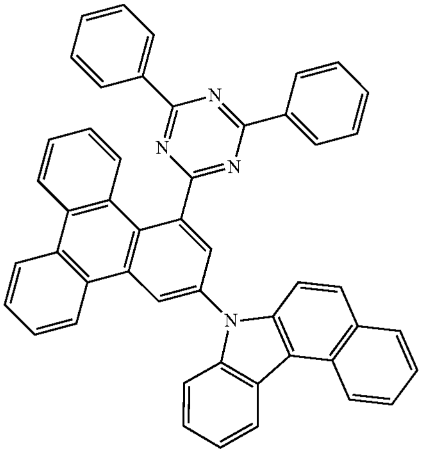
1-51
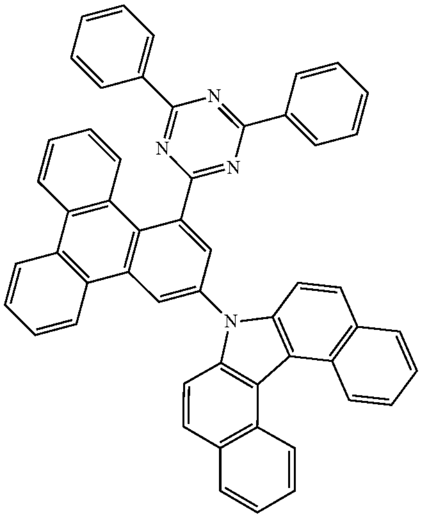
1-52
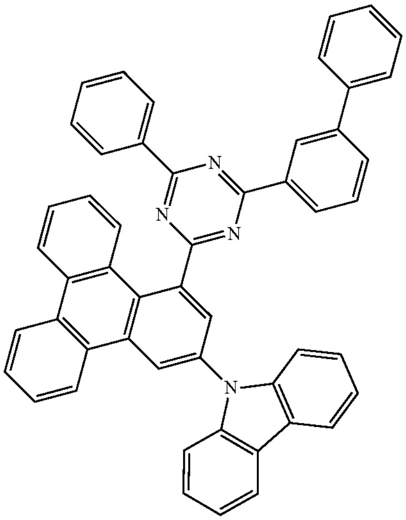

-continued
1-53
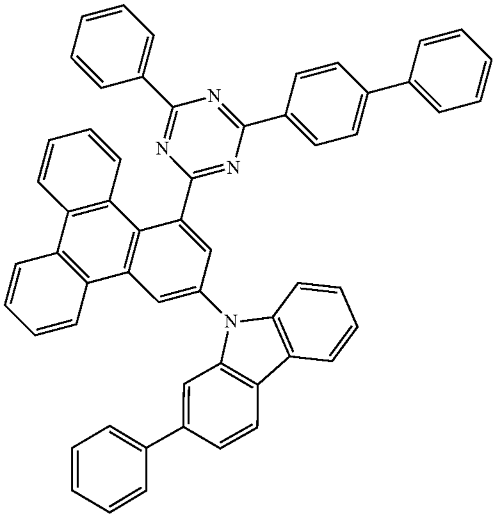
1-54
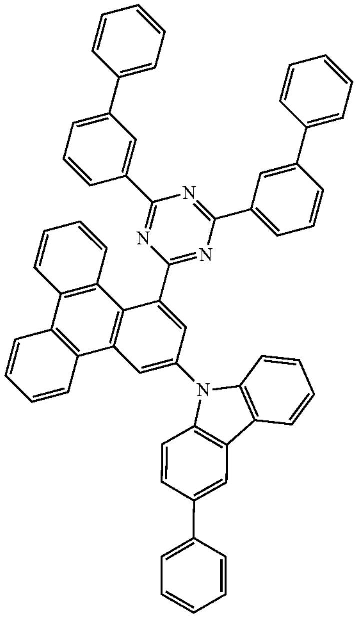
1-55
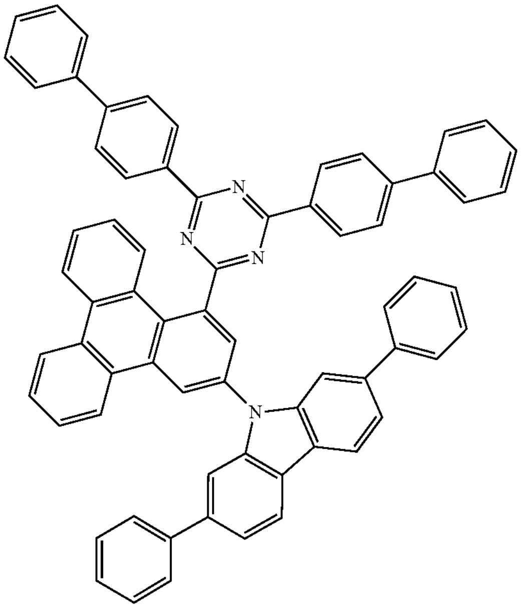
1-56
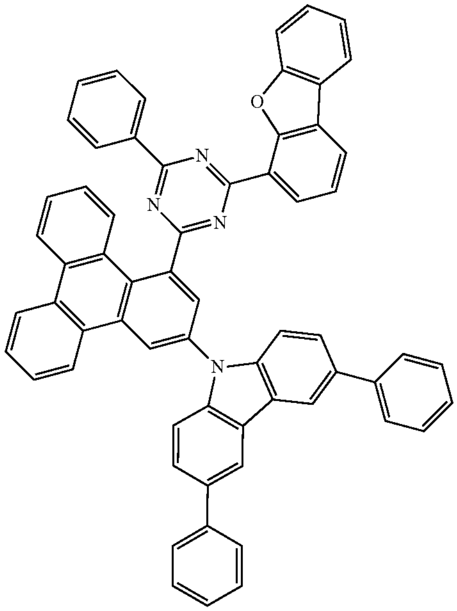

-continued
1-57
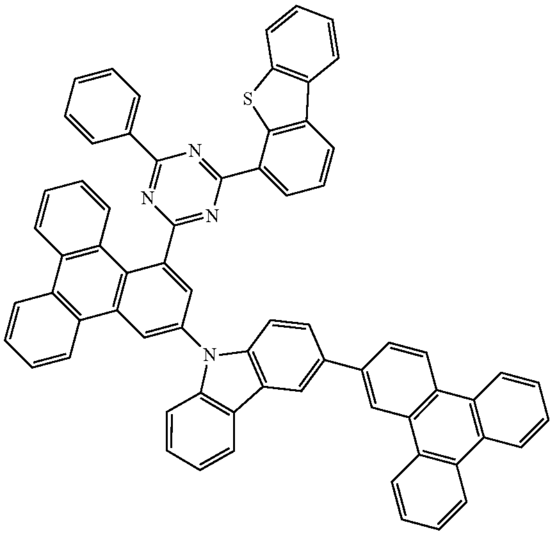
1-58
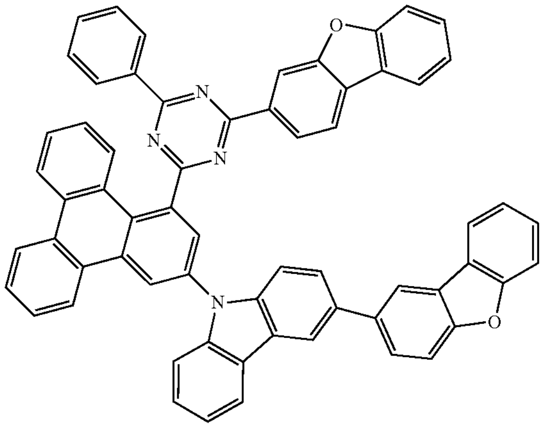
1-59
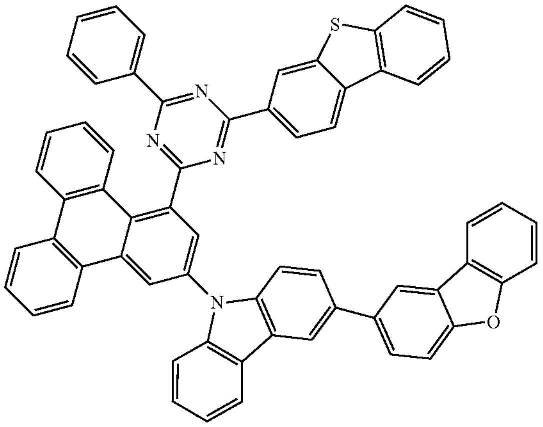
1-60
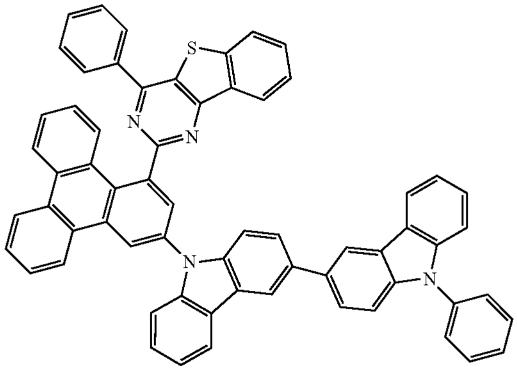
1-61
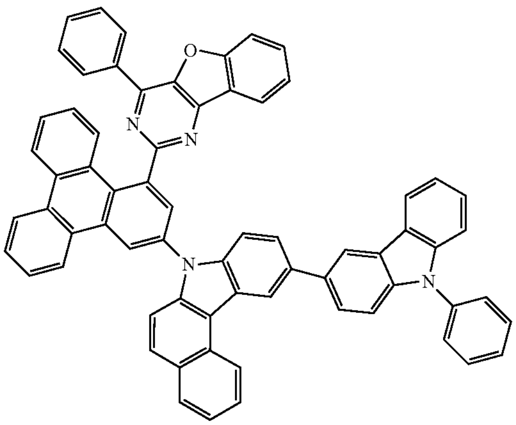
1-62
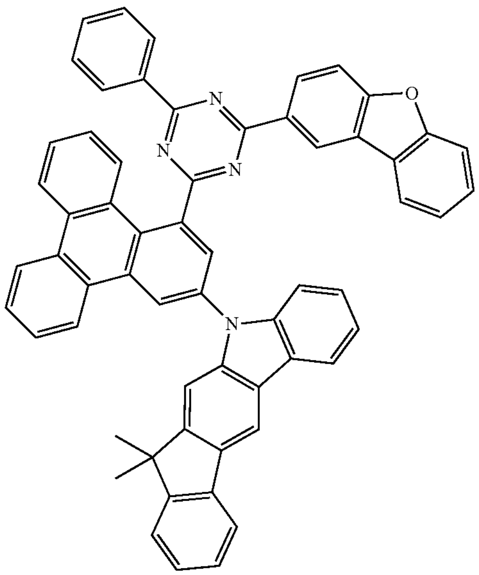

-continued
1-63
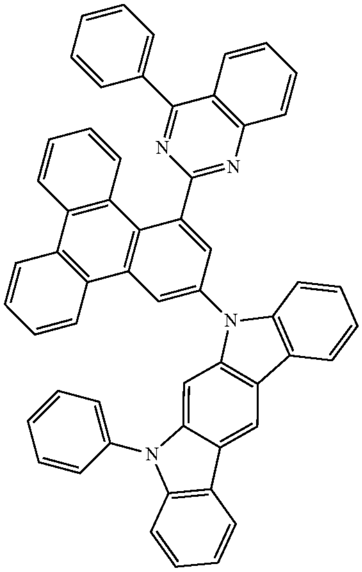
1-64
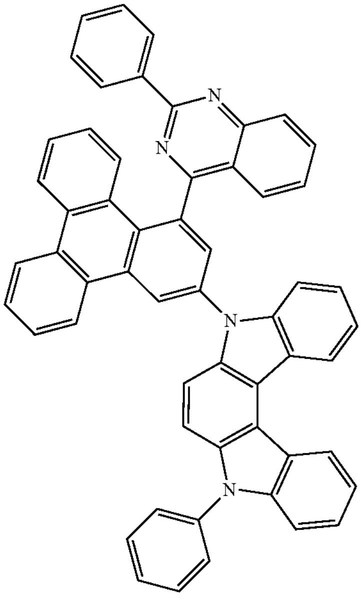
1-65
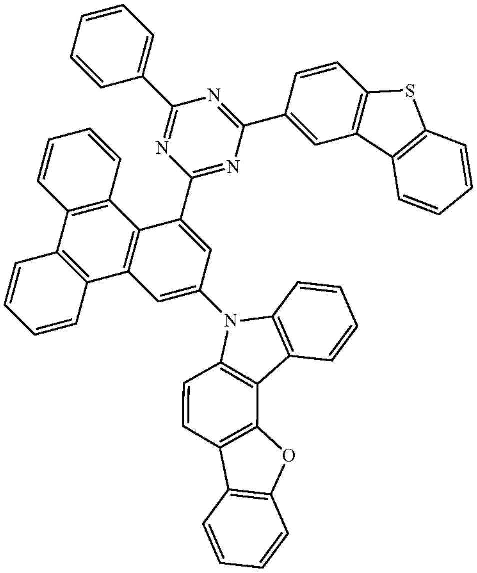
1-66
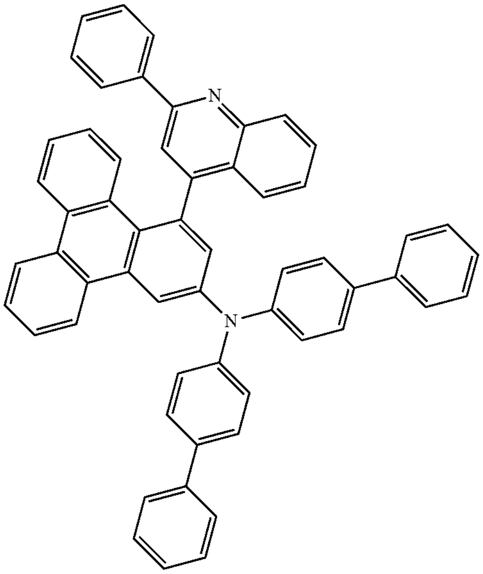

-continued
1-67
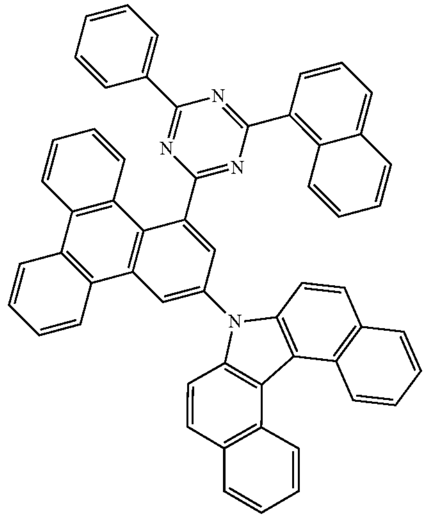
1-68
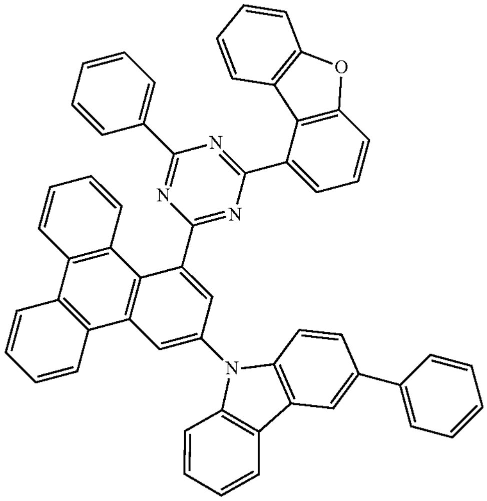
1-69
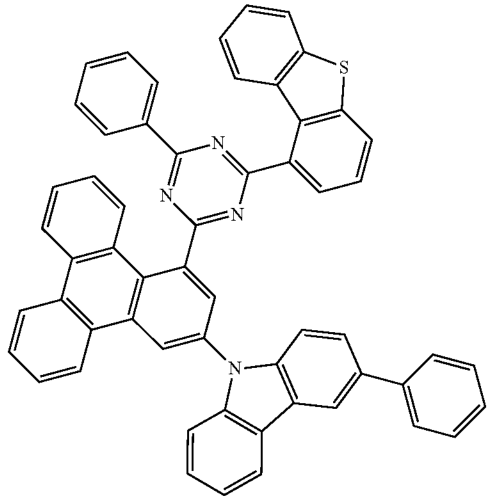
1-70
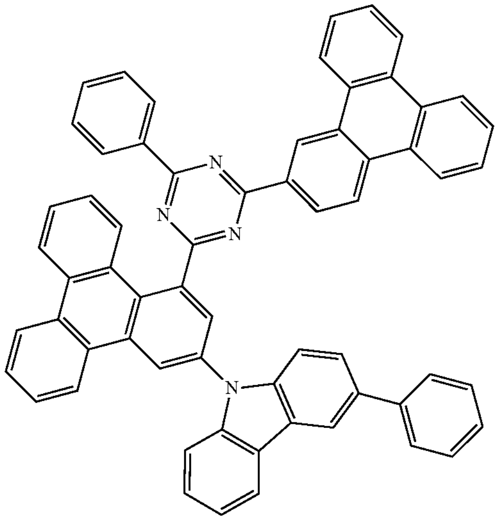
1-71
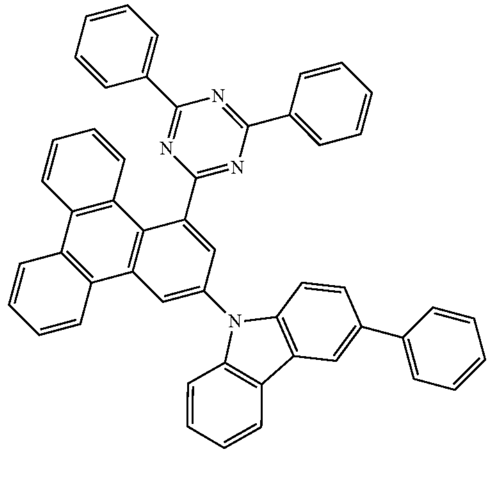
1-72
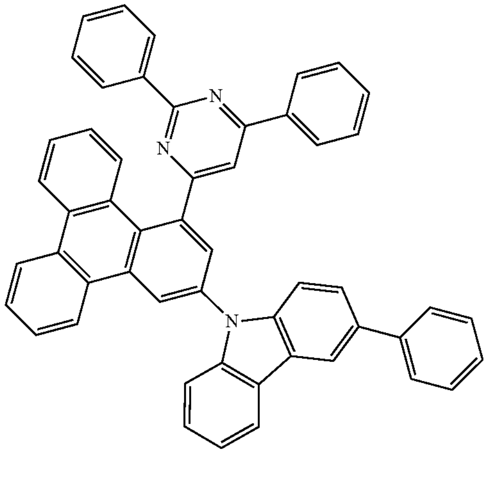

-continued
1-73
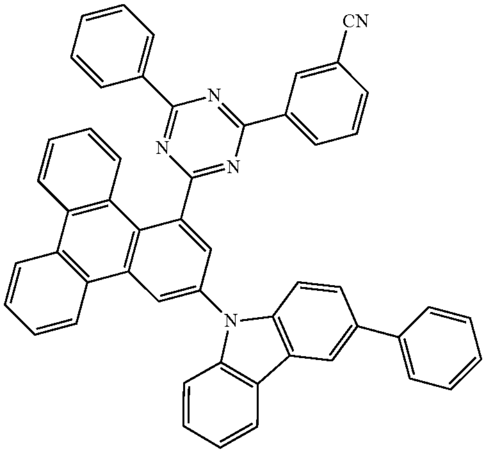
1-74
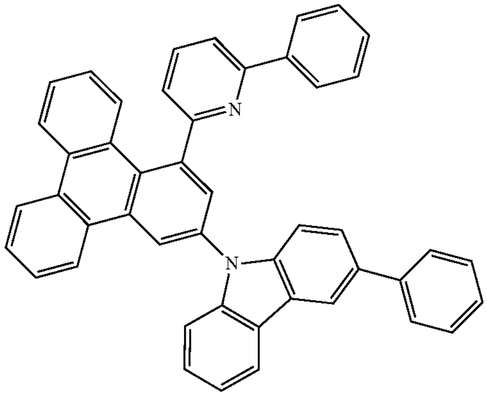
1-75
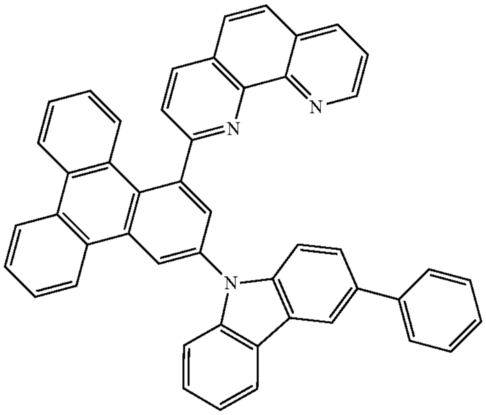
1-76
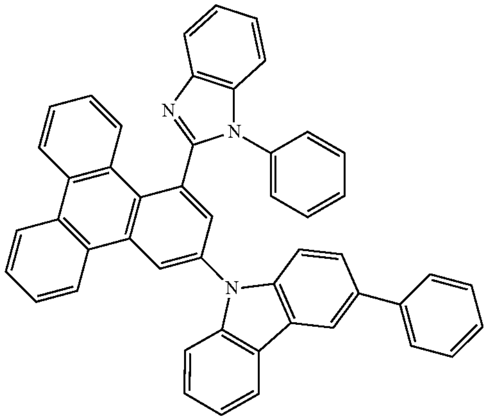
1-77
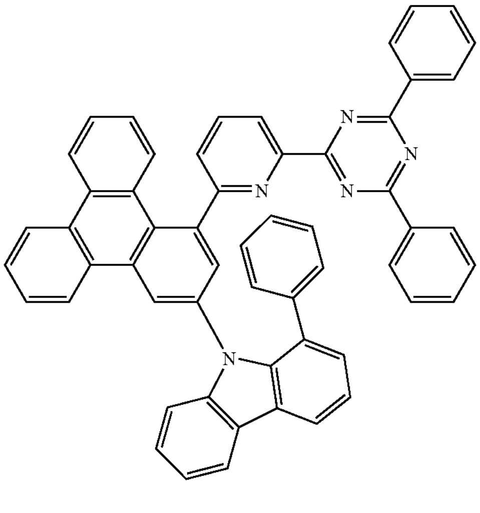
1-78
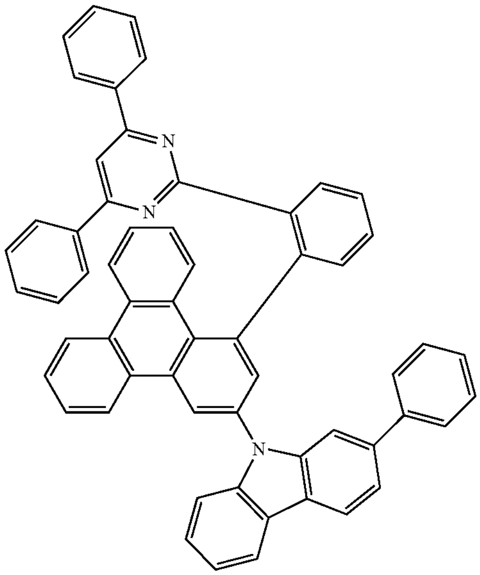

-continued
1-79
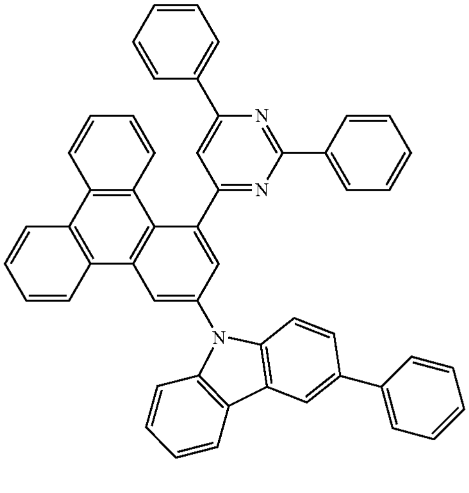
1-80
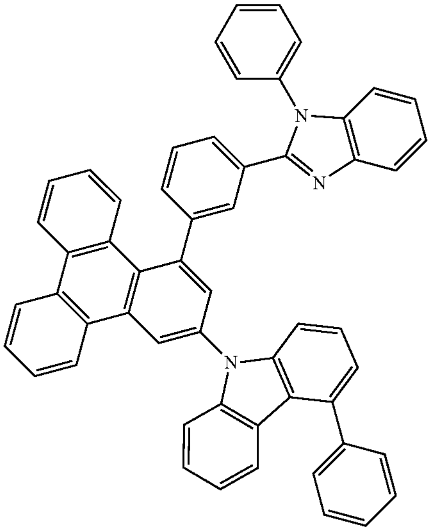
1-81
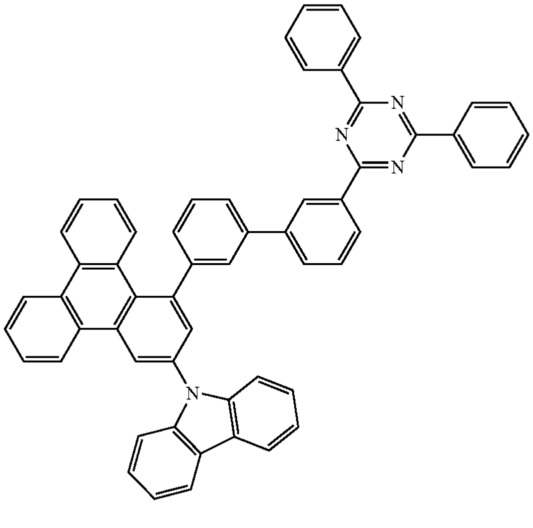
1-82
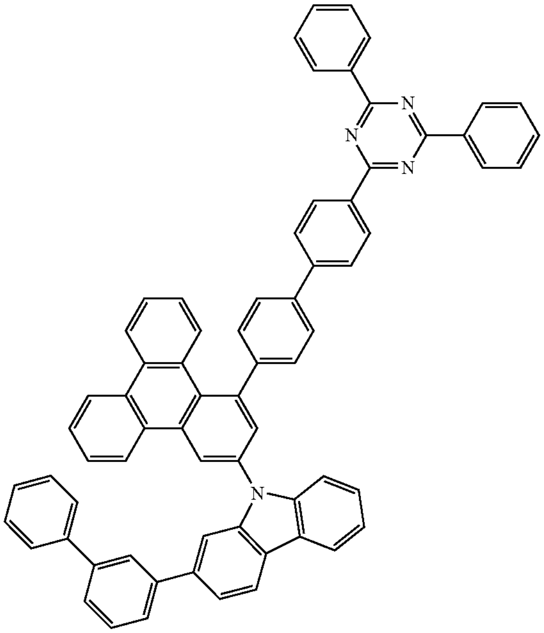

-continued
1-83
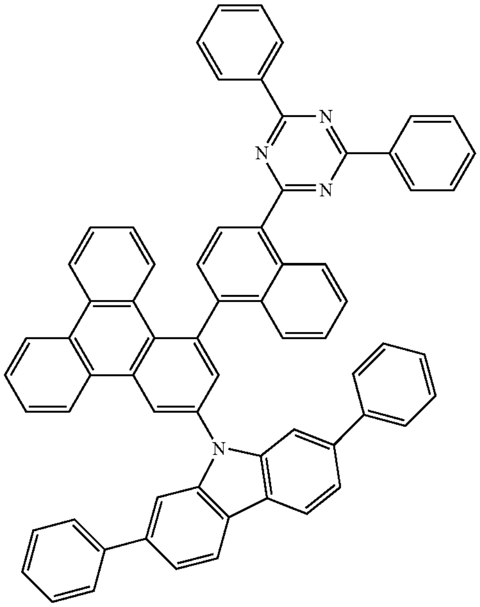
1-84
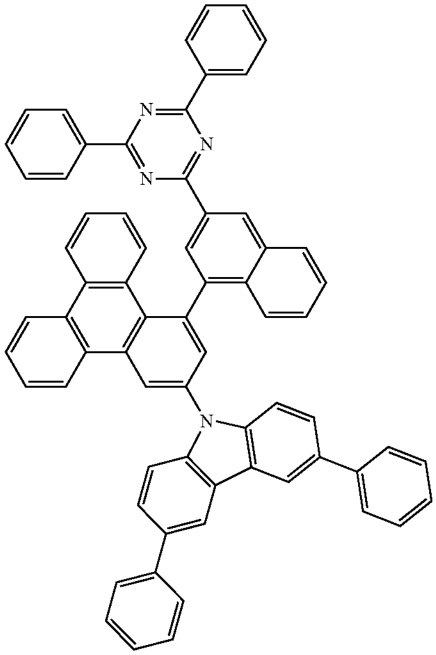
1-85
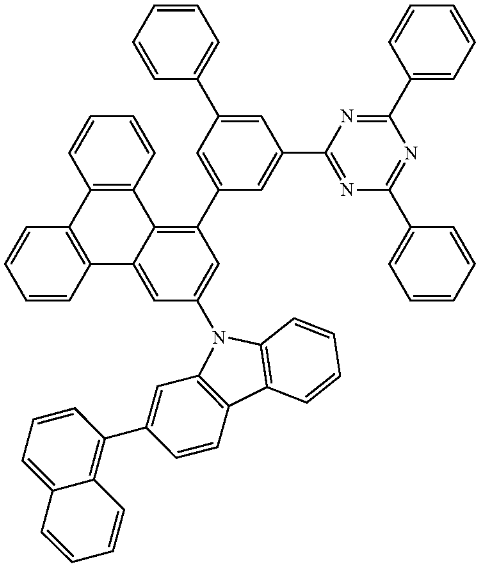
1-86
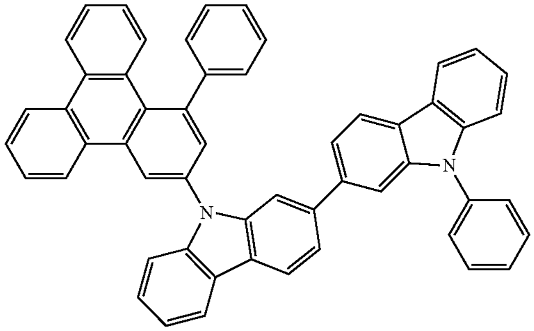

-continued
1-87
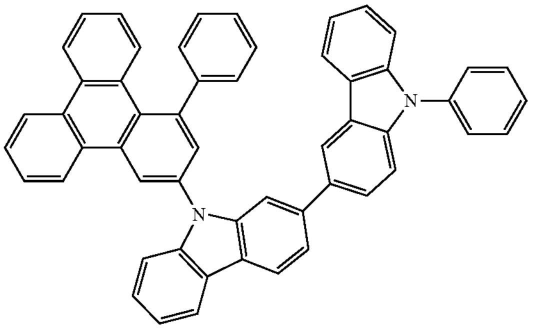
1-88
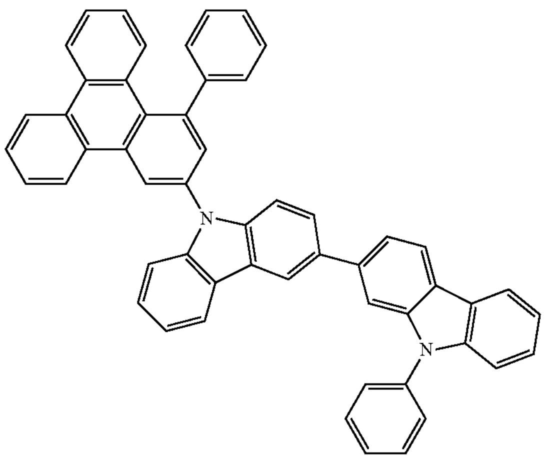
1-89
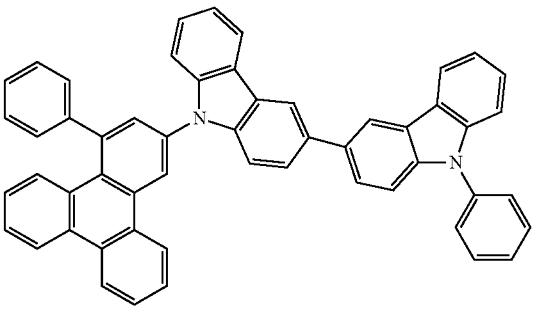
1-90
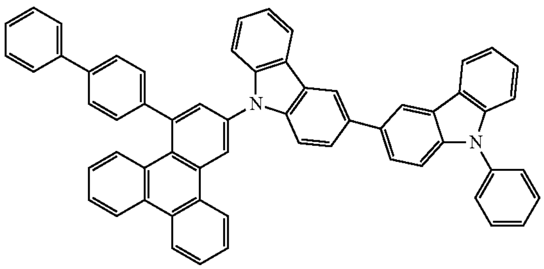
1-91
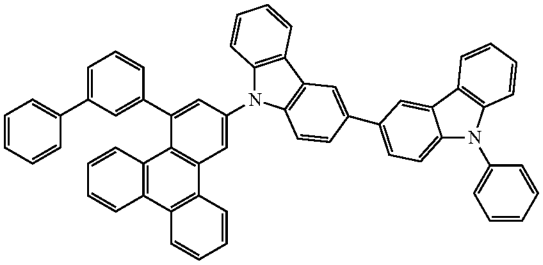
1-92
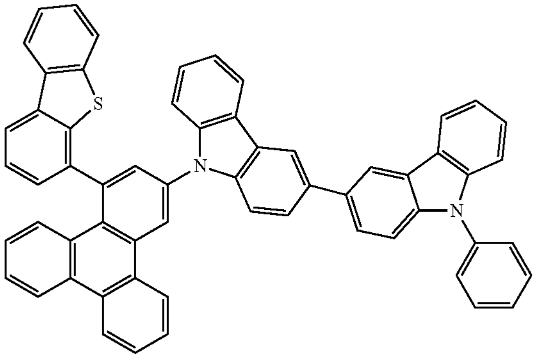
1-93
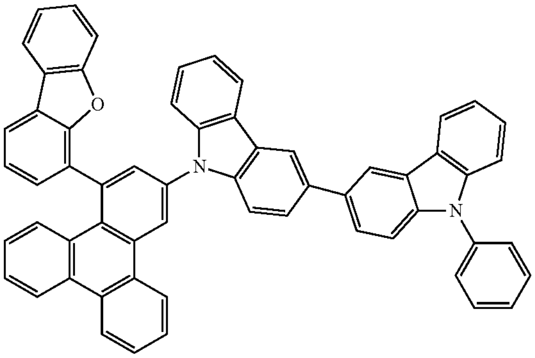
1-94
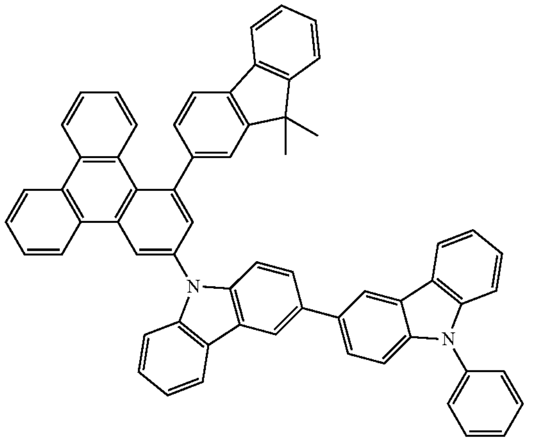

-continued
1-95
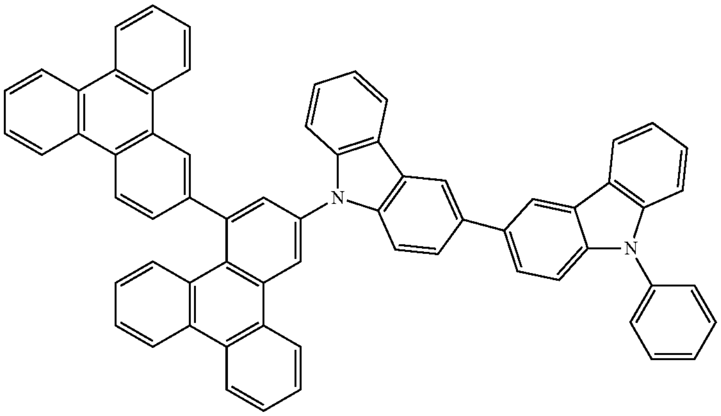
1-96
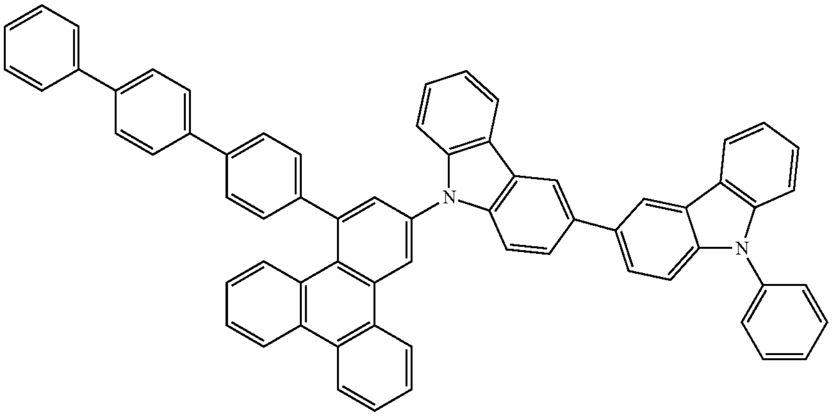
1-97
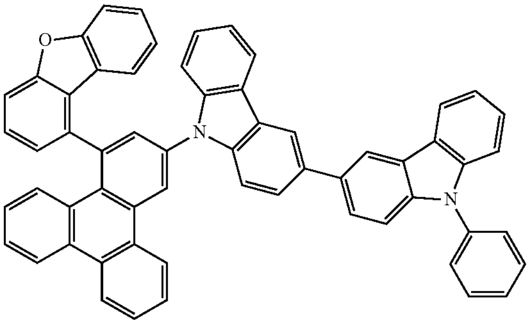
1-98
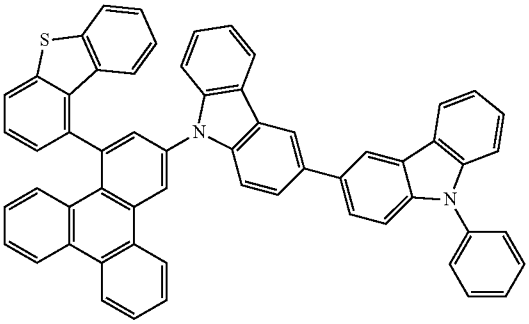
1-99
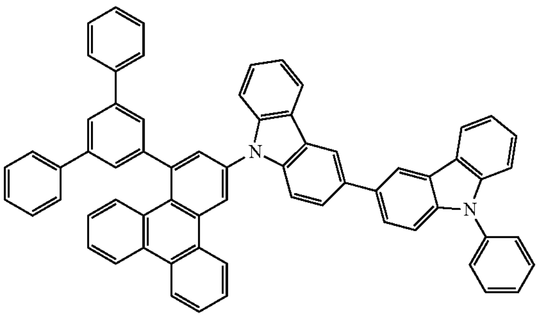
1-100
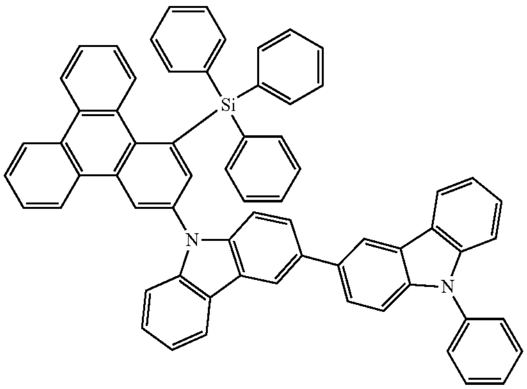

-continued
1-101
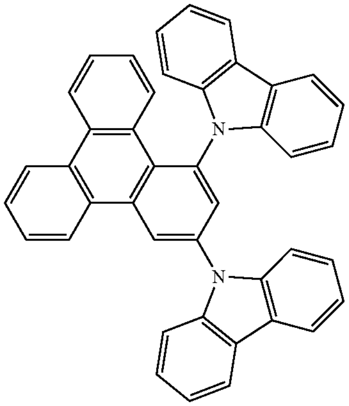
1-102
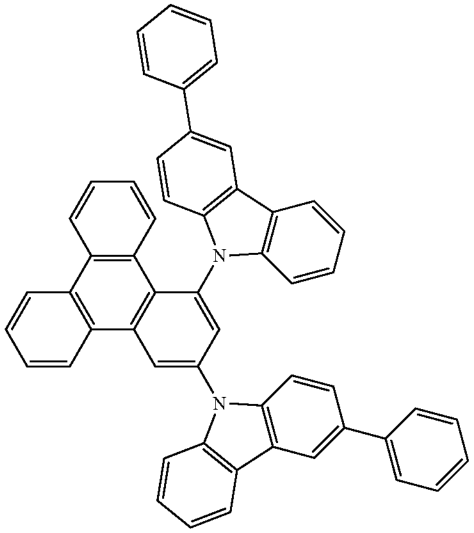
1-103
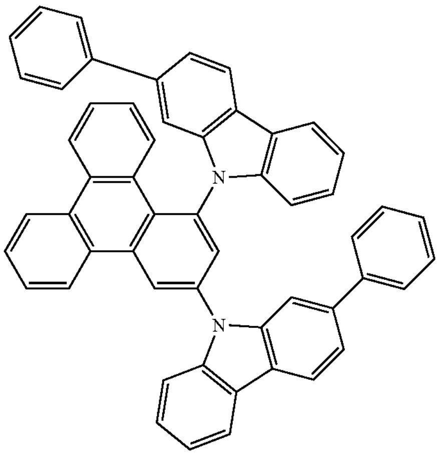
1-104
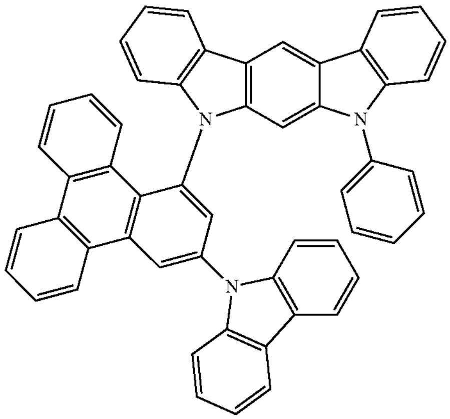
1-105
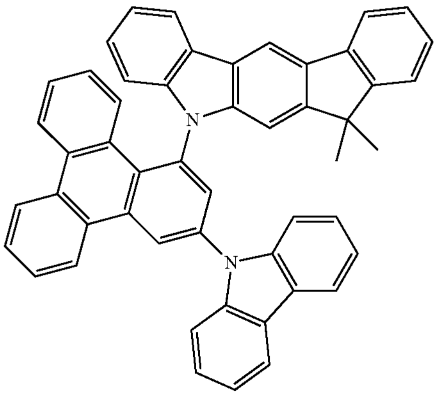
1-106
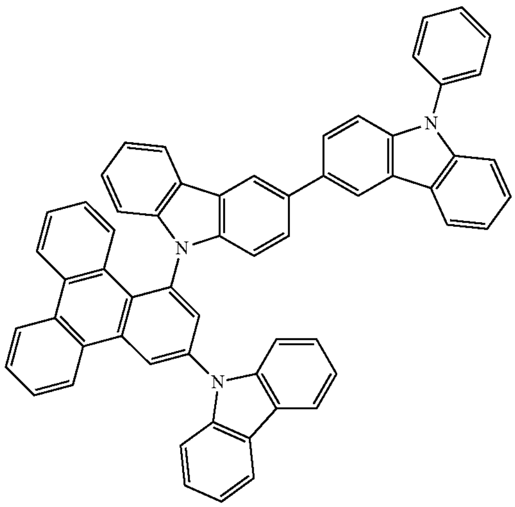

-continued
1-107
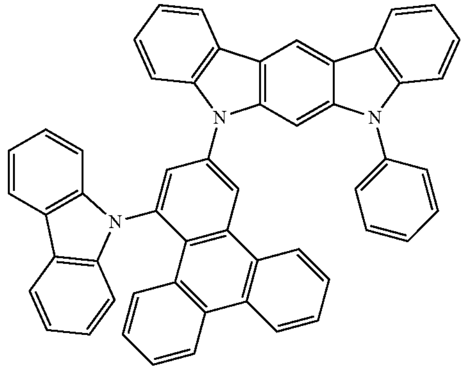
1-108
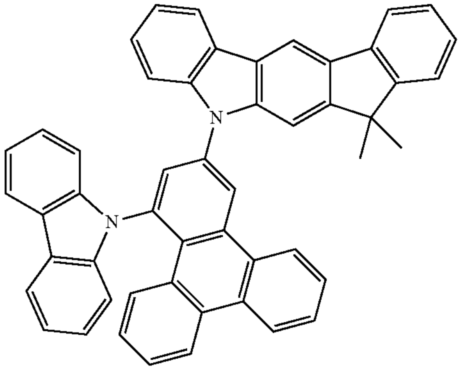
1-109
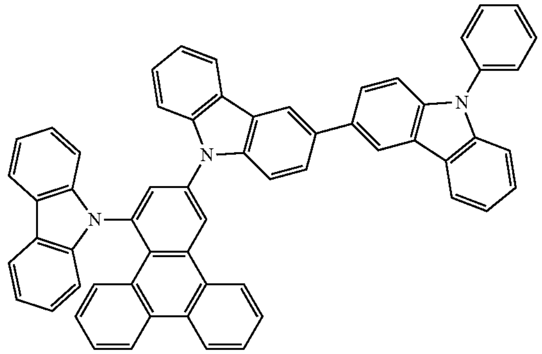
1-110
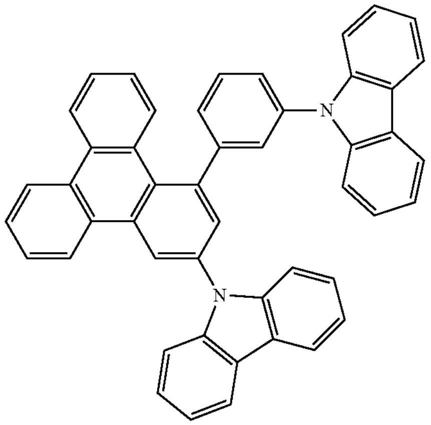
1-111
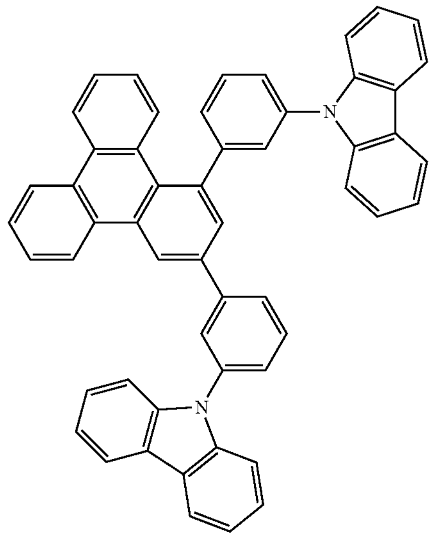
1-112
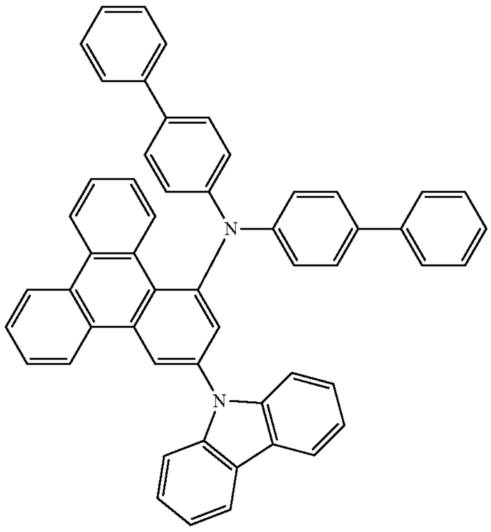

-continued
1-113
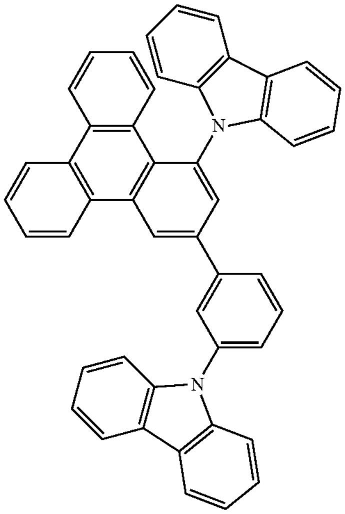
1-114
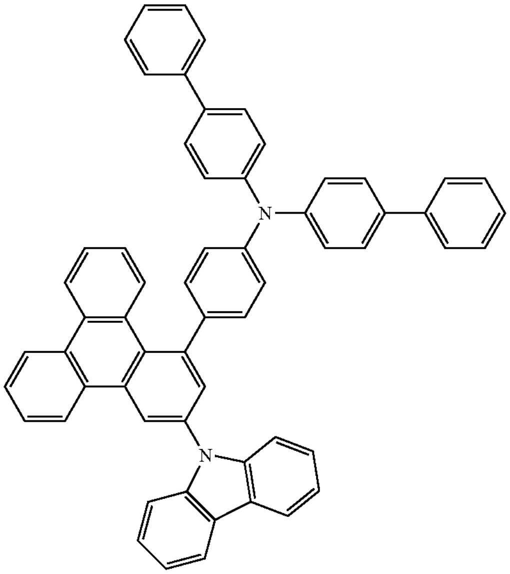
1-115
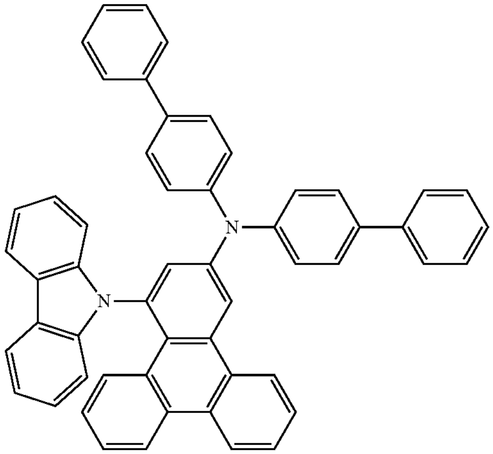
1-116
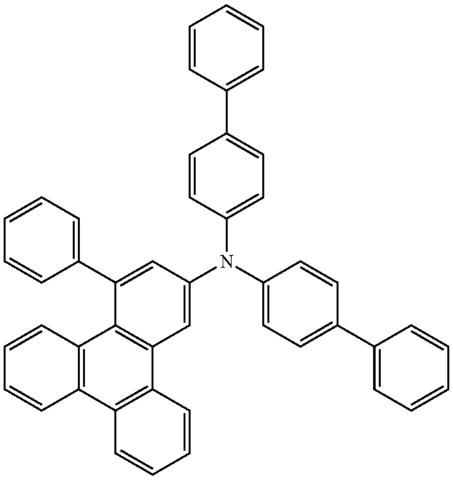
1-117
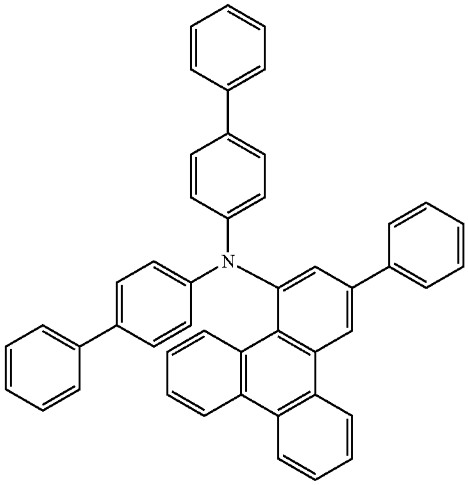
1-118
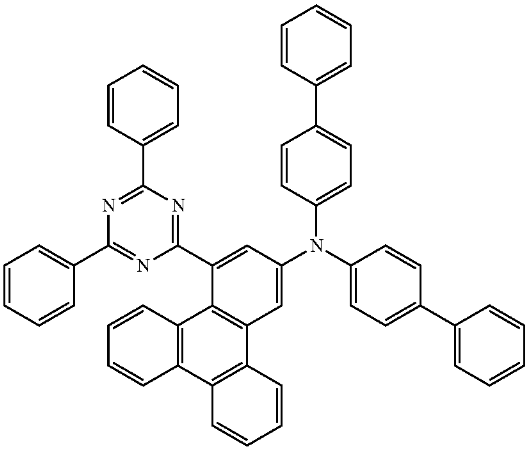

-continued
1-119
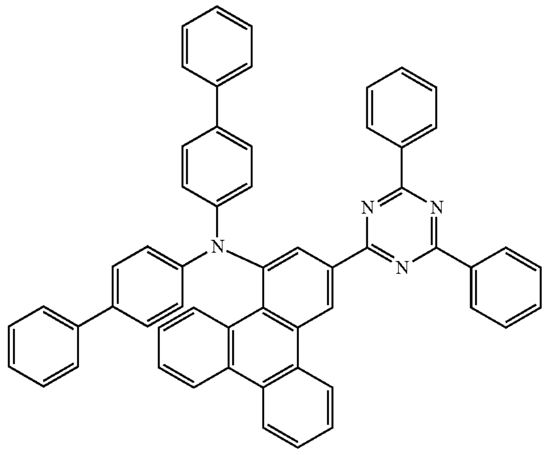
2-1
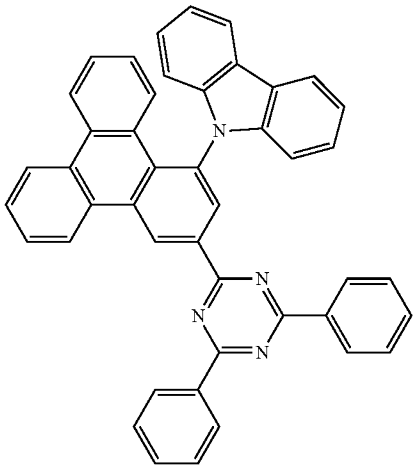
2-2
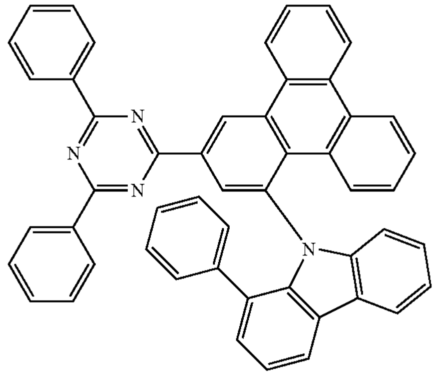
2-3
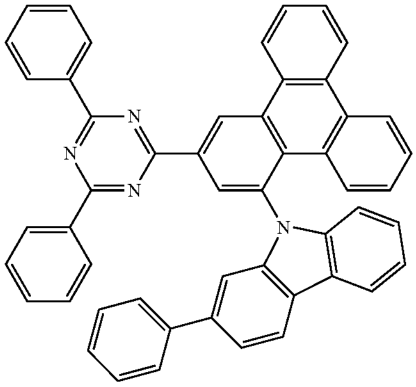
2-4
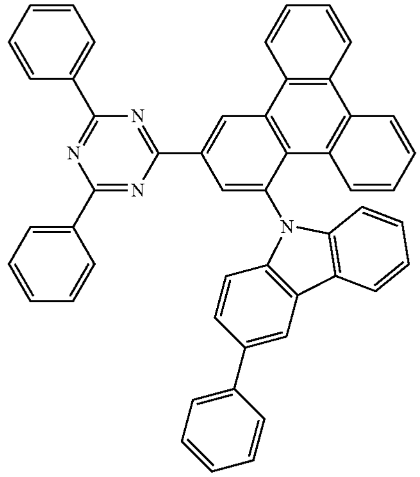
2-5
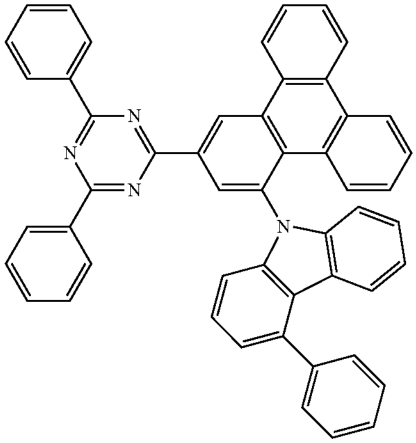

-continued
2-6
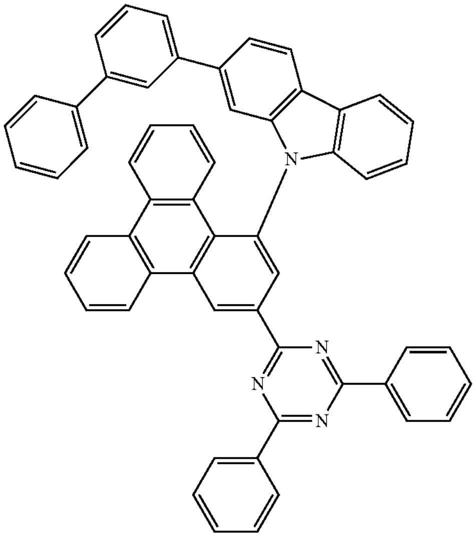
2-7
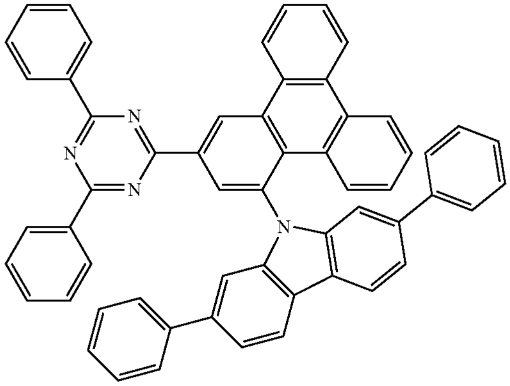
2-8
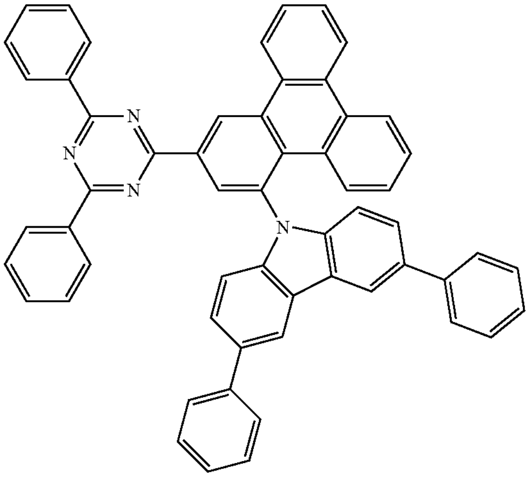
2-9
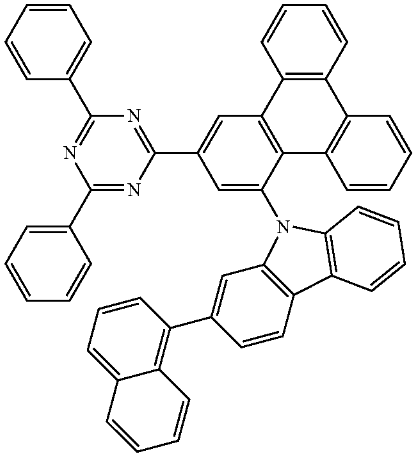
2-10
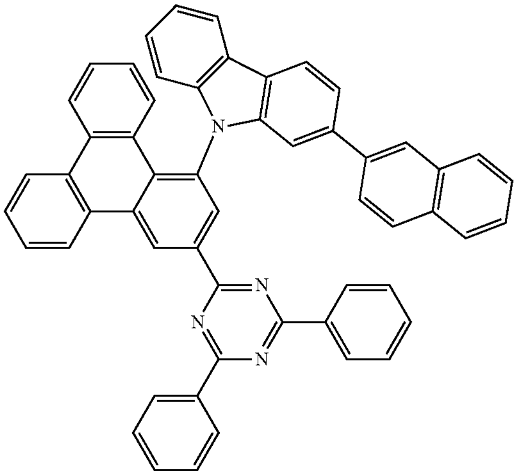
2-11
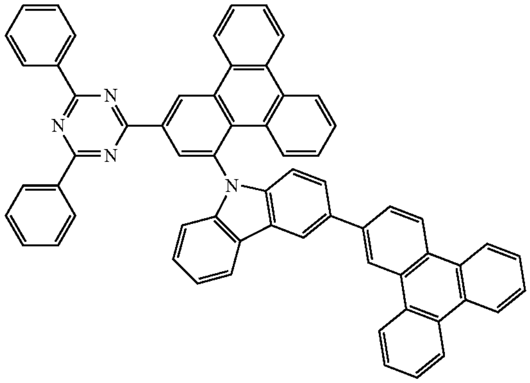

-continued
2-12
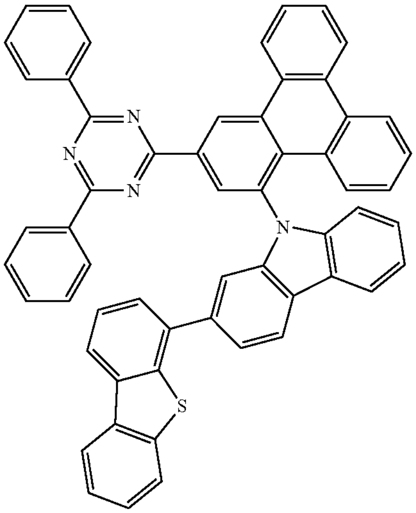
2-13
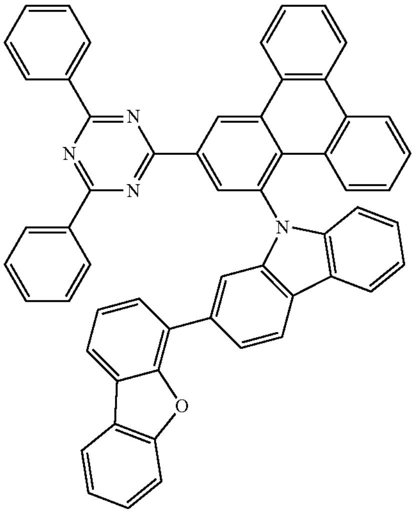
2-14
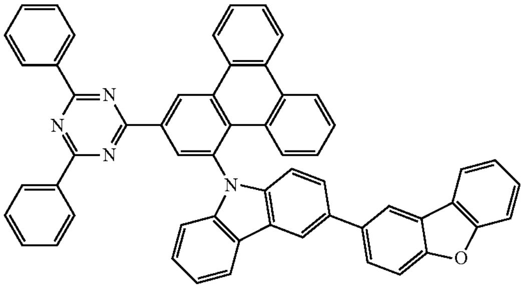
2-15
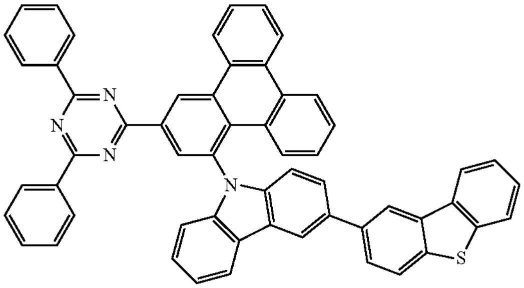
2-16
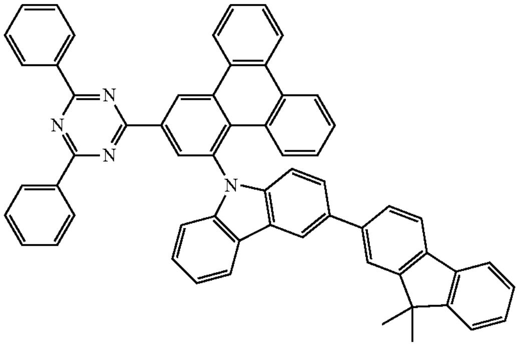
2-17
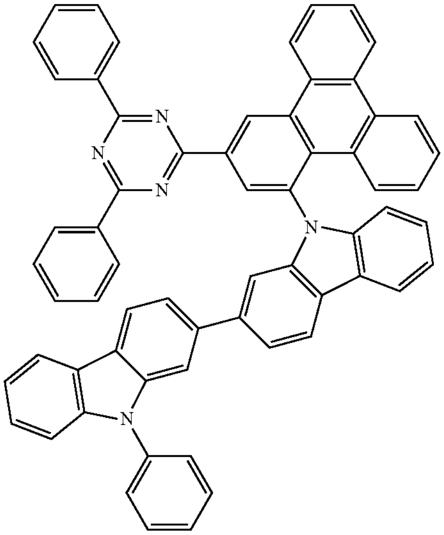

-continued
2-18
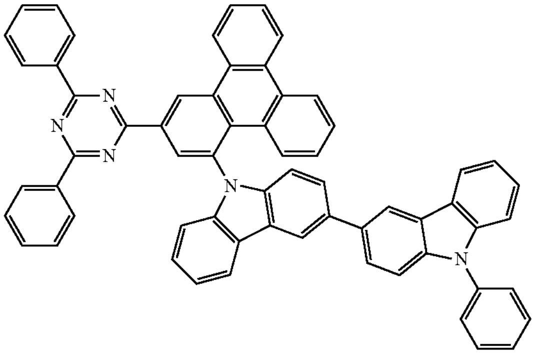
2-19
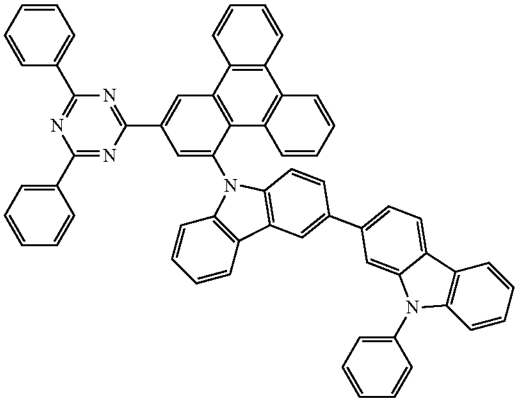
2-20
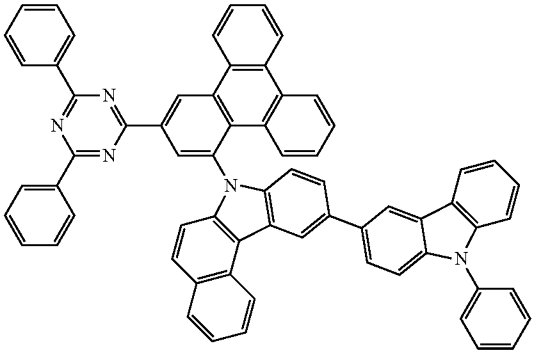
2-21
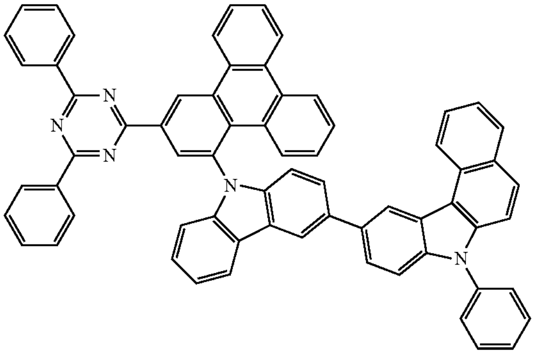
2-22
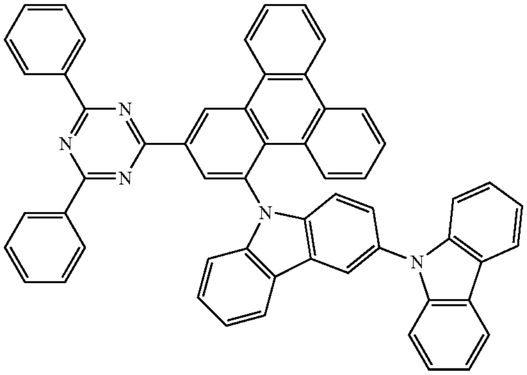
2-23
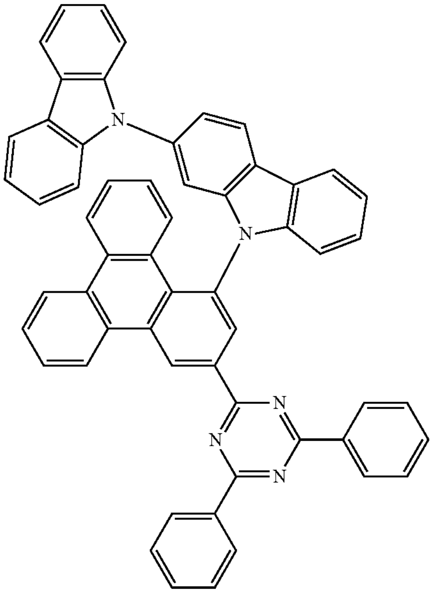

-continued
2-24
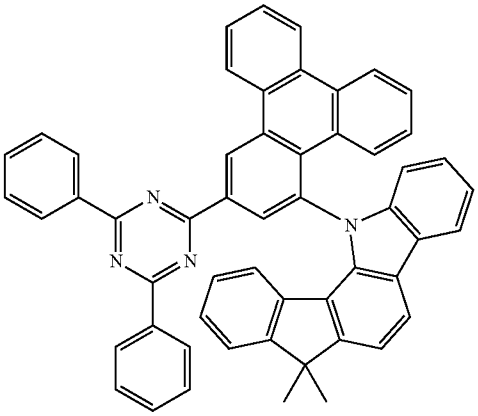
2-25
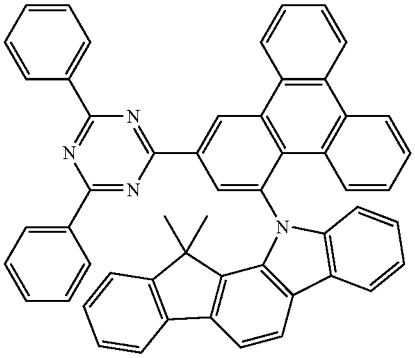
2-26
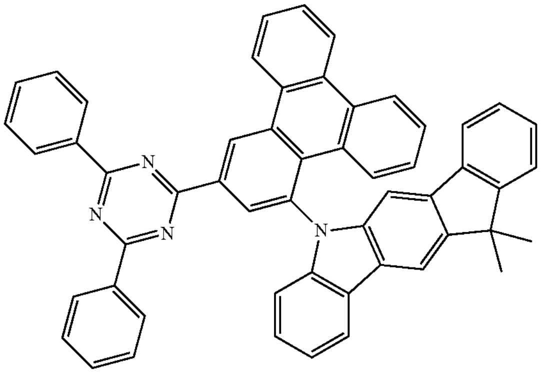
2-27
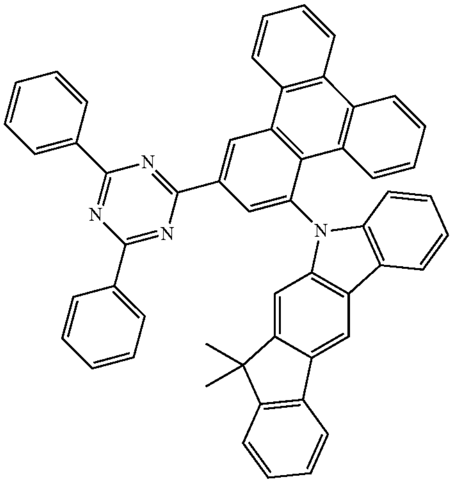
2-28
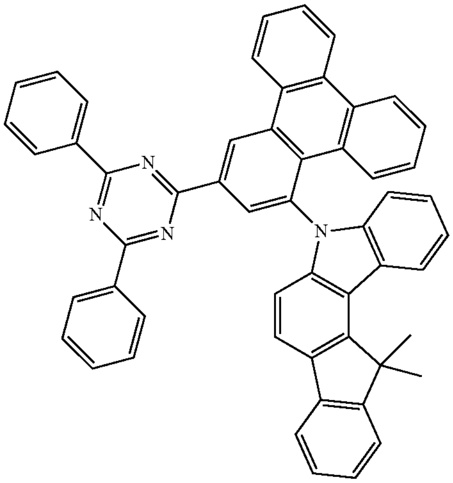
2-29
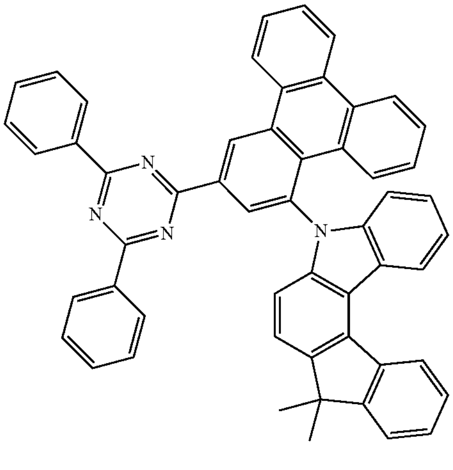

-continued
2-30
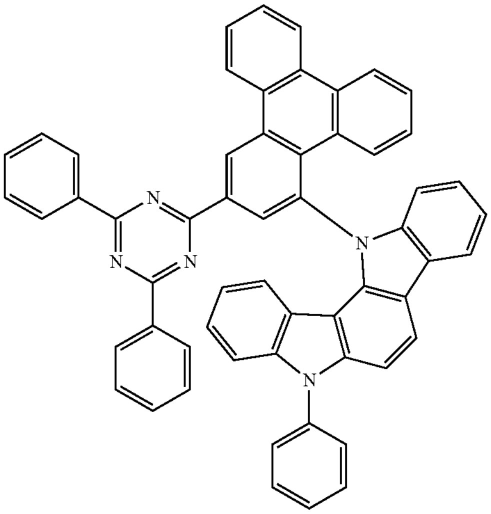
2-31
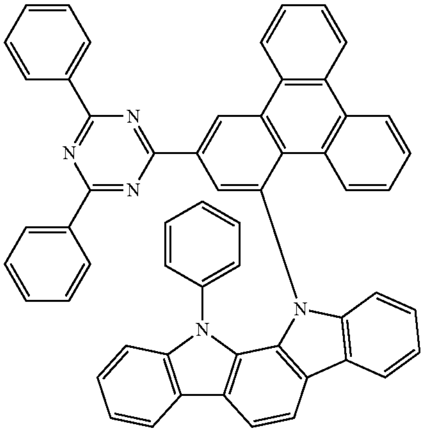
2-32
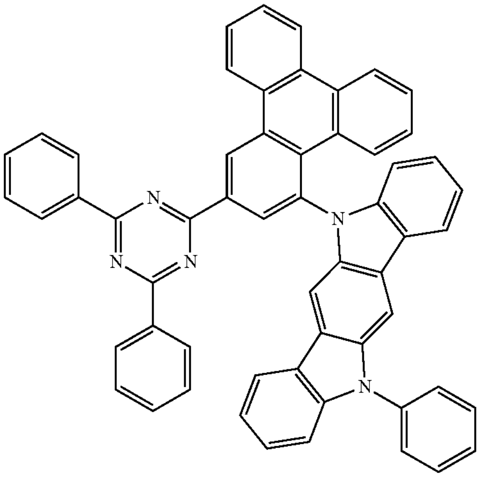
2-33
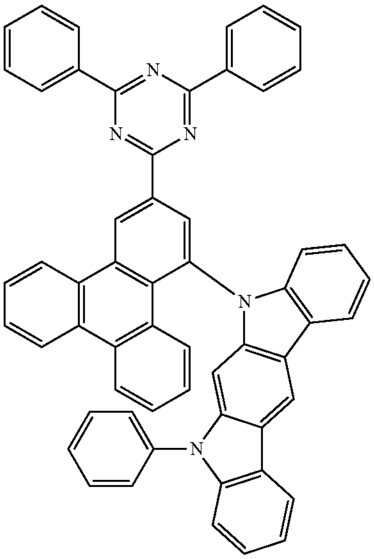
2-34
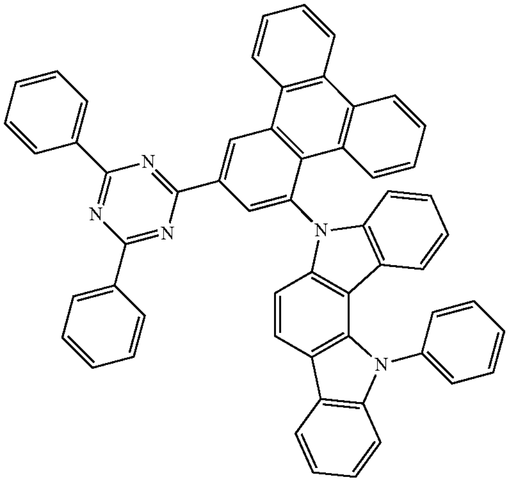
2-35
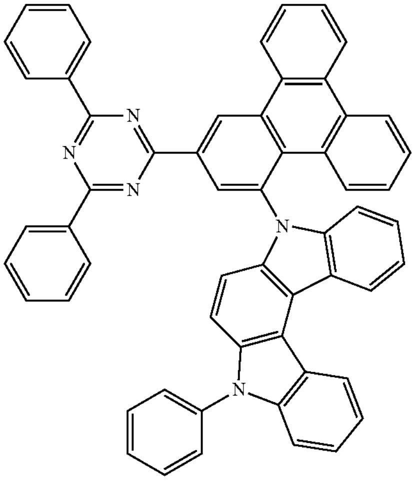

-continued
2-36
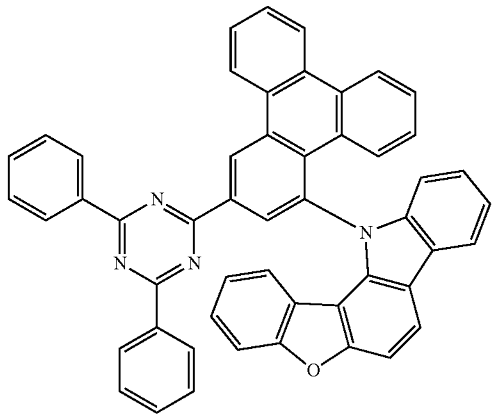
2-37
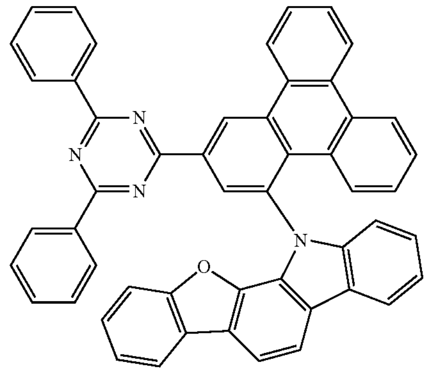
2-38
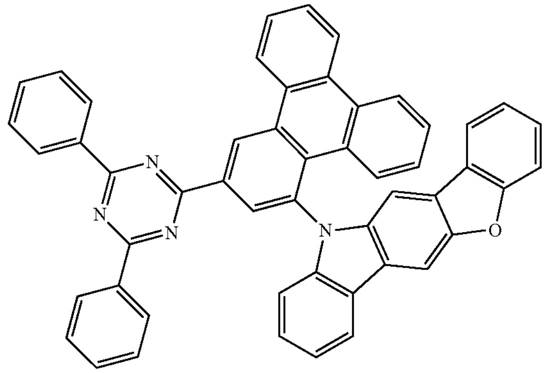
2-39
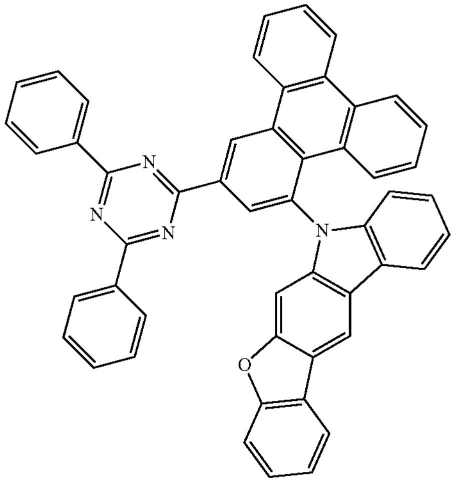
2-40
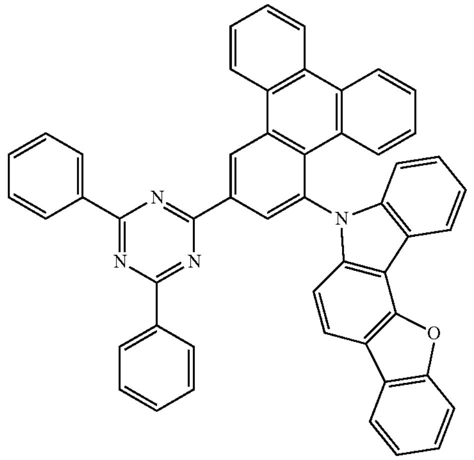
2-41
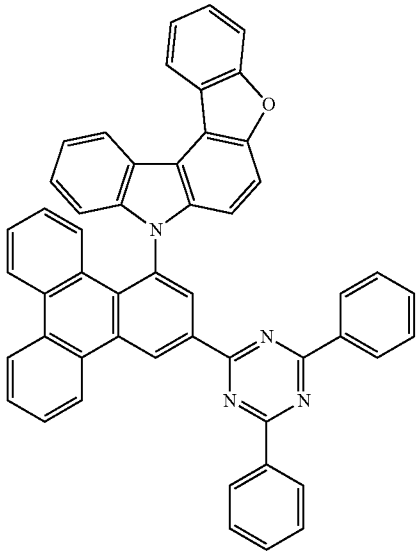

-continued
2-42
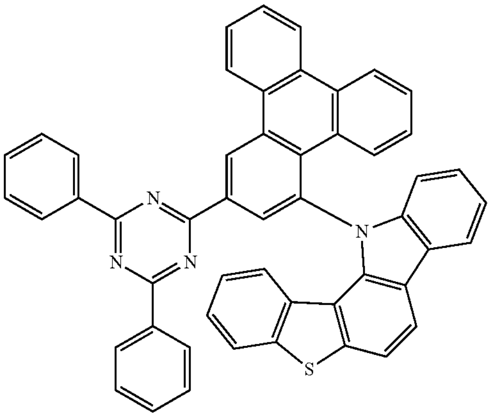
2-43
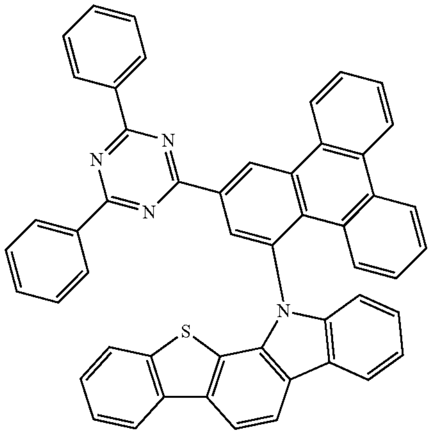
2-44
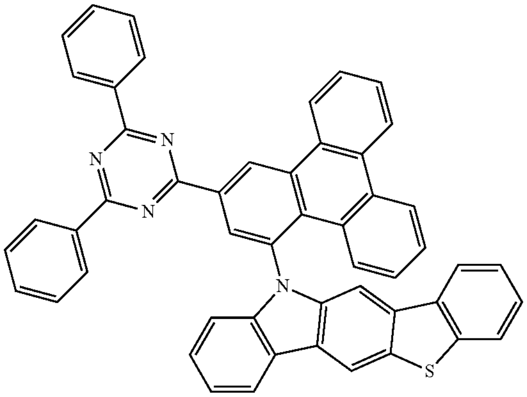
2-45
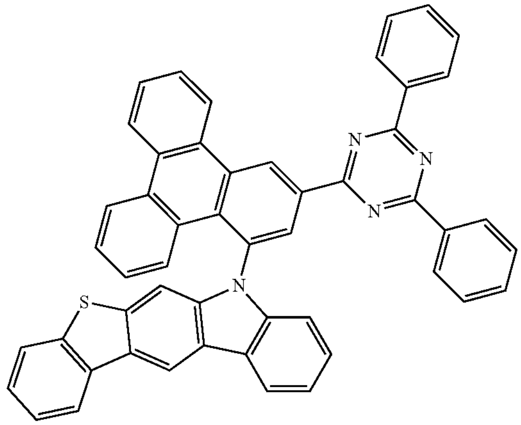
2-46
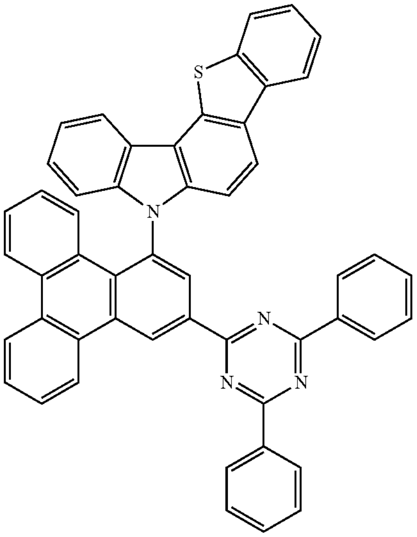
2-47
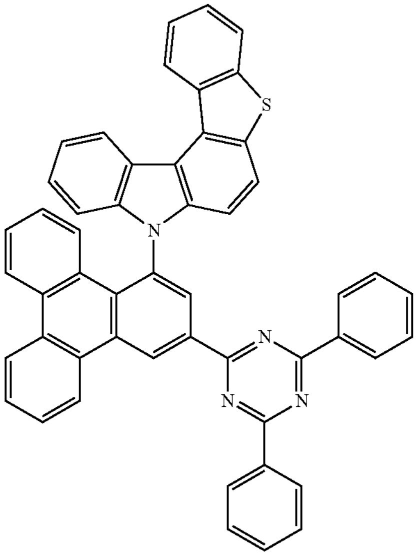

-continued
2-48
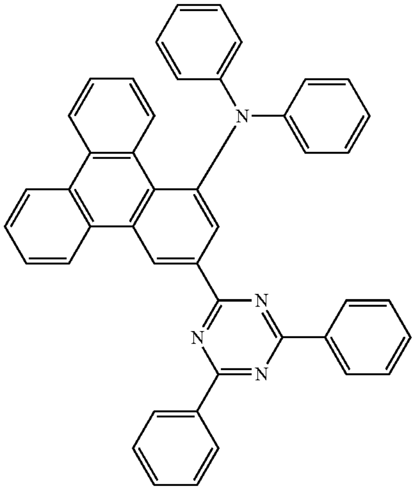
2-49
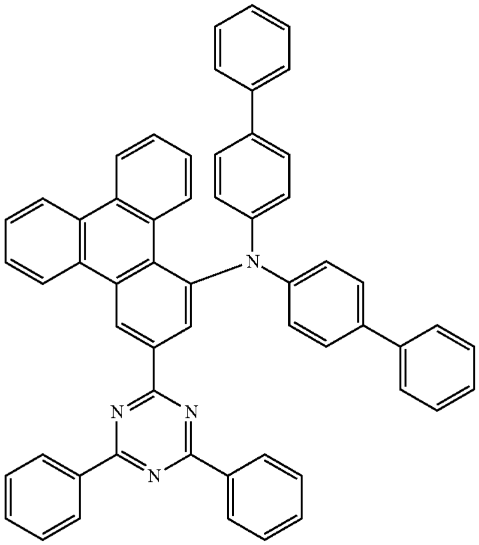
2-50
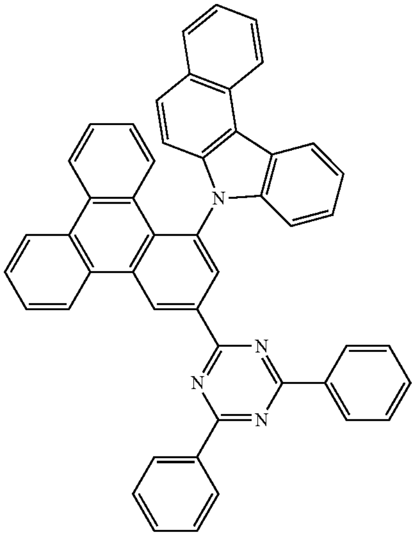
2-51
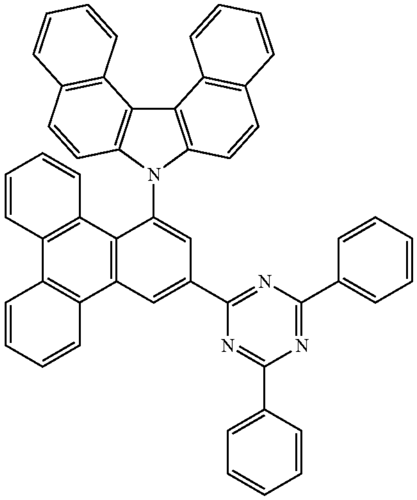
2-52
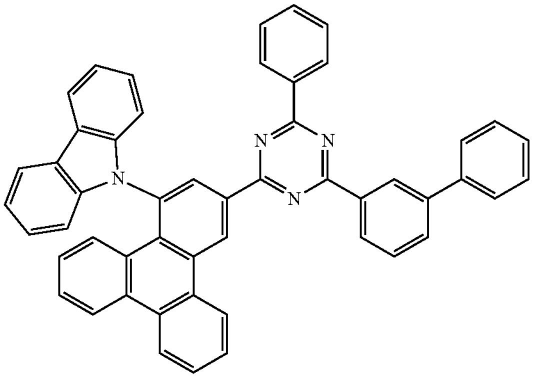
2-53
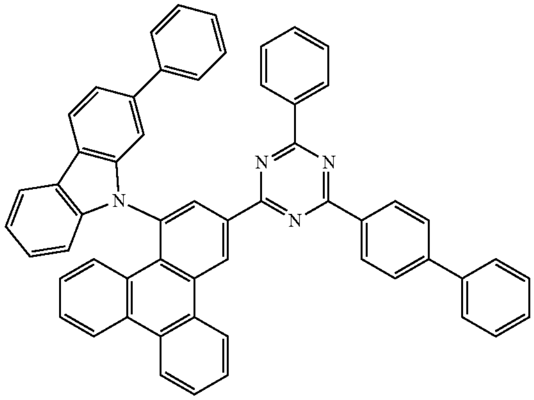

-continued
2-54
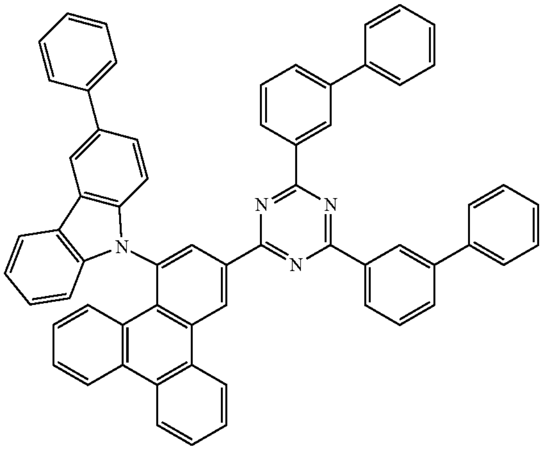
2-55
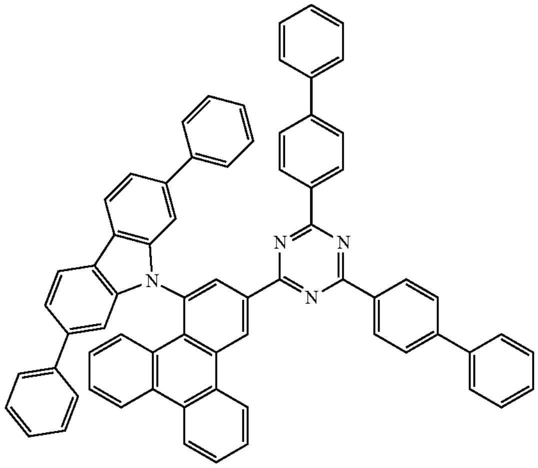
2-56
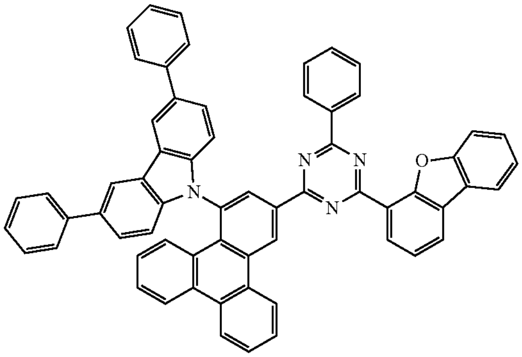
2-57
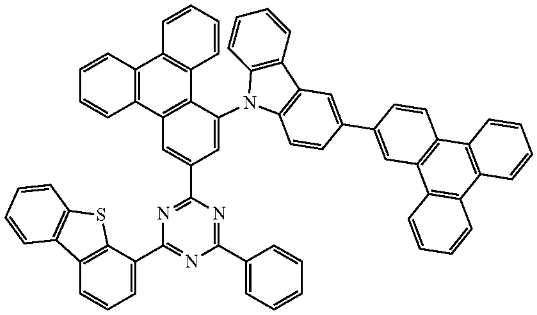
2-58
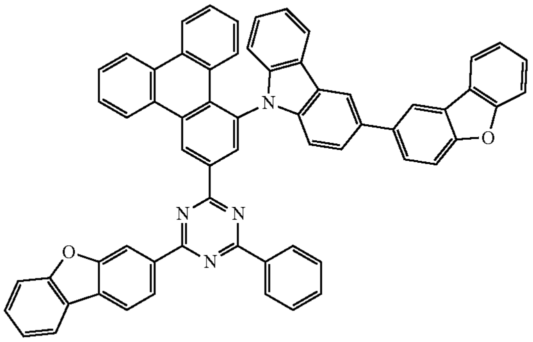
2-59
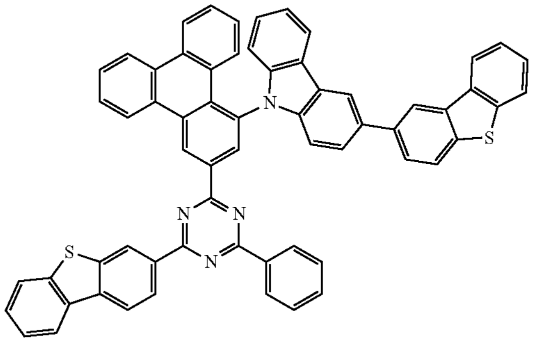
2-60
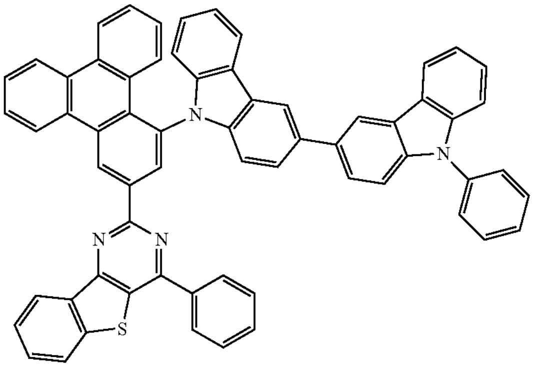
2-61
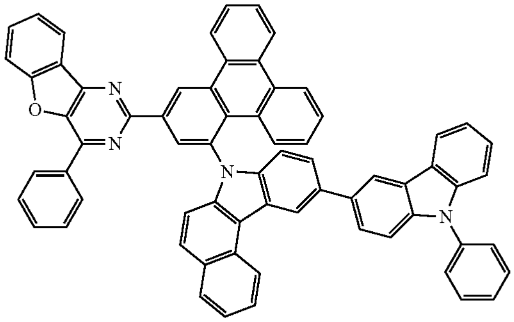

-continued
2-62
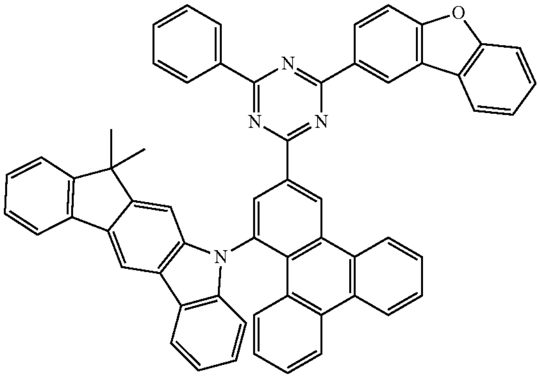
2-63
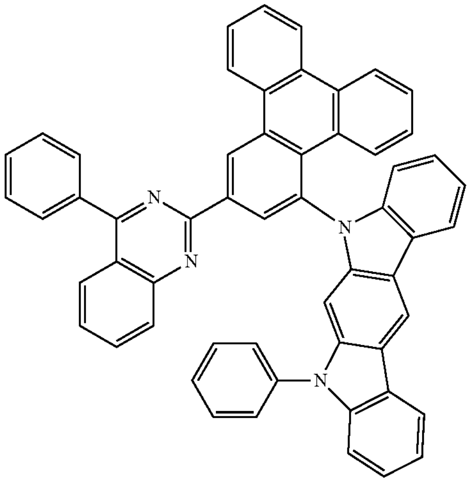
2-64
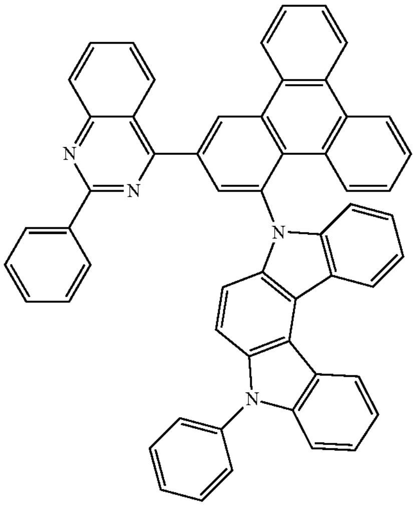
2-65
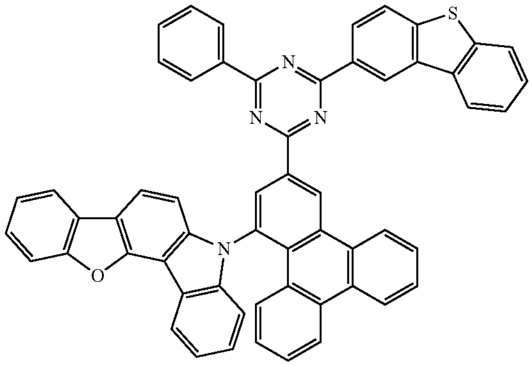
2-66
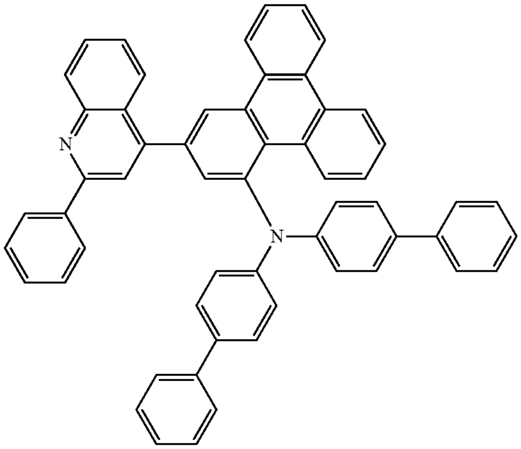
2-67
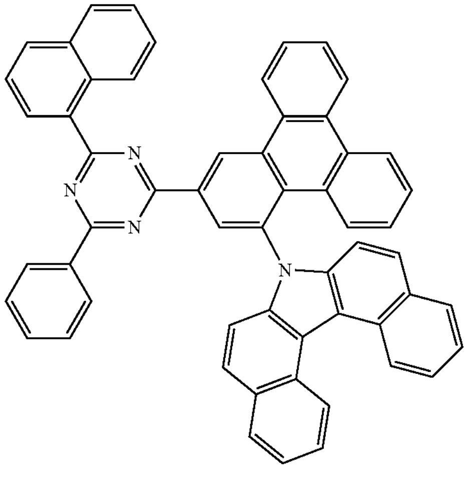

-continued
2-68
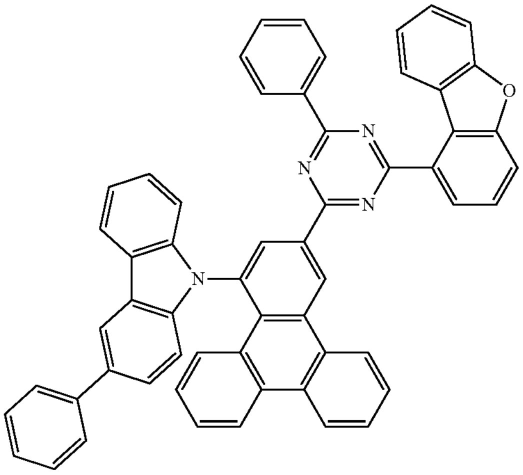
2-69
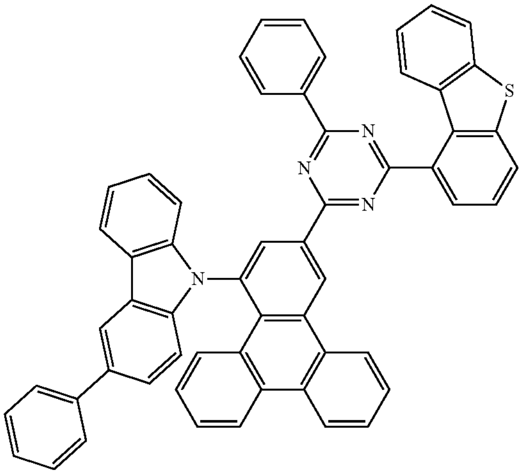
2-70
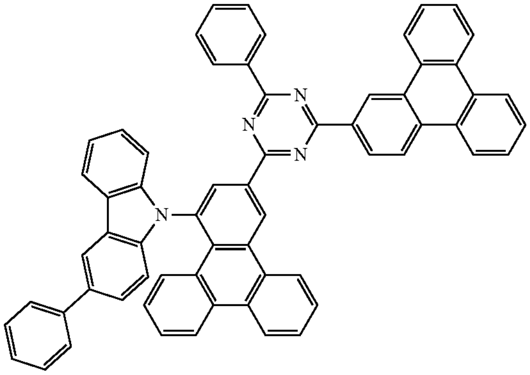
2-71
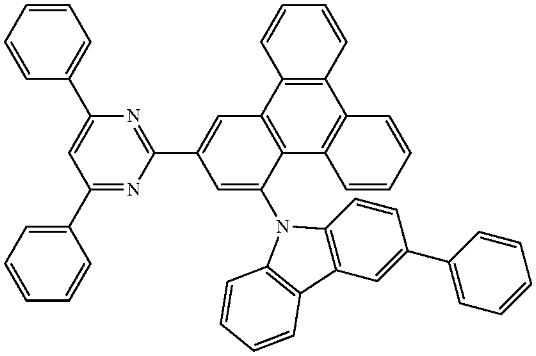
2-72
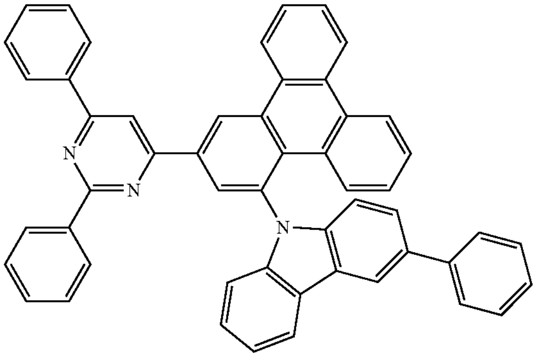
2-73
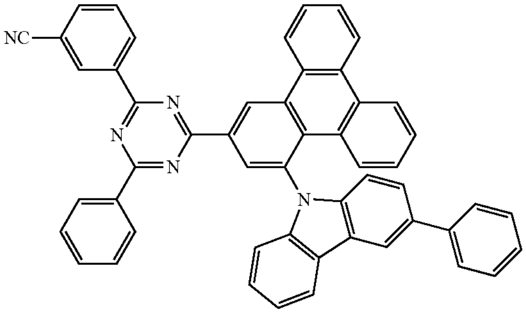
2-74
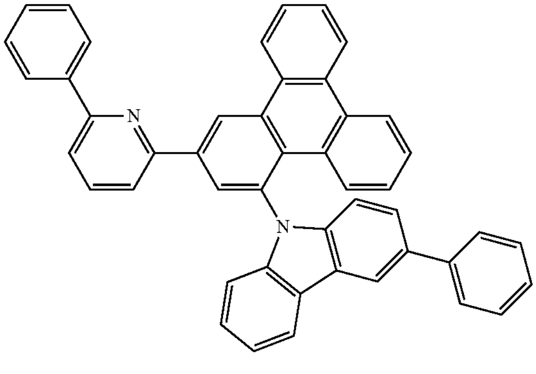
2-75
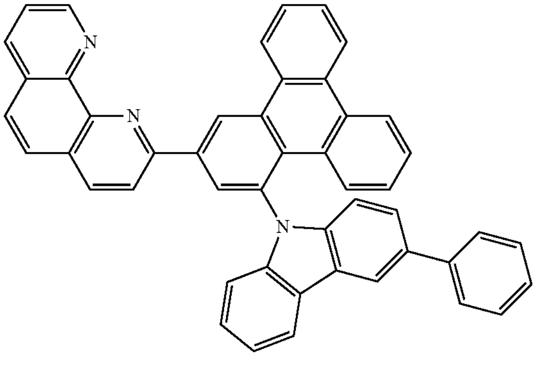

-continued
2-76
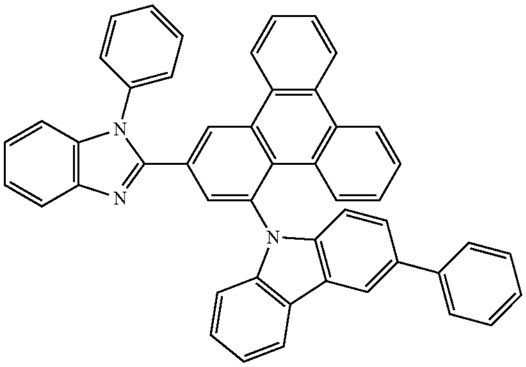
2-77
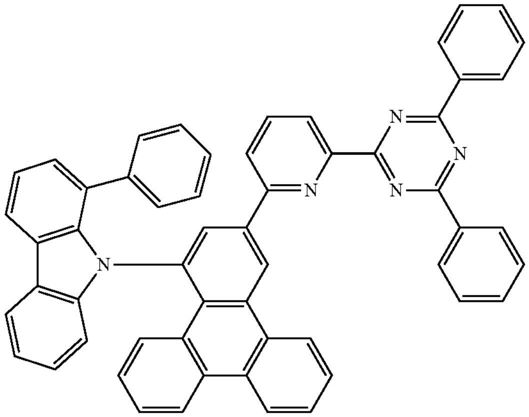
2-78
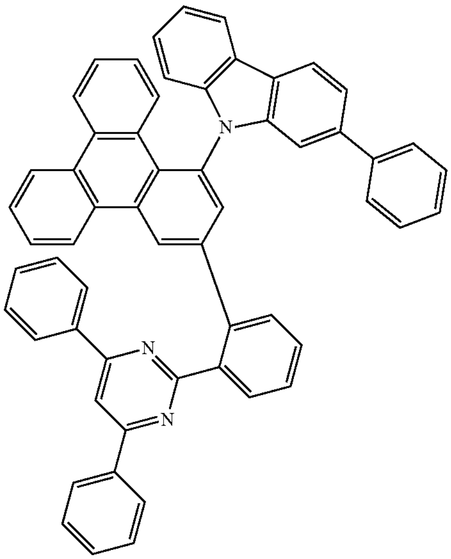
2-79
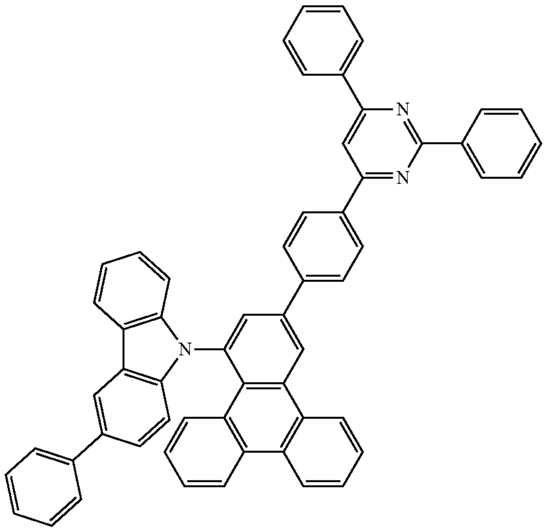
2-80
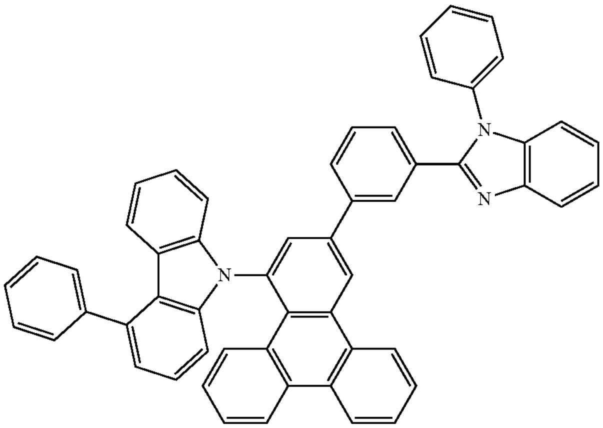

-continued
2-81
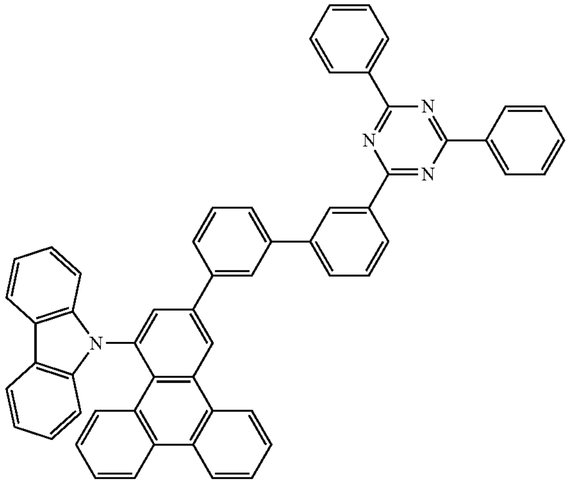
2-82
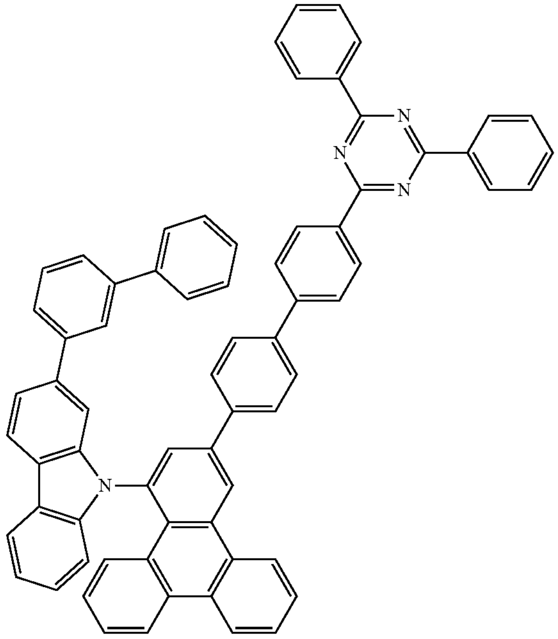
2-83
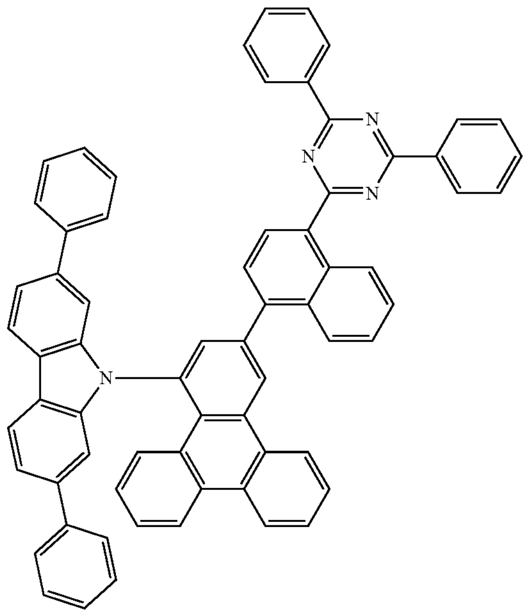
2-84
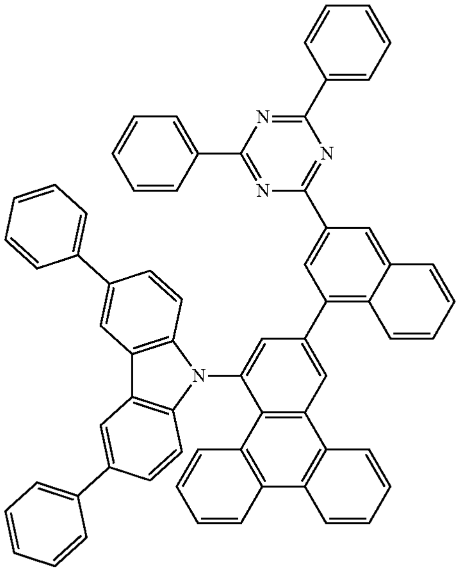
2-85
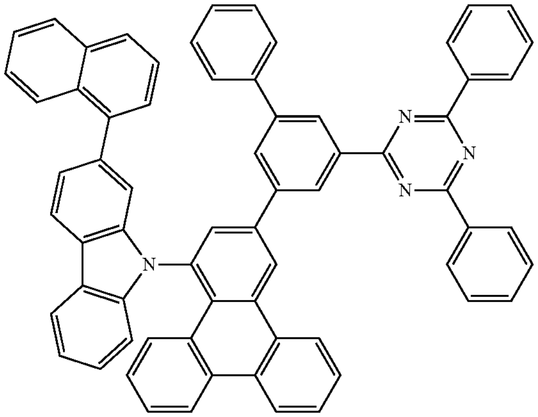

-continued
2-86
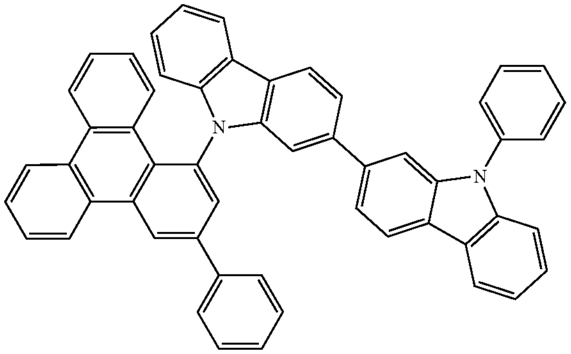
2-87
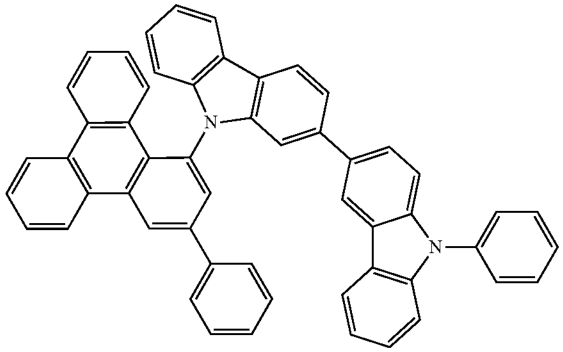
2-88
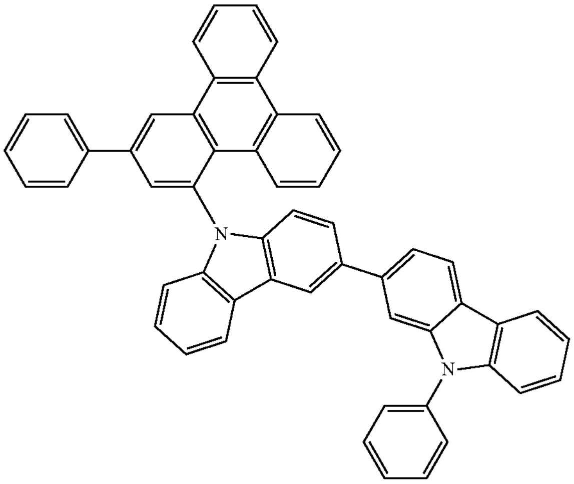
-continued
2-89
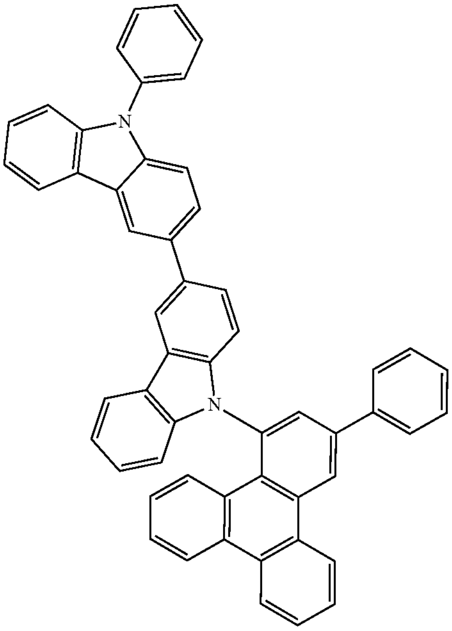
2-90
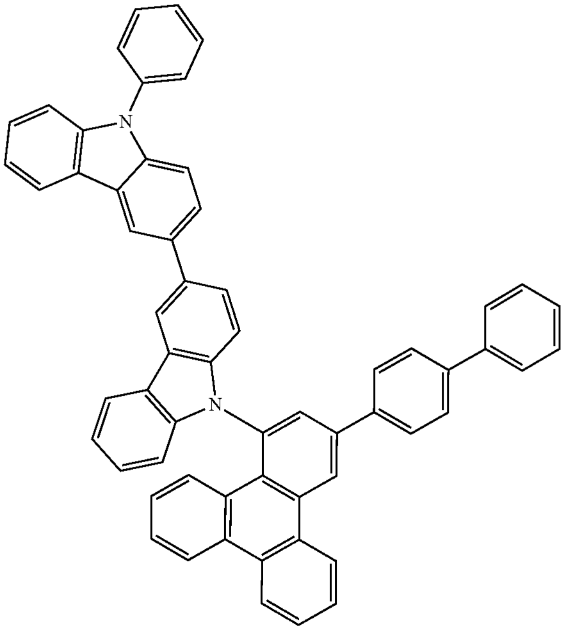

-continued
2-91
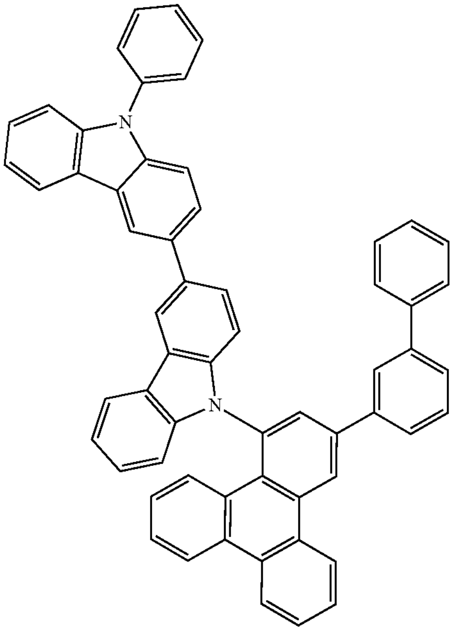
2-92
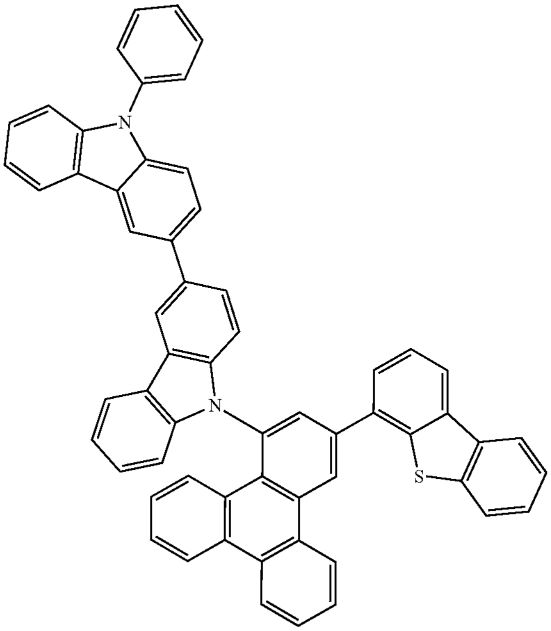
-continued
2-93
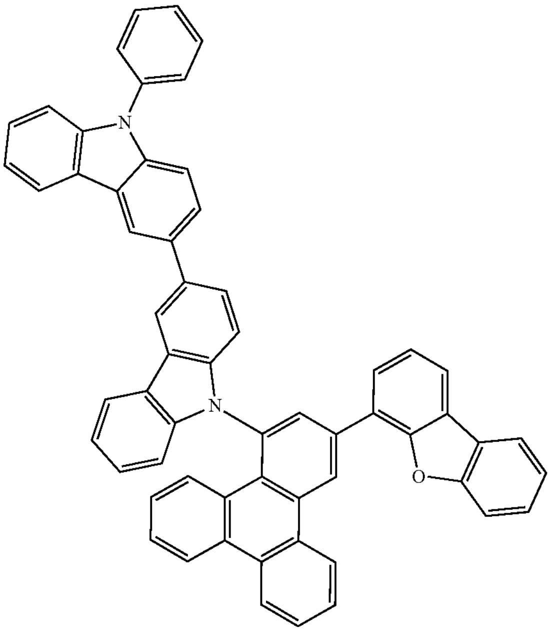
2-94
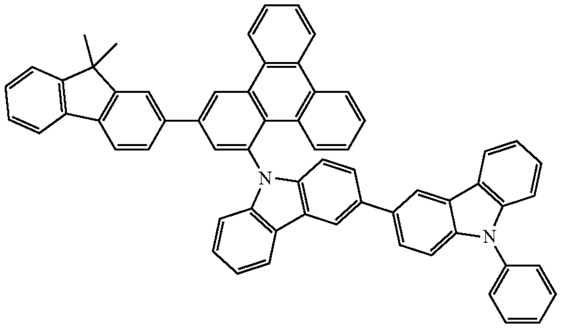
2-95
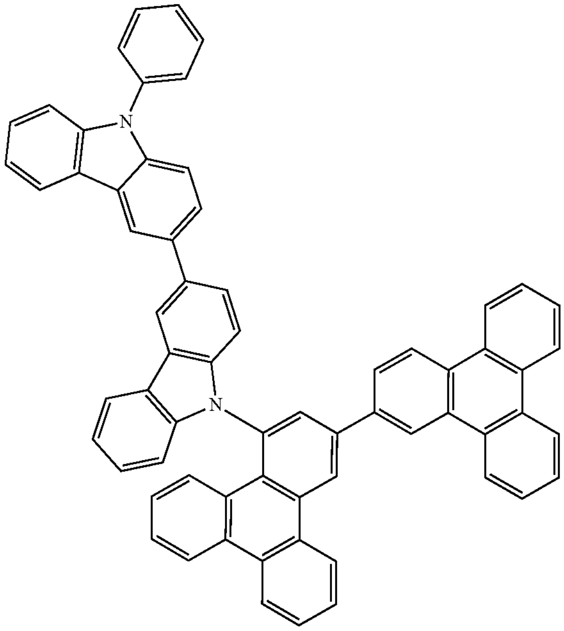

-continued
2-96
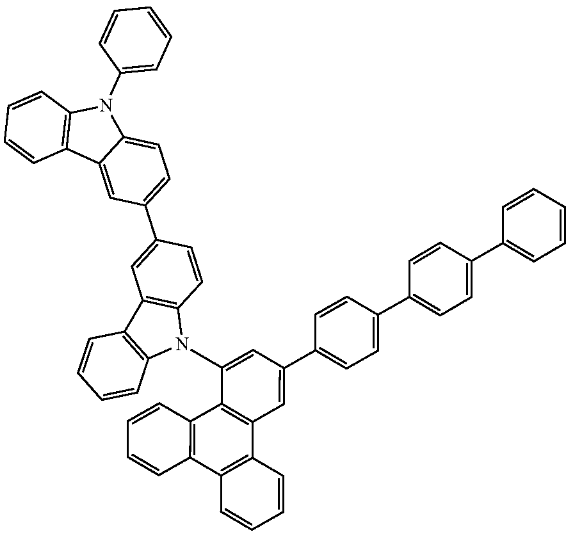
2-97
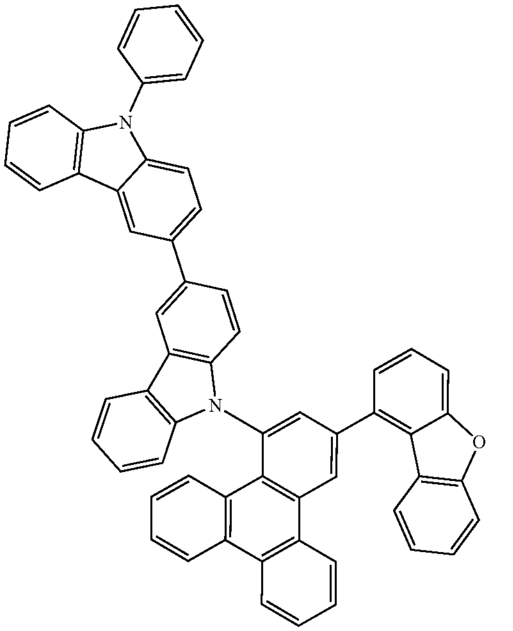
-continued
2-98
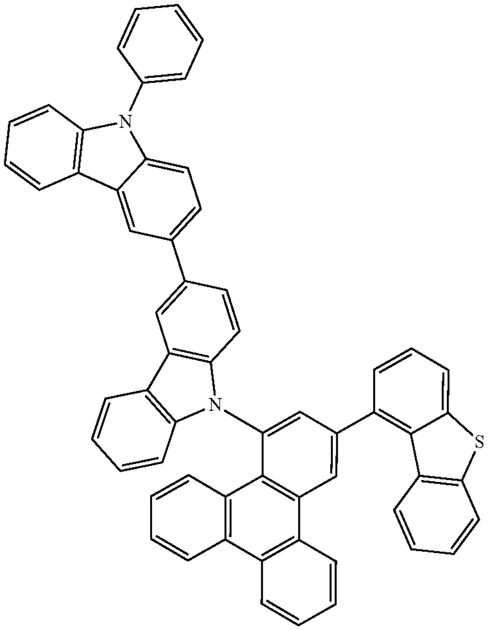
2-99
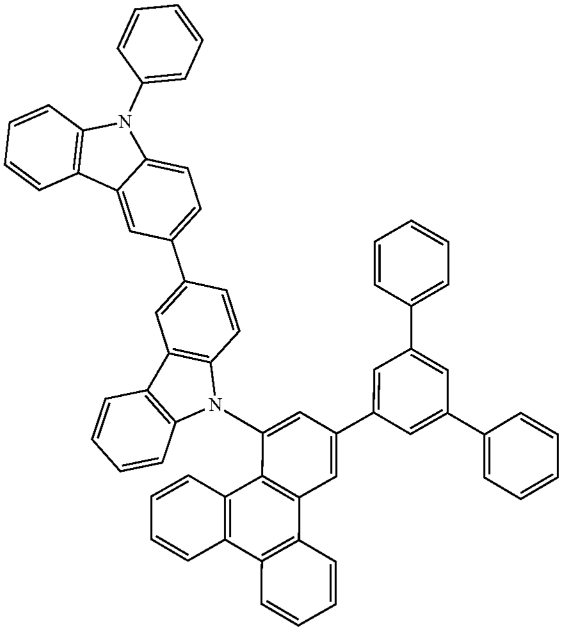

-continued 2-100

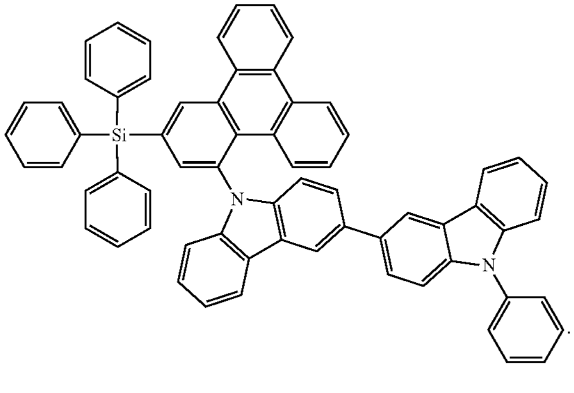

6. An organic light emitting device comprising:

a first electrode;

a second electrode provided opposite to the first electrode; and one or more organic material layers provided between the first electrode and the second electrode, wherein one or more layers of the organic material layers comprise the heterocyclic compound of claim 1.

7. The organic light emitting device of claim 6, wherein the organic material layer comprising the heterocyclic compound further comprises a heterocyclic compound represented by the following Chemical Formula 2:

[Chemical Formula 2]

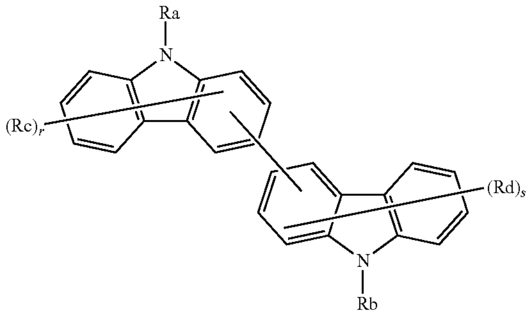

in Chemical Formula 2,

Rc and Rd are the same as or different from each other, and are each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; $—SiR_{101}R_{102}R_{103}$; $—P(=O)R_{101}R_{102}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring;

$R_{101}$, $R_{102}$ and $R_{103}$ are the same as or different from each other, and are each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;

Ra and Rb are the same as or different from each other, and are each independently a substituted or unsubstituted aryl group; or a substituted or unsubstituted heteroaryl group;

r and s are an integer of 0 to 7; and when r and s are each an integer of 2 or greater, substituents in the parentheses are the same as or different from each other.

8. The organic light emitting device of claim 7, wherein Chemical Formula 2 is represented by any one of the following heterocyclic compounds:

3-1

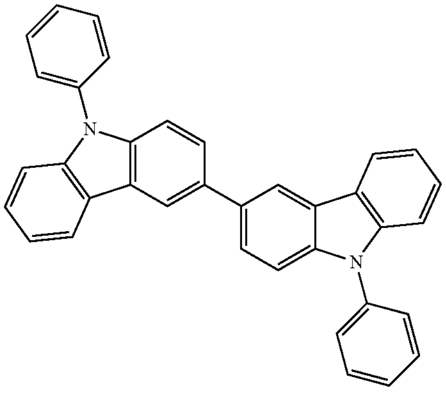

3-2

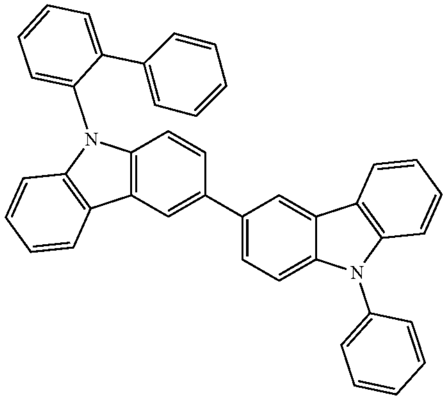

-continued
3-3
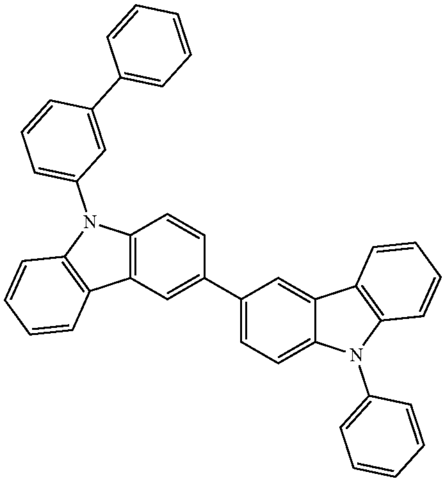
3-4
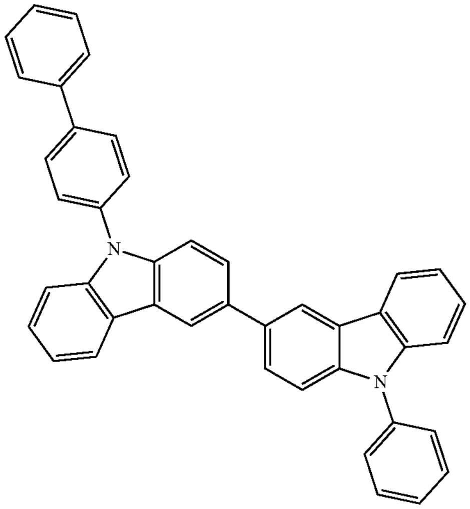
3-5
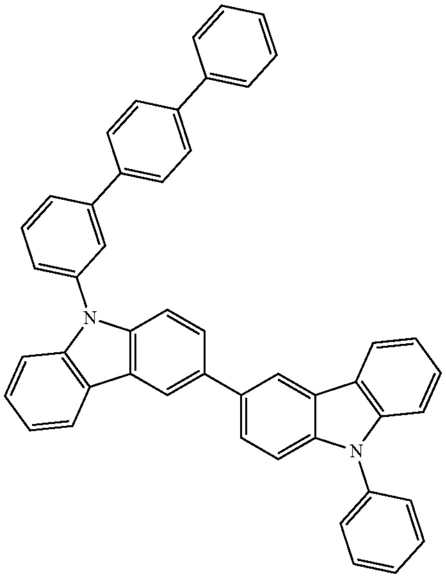
3-6
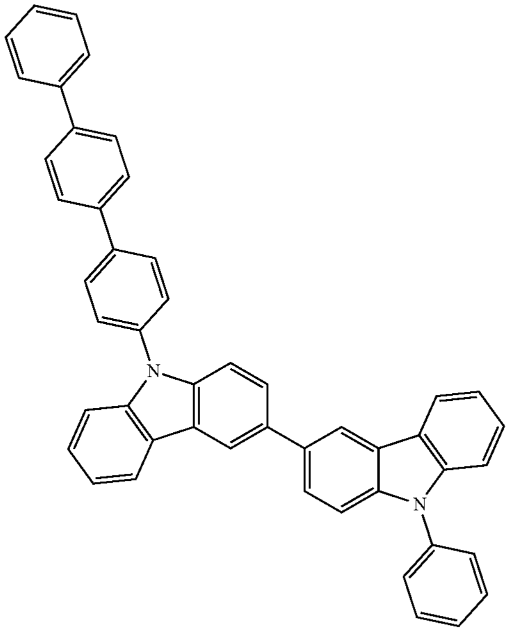
3-7
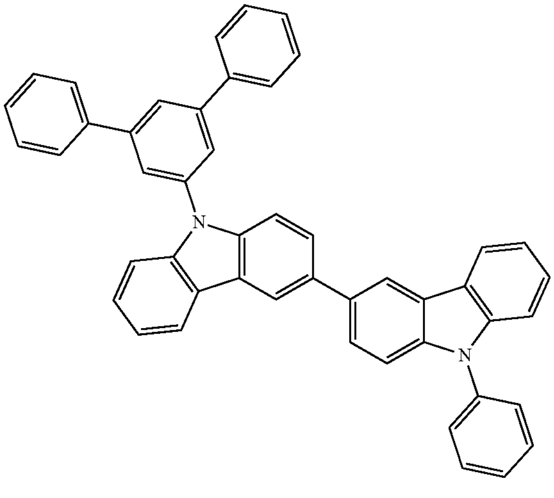
3-8
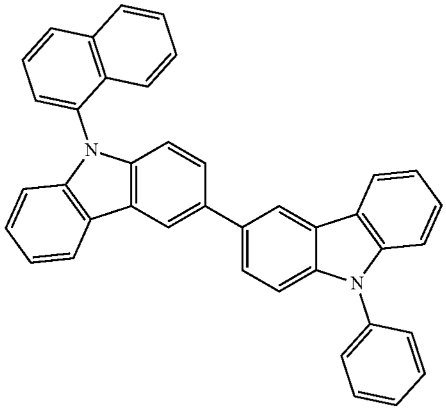

-continued
3-9
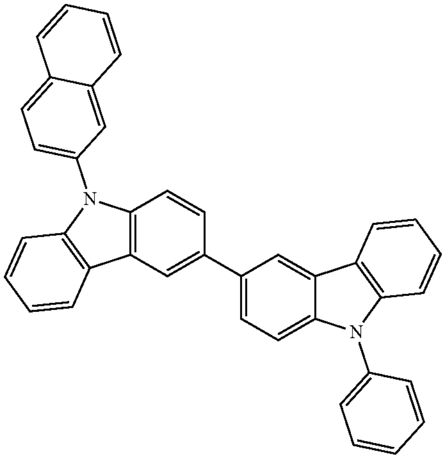
3-10
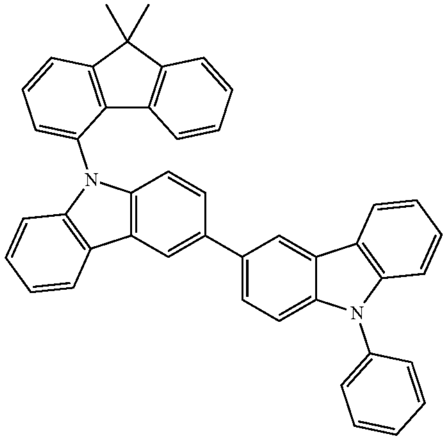
3-11
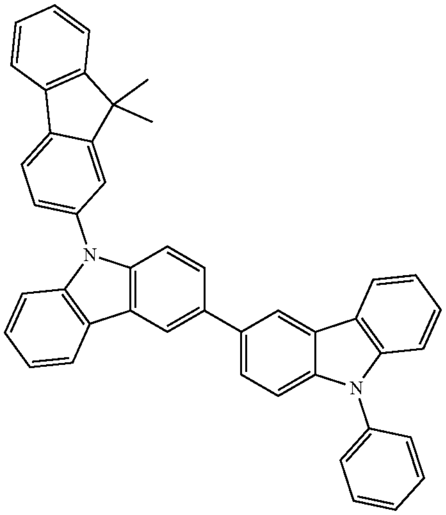
3-12
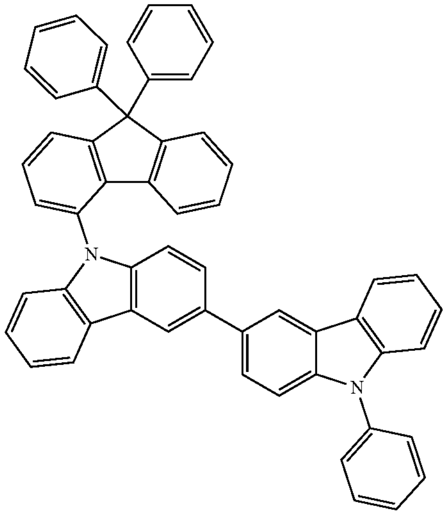
3-13
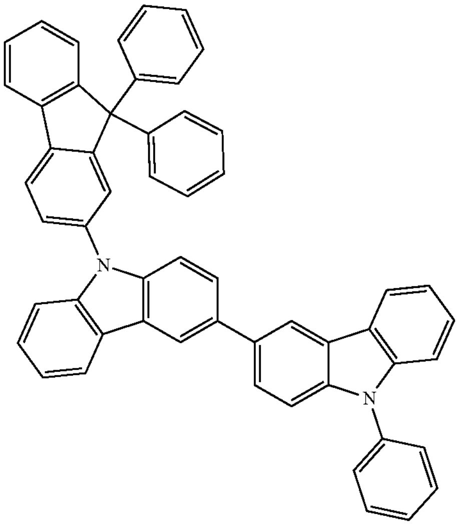
3-14
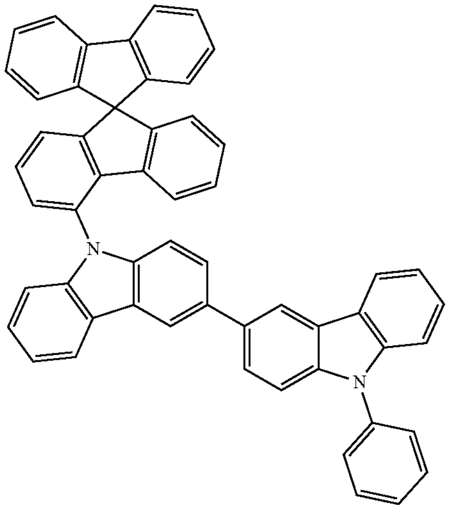

-continued
3-15
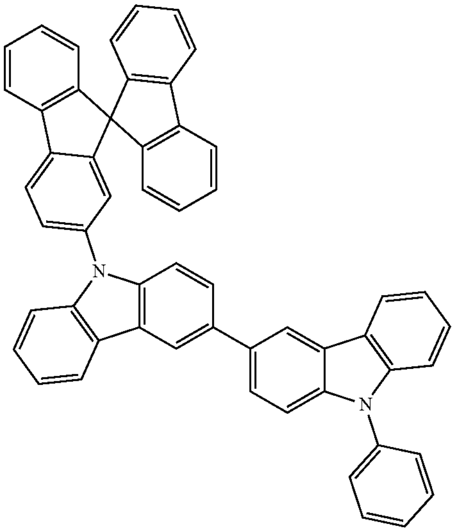
3-16
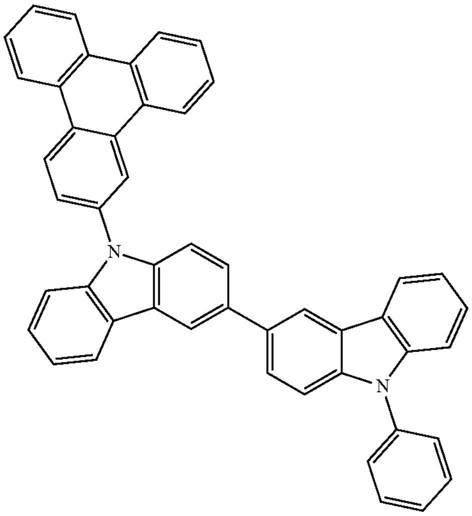
3-17
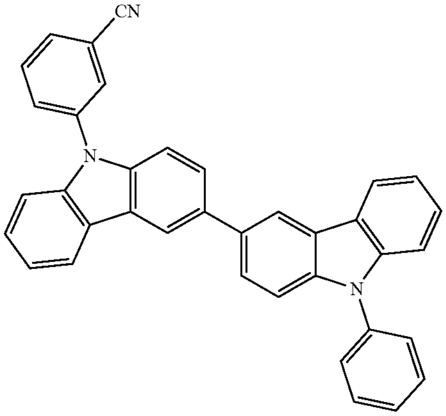
3-18
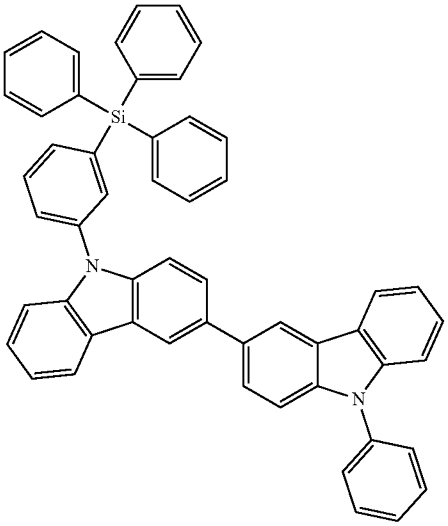
3-19
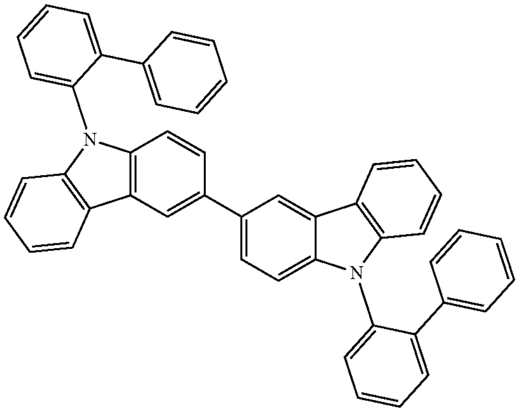
3-20
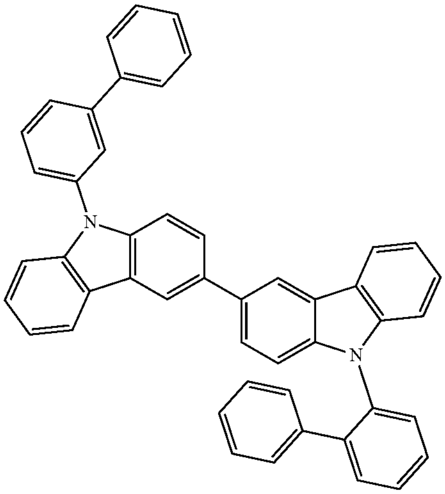

-continued
3-21
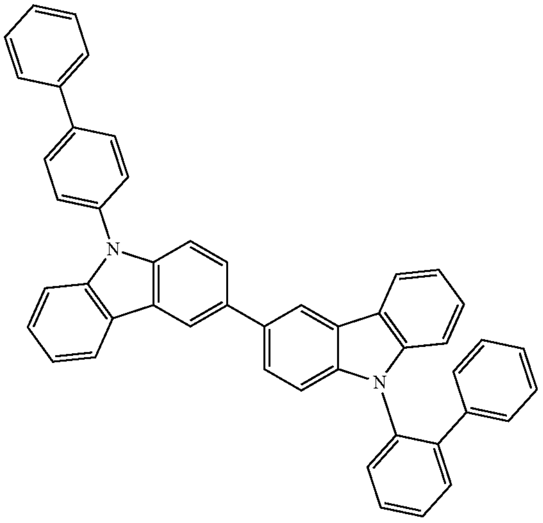
3-22
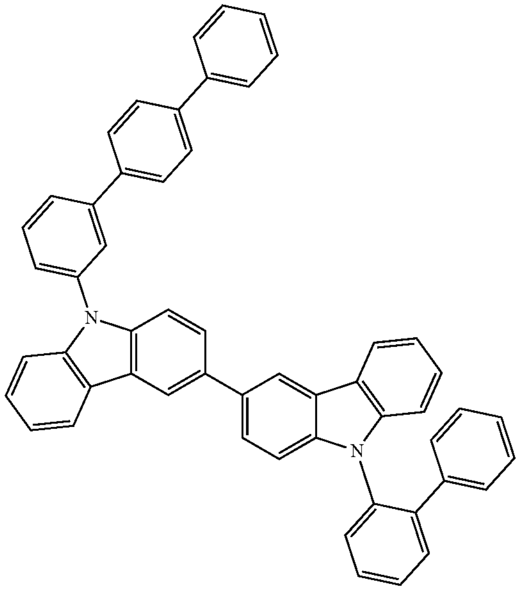
3-23
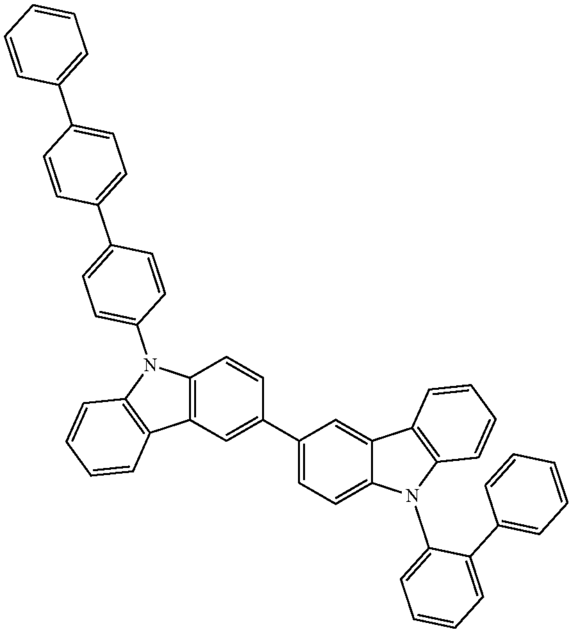
3-24
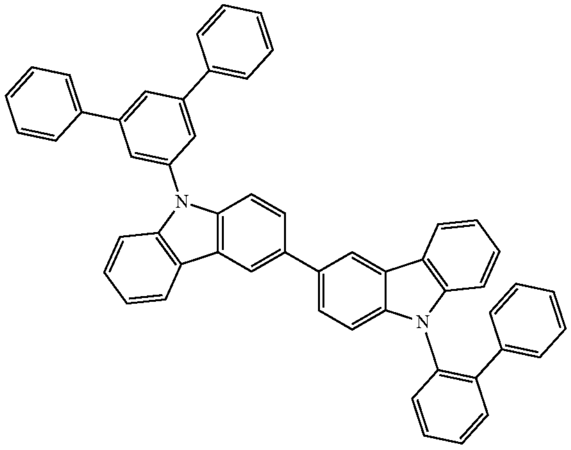

-continued
3-25
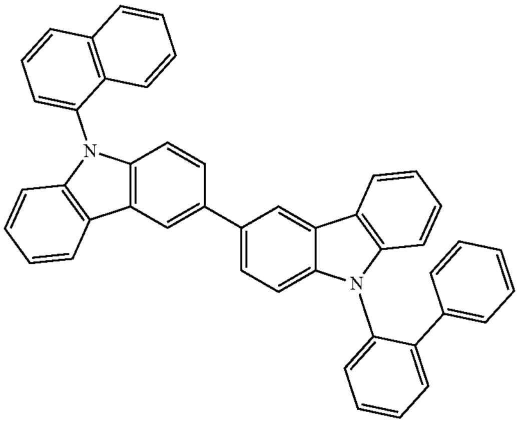
3-26
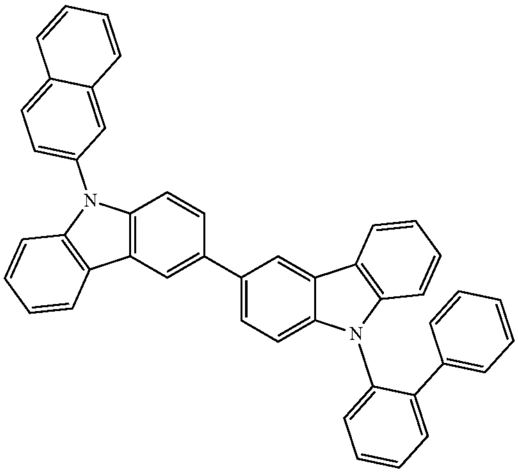
3-27
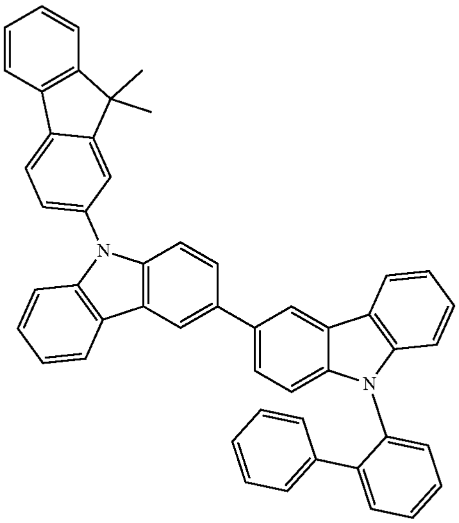
3-28
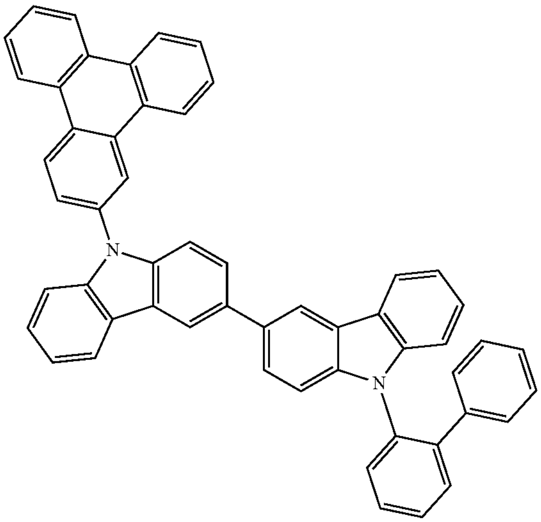
3-29
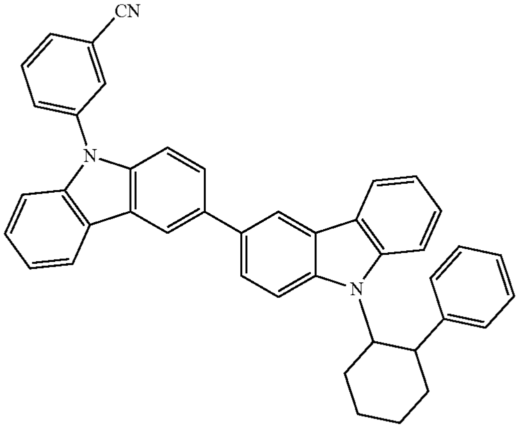
3-30
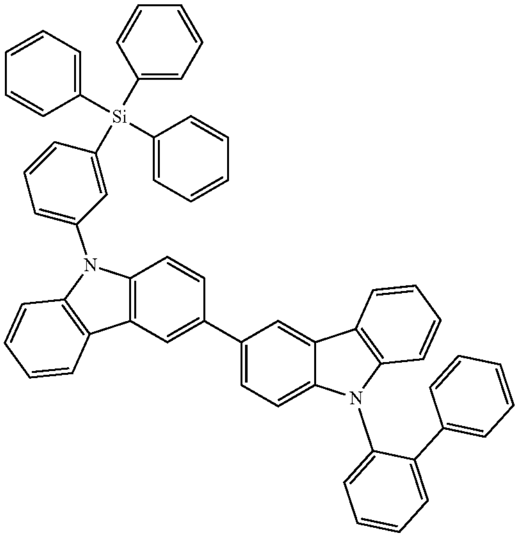

-continued
3-30
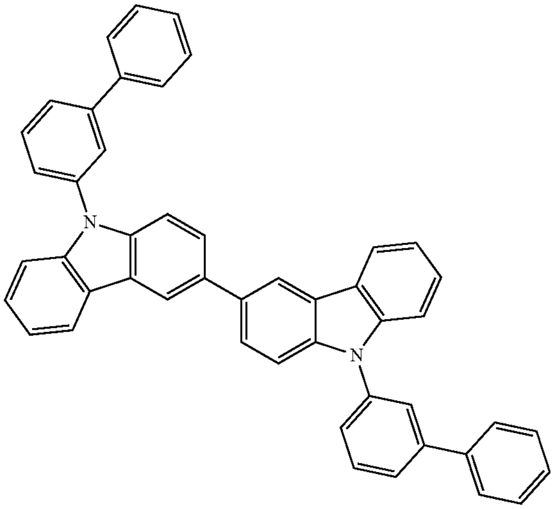
3-32
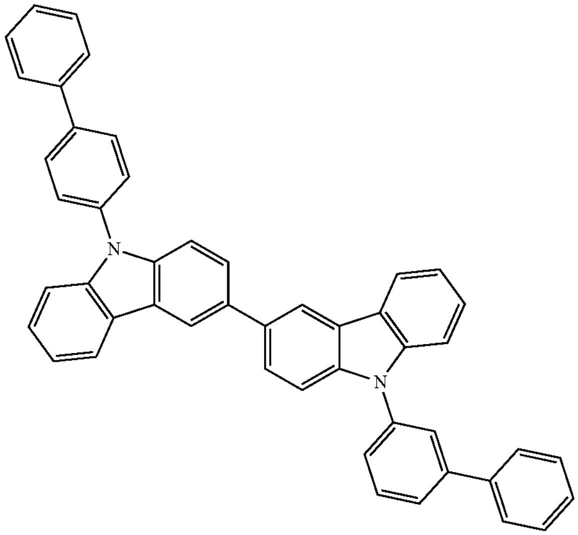
3-33
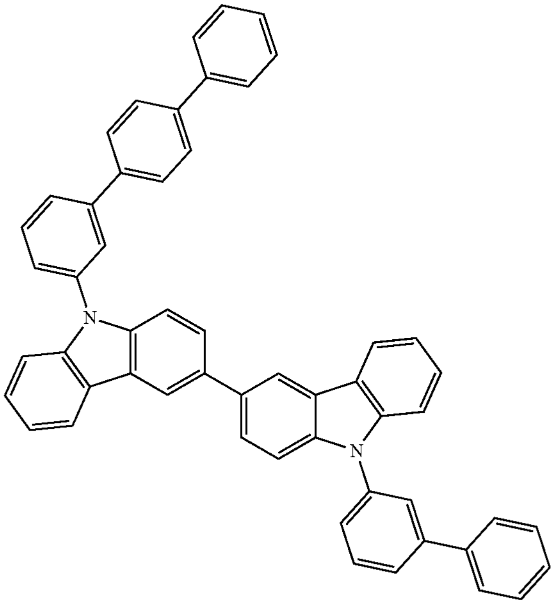
3-34
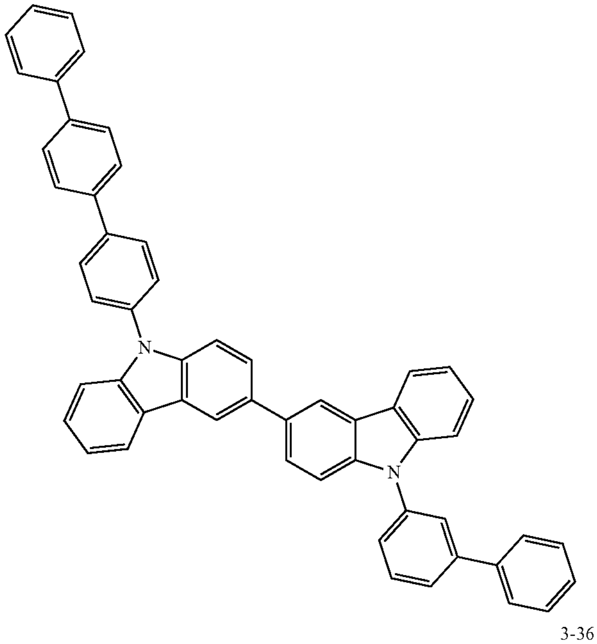
3-35
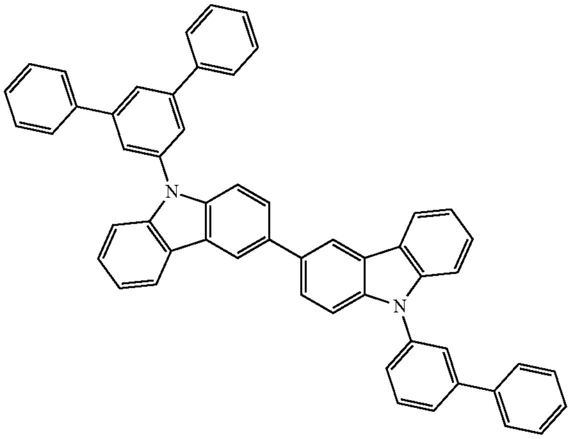
3-36
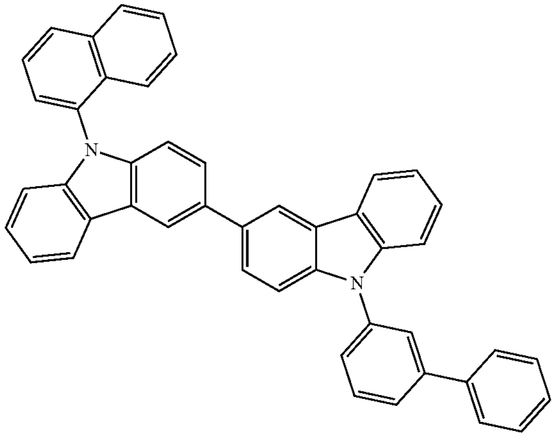

-continued
3-37
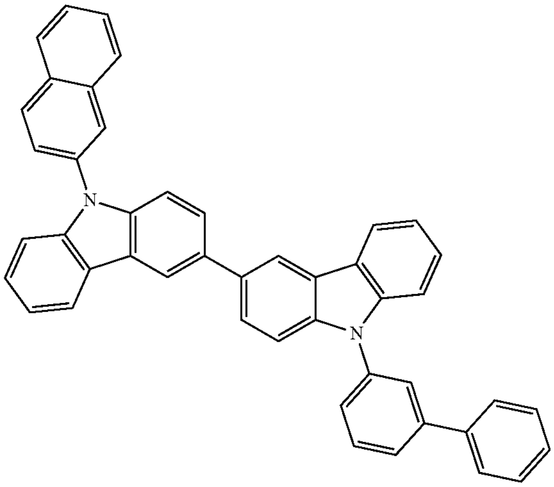
3-38
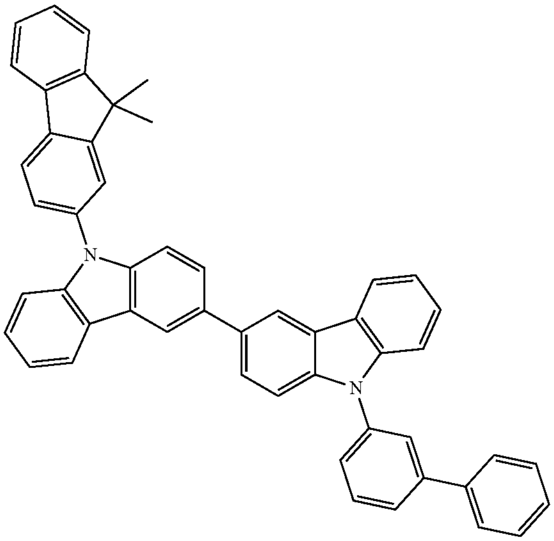
3-39
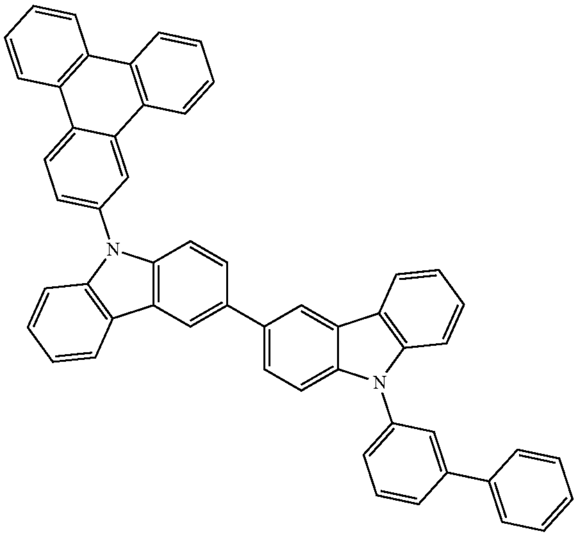
3-40
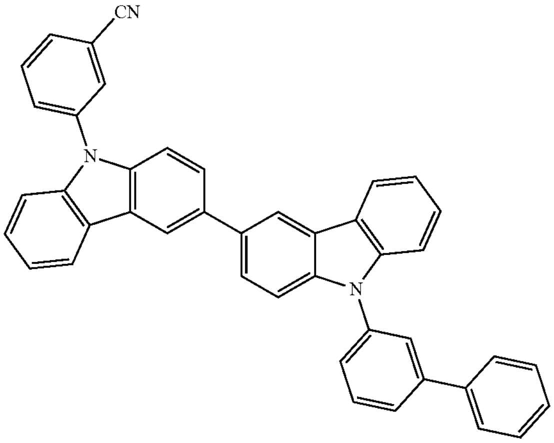

-continued
3-41
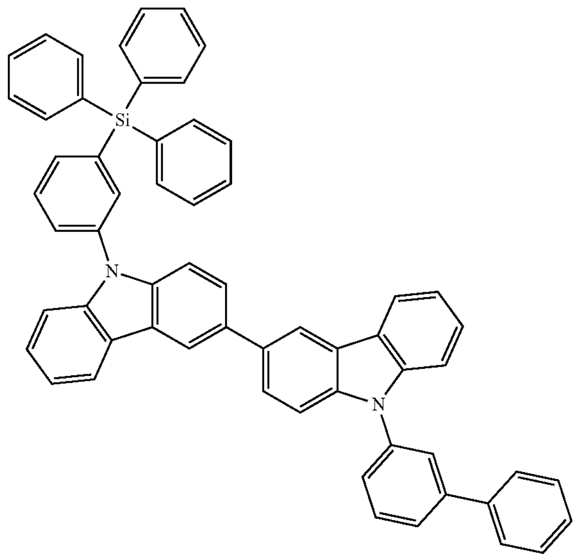
3-42
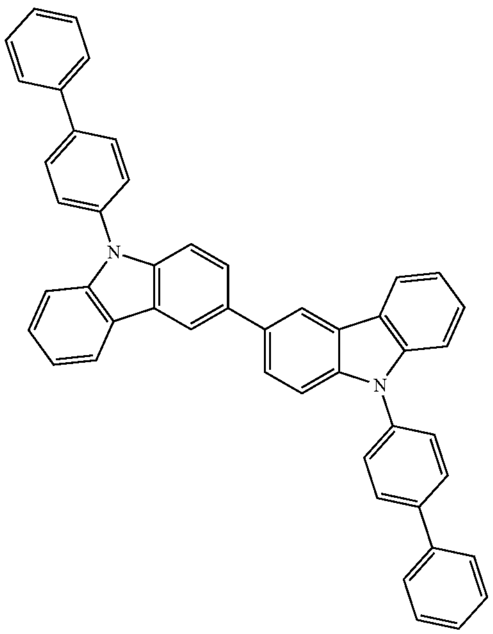
3-43
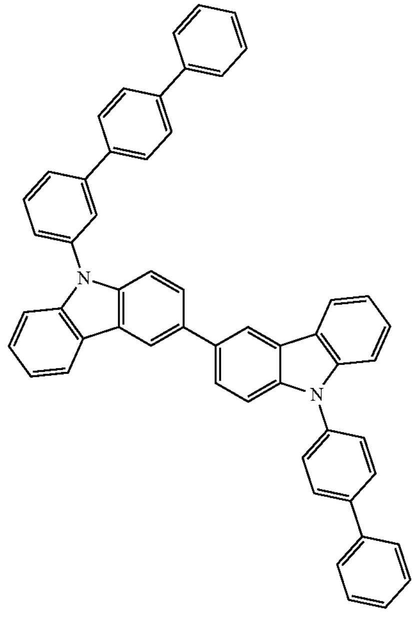
3-44
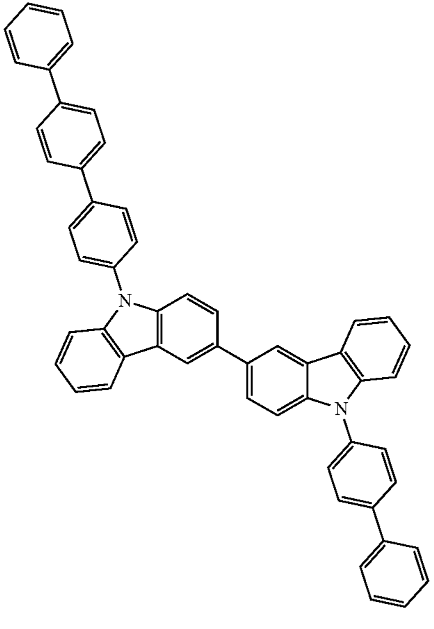

-continued
3-45
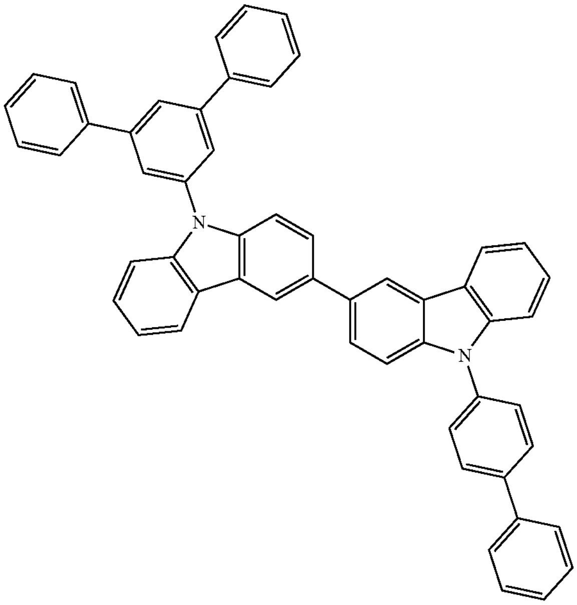
3-46
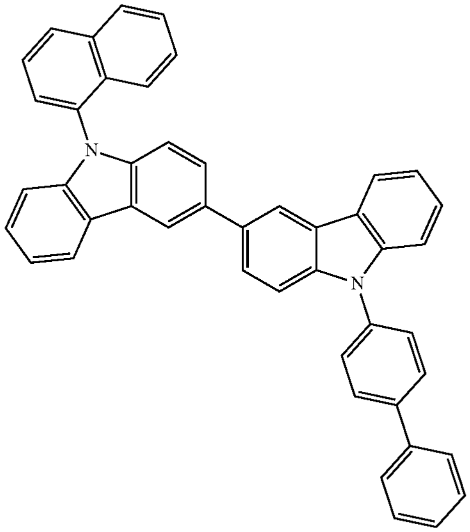
3-47
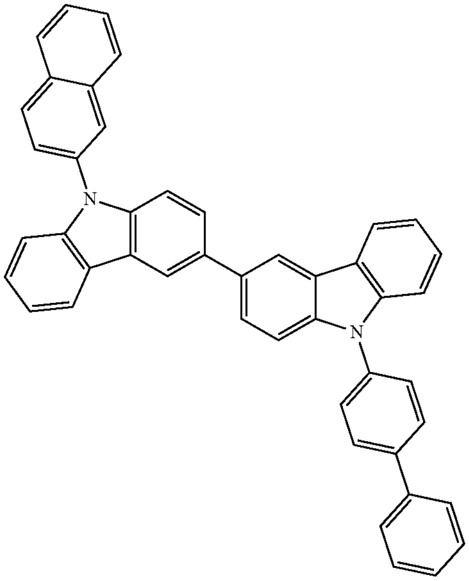
3-48
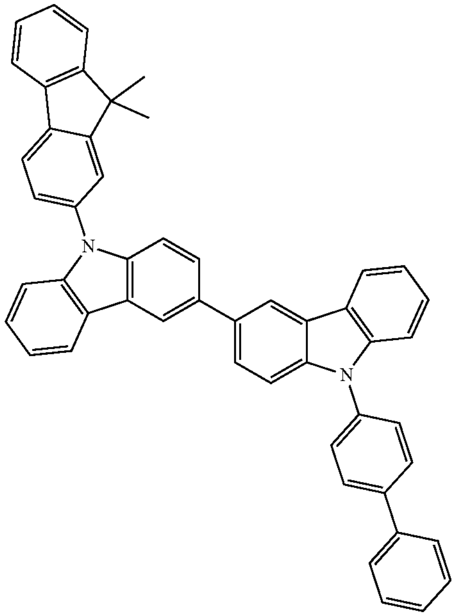

-continued
3-49
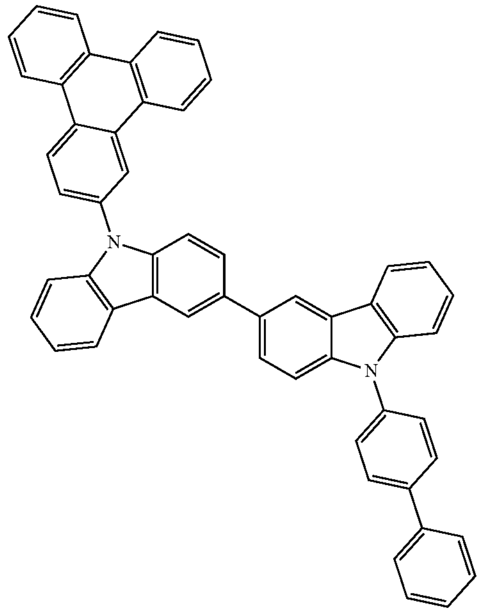
3-50
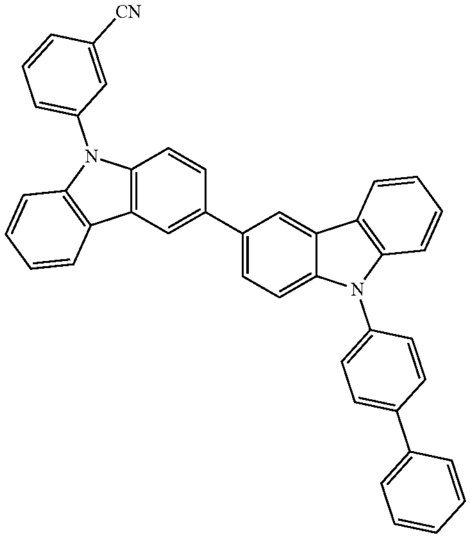
3-51
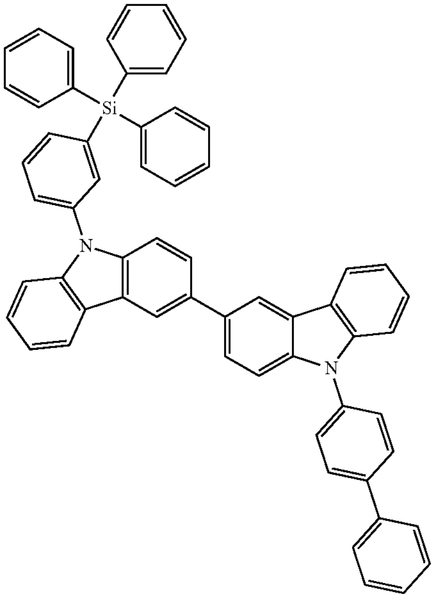
3-52
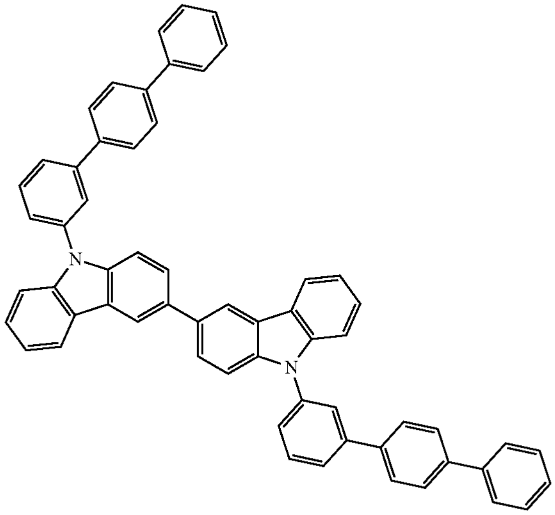

-continued
3-53
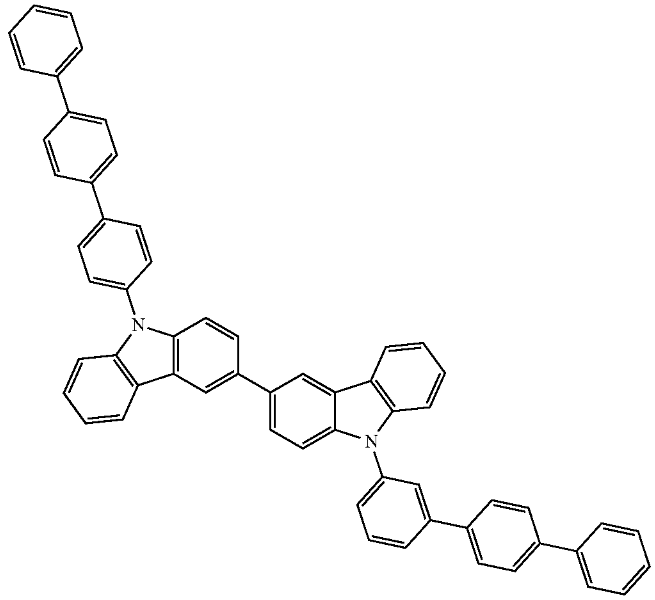
3-54
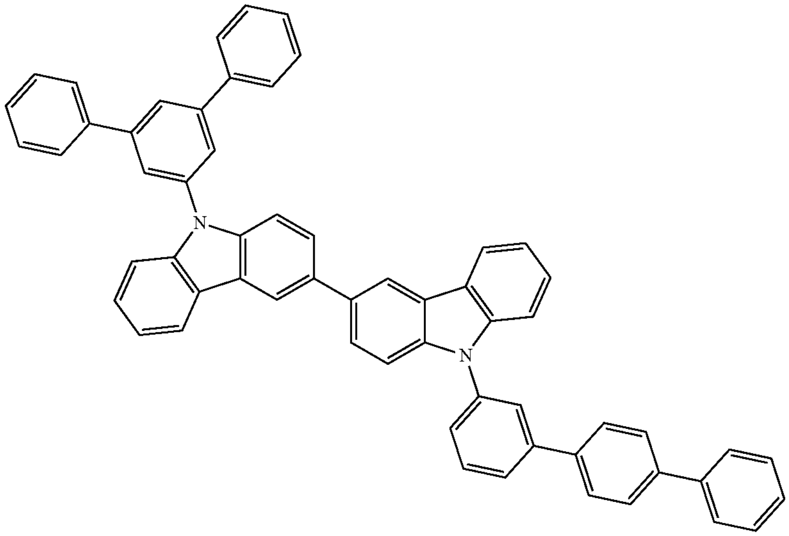
3-55
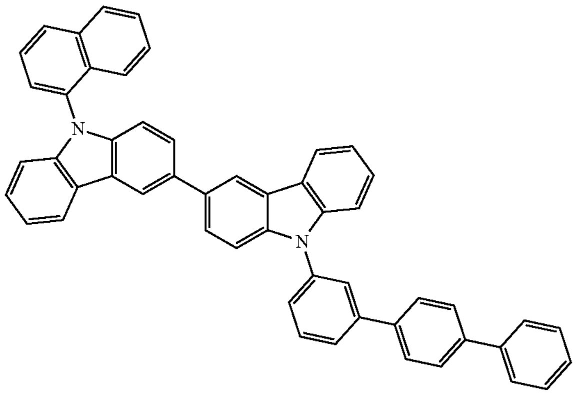
3-56
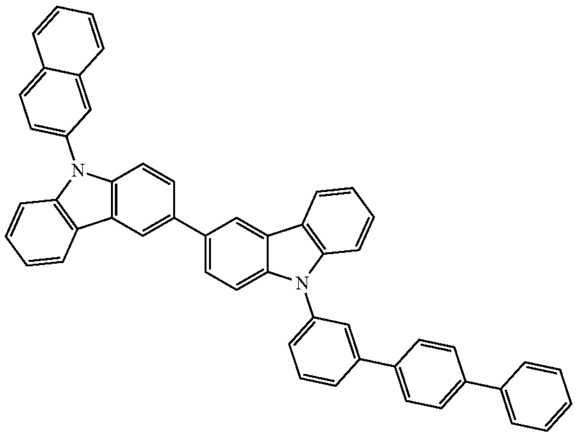

-continued
3-57
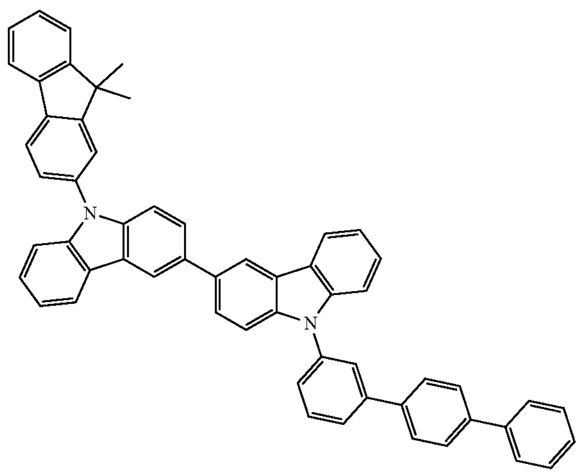
3-58
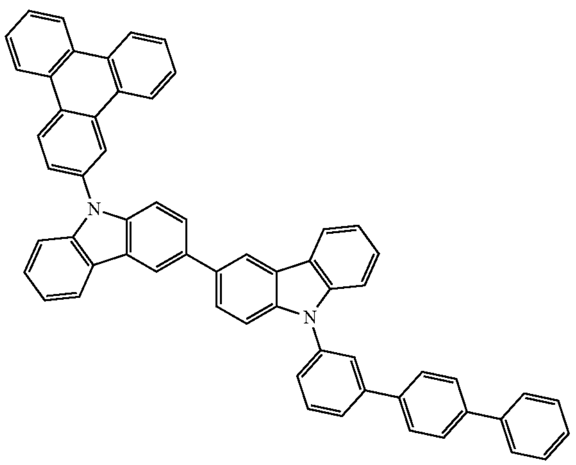
3-59
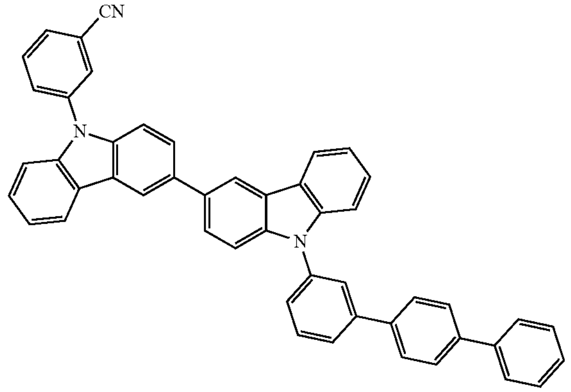
3-60
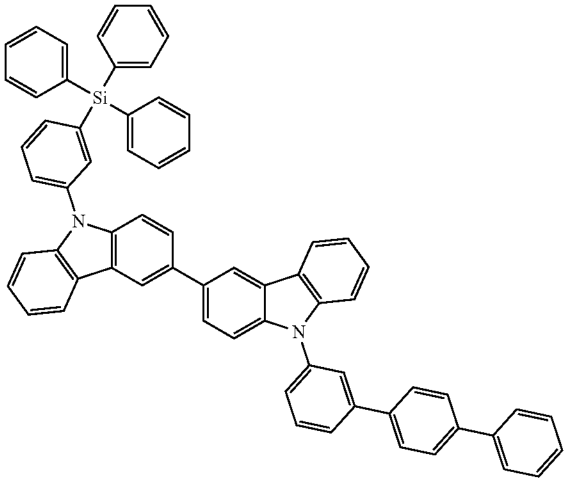
3-61
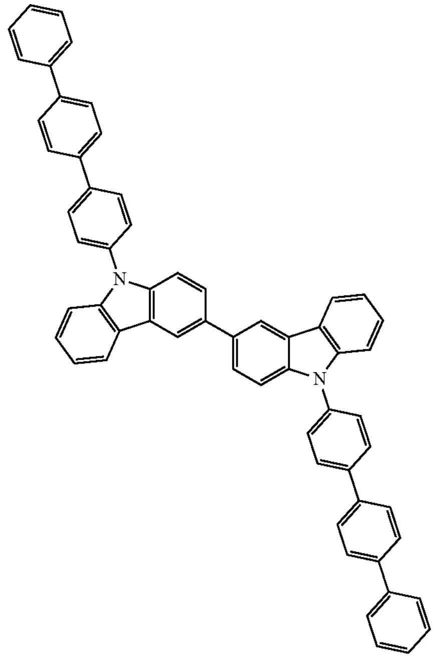
3-62
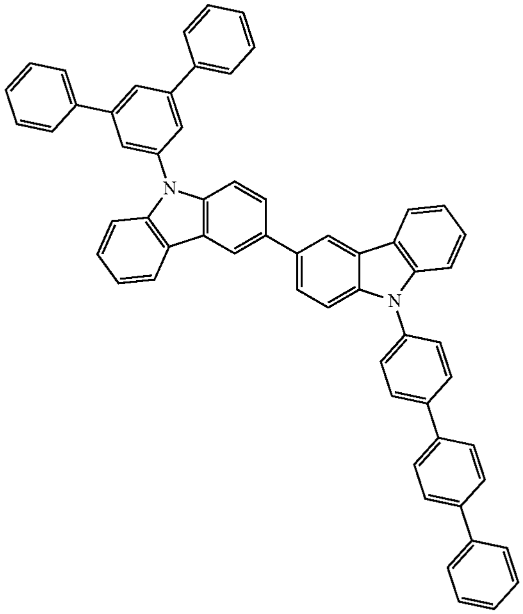

-continued
3-63
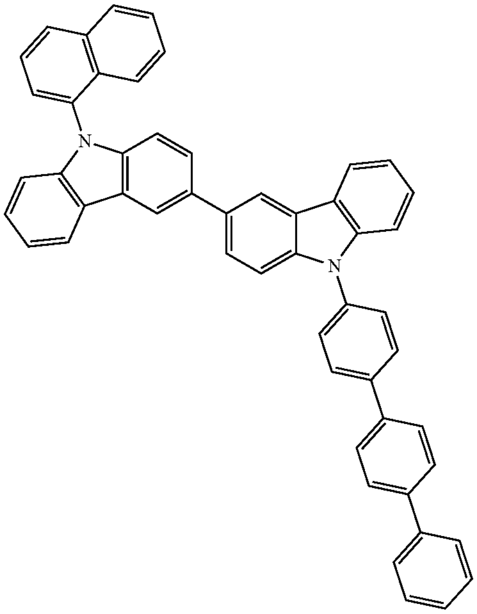
3-64
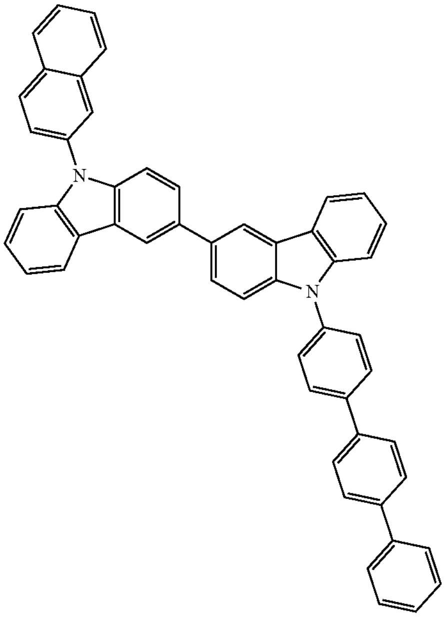
3-65
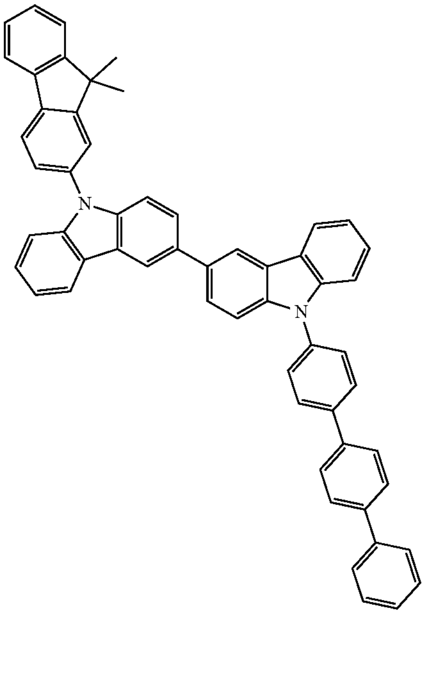
3-66
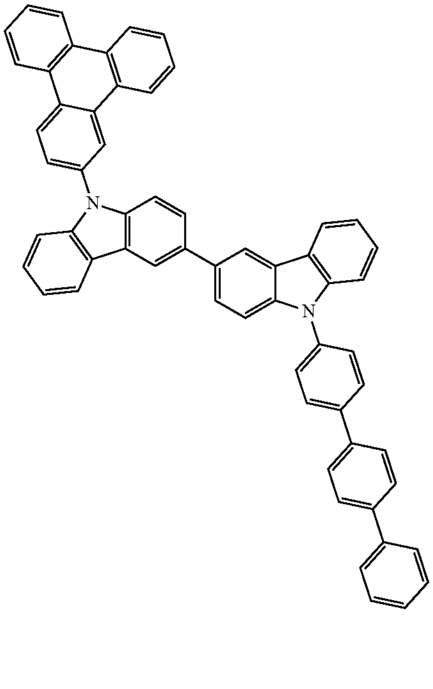

-continued
3-67
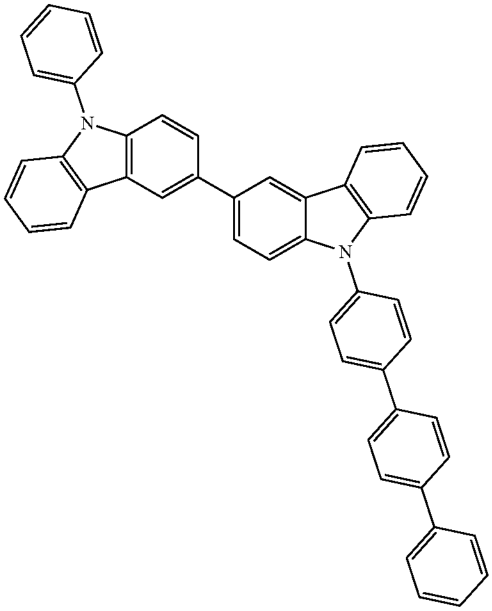
3-68
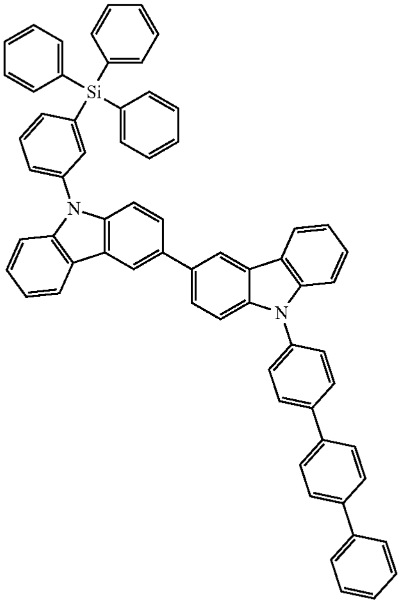
3-69
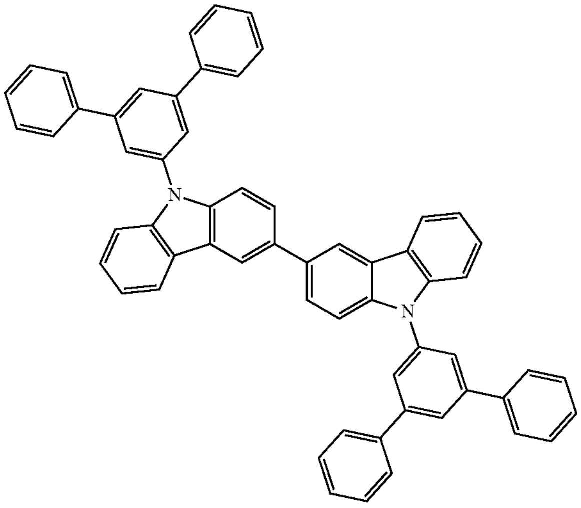
3-70
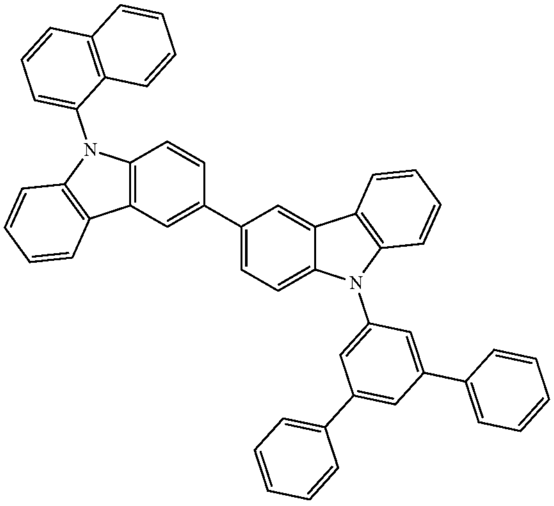

-continued
3-71
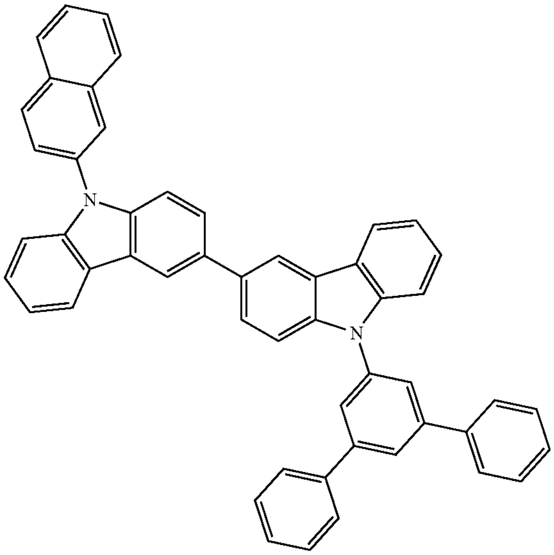
3-72
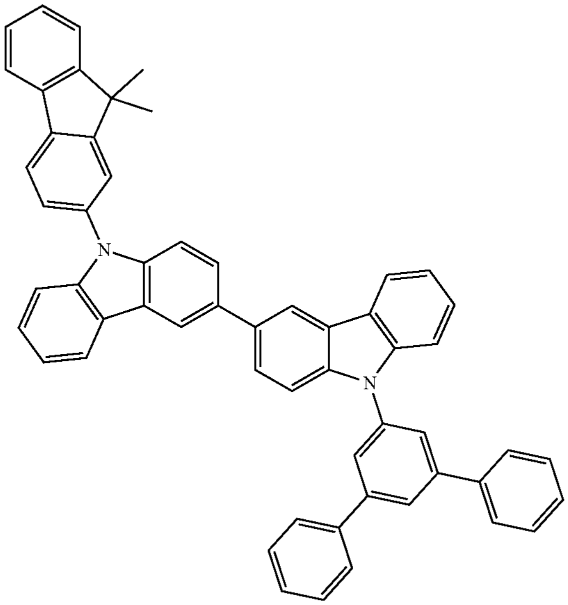
3-74
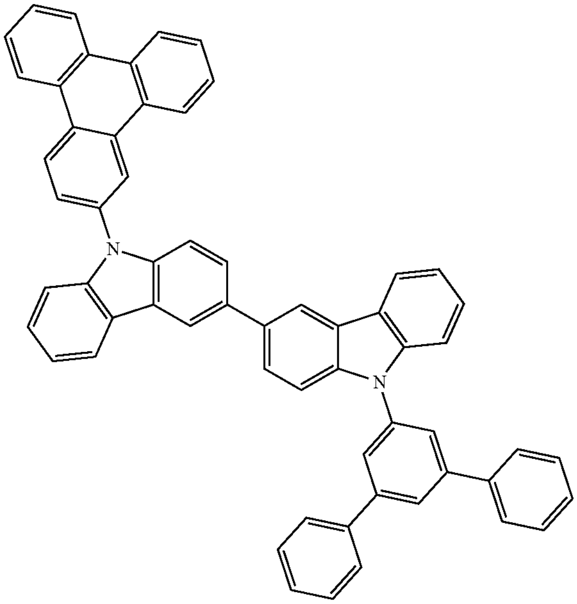
3-73
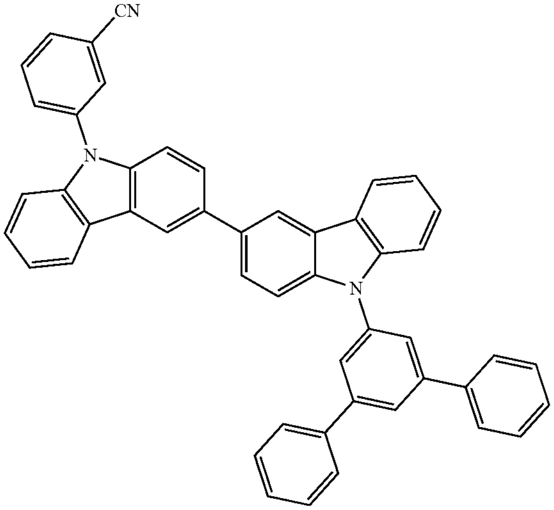

-continued
3-75
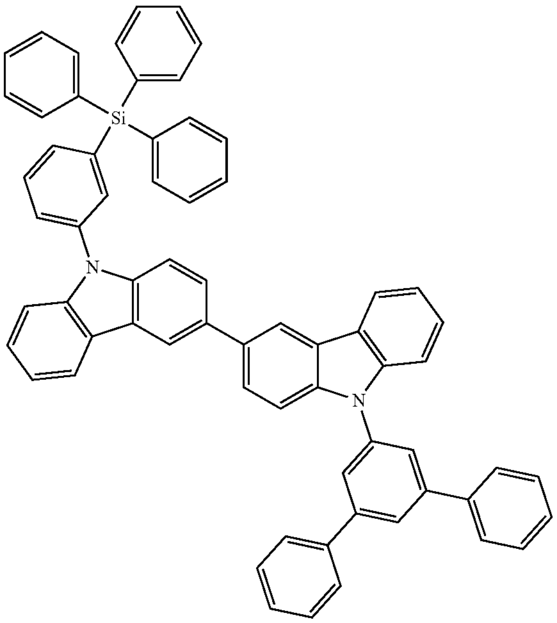
3-76
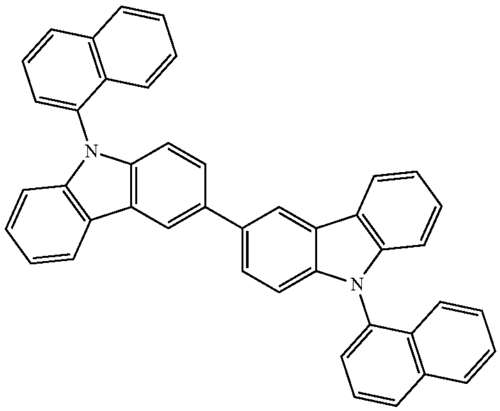
3-77
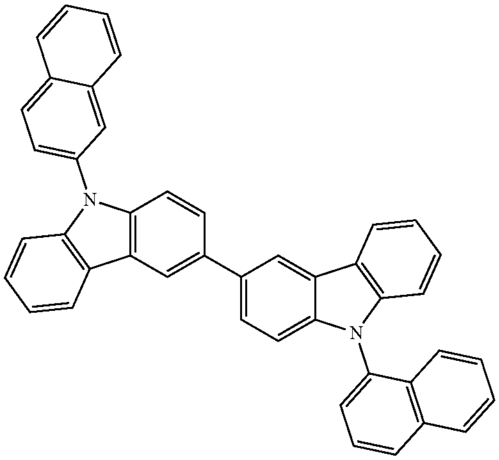
3-78
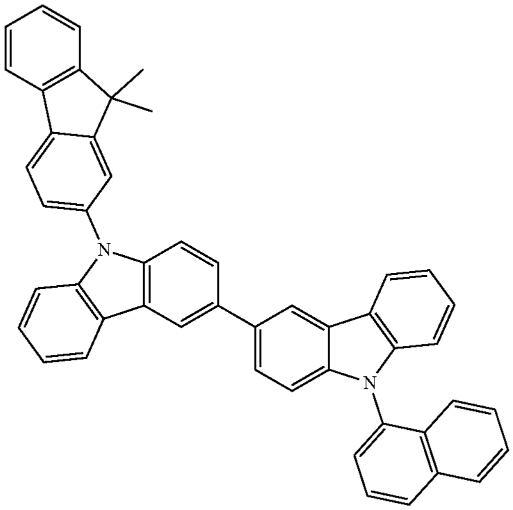
3-79
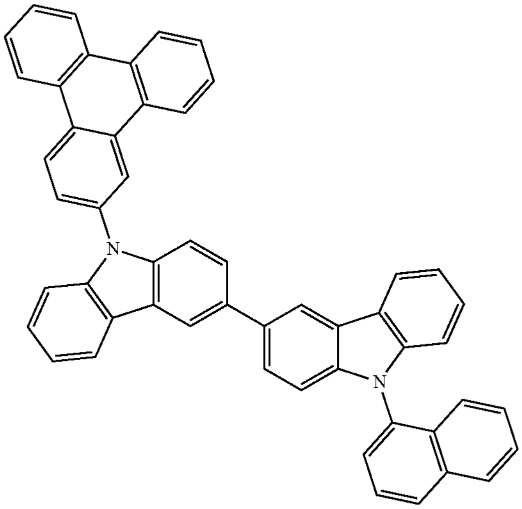
3-80
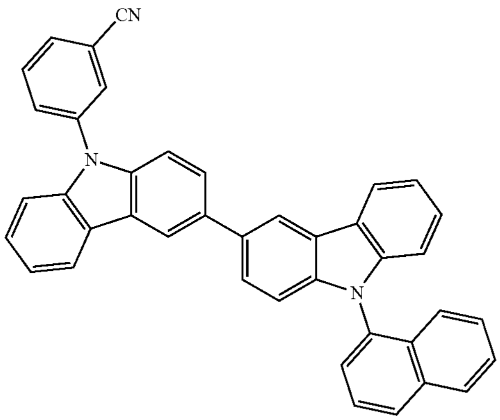

-continued
3-81
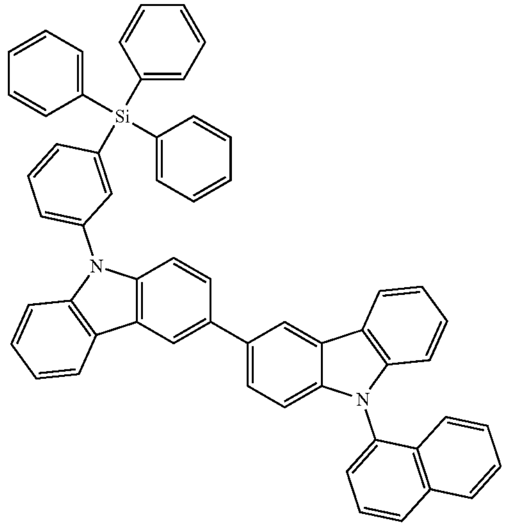
3-82
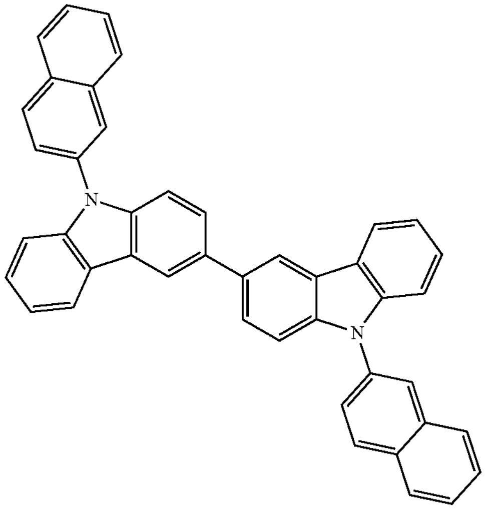
3-83
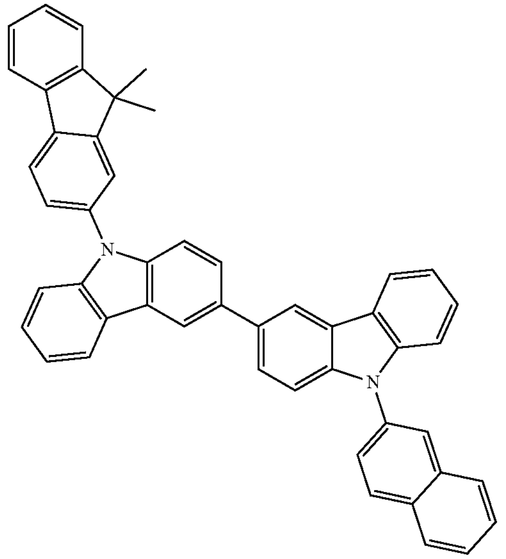
3-84
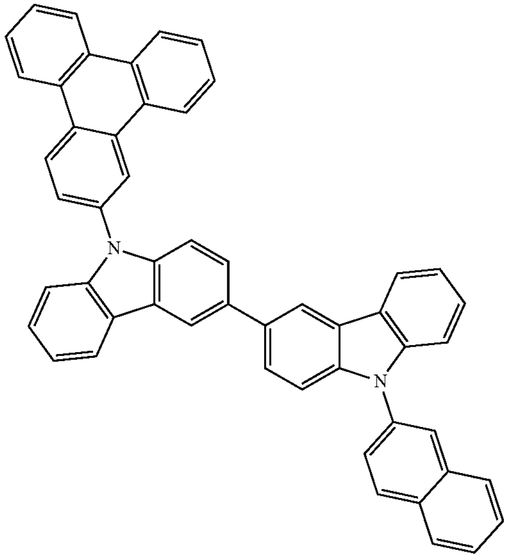
3-85
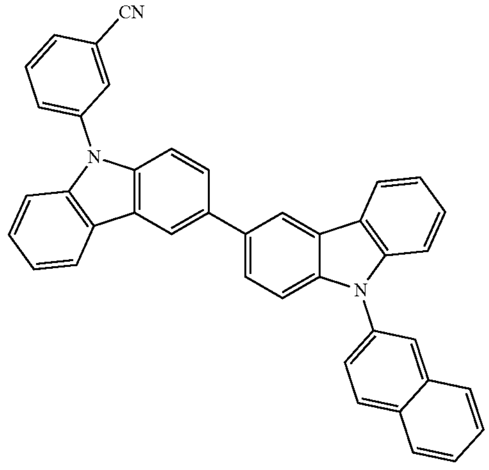
3-86
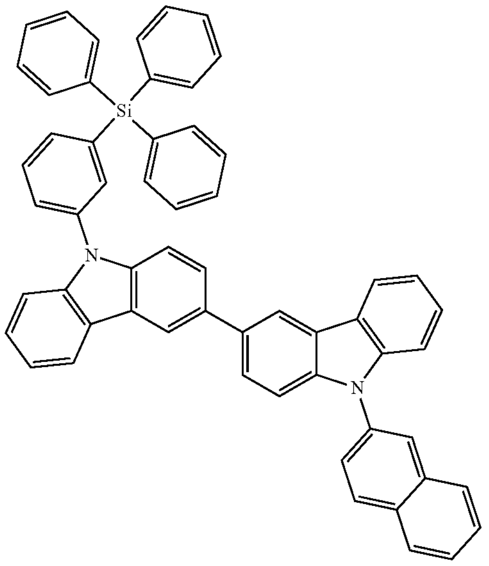

-continued
3-87
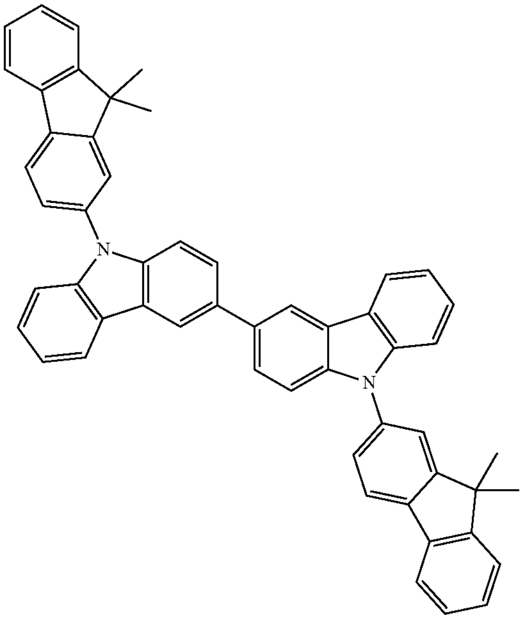
3-88
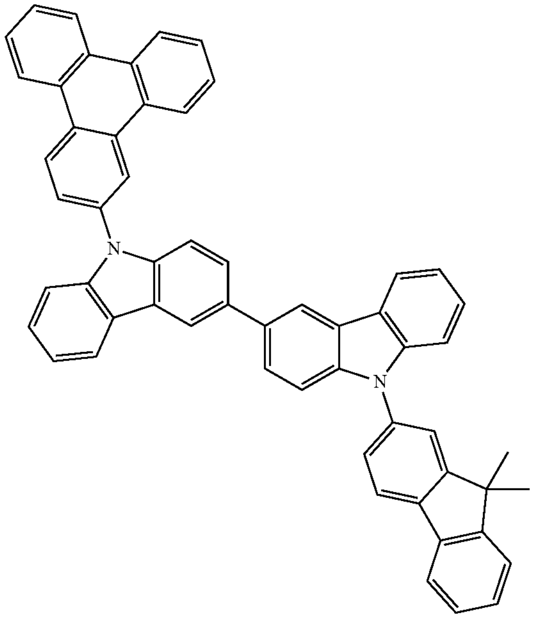
3-89
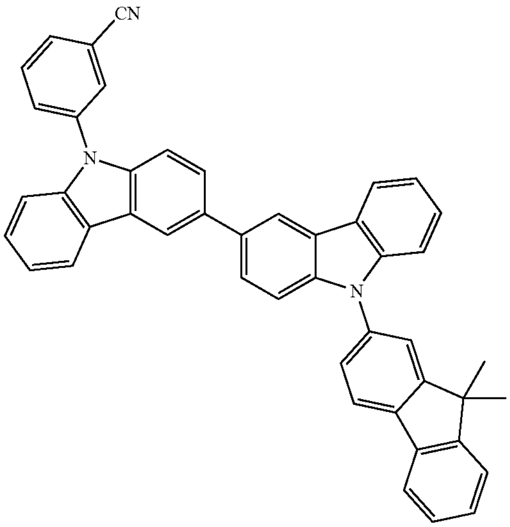
3-90
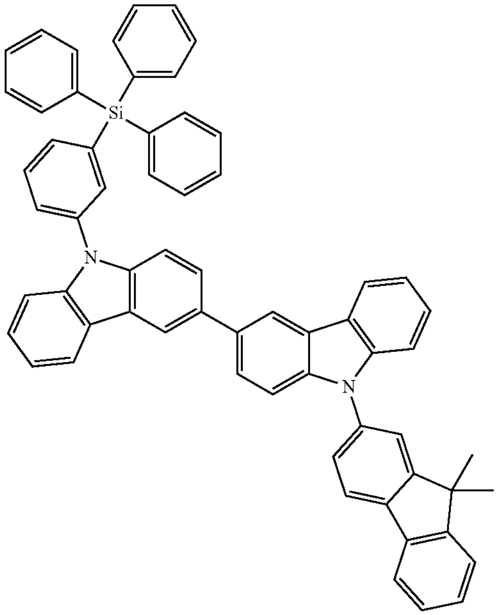

-continued
3-91
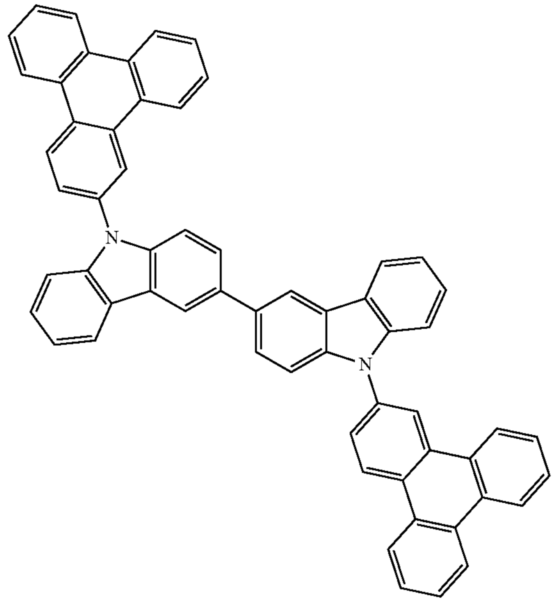
3-92
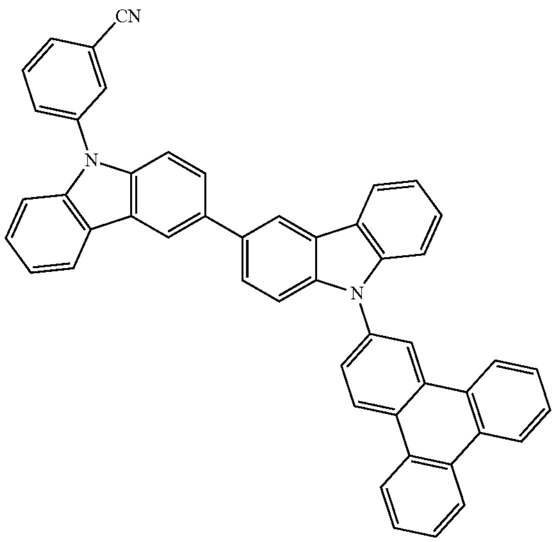
3-93
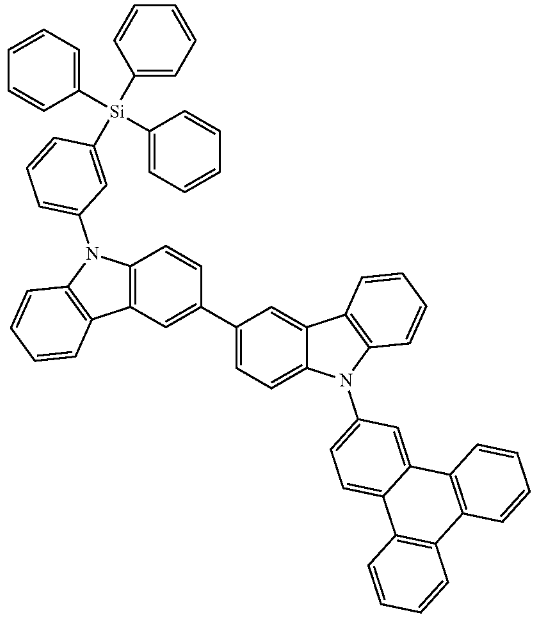
3-84
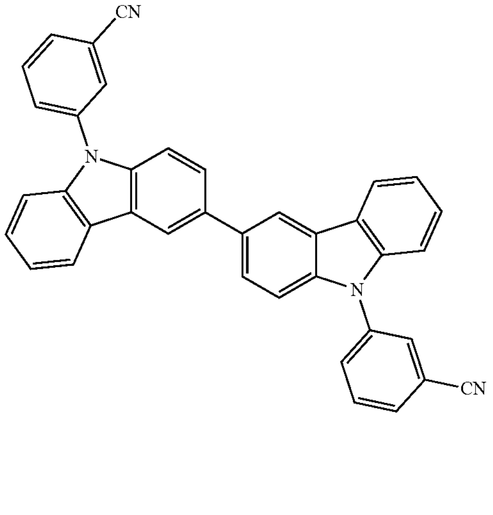

-continued
3-95
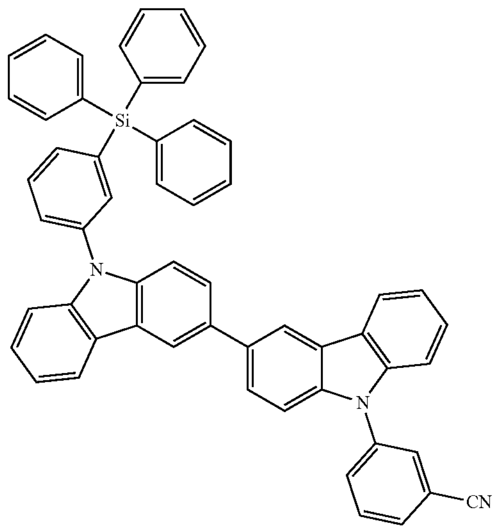
3-96
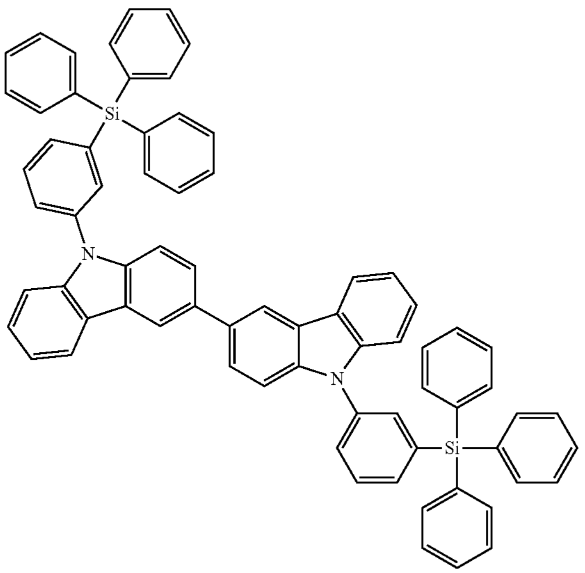
4-1
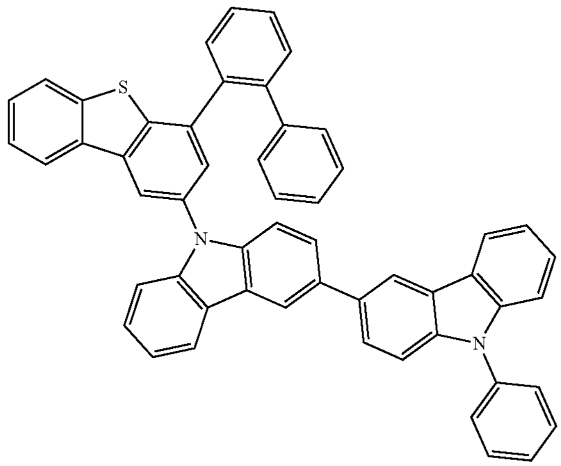
4-2
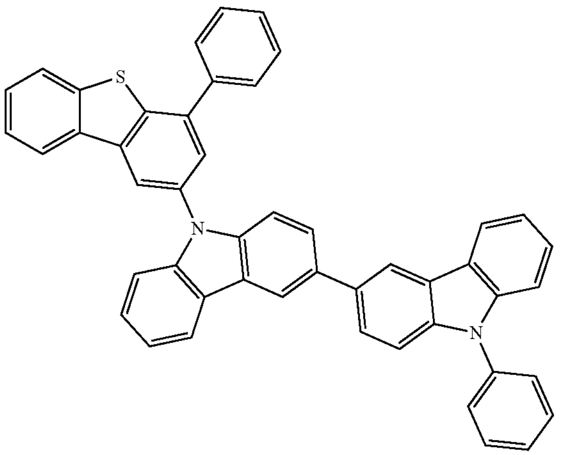
4-3
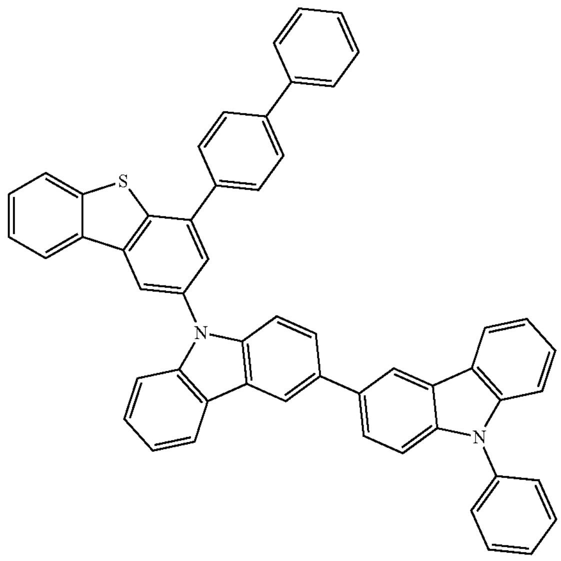
4-4
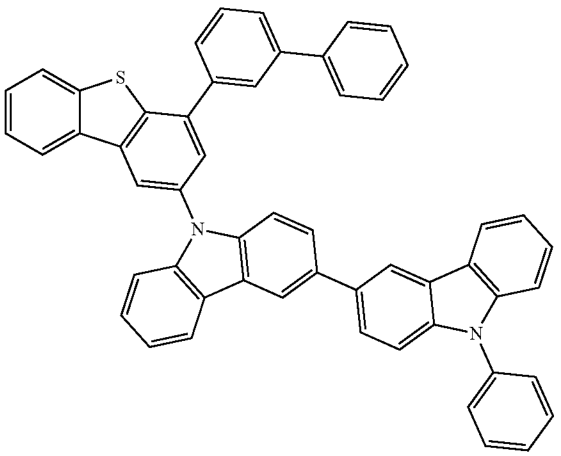

-continued
4-5
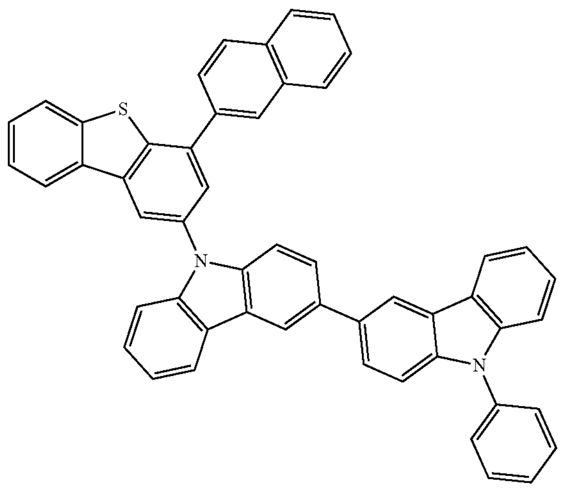
4-6
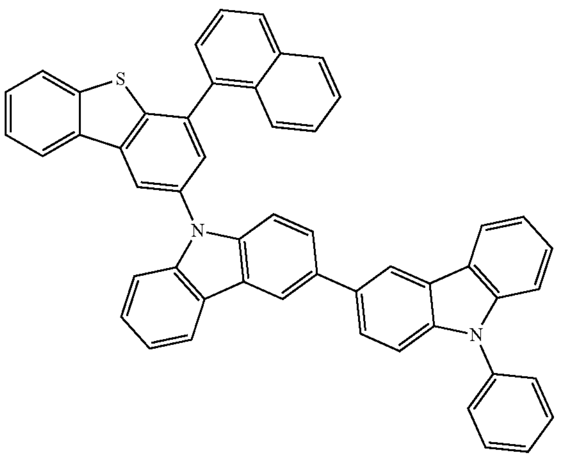
4-7
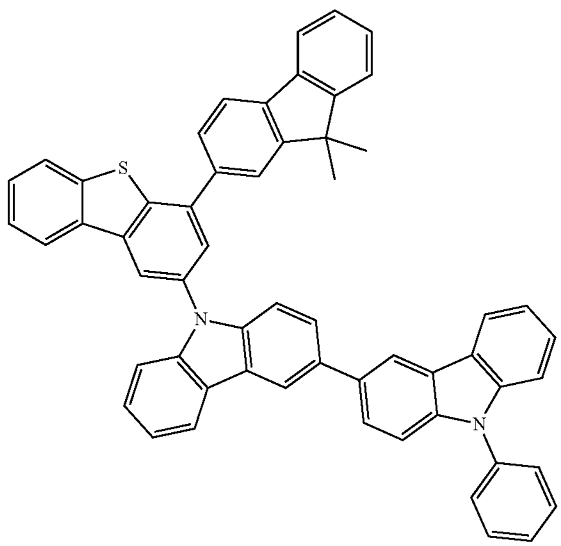
4-8
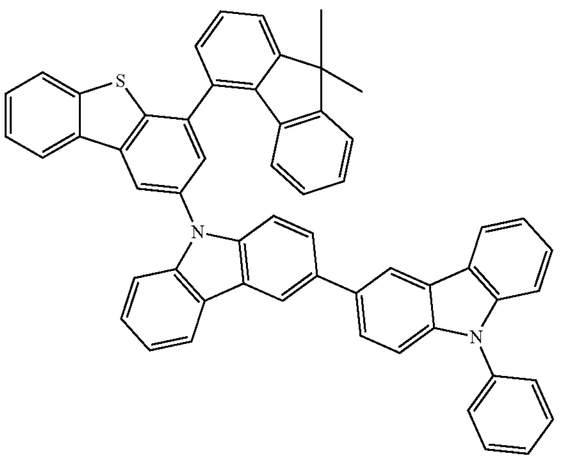
4-9
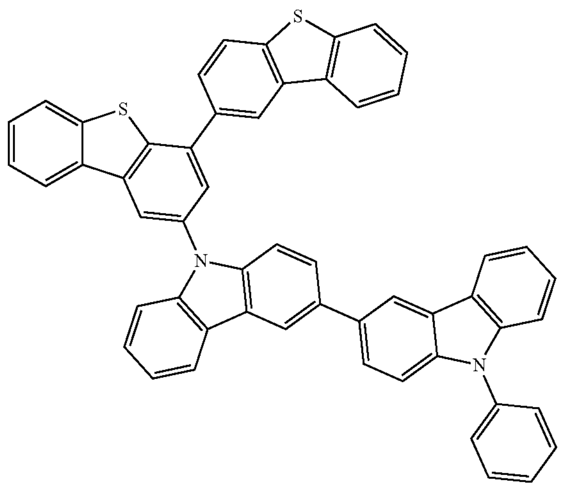
4-10
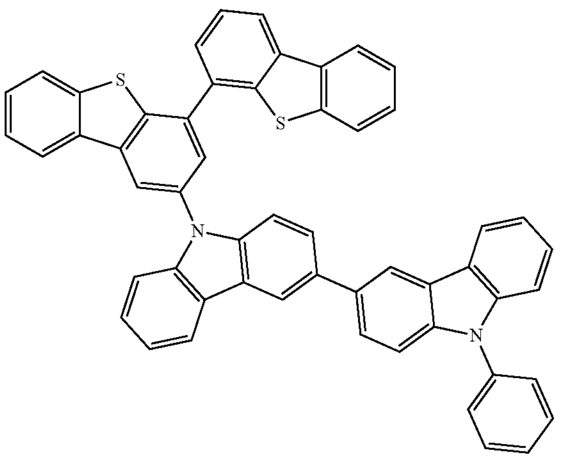

-continued
4-11
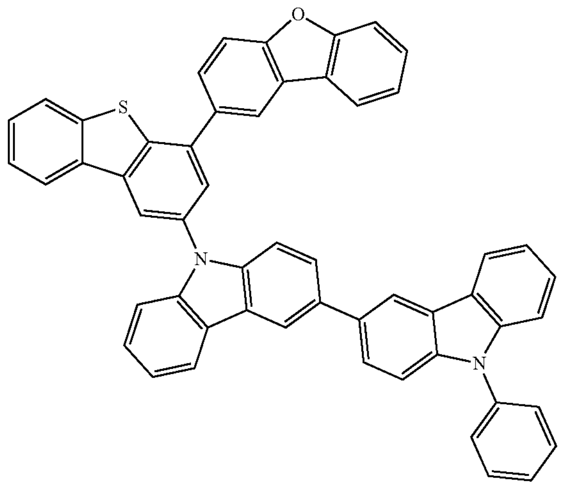
4-12
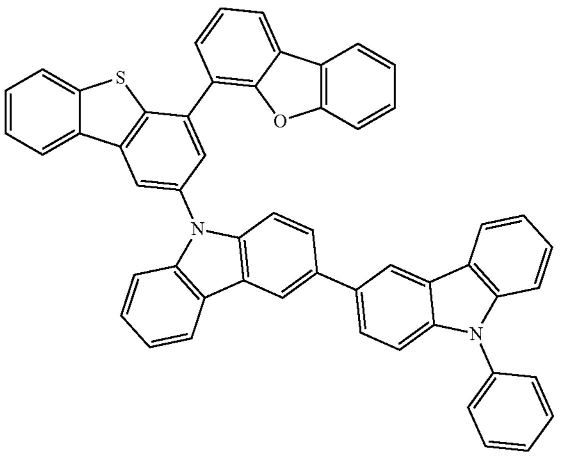
4-13
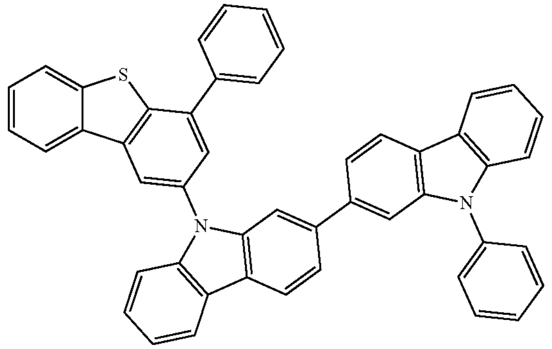
4-14
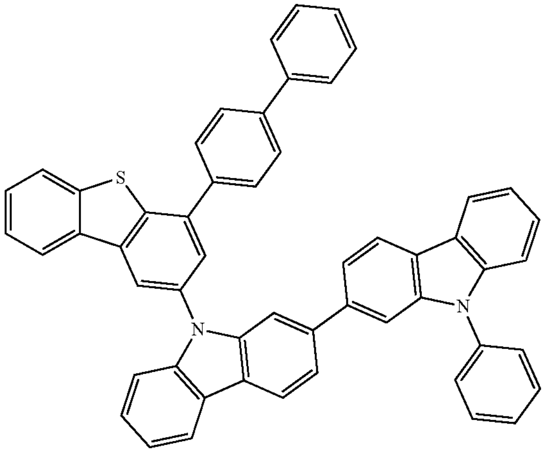
4-15
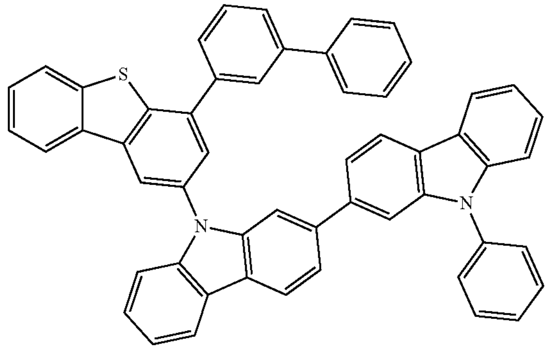
4-16
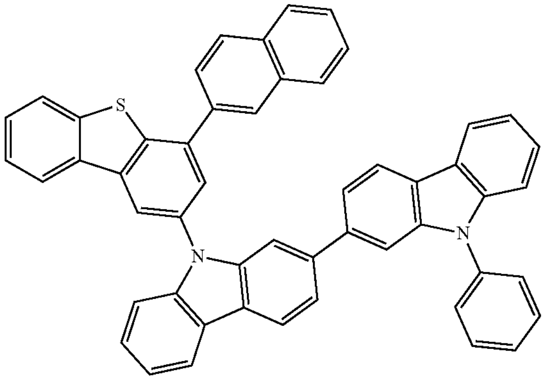

-continued
4-17
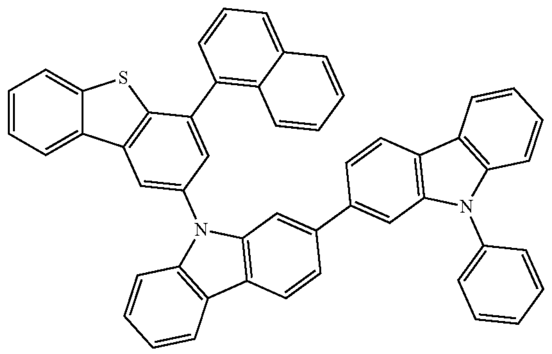
4-18
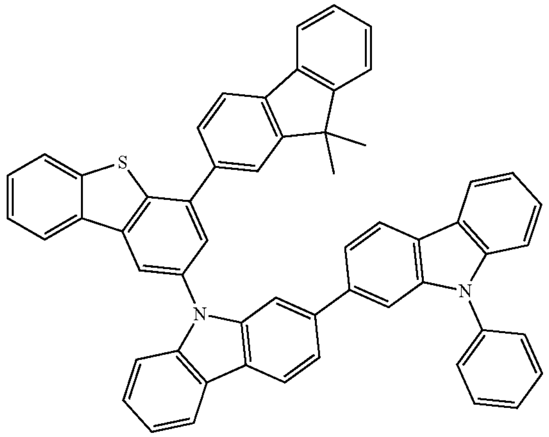
4-20
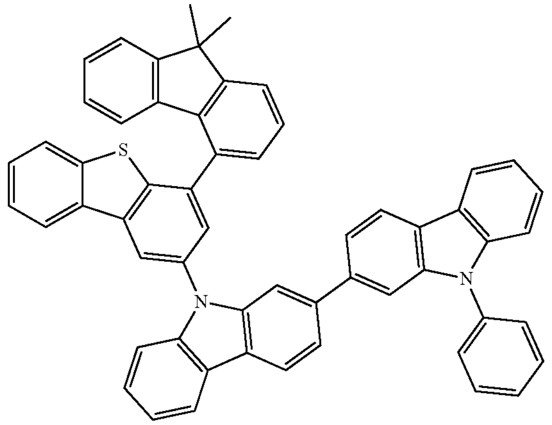
4-19
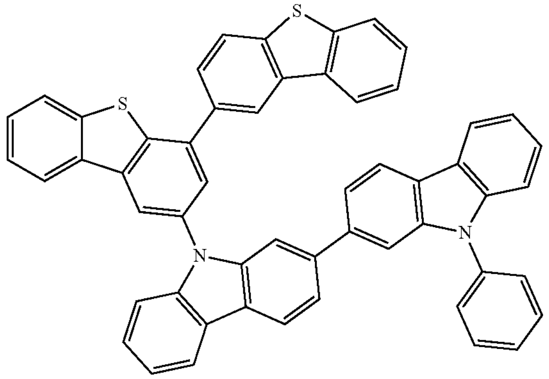
4-21
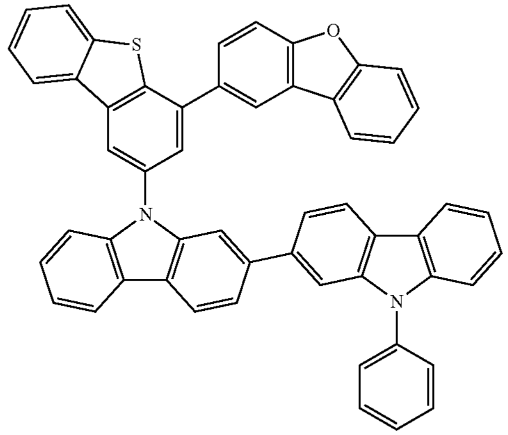
4-22
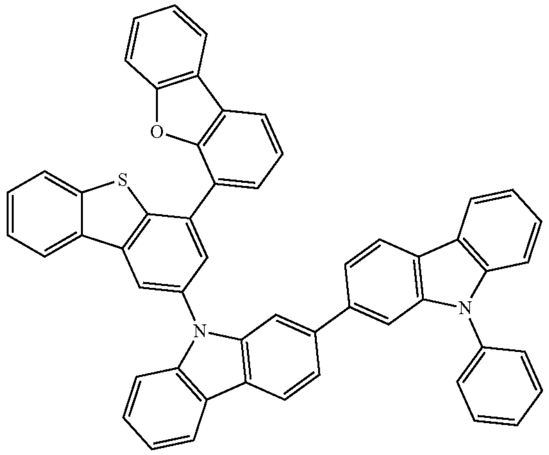

-continued
4-23
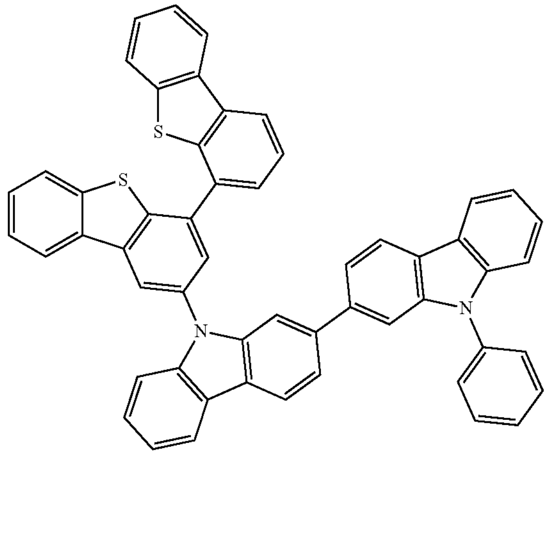
4-24
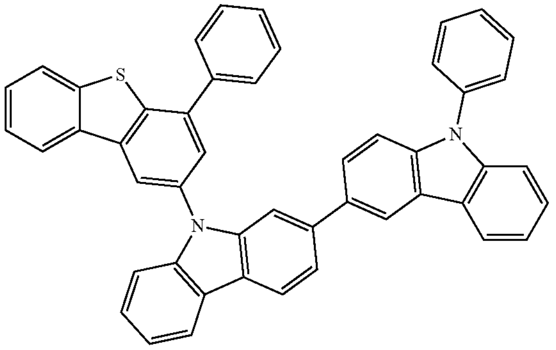
4-25
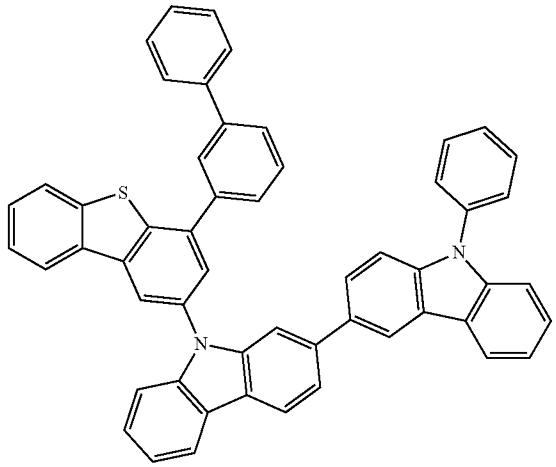
4-26
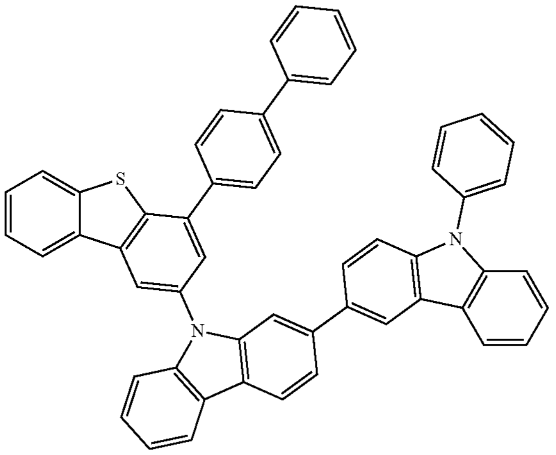
4-27
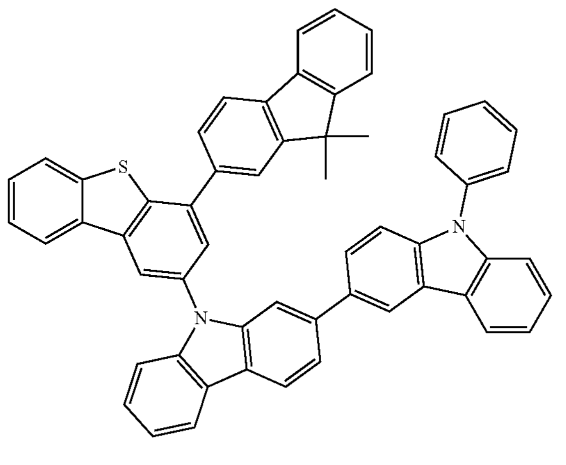
4-28
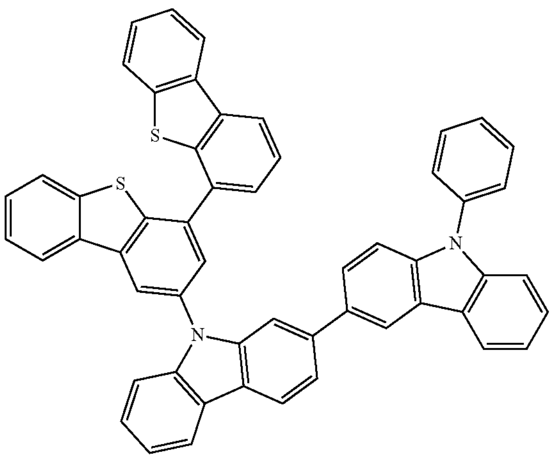

-continued
4-29
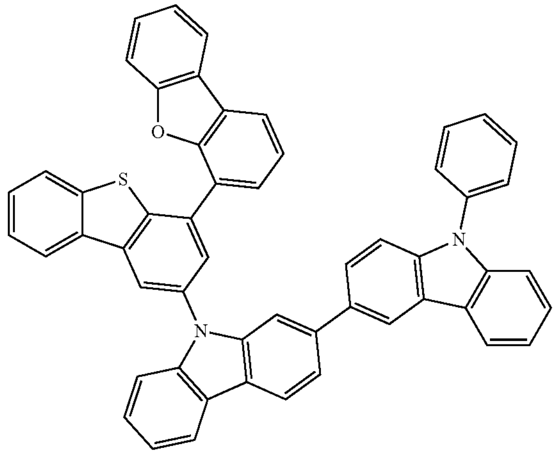
4-30
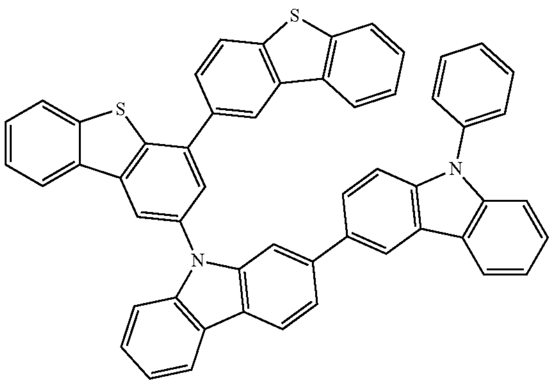
4-31
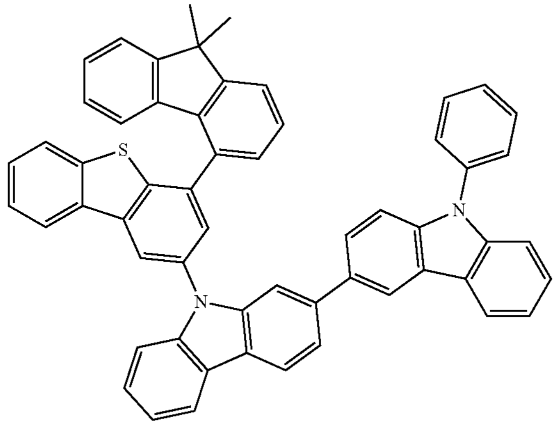
4-32
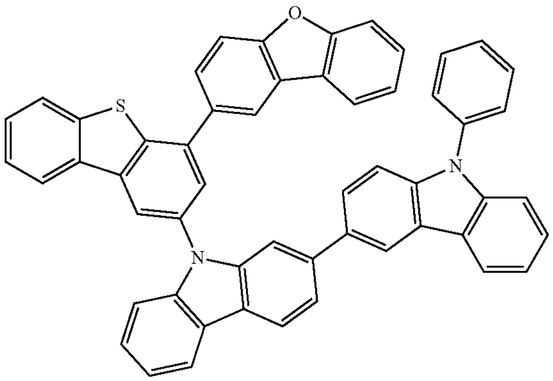
4-33
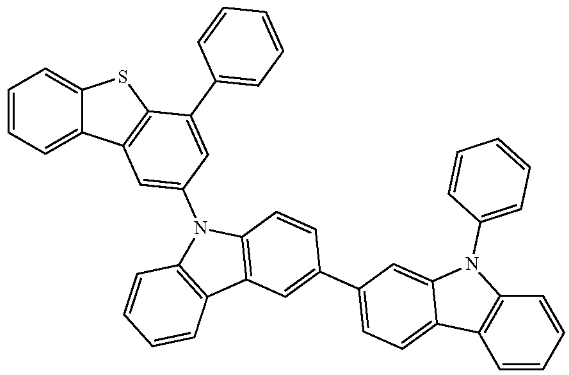
4-34
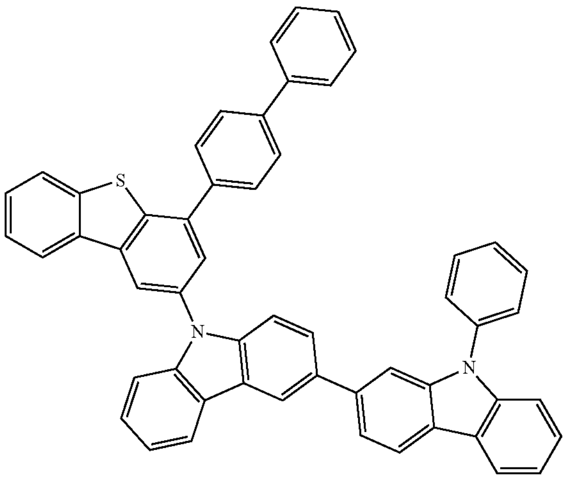

-continued
4-35
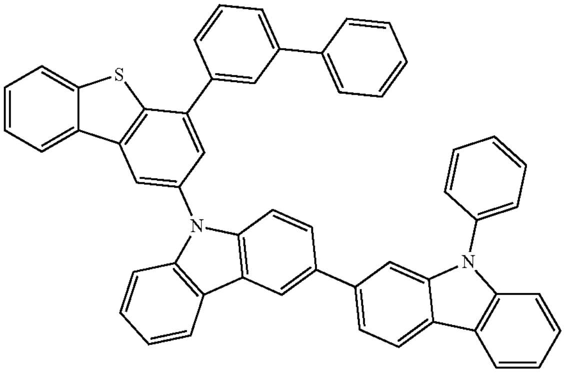
4-36
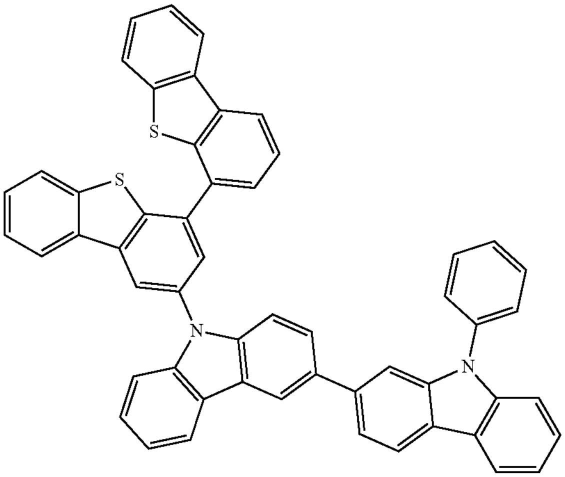
4-37
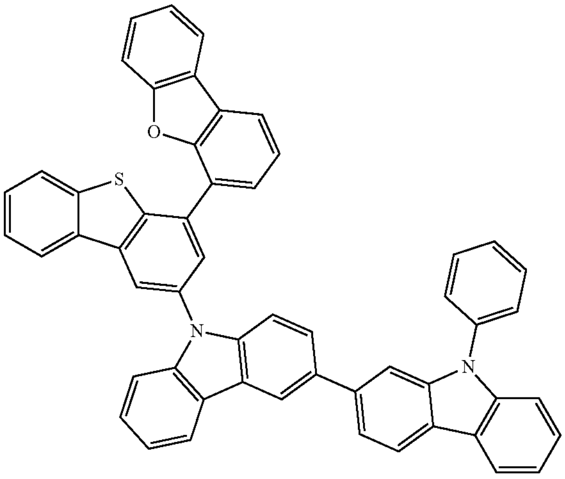
4-38
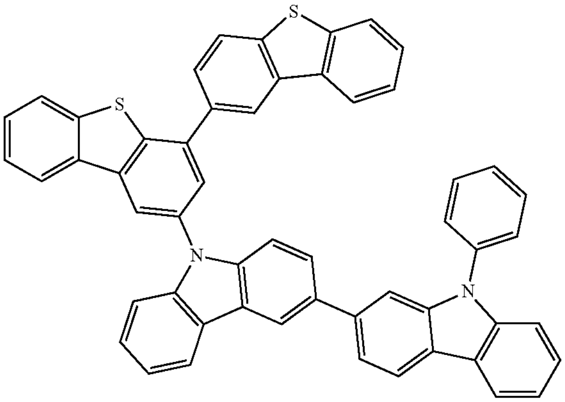
4-39
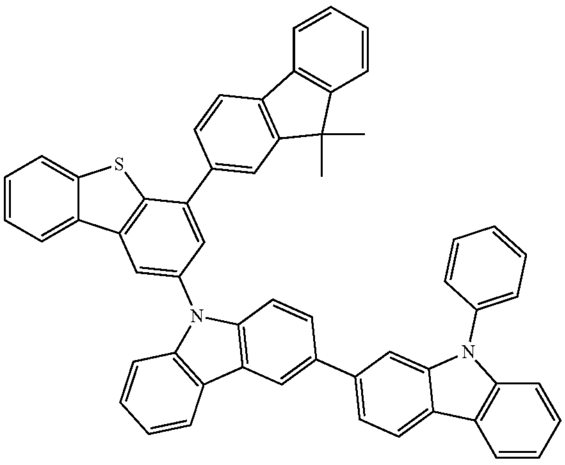
4-40
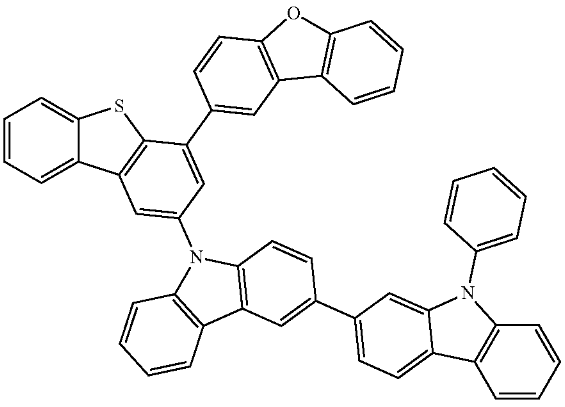

-continued
4-41
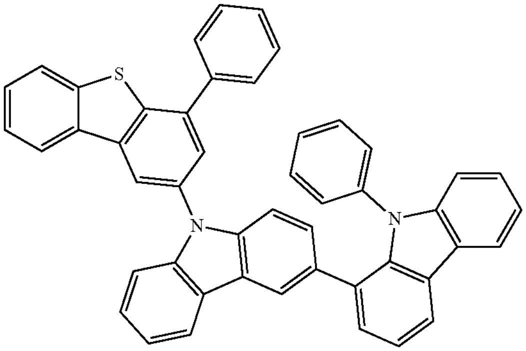
4-42
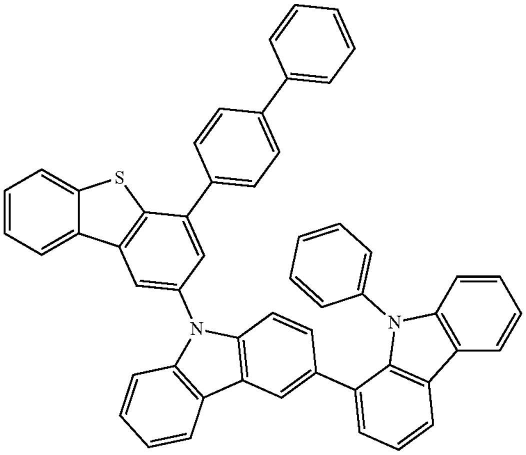
4-43
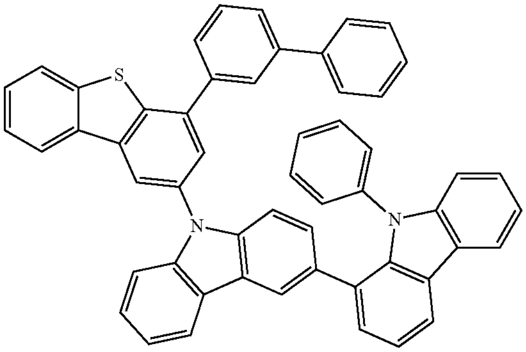
4-44
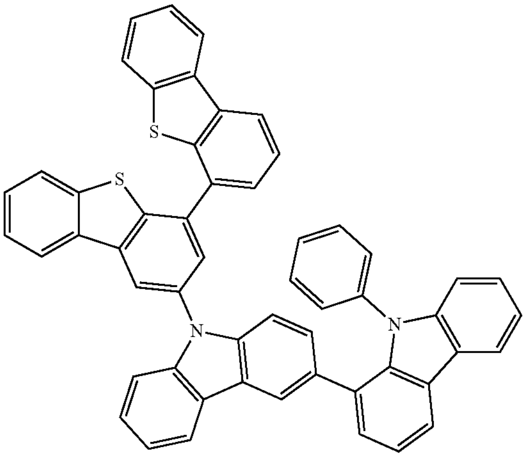
4-45
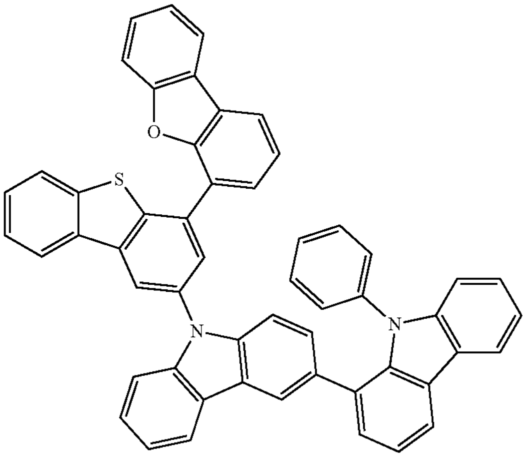
4-46
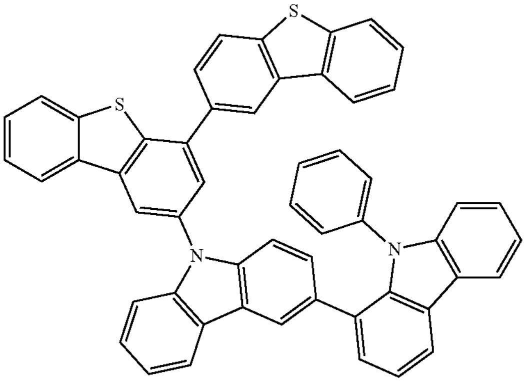

-continued
4-47
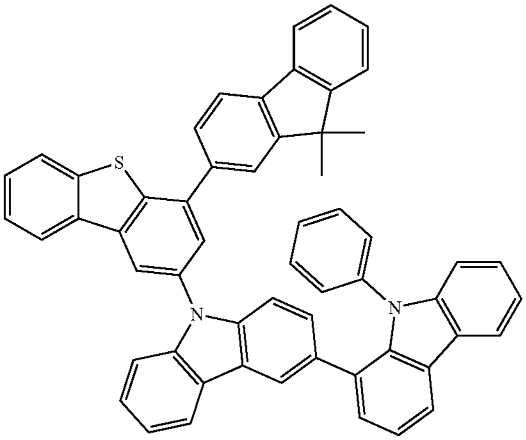
4-48
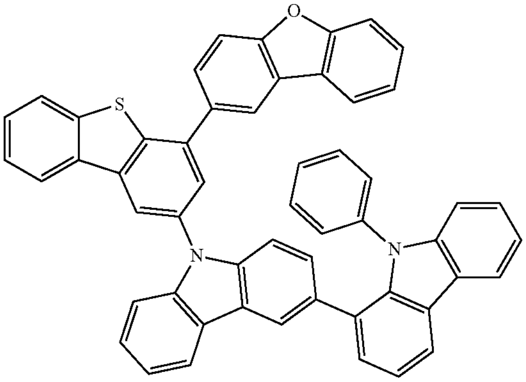
4-49
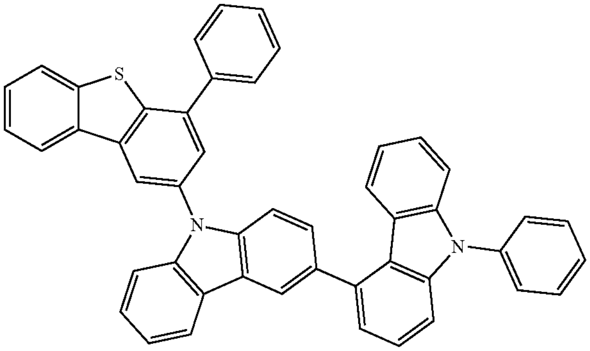
4-50
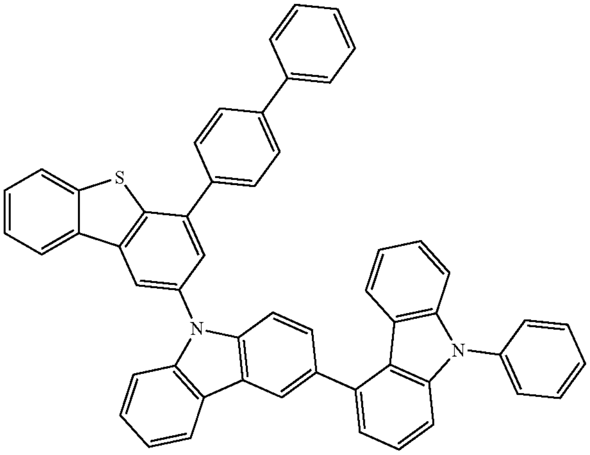
4-51
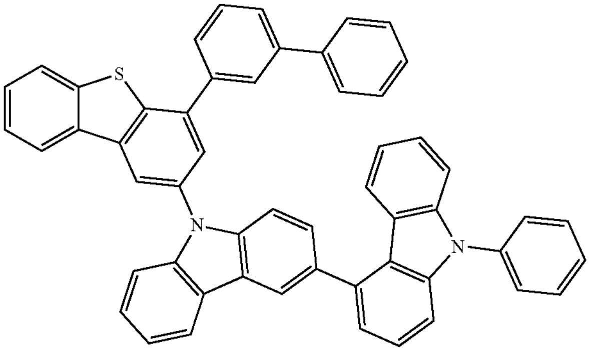
4-52
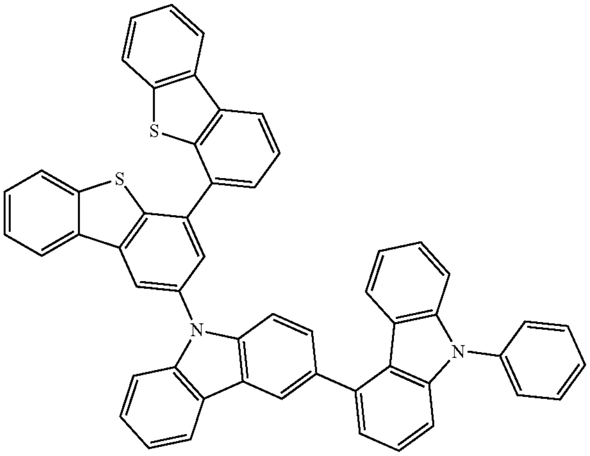

-continued
4-53
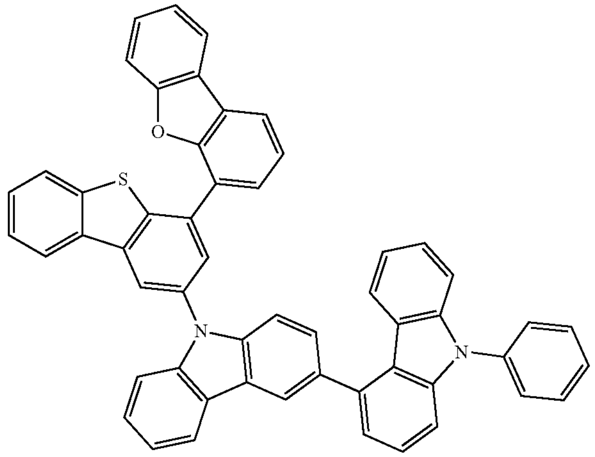
4-54
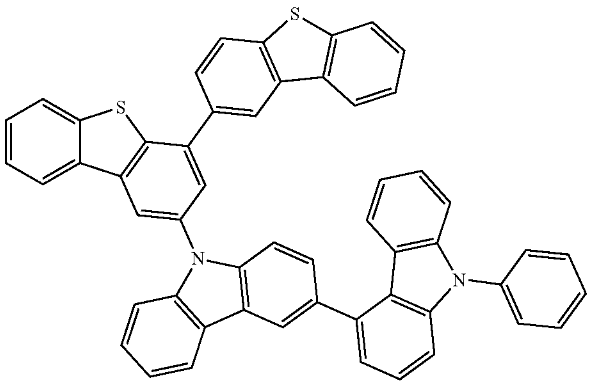
4-55
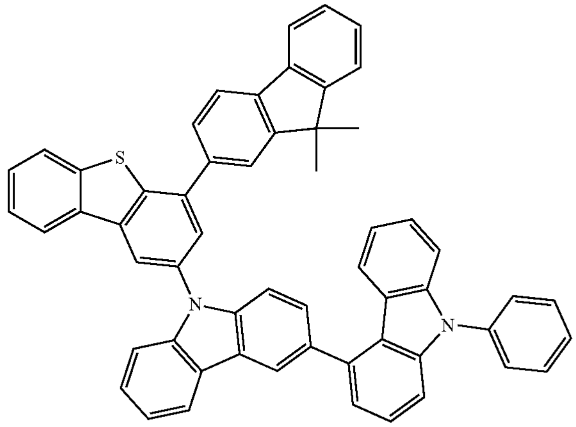
4-56
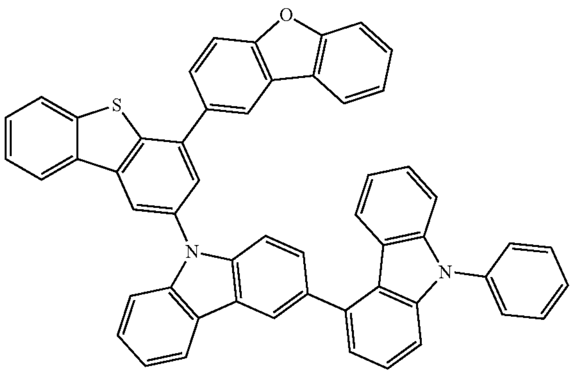
4-57
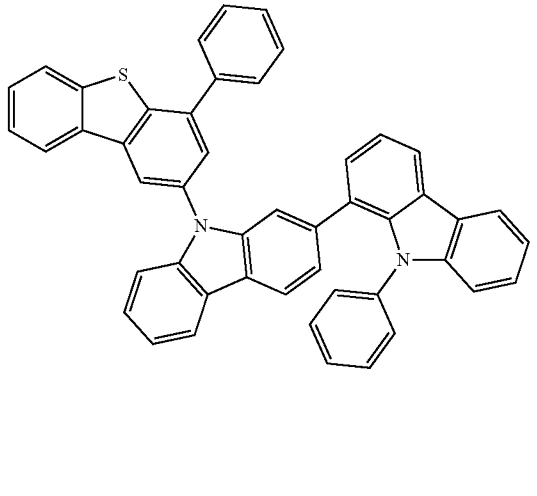
4-58
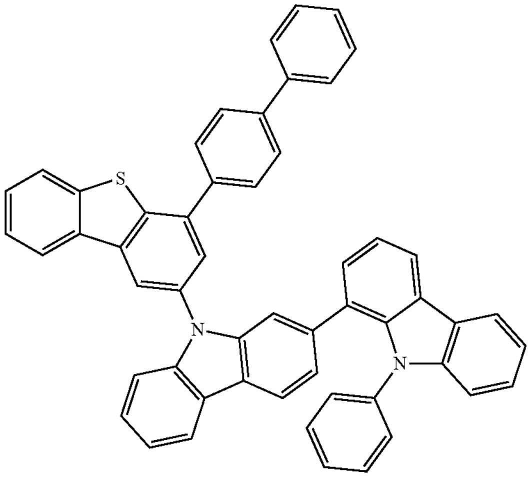

-continued
4-59
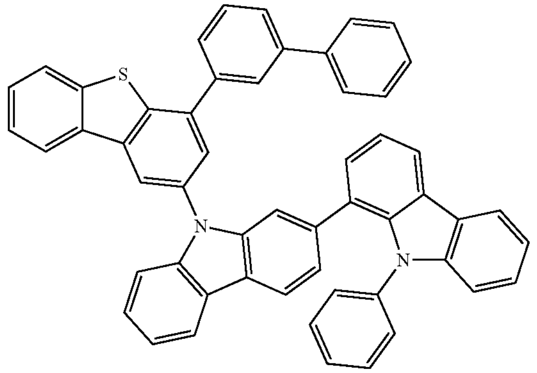
4-60
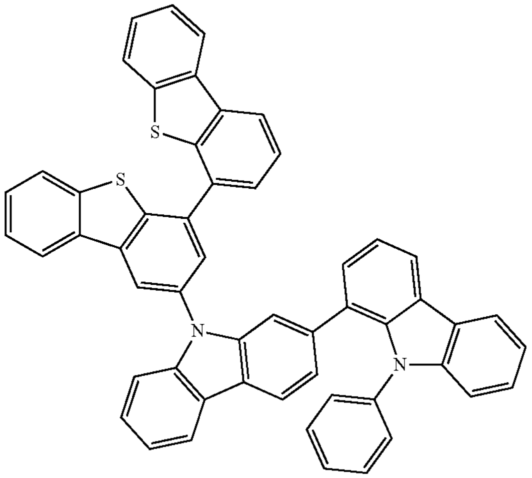
4-61
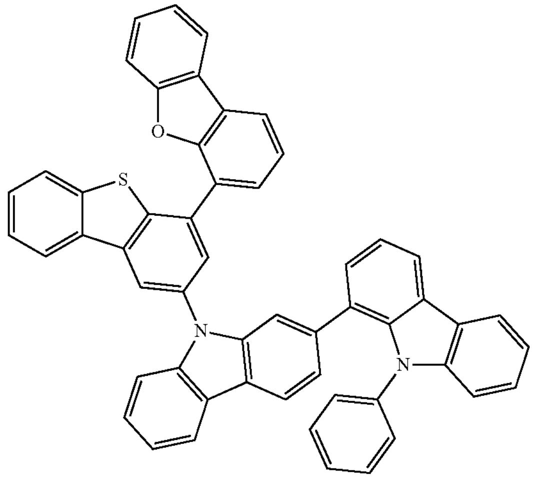
4-62
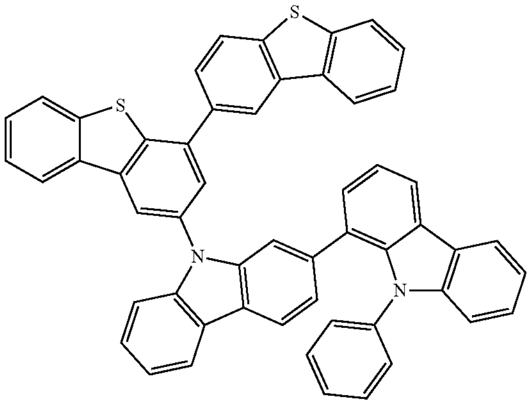
4-63
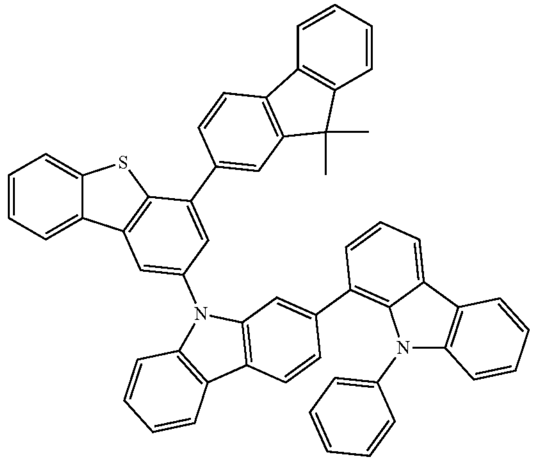
4-64
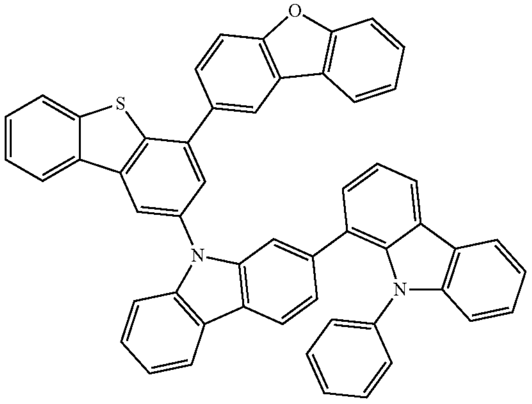

-continued
4-65
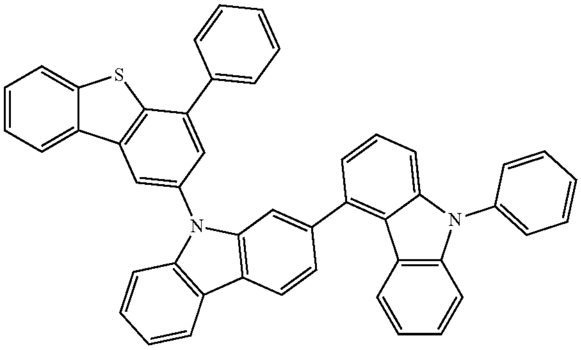
4-66
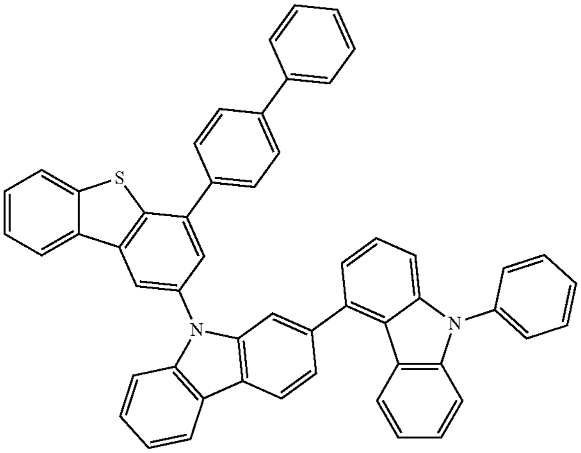
4-67
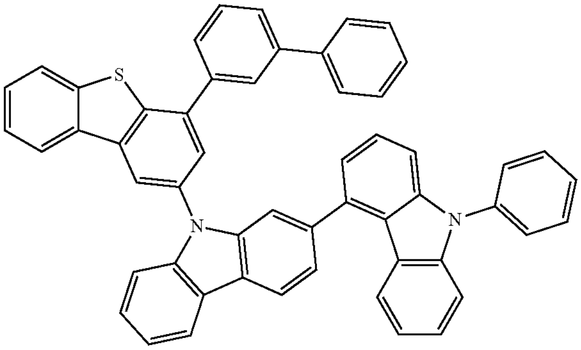
4-68
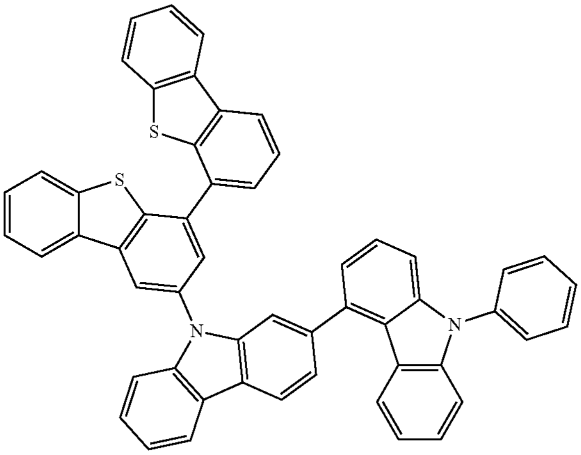
4-69
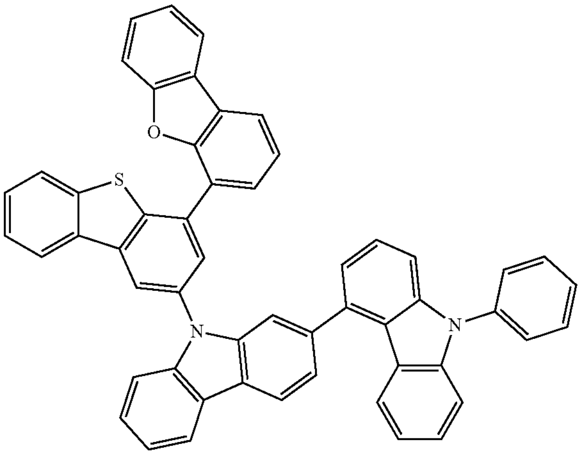
4-70
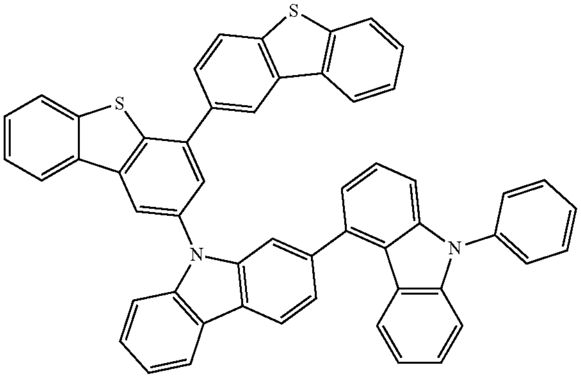

-continued
4-71
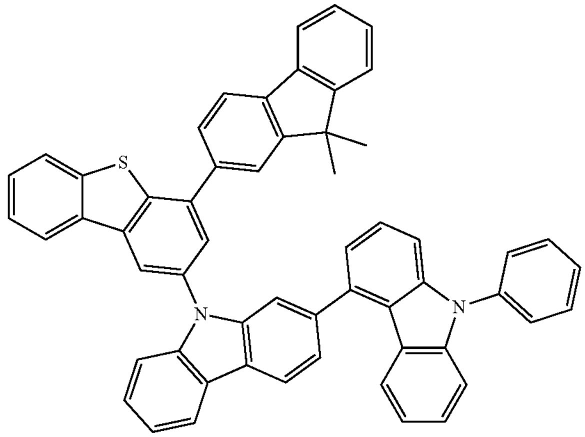
4-72
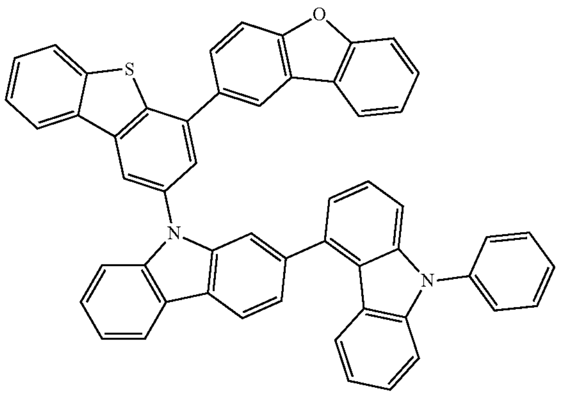
4-73
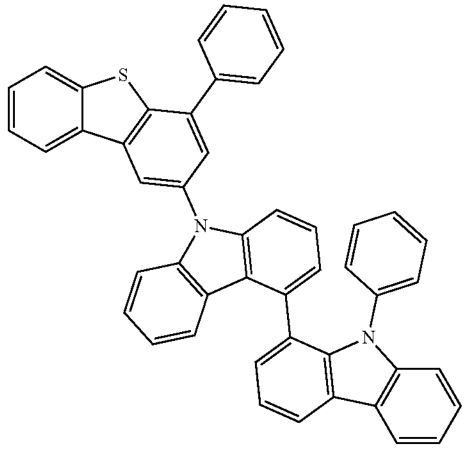
4-74
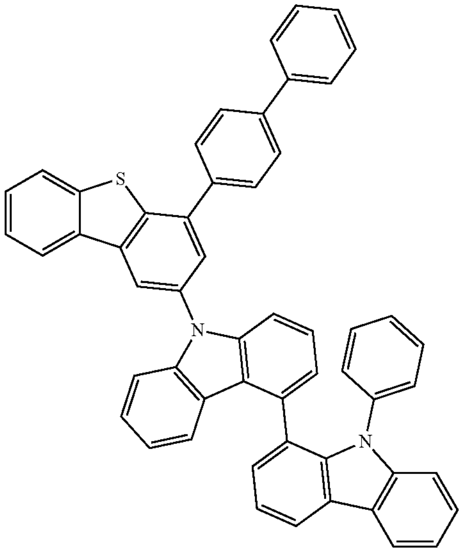
4-75
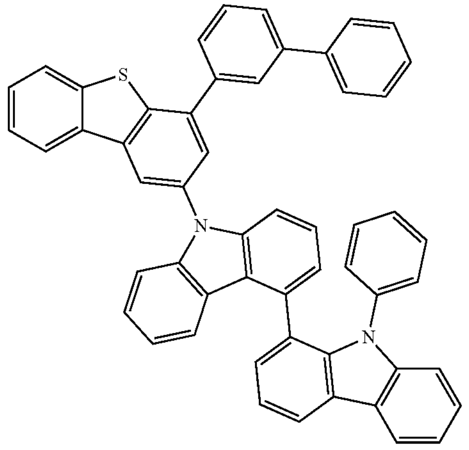
4-76
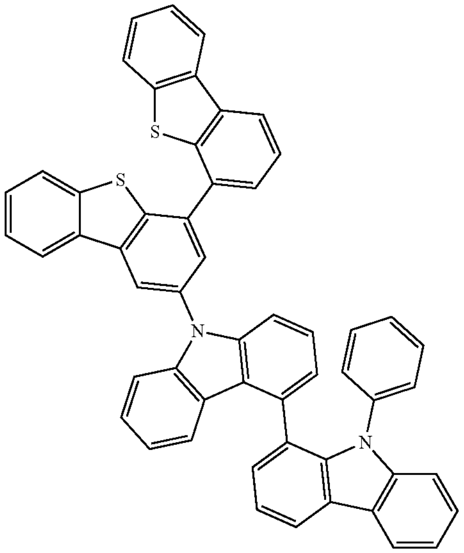

-continued
4-77
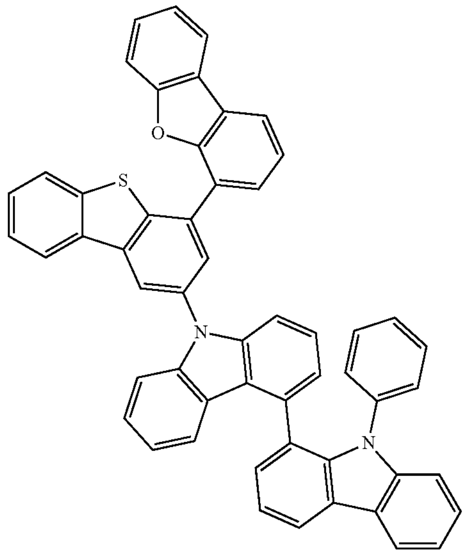
4-78
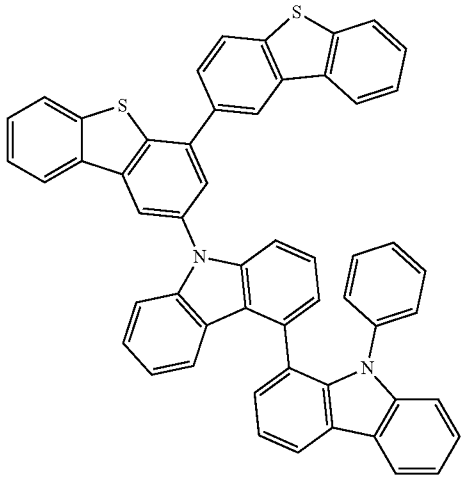
4-79
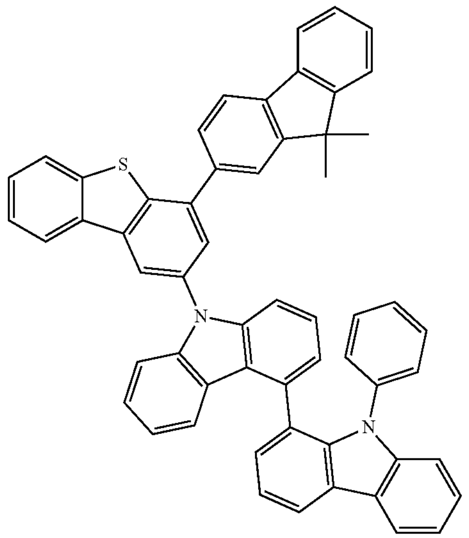
4-80
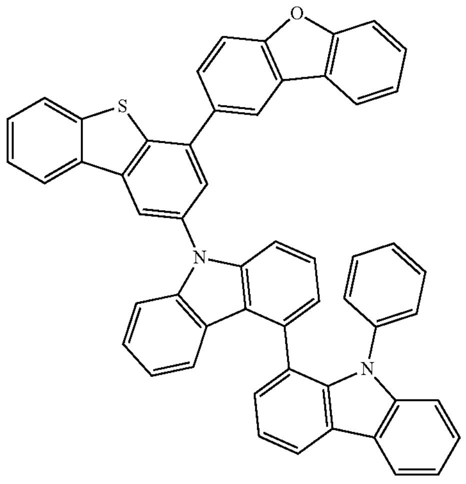

-continued
4-81
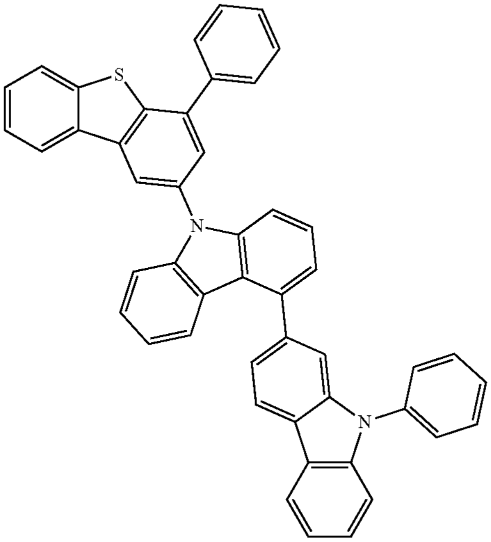
4-82
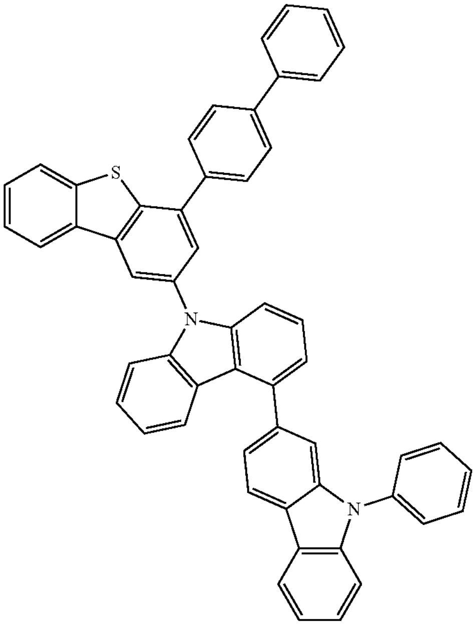
4-83
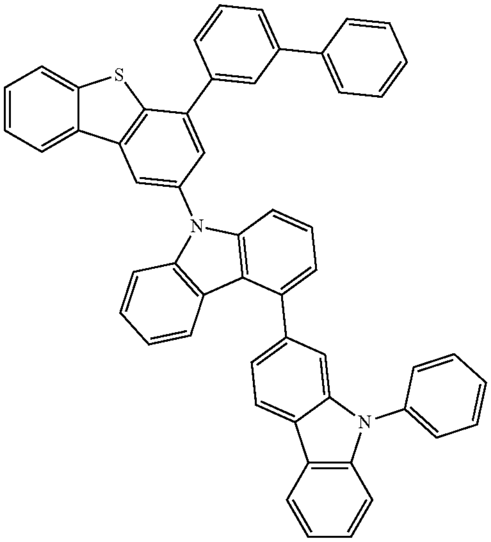
4-84
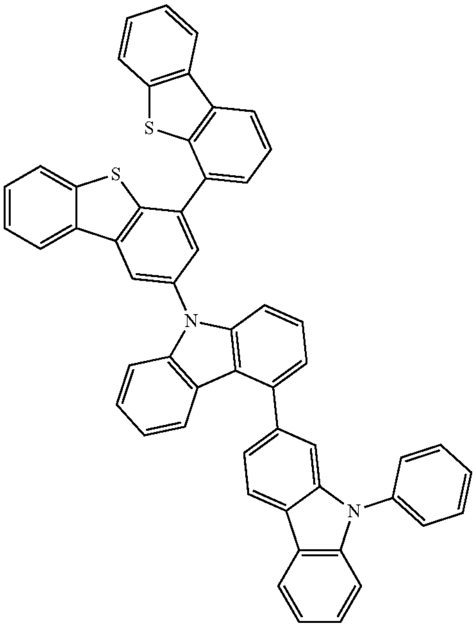

-continued
4-85
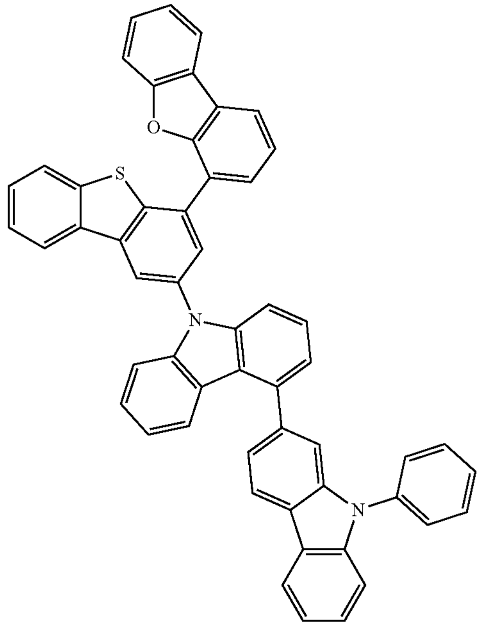
4-86
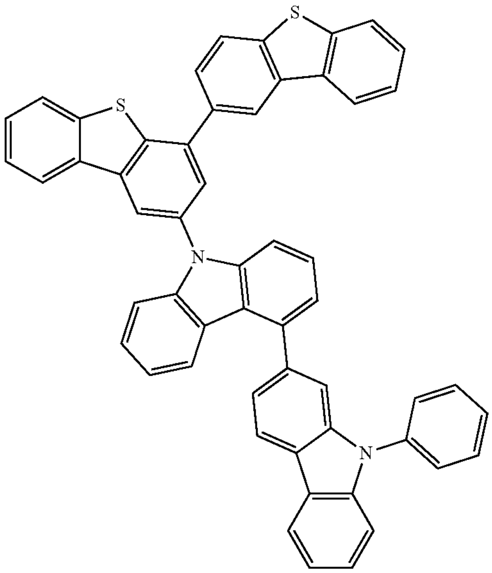
4-87
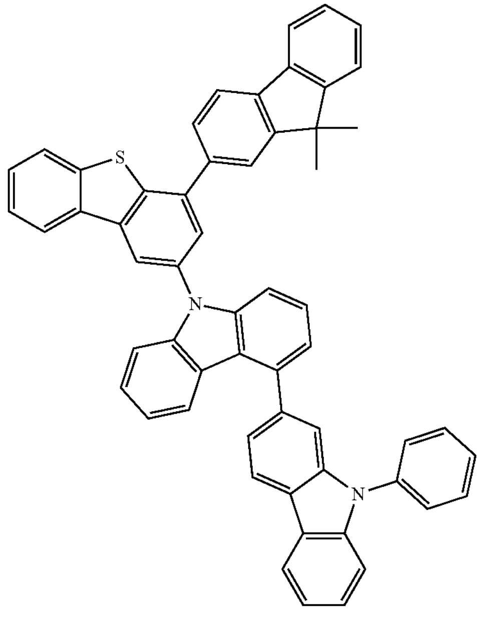
4-88
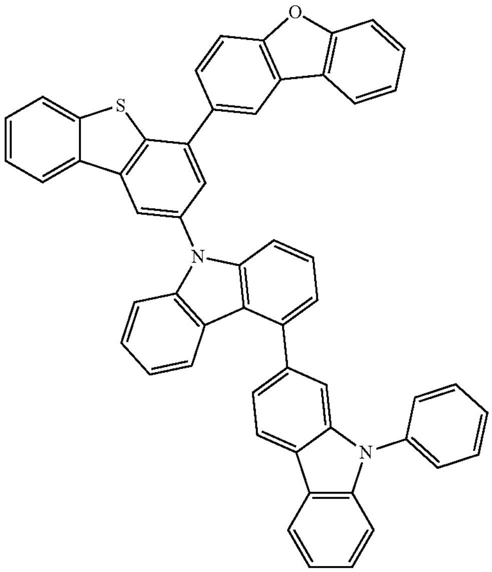

-continued
4-89
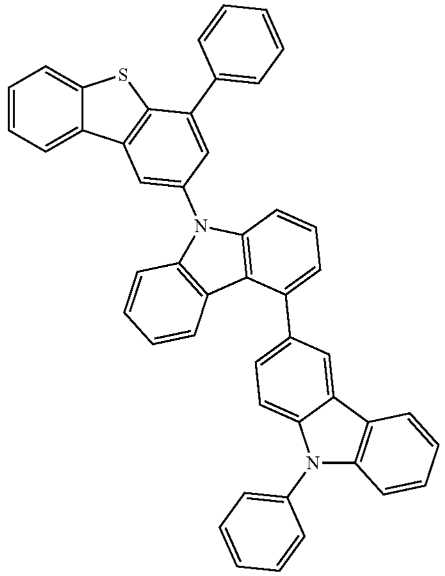
4-90
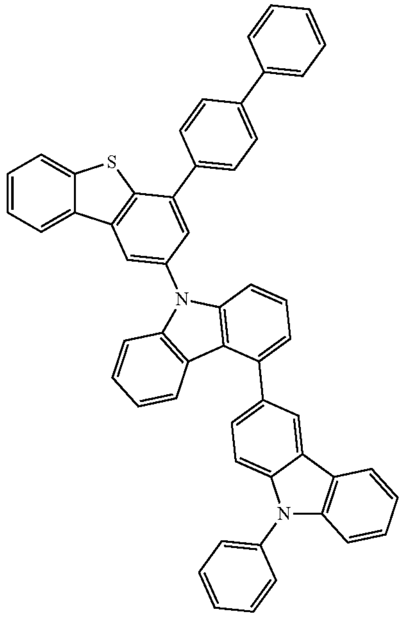
4-91
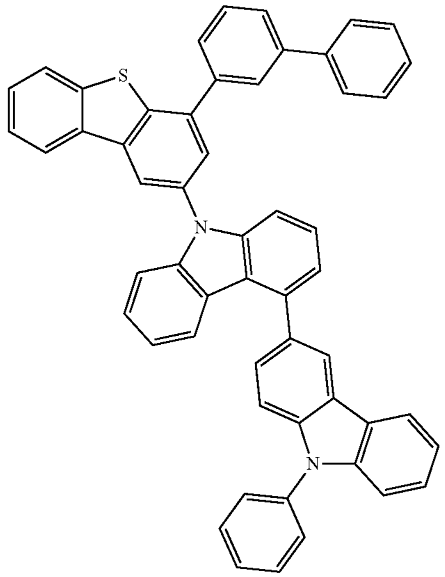
4-92
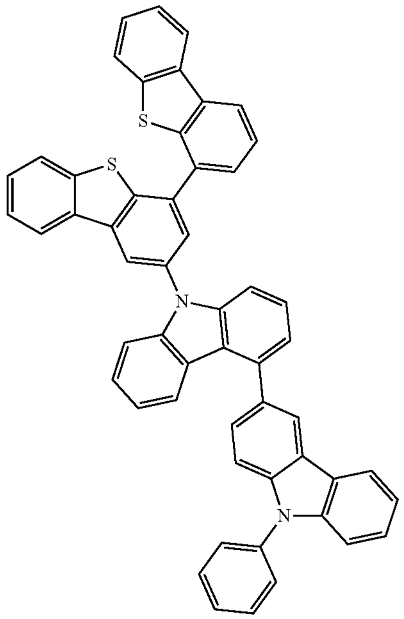

-continued
4-94
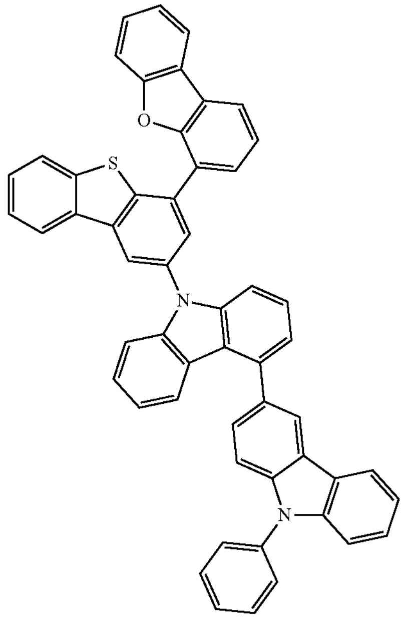
4-93
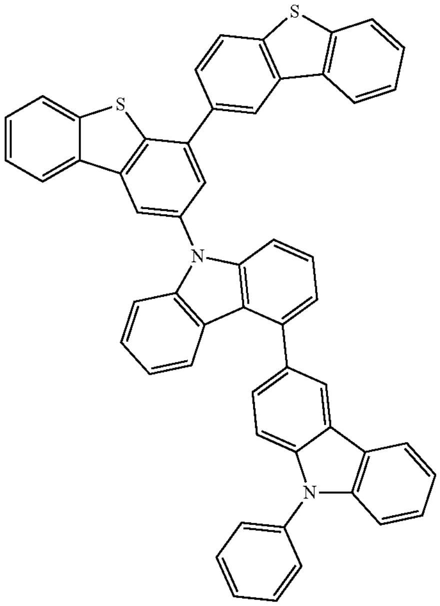
4-95
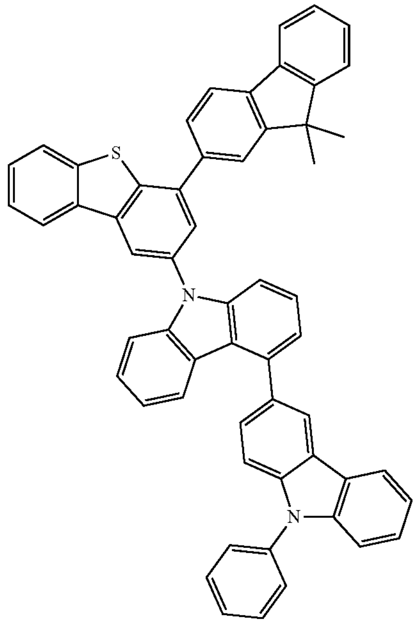
4-96
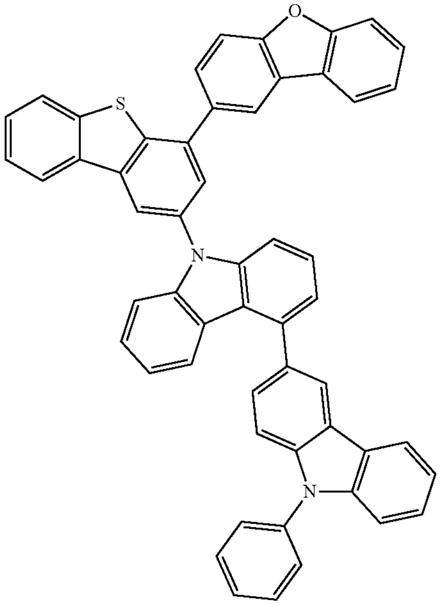

-continued
4-97
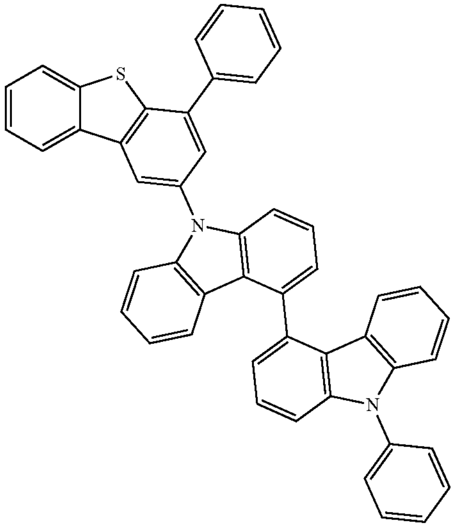
4-98
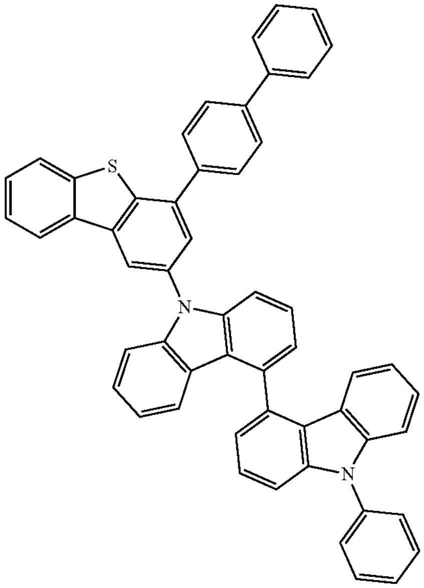
4-99
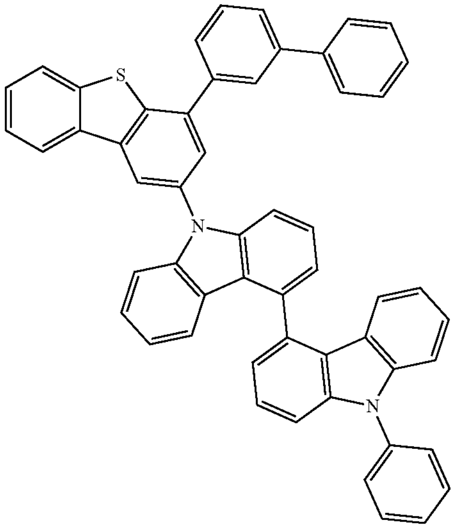
4-100
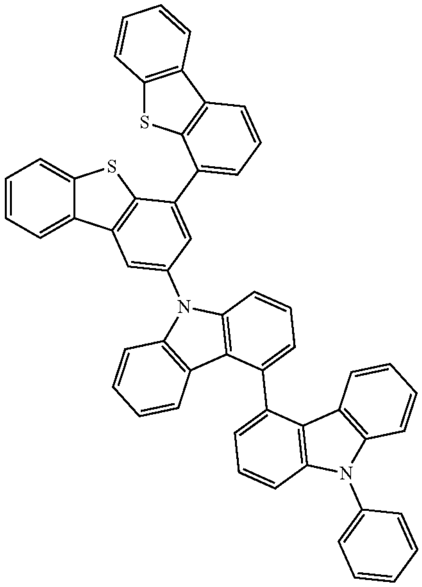
4-101
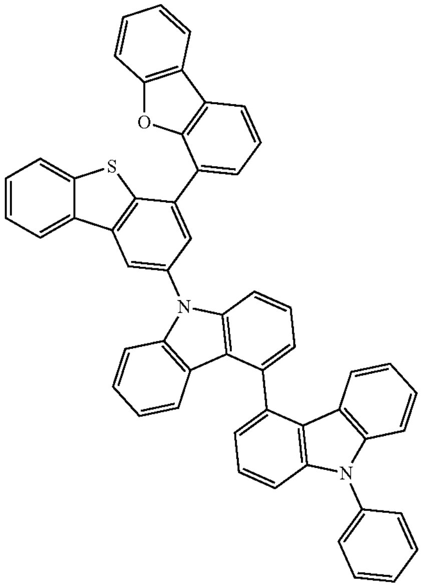

-continued
4-102
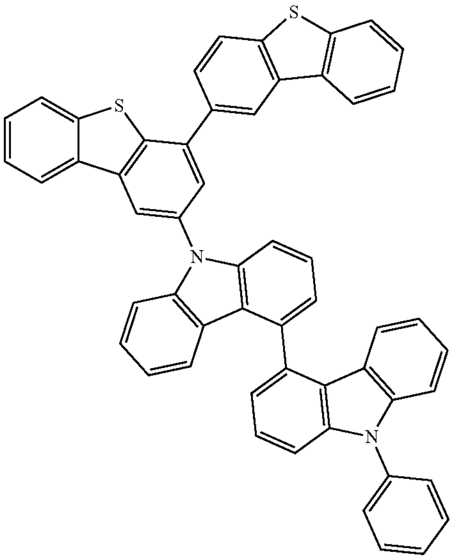
4-103
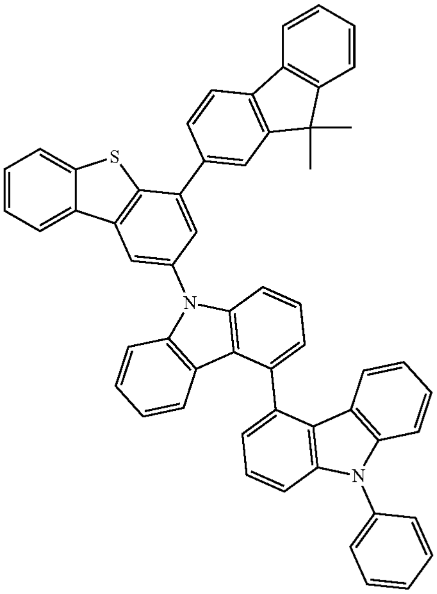
-continued
4-104
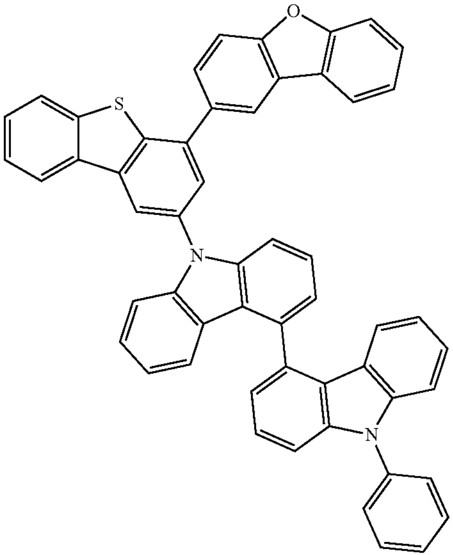
4-105
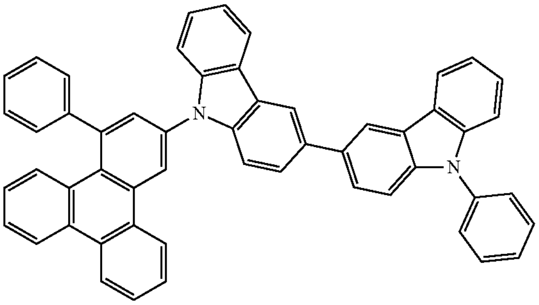
4-106
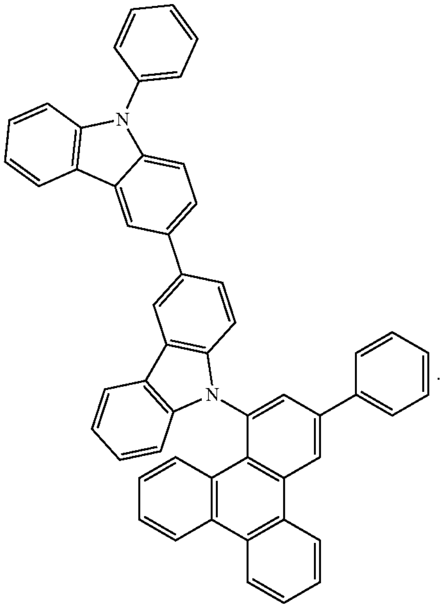
9. The organic light emitting device of claim 7, wherein Rc and Rd are hydrogen.
10. The organic light emitting device of claim 7, wherein Ra and Rb are the same as or different from each other, and are each independently a substituted or unsubstituted C6 to C40 aryl group; or a substituted or unsubstituted C6 to C40 heteroaryl group.

11. The organic light emitting device of claim 6, wherein the organic material layer comprises a light emitting layer, and the light emitting layer comprises the heterocyclic compound.

12. The organic light emitting device of claim 6, wherein the organic material layer comprises a light emitting layer, the light emitting layer comprises a host material, and the host material includes the heterocyclic compound.

13. The organic light emitting device of claim 6, further comprising one, two or more layers selected from the group consisting of a light emitting layer, a hole injection layer, a hole transfer layer, an electron injection layer, an electron transfer layer, an electron blocking layer and a hole blocking layer.

14. A composition for an organic material layer of an organic light emitting device comprising:

the heterocyclic compound of claim 1; and a heterocyclic compound represented by the following Chemical Formula 2:

[Chemical Formula 2]

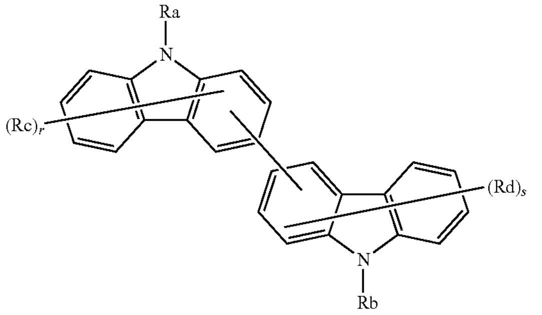

wherein, in Chemical Formula 2,

Rc and Rd are the same as or different from each other, and are each independently selected from the group consisting of hydrogen; deuterium; a halogen group; —CN; a substituted or unsubstituted alkyl group; a substituted or unsubstituted alkenyl group; a substituted or unsubstituted alkynyl group; a substituted or unsubstituted alkoxy group; a substituted or unsubstituted cycloalkyl group; a substituted or unsubstituted heterocycloalkyl group; a substituted or unsubstituted aryl group; a substituted or unsubstituted heteroaryl group; $—SiR_{10}R_{11}R_{12}$; $—P(=O)R_{10}R_{11}$; and an amine group unsubstituted or substituted with a substituted or unsubstituted alkyl group, a substituted or unsubstituted aryl group or a substituted or unsubstituted heteroaryl group, or two or more groups adjacent to each other bond to each other to form a substituted or unsubstituted aromatic hydrocarbon ring or a substituted or unsubstituted heteroring;

$R_{10}$, $R_{11}$, and $R_{12}$ are the same as or different from each other, and are each independently hydrogen; deuterium; —CN; a substituted or unsubstituted alkyl group; a substituted or unsubstituted cycloalkyl group; a substituted or unsubstituted aryl group; or a substituted or unsubstituted heteroaryl group;

Ra and Rb are the same as or different from each other, and are each independently a substituted or unsubstituted aryl group; or a substituted or unsubstituted heteroaryl group;

r and s are an integer of 0 to 7; and when r and s are each an integer of 2 or greater, substituents in the parentheses are the same as or different from each other.

15. The composition for an organic material layer of an organic light emitting device of claim 14, wherein, in the composition, the heterocyclic compound:the heterocyclic compound represented by Chemical Formula 2 have a weight ratio of 1:10 to 10:1.

16. A method for manufacturing an organic light emitting device, the method comprising:

preparing a substrate;

forming a first electrode on the substrate;

forming one or more organic material layers on the first electrode; and forming a second electrode on the organic material layer, wherein the forming of organic material layers comprises forming one or more organic material layers using the composition for an organic material layer of an organic light emitting device of claim 14.

17. The method for manufacturing an organic light emitting device of claim 16, wherein the forming of organic material layers is forming using a thermal vacuum deposition method after pre-mixing the heterocyclic compound of Chemical Formulae 7 to 9, 11 or 12 and the heterocyclic compound of Chemical Formula 2.

* * * * *